(12) United States Patent
Roush et al.

(10) Patent No.: US 11,618,749 B2
(45) Date of Patent: Apr. 4, 2023

(54) COMPOUNDS AND COMPOSITIONS FOR TREATING CONDITIONS ASSOCIATED WITH STING ACTIVITY

(71) Applicant: IFM Due, Inc., Boston, MA (US)

(72) Inventors: William R. Roush, Jupiter, FL (US); Shankar Venkatraman, Lansdale, PA (US); Gary Glick, Ann Arbor, MI (US); Hans Martin Seidel, Concord, MA (US)

(73) Assignee: IFM Due, Inc., Boston, MA (US)

( * ) Notice: Subject to any disclaimer, the term of this patent is extended or adjusted under 35 U.S.C. 154(b) by 0 days.

(21) Appl. No.: 16/460,381

(22) Filed: Jul. 2, 2019

(65) Prior Publication Data

US 2020/0172534 A1 Jun. 4, 2020

Related U.S. Application Data

(60) Provisional application No. 62/861,825, filed on Jun. 14, 2019, provisional application No. 62/693,768, filed on Jul. 3, 2018.

(51) Int. Cl.
*C07D 471/04* (2006.01)

(52) U.S. Cl.
CPC .................. *C07D 471/04* (2013.01)

(58) Field of Classification Search
CPC .. C07D 209/40; C07D 471/04; C07D 487/04; C07D 491/052; C07D 495/04; C07D 513/04
See application file for complete search history.

(56) References Cited

U.S. PATENT DOCUMENTS

| | | | |
|---|---|---|---|
| 7,927,613 B2 | 4/2011 | Almarsson | |
| 2004/0110956 A1 | 6/2004 | Didier | |
| 2004/0132794 A1 | 7/2004 | Didier | |
| 2012/0046290 A1 | 2/2012 | Dumas | |
| 2012/0202848 A1 | 8/2012 | Greene | |
| 2015/0056224 A1 | 2/2015 | Dubensky | |
| 2021/0236466 A1 | 8/2021 | Roush | |
| 2022/0024906 A1 | 1/2022 | Venkatraman et al. | |
| 2022/0024919 A1 | 1/2022 | Venkatraman et al. | |

FOREIGN PATENT DOCUMENTS

| | | | |
|---|---|---|---|
| WO | WO 03/028720 | | 4/2003 |
| WO | WO 2003-028724 | * | 4/2003 |
| WO | WO 2003/028724 | | 4/2003 |
| WO | WO 03/068773 | | 8/2003 |
| WO | WO 2003/068773 | | 8/2003 |
| WO | WO 03/097610 | | 11/2003 |
| WO | WO 2004/022544 | | 3/2004 |
| WO | WO 2005/073224 | | 8/2005 |
| WO | WO 2008/116898 | | 10/2008 |
| WO | WO 2009-140320 | * | 11/2009 |
| WO | WO 2009/140320 | | 11/2009 |
| WO | WO 2012/158413 | | 11/2012 |
| WO | WO 2012/178123 | | 12/2012 |
| WO | WO 2015/061294 | | 4/2015 |
| WO | WO 2016/049774 | | 4/2016 |
| WO | WO 2017/034420 | | 3/2017 |
| WO | WO 2017/035353 | | 3/2017 |
| WO | WO 2017/175156 | | 10/2017 |
| WO | WO 2018/132372 | | 7/2018 |
| WO | WO 2019/122202 | | 6/2019 |
| WO | WO 2019/034179 | | 9/2019 |
| WO | WO 2019/201939 | | 10/2019 |
| WO | WO 2020/010092 | | 1/2020 |
| WO | WO 2020/010155 | | 1/2020 |
| WO | WO 2020/150417 | | 1/2020 |
| WO | WO 2020/106736 | | 5/2020 |

(Continued)

OTHER PUBLICATIONS

Kubinyi (3D QSAR in Drug Design: Ligand-Protein Interactions and Molecular Similarity, vol. 2-3, Springer, 1998; see p. 243).*
Wermuth, The Practice of Medicinal Chemsitry, 2d ed. (2003), 768 pages, for example p. 142.*
Kumaran et al. (Int. J. Pharm. Tech. Res. 2012, 4 (1), pp. 169-175).*
Swarbrick et al. (Encyclopedia of Pharmaceutical Technology 13 (Marcel Dekker, NY 1996) pp. 453-499).*
Serajuddin (Advanced Drug Delivery Reviews 59 (2007) 603-616).*
Stahl et al. (eds., Handbook of pharmaceutical salts. Properties, selection and use (Wiley-VCH, 2008), pp. 265-327).*

(Continued)

*Primary Examiner* — Valerie Rodriguez-Garcia
(74) *Attorney, Agent, or Firm* — Fish & Richardson P.C.

(57) ABSTRACT

This disclosure features chemical entities of formula I (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

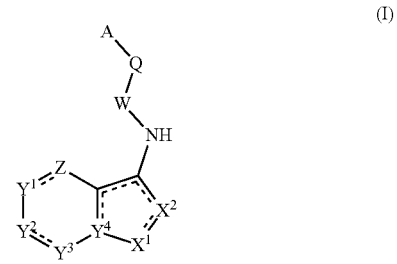

(I)

12 Claims, No Drawings

(56) References Cited

FOREIGN PATENT DOCUMENTS

| WO | WO 2020/106741 | 5/2020 |
|---|---|---|
| WO | WO 2020/150439 | 7/2020 |
| WO | WO 2020/191227 | 9/2020 |
| WO | WO 2020/236586 | 11/2020 |
| WO | WO 2020/243519 | 12/2020 |
| WO | WO 2020/252240 | 12/2020 |
| WO | WO 2020/257621 | 12/2020 |
| WO | WO 2021/067791 | 4/2021 |
| WO | WO 2021/067801 | 4/2021 |
| WO | WO 2021/067805 | 4/2021 |
| WO | WO 2021/138419 | 7/2021 |
| WO | WO 2021/138434 | 7/2021 |
| WO | WO 2022/015938 | 1/2022 |
| WO | WO 2022/015957 | 1/2022 |
| WO | WO 2022/015975 | 1/2022 |
| WO | WO 2022/015977 | 1/2022 |
| WO | WO 2022/015979 | 1/2022 |

OTHER PUBLICATIONS

Bastin et al., (Organic Process Research & Development 2000, 4, 427-435).*

PCT International Preliminary Report on Patentability in International Appln. No. PCT/US2019/040317, dated Jan. 5, 2021, 7 pages.

PCT International Search Report and Written Opinion in Appln. No. PCT/US2020/054064, dated Jan. 12, 2021, 18 pages.

Djung et al., "The synthesis and evaluation of indolylureas as PKCa inhibitors", Bioorganic & Medicinal Chemistry, vol. 19, No. 8, pp. 2742-2750, 2011.

Filipski et al., "Intestinal targeting of drugs: rational design approaches and challenges," Current Topics in Medicinal Chemistry, 13(7):776-802, 2013.

Haag et al., "Targeting STING with covalent small-molecule inhibitors", Nature, 559, 269-273, 2018.

International Search Report and Written Opinion in Application No. PCT/US2019/040317, dated Sep. 20, 2019, 16 pages.

Kumaran et al., "Synthesis, Spectral Characterization and Antimicrobial Studies of New 3- and 4-substituted in 7- Aza Indole Derivatives", International Journal of PharmTech Research, 4(1), 169-175, 2012.

Lammers et al., "Effect of intratumoral injection on the biodistribution and the therapeutic potential of HPMA copolymer-based drug delivery systems," Neoplasia, 10: 788-795, 2006.

Mohamed et al., "Design, Synthesis and Cancer Cell Line Activities of Pyrazolo[3,4-Z/\]pyridine Derivatives", Open Journal of Medicinal Chemistry, vol. 02, No. 03, pp. 78-88, 2012.

Postow et al., "Immune Checkpoint Blockade in Cancer Therapy," J. Clin. Oncol., 33(17): 1974-1982, 2015.

Sheridan Cormac, "Drug developers switch gears to inhibit STING", Nature Biotechnology, Gale Group Inc, New York, vol. 37, No. 3, pp. 199-201, 2019.

Zhang et al., "Discovery of Azaindole Ureas as a Novel Class of Bacterial Gyrase B Inhibitors", Journal of Medicinal Chemistiy, 58(21), 8503-8512, 2015.

International Preliminary Report on Patentability in Application No. PCT/US2020/054064, dated Apr. 5, 2022, 10 pages.

International Search Report and Written Opinion in Application No. PCT/US2020/067463, dated Feb. 25, 2021, 9 pages.

International Search Report and Written Opinion in Application No. PCT/US2020/067483, dated Apr. 9, 2021, 16 pages.

Raffa et al., "Synthesis and antiproliferative activity of 3-amino-N-phenyl-1H-indazole-1-carbonxamides," European J. of Medicinal Chem., Jan. 2009, 165-178.

\* cited by examiner

COMPOUNDS AND COMPOSITIONS FOR TREATING CONDITIONS ASSOCIATED WITH STING ACTIVITY

PRIORITY CLAIM

This application claims the benefit of United States Provisional Application No. 62/693,768, filed on Jul. 3, 2018 and U.S. Provisional Application No. 62/861,825, filed on Jun. 14, 2019, each of which is incorporated herein by reference in its entirety.

TECHNICAL FIELD

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

BACKGROUND

STING, also known as transmembrane protein 173 (TMEM173) and MPYS/MITA/ERIS, is a protein that in humans is encoded by the TMEM173 gene. STING has been shown to play a role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner.

The STING pathway is pivotal in mediating the recognition of cytosolic DNA. In this context, STING, a transmembrane protein localized to the endoplasmic reticulum (ER), acts as a second messenger receptor for 2', 3' cyclic GMP-AMP (hereafter cGAMP), which is produced by cGAS after dsDNA binding. In addition, STING can also function as a primary pattern recognition receptor for bacterial cyclic dinucleotides (CDNs) and small molecule agonists. The recognition of endogenous or prokaryotic CDNs proceeds through the carboxy-terminal domain of STING, which faces into the cytosol and creates a V-shaped binding pocket formed by a STING homodimer. Ligand-induced activation of STING triggers its re-localization to the Golgi, a process essential to promote the interaction of STING with TBK1. This protein complex, in turn, signals through the transcription factors IRF-3 to induce type I interferons (IFNs) and other co-regulated antiviral factors. In addition, STING was shown to trigger NF-κB and MAP kinase activation. Following the initiation of signal transduction, STING is rapidly degraded, a step considered important in terminating the inflammatory response.

Excessive activation of STING is associated with a subset of monogenic autoinflammatory conditions, the so-called type I interferonopathies. Examples of these diseases include a clinical syndrome referred to as STING-associated vasculopathy with onset in infancy (SAVI), which is caused by gain-of-function mutations in TMEM173 (the gene name of STING). Moreover, STING is implicated in the pathogenesis of Aicardi-Goutières Syndrome (AGS) and genetic forms of lupus. As opposed to SAVI, it is the dysregulation of nucleic acid metabolism that underlies continuous innate immune activation in AGS. Apart from these genetic disorders, emerging evidence points to a more general pathogenic role for STING in a range of inflammation-associated disorders such as systemic lupus erythematosus, rheumatoid arthritis and cancer. Thus, small molecule-based pharmacological interventions into the STING signaling pathway hold significant potential for the treatment of a wide spectrum of diseases

SUMMARY

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

An "antagonist" of STING includes compounds that, at the protein level, directly bind or modify STING such that an activity of STING is decreased, e.g., by inhibition, blocking or dampening agonist-mediated responses, altered distribution, or otherwise. STING antagonists include chemical entities, which interfere or inhibit STING signaling.

In one aspect, compounds of Formula (I), or a pharmaceutically acceptable salt thereof, are featured:

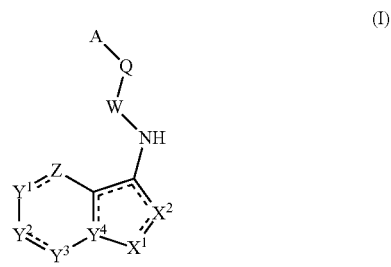

(I)

In which $X^1$, $X^2$, $Y^1$, $Y^2$, $Y^3$, $Y^4$, Z, W, Q, and A can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for inhibiting (e.g., antagonizing) STING activity are featured that include contacting STING with a chemical entity described herein (e.g., a compound described generically or specifically herein or a pharmaceutically acceptable salt thereof or compositions containing the same). Methods include in vitro methods, e.g., contacting a sample that includes one or more cells comprising STING (e.g., innate immune cells, e.g., mast cells, macrophages, dendritic cells (DCs), and natural killer cells) with the chemical entity. Methods can also include in vivo methods; e.g., administering the chemical entity to a subject (e.g., a human) having a disease in which increased (e.g., excessive) STING signaling contributes to the pathology and/or symptoms and/or progression of the disease.

In one aspect, methods of treating a condition, disease or disorder ameliorated by antagonizing STING are featured, e.g., treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). The methods include administering to a subject in need of such treatment an effective amount of a chemical entity described herein (e.g., a compound described generically or specifically herein or a pharmaceutically acceptable salt thereof or compositions containing the same).

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same).

In a further aspect, methods of treating other STING-associated conditions are featured, e.g., type I interferonopathies (e.g., STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis. The methods include administering to a subject in need of such treatment an effective amount of a chemical entity described herein (e.g., a compound described generically or specifically herein or a pharmaceutically acceptable salt thereof or compositions containing the same).

In another aspect, methods of suppressing STING-dependent type I interferon production in a subject in need thereof are featured that include administering to the subject an effective amount of a chemical entity described herein (e.g., a compound described generically or specifically herein or a pharmaceutically acceptable salt thereof or compositions containing the same).

In a further aspect, methods of treating a disease in which increased (e.g., excessive) STING activation (e.g., STING signaling) contributes to the pathology and/or symptoms and/or progression of the disease are featured. The methods include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering an effective amount of a chemical entity described herein (e.g., a compound described generically or specifically herein or a pharmaceutically acceptable salt thereof or compositions containing the same) to a subject; wherein the subject has (or is predisposed to have) a disease in which increased (e.g., excessive) STING activation (e.g., STING signaling) contributes to the pathology and/or symptoms and/or progression of the disease.

In a further aspect, methods of treatment that include administering to a subject a chemical entity described herein (e.g., a compound described generically or specifically herein or a pharmaceutically acceptable salt thereof or compositions containing the same), wherein the chemical entity is administered in an amount effective to treat a disease in which increased (e.g., excessive) STING activation (e.g., STING signaling) contributes to the pathology and/or symptoms and/or progression of the disease, thereby treating the disease.

Embodiments can include one or more of the following features.

The chemical entity can be administered in combination with one or more additional therapeutic agents and/or regimens. For examples, methods can further include administering one or more (e.g., two, three, four, five, six, or more) additional agents.

The chemical entity can be administered in combination with one or more additional therapeutic agents and/or regimens that are useful for treating other STING-associated conditions, e.g., type I interferonopathies (e.g., STING-associated vasculopathy with onset in infancy (SAVI)), Aicardi-Goutieres Syndrome (AGS), genetic forms of lupus, and inflammation-associated disorders such as systemic lupus erythematosus, and rheumatoid arthritis.

The chemical entity can be administered in combination with one or more additional cancer therapies (e.g., surgery, radiotherapy, chemotherapy, toxin therapy, immunotherapy, cryotherapy or gene therapy, or a combination thereof; e.g., chemotherapy that includes administering one or more (e.g., two, three, four, five, six, or more) additional chemotherapeutic agents. Non-limiting examples of additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-

CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

The subject can have cancer; e.g., the subject has undergone and/or is undergoing and/or will undergo one or more cancer therapies.

Non-limiting examples of cancer include melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma. In certain embodiments, the cancer can be a refractory cancer.

The chemical entity can be administered intratumorally.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "STING" is meant to include, without limitation, nucleic acids, polynucleotides, oligonucleotides, sense and antisense polynucleotide strands, complementary sequences, peptides, polypeptides, proteins, homologous and/or orthologous STING molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to:

rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, and the like.

The term "cycloalkyl" as used herein includes cyclic hydrocarbon groups having 3 to 20 ring carbons, preferably 3 to 16 ring carbons, and more preferably 3 to 12 ring carbons or 3-10 ring carbons or 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

The term "cycloalkenyl" as used herein includes partially unsaturated cyclic hydrocarbon groups having 3 to 20 ring carbons, preferably 3 to 16 ring carbons, and more preferably 3 to 12 ring carbons or 3-10 ring carbons or 3-6 ring carbons, wherein the cycloalkenyl group may be optionally substituted. Examples of cycloalkenyl groups include, without limitation, cyclopentenyl, cyclohexenyl, cycloheptenyl, and cyclooctenyl. Cycloalkenyl groups may have any degree of saturation provided that none of the rings in the ring system are aromatic; and the cycloalkenyl group is not fully saturated overall. Cycloalkenyl may include multiple fused and/or bridged and/or spirocyclic rings.

The term "heteroaryl", as used herein, means a mono-, bi-, tri- or polycyclic group having 5 to 20 ring atoms, alternatively 5, 6, 9, 10, or 14 ring atoms; and having 6, 10, or 14 pi electrons shared in a cyclic array; wherein at least one ring in the system is aromatic (but does not have to be a ring which contains a heteroatom, e.g. tetrahydroisoquinolinyl, e.g., tetrahydroquinolinyl), and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

The term "heterocyclyl" refers to a mono-, bi-, tri-, or polycyclic nonaromatic ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heterocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, "the ring that includes Z, $Y^1$, $Y^2$, $Y^3$, and $Y^4$ is partially unsaturated" means that said ring may have any degree of unsaturation provided that the ring is not aromatic and is not fully saturated overall. Examples of such rings include:

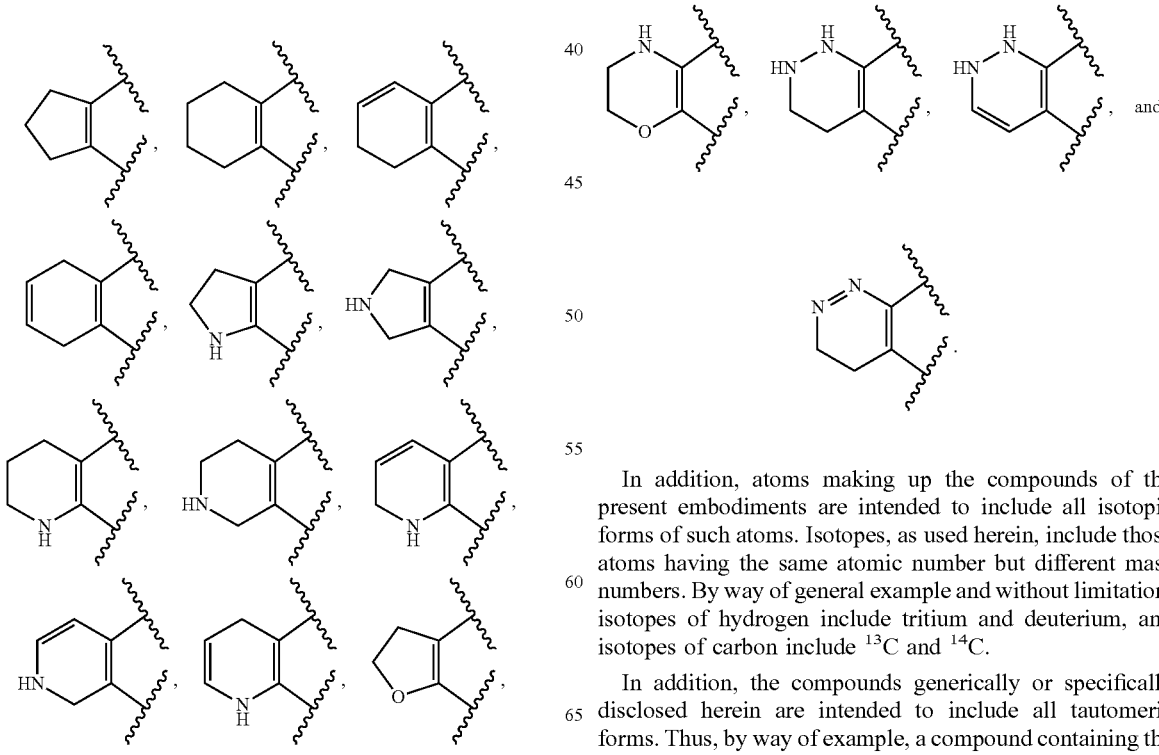

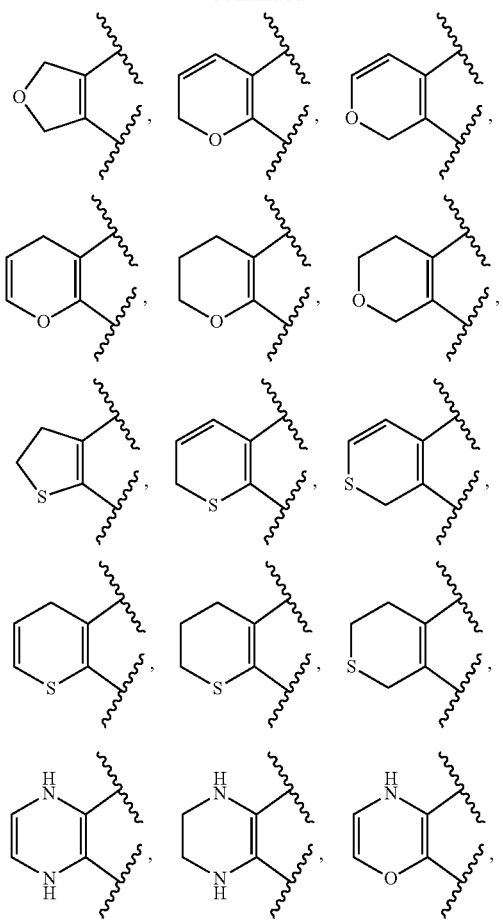

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In addition, the compounds generically or specifically disclosed herein are intended to include all tautomeric forms. Thus, by way of example, a compound containing the moiety:

encompasses the tautomeric form containing the moiety:

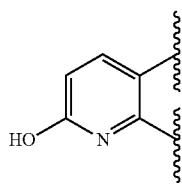

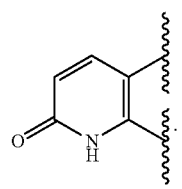

Similarly, a pyridinyl or pyrimidinyl moiety that is described to be optionally substituted with hydroxyl encompasses pyridone or pyrimidone tautomeric forms.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

Formula I Compounds

In one aspect, compounds of Formula (I), or a pharmaceutically acceptable salt thereof, are featured:

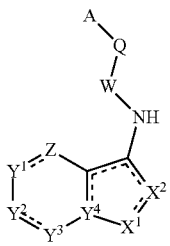

(I)

or a pharmaceutically acceptable salt thereof, or an N-oxide thereof,
wherein:
Z is selected from the group consisting of a bond, $CR^1$, $C(R^3)_2$, N, and $NR^2$;
each of $Y^1$, $Y^2$, and $Y^3$ is independently selected from the group consisting of O, S, $CR^1$, $C(R^3)_2$, N, and $NR^2$;
$Y^4$ is C or N;
$X^1$ is selected from the group consisting of O, S, N, $NR^2$, and $CR^1$;
$X^2$ is selected from the group consisting of O, S, N, $NR^4$, and $CR^5$;
each ═ is independently a single bond or a double bond, provided that the five-membered ring comprising $Y^4$, $X^1$, and $X^2$ is heteroaryl;
W is selected from the group consisting of:
(i) C(═O);
(ii) C(═S);
(iii) $S(O)_{1-2}$;
(iv) C(═$NR^d$);
(v) C(═NH);
(vi) C(═C—$NO_2$);
(vii) S(O)N($R^d$); and
(viii) S(O)NH;
Q-A is defined according to (A) or (B) below:
(A)
Q is NH or N($C_{1-6}$ alkyl) wherein the $C_{1-6}$ alkyl is optionally substituted with 1-2 independently selected $R^a$, and
A is:
(i) —$(Y^{A1})_n$—$Y^{A2}$, wherein:
n is 0 or 1;
$Y^{A1}$ is $C_{1-6}$ alkylene, which is optionally substituted with from 1-6 $R^a$; and
$Y^{A2}$ is:
(a) $C_{3-20}$ cycloalkyl, which is optionally substituted with from 1-4 $R^b$,
(b) $C_{6-20}$ aryl, which is optionally substituted with from 1-4 $R^c$;
(c) heteroaryl including from 5-20 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
(d) heterocyclyl including from 3-16 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
OR
(ii) —$Z^1$—$Z^2$-$Z^3$, wherein:
$Z^1$ is $C_{1-3}$ alkylene, which is optionally substituted with from 1-4 $R^a$;
$Z^2$ is —N(H)—, —N($R^d$)—, —O—, or —S—; and
$Z^3$ is $C_{2-7}$ alkyl, which is optionally substituted with from 1-4 $R^a$;
OR
(iii) $C_{1-10}$ alkyl, which is optionally substituted with from 1-6 independently selected $R^a$, or
(B)
Q and A, taken together, form:

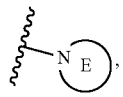

wherein ∤ denotes point of attachment to W; and
E is heterocyclyl including from 3-16 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-4 independently selected $R^b$, each occurrence of $R^1$ is independently selected from the group consisting of H, halo, cyano, $C_{1-6}$ alkyl optionally substituted with 1-2 $R^a$, $C_{2-6}$ alkenyl, $C_{2-6}$ alkynyl, $C_{1-4}$ haloalkyl, $C_{1-4}$ alkoxy, $C_{1-4}$ haloalkoxy, —($C_{0-3}$ alkylene)-$C_{3-6}$ cycloalkyl optionally substituted with from 1-4 independently selected $C_{1-4}$ alkyl, —($C_{0-3}$ alkylene)-$C_{6-10}$ aryl optionally substituted with from 1-4 independently selected $C_{1-4}$ alkyl, —($C_{0-3}$ alkylene)-5-10 membered heteroaryl optionally substituted with from 1-4 independently selected $C_{1-4}$ alkyl, —S(O)$_{1-2}$($C_{1-4}$ alkyl), —NR$^e$R$^f$, —OH, oxo, —S(O)$_{1-2}$(NR'R''), —$C_{1-4}$ thioalkoxy, —NO$_2$, —C(═O)($C_{1-4}$ alkyl), —C(═O)O($C_{1-4}$ alkyl), —C(═O)OH, and —C(═O)N(R')(R'');

each occurrence of $R^2$ is independently selected from the group consisting of:
(i) $C_{1-6}$ alkyl, which is optionally substituted with from 1-2 independently selected $R^a$;
(ii) $C_{3-6}$ cycloalkyl;
(iii) heterocyclyl including from 3-10 ring atoms, wherein from 1-3 ring atoms are heteroatoms, each independently selected from the group consisting of N, N(H), N($R^d$), and O.
(iv) —C(O)($C_{1-4}$ alkyl);
(v) —C(O)O($C_{1-4}$ alkyl);
(vi) —CON(R')(R'');
(vii) —S(O)$_{1-2}$(NR'R'');
(viii) —S(O)$_{1-2}$($C_{1-4}$ alkyl);
(ix) —OH;
(x) $C_{1-4}$ alkoxy; and
(xi) H;

each occurrence of $R^3$ is independently selected from H, $C_{1-6}$ alkyl optionally substituted with from 1-6 independently selected $R^a$; $C_{1-4}$ haloalkyl; —OH; —F; —Cl; —Br; —NR$^e$R$^f$; $C_{1-4}$ alkoxy; $C_{1-4}$ haloalkoxy; —C(═O)($C_{1-4}$ alkyl); —C(═O)O($C_{1-4}$ alkyl); —C(═O)OH; —C(═O)N(R')(R''); —S(O)$_{1-2}$(NR'R''); —S(O)$_{1-2}$($C_{1-4}$ alkyl); cyano; and $C_{3-6}$ cycloalkyl optionally substituted with from 1-4 independently selected $C_{1-4}$ alkyl; or two $R^3$ on the same carbon combine to form an oxo;

$R^4$ is selected from H and $C_{1-6}$ alkyl;
$R^5$ is selected from H, halo, $C_{1-4}$ alkoxy, OH, oxo, and $C_{1-6}$ alkyl;

each occurrence of $R^a$ is independently selected from the group consisting of: —OH; —F; —Cl; —Br; —NR$^e$R$^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R''); —S(O)$_{1-2}$(NR'R''); —S(O)$_{1-2}$($C_{1-4}$ alkyl); cyano, and $C_{3-6}$ cycloalkyl optionally substituted with from 1-4 independently selected $C_{1-4}$ alkyl;

each occurrence of $R^b$ is independently selected from the group consisting of: $C_{1-10}$ alkyl optionally substituted with from 1-6 independently selected $R^a$; $C_{1-4}$ haloalkyl; —OH; oxo; —F; —Cl; —Br; —NR$^e$R$^f$; $C_{1-4}$ alkoxy; $C_{1-4}$ haloalkoxy; —C(═O)($C_{1-4}$ alkyl); —C(═O)O($C_{1-4}$ alkyl); —C(═O)OH; —C(═O)N(R')(R''); —S(O)$_{1-2}$(NR'R''); —S(O)$_{1-2}$($C_{1-4}$ alkyl); cyano; $C_{6-10}$ aryl optionally substituted with 1-4 independently selected $C_{1-4}$ alkyl; and $C_{3-6}$ cycloalkyl optionally substituted with from 1-4 independently selected $C_{1-4}$ alkyl;

each occurrence of $R^c$ is independently selected from the group consisting of:
(i) halo;
(ii) cyano;
(iii) $C_{1-10}$ alkyl which is optionally substituted with from 1-6 independently selected $R^a$;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O;
(xi) —S(O)$_{1-2}$($C_{1-4}$ alkyl);
(xii) —NR$^e$R$^f$;
(xiii) —OH;
(xiv) —S(O)$_{1-2}$(NR'R'');
(xv) —$C_{1-4}$ thioalkoxy;
(xvi) —NO$_2$;
(xvii) —C(═O)($C_{1-4}$ alkyl);
(xviii) —C(═O)O($C_{1-4}$ alkyl);
(xix) —C(═O)OH, and
(xx) —C(═O)N(R')(R'');

$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl; $C_{1-6}$ haloalkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N($R^d$), O, and S; and each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N($R^d$), O, and S.

In one aspect, compounds of Formula (I), or a pharmaceutically acceptable salt thereof, are featured:

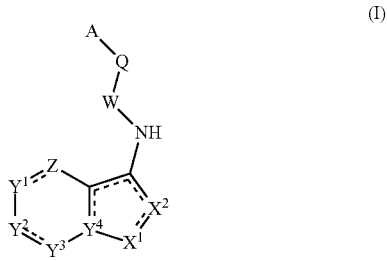

(I)

or a pharmaceutically acceptable salt thereof, or an N-oxide thereof,
wherein:
Z is selected from the group consisting of a bond, $CR^1$, $C(R^3)_2$, N, and $NR^2$;
each of $Y^1$, $Y^2$, and $Y^3$ is independently selected from the group consisting of O, S, $CR^1$, $C(R^3)_2$, N, and $NR^2$;
$Y^4$ is C or N;
$X^1$ is selected from the group consisting of O, S, N, $NR^2$, and $CR^1$;
$X^2$ is selected from the group consisting of O, S, N, $NR^4$, and $CR^5$;
each ═ is independently a single bond or a double bond, provided that the five-membered ring comprising $Y^4$, $X^1$, and $X^2$ is heteroaryl;
W is selected from the group consisting of:
(i) C(═O);
(ii) C(═S);
(iii) $S(O)_{1-2}$;
(iv) C(═$NR^d$);
(v) C(═NH);
(vi) C(═C—$NO_2$);
(vii) S(O)N($R^d$); and
(viii) S(O)NH;
Q-A is defined according to (A) or (B) below:
(A)
Q is NH or N($C_{1-6}$ alkyl) wherein the $C_{1-6}$ alkyl is optionally substituted with 1-2 independently selected $R^a$, and
A is:
(i) —$(Y^{A1})_n$—$Y^{A2}$, wherein:
n is 0 or 1;
$Y^{A1}$ is $C_{1-6}$ alkylene, which is optionally substituted with from 1-6 $R^a$; and
$Y^{A2}$ is:
(a) $C_{3-20}$ cycloalkyl, which is optionally substituted with from 1-4 $R^b$,
(b) $C_{6-20}$ aryl, which is optionally substituted with from 1-4 $R^c$;
(c) heteroaryl including from 5-20 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
(d) heterocyclyl including from 3-16 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
OR
(ii) —$Z^1$—$Z^2$—$Z^3$, wherein:
$Z^1$ is $C_{1-3}$ alkylene, which is optionally substituted with from 1-4 $R^a$;
$Z^2$ is —N(H)—, —N($R^d$)—, —O—, or —S—; and
$Z^3$ is $C_{2-7}$ alkyl, which is optionally substituted with from 1-4 $R^a$;
OR
(iii) $C_{1-10}$ alkyl, which is optionally substituted with from 1-6 independently selected $R^a$, or
(B)
Q and A, taken together, form:

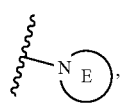

wherein ⌡ denotes point of attachment to W; and
E is heterocyclyl including from 3-16 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
each occurrence of $R^1$ is independently selected from the group consisting of H, halo, cyano, $C_{1-6}$ alkyl optionally substituted with 1-2 $R^a$, $C_{2-6}$ alkenyl, $C_{2-6}$ alkynyl, $C_{1-4}$ haloalkyl, $C_{1-4}$ alkoxy, $C_{1-4}$ haloalkoxy, —($C_{0-3}$ alkylene)-$C_{3-6}$ cycloalkyl optionally substituted with from 1-4 independently selected $C_{1-4}$ alkyl, —$S(O)_{1-2}(C_{1-4}$ alkyl), —$NR^eR^f$, —OH, oxo, —$S(O)_{1-2}$ (NR'R''), —$C_{1-4}$ thioalkoxy, —$NO_2$, —C(═O)($C_{1-4}$ alkyl), —C(═O)O($C_{1-4}$ alkyl), —C(═O)OH, and —C(═O)N(R')(R'');
each occurrence of $R^2$ is independently selected from the group consisting of:
(i) $C_{1-6}$ alkyl, which is optionally substituted with from 1-2 independently selected $R^a$;
(ii) $C_{3-6}$ cycloalkyl;
(iii) heterocyclyl including from 3-10 ring atoms, wherein from 1-3 ring atoms are heteroatoms, each independently selected from the group consisting of N, N(H), N($R^d$), and O.
(iv) —C(O)($C_{1-4}$ alkyl);
(v) —C(O)O($C_{1-4}$ alkyl);
(vi) —CON(R')(R'');
(vii) —$S(O)_{1-2}$(NR'R'');
(viii) —$S(O)_{1-2}(C_{1-4}$ alkyl);
(ix) —OH;
(x) $C_{1-4}$ alkoxy; and
(xi) H;
each occurrence of $R^3$ is independently selected from H, $C_{1-6}$ alkyl optionally substituted with from 1-6 independently selected $R^a$; $C_{1-4}$ haloalkyl; —OH; —F; —Cl; —Br; —$NR^eR^f$; $C_{1-4}$ alkoxy; $C_{1-4}$ haloalkoxy; —C(═O)($C_{1-4}$ alkyl); —C(═O)O($C_{1-4}$ alkyl); —C(═O)OH; —C(═O)N(R')(R''); —$S(O)_{1-2}$(NR'R''); —$S(O)_{1-2}(C_{1-4}$ alkyl); cyano; and $C_{3-6}$ cycloalkyl optionally substituted with from 1-4 independently selected $C_{1-4}$ alkyl; or two $R^3$ on the same carbon combine to form an oxo;
$R^4$ is selected from H and $C_{1-6}$ alkyl;
$R^5$ is selected from H, halo, $C_{1-4}$ alkoxy, OH, oxo, and $C_{1-6}$ alkyl;
each occurrence of $R^a$ is independently selected from the group consisting of: —OH; —F; —Cl; —Br; —$NR^eR^f$; $C_{1-4}$ alkoxy; $C_{1-4}$ haloalkoxy; —C(═O)O($C_{1-4}$ alkyl); —C(═O) ($C_{1-4}$ alkyl); —C(═O)OH; —CON(R')(R''); —$S(O)_{1-2}$(NR'R''); —$S(O)_{1-2}(C_{1-4}$ alkyl); cyano, and $C_{3-6}$ cycloalkyl optionally substituted with from 1-4 independently selected $C_{1-4}$ alkyl;
each occurrence of $R^b$ is independently selected from the group consisting of: $C_{1-10}$ alkyl optionally substituted with from 1-6 independently selected $R^a$; $C_{1-4}$ haloalkyl; —OH; oxo; —F; —Cl; —Br; —$NR^eR^f$; $C_{1-4}$ alkoxy; $C_{1-4}$ haloalkoxy; —C(═O)($C_{1-4}$ alkyl); —C(═O)O($C_{1-4}$ alkyl); —C(═O)OH; —C(═O)N(R')(R''); —$S(O)_{1-2}$(NR'R''); —$S(O)_{1-2}(C_{1-4}$ alkyl); cyano; $C_{6-10}$ aryl optionally substituted with 1-4 independently selected $C_{1-4}$ alkyl; and $C_{3-6}$ cycloalkyl optionally substituted with from 1-4 independently selected $C_{1-4}$ alkyl;
each occurrence of $R^c$ is independently selected from the group consisting of:
(i) halo;
(ii) cyano;

(iii) $C_{1-10}$ alkyl which is optionally substituted with from 1-6 independently selected $R^a$;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O;
(xi) —S(O)$_{1-2}$($C_{1-4}$ alkyl);
(xii) —NR$^e$R$^f$;
(xiii) —OH;
(xiv) —S(O)$_{1-2}$(NR'R");
(xv) —$C_{1-4}$ thioalkoxy;
(xvi) —NO$_2$;
(xvii) —C(=O)($C_{1-4}$ alkyl);
(xviii) —C(=O)O($C_{1-4}$ alkyl);
(xix) —C(=O)OH, and
(xx) —C(=O)N(R')(R");

$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R"); —S(O)$_{1-2}$(NR'R"); —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl; $C_{1-6}$ haloalkyl; $C_{3-6}$ cycloalkyl; —C(O)($C_{1-4}$ alkyl); —C(O)O($C_{1-4}$ alkyl); —CON(R')(R"); —S(O)$_{1-2}$(NR'R"); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of N($R^d$), O, and S; and each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of N($R^d$), O, and S.

In one aspect, provided herein is a compound of Formula (I):

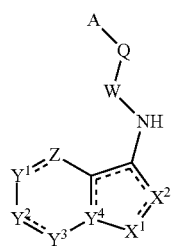

(I)

or a pharmaceutically acceptable salt thereof, or an N-oxide thereof, wherein:

Z is selected from the group consisting of a bond, $CR^1$, $C(R^3)_2$, N, and $NR^2$;

each of $Y^1$, $Y^2$, and $Y^3$ is independently selected from the group consisting of O, S, $CR^1$, $C(R^3)_2$, N, and $NR^2$;

$Y^4$ is C or N;

$X^1$ is selected from the group consisting of O, S, N, $NR^2$, and $CR^1$;

$X^2$ is selected from the group consisting of O, S, N, $NR^4$, and $CR^5$;

each = is independently a single bond or a double bond, provided that the five-membered ring comprising $Y^4$, $X^1$, and $X^2$ is heteroaryl;

W is selected from the group consisting of:
(i) C(=O);
(ii) C(=S);
(iii) S(O)$_{1-2}$;
(iv) C(=N$R^d$);
(v) C(=NH);
(vi) C(=C—NO$_2$);
(vii) S(O)N($R^d$); and
(viii) S(O)NH;

Q-A is defined according to (A) or (B) below:

(A)

Q is NH or N($C_{1-6}$ alkyl) wherein the $C_{1-6}$ alkyl is optionally substituted with 1-2 independently selected $R^a$, and A is:

(i) —($Y^{A1}$)$_n$—$Y^{A2}$, wherein:

n is 0 or 1;

$Y^{A1}$ is $C_{1-6}$ alkylene, which is optionally substituted with from 1-6 $R^a$; and $Y^{A2}$ is:

(a) $C_{3-20}$ cycloalkyl, which is optionally substituted with from 1-4 $R^b$, (b) $C_{6-20}$ aryl, which is optionally substituted with from 1-4 $R^c$;

(c) heteroaryl including from 5-20 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or (d) heterocyclyl including from 3-16 ring atoms, wherein from 1-3 ring atoms are heteroatoms, each independently selected from the group consisting of N, N(H), N($R^b$), N($R^d$), and O, and wherein one or more of the heterocyclyl ring carbon atoms are optionally substituted with from 1-4 independently selected $R^b$,

OR (ii) —$Z^1$—$Z^2$—$Z^3$, wherein:

$Z^1$ is $C_{1-3}$ alkylene, which is optionally substituted with from 1-4 $R^a$;

$Z^2$ is —N(H)—, —N($R^d$)—, —O—, or —S—; and $Z^3$ is $C_{2-7}$ alkyl, which is optionally substituted with from 1-4 $R^a$;

OR (iii) $C_{1-10}$ alkyl, which is optionally substituted with from 1-6 independently selected $R^a$, or (B) Q and A, taken together, form:

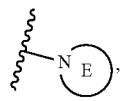

wherein ∫ denotes point of attachment to W; and

E is a ring including from 3-16 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-4 independently selected $R^b$, each occurrence of $R^1$ is independently selected from the group consisting of H; halo; cyano; $C_{1-6}$ alkyl optionally substituted with 1-2 $R^a$; $C_{2-6}$ alkenyl; $C_{2-6}$ alkynyl; $C_{1-4}$ haloalkyl; $C_{1-4}$ alkoxy; $C_{1-4}$ haloalkoxy; —($C_{0-3}$ alkylene)-$C_{3-6}$ cycloalkyl optionally substituted with from 1-4 independently selected $R^g$; —($C_{0-3}$ alkylene)-$C_{6-10}$ aryl optionally substituted with from 1-4 independently selected $R^g$; —($C_{0-3}$ alkylene)-5-10 membered heteroaryl, wherein from 1-3 ring atoms of the heteroaryl are heteroatoms each independently selected from the group consisting of N, NH, N$R^d$, O, and S, wherein the heteroaryl is optionally substituted with from 1-4 independently selected $R^g$; —($C_{0-3}$ alkylene)-5-10 membered heterocyclyl, wherein from 1-3 ring atoms of the heterocyclyl are heteroatoms each independently selected from the group consisting of N, NH, N$R^d$, O, and S, wherein the heterocyclyl is optionally substituted with 1-4 independently selected $R^g$; —S(O)$_{1-2}$($C_{1-4}$ alkyl); —N$R^eR^f$; —OH; oxo; —S(O)$_{1-2}$(NR'R''); —$C_{1-4}$ thioalkoxy; —NO$_2$; —C(=O)($C_{1-4}$ alkyl); —C(=O)O($C_{1-4}$ alkyl); —C(=O)OH; and —C(=O)N(R')(R'');

each occurrence of $R^2$ is independently selected from the group consisting of:
(i) $C_{1-6}$ alkyl, which is optionally substituted with from 1-2 independently selected $R^a$;
(ii) $C_{3-6}$ cycloalkyl;
(iii) heterocyclyl including from 3-10 ring atoms, wherein from 1-3 ring atoms are heteroatoms, each independently selected from the group consisting of N, N(H), N($R^d$), and O;
(iv) —C(O)($C_{1-4}$ alkyl);
(v) —C(O)O($C_{1-4}$ alkyl);
(vi) —CON(R')(R'');
(vii) —S(O)$_{1-2}$(NR'R'');
(viii) —S(O)$_{1-2}$($C_{1-4}$ alkyl);
(ix) —OH;
(x) $C_{1-4}$ alkoxy; and
(xi) H;

each occurrence of $R^3$ is independently selected from the group consisting of H, $C_{1-6}$ alkyl optionally substituted with from 1-6 independently selected $R^a$; $C_{1-4}$ haloalkyl; —OH; —F; —Cl; —Br; —N$R^eR^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —S(O)$_{1-2}$(NR'R''); —S(O)$_{1-2}$($C_{1-4}$ alkyl); cyano; and $C_{3-6}$ cycloalkyl optionally substituted with from 1-4 independently selected $C_{1-4}$ alkyl; or two $R^3$ on the same carbon combine to form an oxo;

$R^4$ is selected from the group consisting of H and $C_{1-6}$ alkyl;
$R^5$ is selected from the group consisting of H, halo, $C_{1-4}$ alkoxy, OH, oxo, and $C_{1-6}$ alkyl;

each occurrence of $R^a$ is independently selected from the group consisting of: —OH; —F; —Cl; —Br; —N$R^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{1-2}$($C_{1-4}$ alkyl); cyano, and $C_{3-6}$ cycloalkyl optionally substituted with from 1-4 independently selected $C_{1-4}$ alkyl;

each occurrence of $R^b$ is independently selected from the group consisting of: $C_{1-10}$ alkyl optionally substituted with from 1-6 independently selected $R^a$; $C_{1-4}$ haloalkyl; —OH; oxo; —F; —Cl; —Br; —N$R^eR^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —S(O)$_{1-2}$(NR'R''); —S(O)$_{1-2}$($C_{1-4}$ alkyl); cyano; ($C_{0-3}$ alkylene)-$C_{6-10}$ aryl optionally substituted with 1-4 independently selected $C_{1-4}$ alkyl; and ($C_{0-3}$ alkylene)-$C_{3-6}$ cycloalkyl optionally substituted with from 1-4 independently selected $C_{1-4}$ alkyl;

each occurrence of $R^c$ is independently selected from the group consisting of:
(i) halo;
(ii) cyano;
(iii) $C_{1-10}$ alkyl which is optionally substituted with from 1-6 independently selected $R^a$;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O;
(xi) —S(O)$_{1-2}$($C_{1-4}$ alkyl);
(xii) —N$R^eR^f$;
(xiii) —OH;
(xiv) —S(O)$_{1-2}$(NR'R'');
(xv) —$C_{1-4}$ thioalkoxy;
(xvi) —NO$_2$;
(xvii) —C(=O)($C_{1-4}$ alkyl);
(xviii) —C(=O)O($C_{1-4}$ alkyl);
(xix) —C(=O)OH;
(xx) —C(=O)N(R')(R''); and
(xxi) —($C_{0-3}$ alkylene)-$C_{6-10}$ aryl optionally substituted with from 1-4 independently selected $C_{1-4}$ alkyl; and
(xxii) —($C_{0-3}$ alkylene)-5-10 membered heteroaryl, wherein from 1-3 ring atoms of the heteroaryl are heteroatoms each independently selected from the group consisting of: N, NH, N$R^d$, O, and S, wherein the heteroaryl is optionally substituted with from 1-4 independently selected $C_{1-4}$ alkyl;

$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —CN; —OH; and $C_{1-4}$ alkoxy;

each occurrence of $R^e$ and $R^f$ is independently selected from the group consisting of: H; $C_{1-6}$ alkyl; $C_{1-6}$ haloalkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from the group consisting of H and $C_{1-3}$ alkyl; and (b) from 0-3 ring heteroatoms (in addition to the nitrogen atom attached to $R^e$ and $R^f$), which are each independently selected from the group consisting of $N(R^d)$, O, and S;

each occurrence of $R^g$ is independently selected from the group consisting of: halo; cyano; $C_{1-6}$ alkyl optionally substituted with from 1-2 independently selected $R^a$; $C_{1-4}$ haloalkyl; $C_{1-6}$ alkoxy optionally substituted with 1-2 independently selected $R^a$; $C_{1-4}$ haloalkoxy; $S(O)_{1-2}(C_{1-4}$ alkyl); —$NR^eR^f$; —OH; oxo; —$S(O)_{1-2}(NR'R'')$; —$C_{1-4}$ thioalkoxy; —$NO_2$; —C(=O)($C_{1-4}$ alkyl); —C(=O)O($C_{1-4}$ alkyl); —C(=O)OH; and —C(=O)N(R')(R'');

and each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from the group consisting of: H and $C_{1-3}$ alkyl; and (b) from 0-3 ring heteroatoms (in addition to the nitrogen atom attached to R' and R"), which are each independently selected from the group consisting of $N(R^d)$, O, and S, provided that one or more of a), b), and c) apply:

a) one or more of Z, $Y^1$, $Y^2$, $Y^3$, and $Y^4$ in the ring below

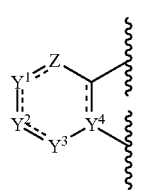

is an independently selected heteroatom;

b) the ring that includes Z, $Y^1$, $Y^2$, $Y^3$, and $Y^4$ is partially unsaturated; OR c) Z is a bond;

further provided that when Q-A is defined according to (A); A is $C_6$ aryl mono-substituted with $C_{1-10}$ alkyl (e.g., $C_{2-6}$ alkyl (e.g., $C_{3-5}$ alkyl (e.g., $C_4$ alkyl (e.g., n-butyl)))) at the para position; and the ring that includes Z, $Y^1$, $Y^2$, $Y^3$, and $Y^4$ is aromatic, then the ring that includes Z, $Y^1$, $Y^2$, $Y^3$, and $Y^4$ must be substituted with one or more R' that is other than hydrogen; and and further provided with the proviso that the compound is not selected from the group consisting of:

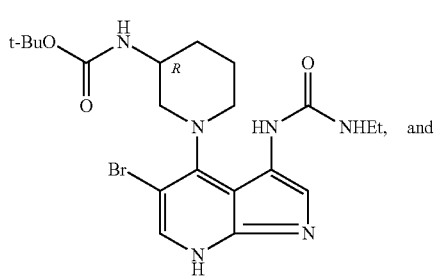

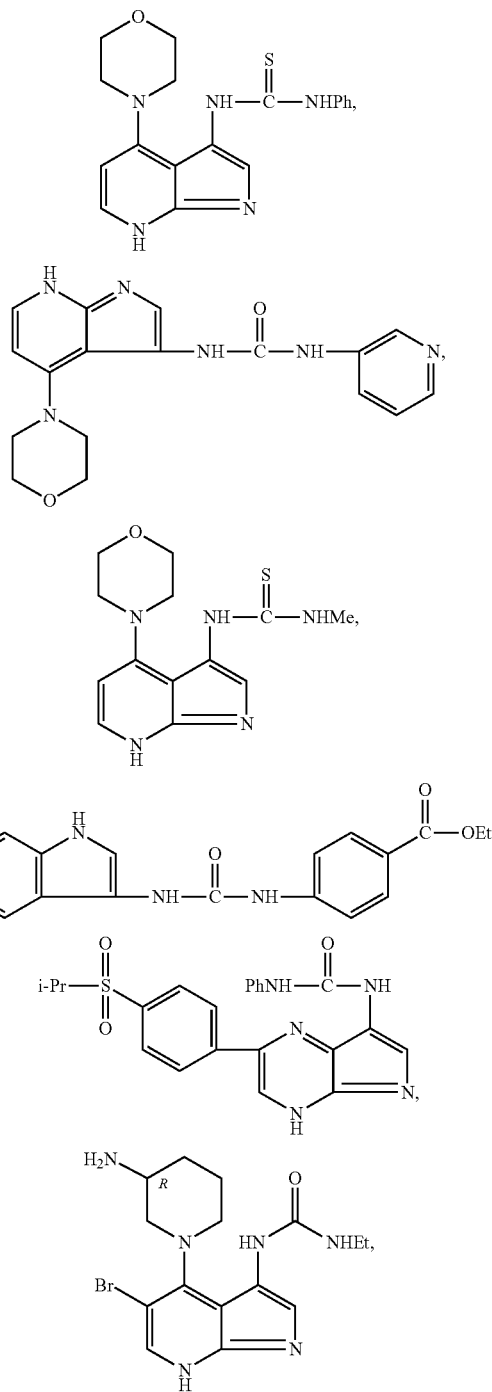

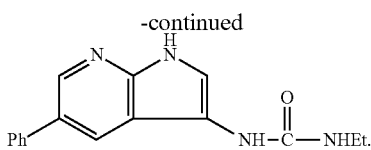

In some embodiments, it is provided that when Q-A is defined according to (A); A is $C_6$ aryl mono-substituted with $C_4$ alkyl such as n-butyl at the para position; and the ring that includes Z, $Y^1$, $Y^2$, $Y^3$, and $Y^4$ is aromatic, then the ring that includes Z, $Y^1$, $Y^2$, $Y^3$, and $Y^4$ must be substituted with one or more $R^1$ that is other than hydrogen.

In another aspect, provided herein is a compound of Formula (I):

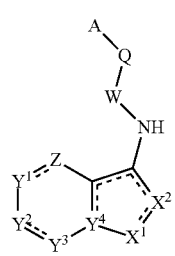

(I)

or a pharmaceutically acceptable salt thereof, or an N-oxide thereof,
wherein:
one or more of Z, $Y^1$, $Y^2$, $Y^3$, and $Y^4$ in the ring below

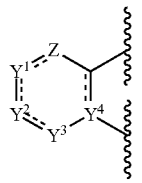

is an independently selected heteroatom;
Z is selected from the group consisting of $CR^1$ and N;
each of $Y^1$, $Y^2$, and $Y^3$ is independently selected from the group consisting of $CR^1$ and N;
provided that one or more of Z, $Y^1$, $Y^2$, and $Y^3$ is an independently selected $CR^1$;
$Y^4$ is C;
$X^1$ is NH;
$X^2$ is CH;
each ═ is independently a single bond or a double bond, provided that the five-membered ring comprising $Y^4$, $X^1$, and $X^2$ is heteroaryl; and
the ring that includes Z, $Y^1$, $Y^2$, $Y^3$, and $Y^4$ is aromatic;
W is selected from the group consisting of:
(i) C(═O);
(ii) C(═S);
(iv) C(═$NR^d$); and
(v) C(═NH);
Q-A is defined according to (A) or (B) below:
(A)
Q is NH or N($C_{1-6}$ alkyl) wherein the $C_{1-6}$ alkyl is optionally substituted with 1-2 independently selected $R^a$, and A is:
(i) —$(Y^{A1})_n$—$Y^{A2}$, wherein:
n is 0 or 1;
$Y^{A1}$ is $C_{1-6}$ alkylene, which is optionally substituted with from 1-6 $R^a$; and
$Y^{A2}$ is:
(a) $C_{3-20}$ cycloalkyl, which is optionally substituted with from 1-4 $R^b$,
(b) $C_{6-20}$ aryl, which is optionally substituted with from 1-4 $R^c$;
(c) heteroaryl including from 5-20 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
(d) heterocyclyl including from 3-16 ring atoms, wherein from 1-3 ring atoms are heteroatoms, each independently selected from the group consisting of N, N(H), N($R^b$), N($R^d$), and O, and wherein one or more of the heterocyclyl ring carbon atoms are optionally substituted with from 1-4 independently selected $R^b$,
OR
(ii) —$Z^1$—$Z^2$—$Z^3$, wherein:
$Z^1$ is $C_{1-3}$ alkylene, which is optionally substituted with from 1-4 $R^a$;
$Z^2$ is —N(H)—, —N($R^d$)—, —O—, or —S—; and
$Z^3$ is $C_{2-7}$ alkyl, which is optionally substituted with from 1-4 $R^a$;
OR
(iii) $C_{1-10}$ alkyl, which is optionally substituted with from 1-6 independently selected $R^a$,
OR
(B)
Q and A, taken together, form:

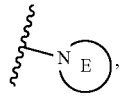

wherein ∤ denotes point of attachment to W; and
E is a ring including from 3-16 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
each occurrence of $R^1$ is independently selected from the group consisting of H; halo; cyano; $C_{1-6}$ alkyl optionally substituted with 1-2 $R^a$; $C_{2-6}$ alkenyl; $C_{2-6}$ alkynyl; $C_{1-4}$ haloalkyl; $C_{1-4}$ alkoxy; $C_{1-4}$ haloalkoxy; —($C_{0-3}$ alkylene)-$C_{3-6}$ cycloalkyl optionally substituted with from 1-4 independently selected $R^g$; —($C_{0-3}$ alkylene)-$C_{6-10}$ aryl optionally substituted with from 1-4 independently selected $R^g$; —($C_{0-3}$ alkylene)-5-10 membered heteroaryl, wherein from 1-3 ring atoms of the heteroaryl are heteroatoms each independently selected from the group consisting of N, NH, $NR^d$, O, and S, wherein the heteroaryl is optionally substituted with from 1-4 independently selected $R^g$; —($C_{0-3}$ alkylene)-5-10 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected R$^g$; —S(O)$_{1-2}$ (C$_{1-4}$ alkyl); —NR$^e$R$^f$; —OH; oxo; —S(O)$_{1-2}$(NR'R''); —C$_{1-4}$ thioalkoxy; —NO$_2$; —C(=O)(C$_{1-4}$ alkyl); —C(=O)O(C$_{1-4}$ alkyl); —C(=O)OH; and —C(=O)N(R')(R'');

each occurrence of R$^a$ is independently selected from the group consisting of: —OH; —F; —Cl; —Br; —NR$^e$R$^f$; C$_{1-4}$ alkoxy; C$_{1-4}$ haloalkoxy; —C(=O)O(C$_{1-4}$ alkyl); —C(=O)(C$_{1-4}$ alkyl); —C(=O)OH; —CON(R')(R''); —S(O)$_{1-2}$(NR'R''); —S(O)$_{1-2}$(C$_{1-4}$ alkyl); cyano; and C$_{3-6}$ cycloalkyl optionally substituted with from 1-4 independently selected C$_{1-4}$ alkyl;

each occurrence of R$^b$ is independently selected from the group consisting of: C$_{1-10}$ alkyl optionally substituted with from 1-6 independently selected R$^a$; C$_{1-4}$ haloalkyl; —OH; oxo; —F; —Cl; —Br; —NR$^e$R$^f$; C$_{1-4}$ alkoxy; C$_{1-4}$ haloalkoxy; —C(=O)(C$_{1-4}$ alkyl); —C(=O)O(C$_{1-4}$ alkyl); —C(=O)OH; —C(=O)N(R')(R''); —S(O)$_{1-2}$(NR'R''); —S(O)$_{1-2}$(C$_{1-4}$ alkyl); cyano; (C$_{0-3}$ alkylene)-C$_{6-10}$ aryl optionally substituted with 1-4 independently selected C$_{1-4}$ alkyl; and (C$_{0-3}$ alkylene)-C$_{3-6}$ cycloalkyl optionally substituted with from 1-4 independently selected C$_{1-4}$ alkyl;

each occurrence of R$^c$ is independently selected from the group consisting of:
(i) halo;
(ii) cyano;
(iii) C$_{1-10}$ alkyl which is optionally substituted with from 1-6 independently selected R$^a$;
(iv) C$_{2-6}$ alkenyl;
(v) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl, wherein the heterocyclyl includes from 3-16 ring atoms, wherein from 1-3 ring atoms are heteroatoms, each independently selected from the group consisting of N, N(H), N(R$^d$), and O;
(xi) —S(O)$_{1-2}$(C$_{1-4}$ alkyl);
(xii) —NR$^e$R$^f$;
(xiii) —OH;
(xiv) —S(O)$_{1-2}$(NR'R'');
(xv) —C$_{1-4}$ thioalkoxy;
(xvi) —NO$_2$;
(xvii) —C(=O)(C$_{1-4}$ alkyl);
(xviii) —C(=O)O(C$_{1-4}$ alkyl);
(xix) —C(=O)OH;
(xx) —C(=O)N(R')(R'');
(xxi) —(C$_{0-3}$ alkylene)-C$_{6-10}$ aryl optionally substituted with from 1-4 independently selected C$_{1-4}$ alkyl; and
(xxii) —(C$_{0-3}$ alkylene)-5-10 membered heteroaryl, wherein from 1-3 ring atoms of the heteroaryl are heteroatoms each independently selected from the group consisting of: N, NH, NR$^d$, O, and S, wherein the heteroaryl is optionally substituted with from 1-4 independently selected C$_{1-4}$ alkyl;

R$^d$ is selected from the group consisting of: C$_{1-6}$ alkyl; C$_{3-6}$ cycloalkyl; —C(O)(C$_{1-4}$ alkyl); —C(O)O(C$_{1-4}$ alkyl); —CON(R')(R''); —S(O)$_{1-2}$(NR'R''); —S(O)$_{1-2}$(C$_{1-4}$ alkyl); —OH; —CN; and C$_{1-4}$ alkoxy;

each occurrence of R$^e$ and R$^f$ is independently selected from the group consisting of: H; C$_{1-6}$ alkyl; C$_{1-6}$ haloalkyl; C$_{3-6}$ cycloalkyl; —C(O)(C$_{1-4}$ alkyl); —C(O)O(C$_{1-4}$ alkyl); —CON(R')(R''); —S(O)$_{1-2}$(NR'R''); —S(O)$_{1-2}$(C$_{1-4}$ alkyl); —OH; and C$_{1-4}$ alkoxy; or R$^e$ and R$^f$ together with the nitrogen atom to which each is attached forms a ring including from 3-8 ring atoms, wherein the ring includes: (a) from 1-7 ring carbon atoms, each of which is substituted with from 1-2 substituents independently selected from H and C$_{1-3}$ alkyl; and (b) from 0-3 ring heteroatoms (in addition to the nitrogen atom attached to R$^e$ and R$^f$), which are each independently selected from the group consisting of N(R$^d$), O, and S;

each occurrence of R$^g$ is independently selected from the group consisting of: halo; cyano; C$_{1-6}$ alkyl optionally substituted with from 1-2 independently selected R$^a$; C$_{1-4}$ haloalkyl; C$_{1-6}$ alkoxy optionally substituted with 1-2 independently selected R$^a$; C$_{1-4}$ haloalkoxy; S(O)$_{1-2}$(C$_{1-4}$ alkyl); —NR$^e$R$^f$; —OH; oxo; —S(O)$_{1-2}$(NR'R''); —C$_{1-4}$ thioalkoxy; —NO$_2$; —C(=O)(C$_{1-4}$ alkyl); —C(=O)O(C$_{1-4}$ alkyl); —C(=O)OH; and —C(=O)N(R')(R'');

and each occurrence of R' and R'' is independently selected from the group consisting of: H and C$_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and C$_{1-3}$ alkyl; and (b) from 0-3 ring heteroatoms (in addition to the nitrogen atom attached to R' and R''), which are each independently selected from the group consisting of N(R$^d$), O, and S;

provided that when Q-A is defined according to (A); A is C$_6$ aryl mono-substituted with a C$_4$ alkyl such as n-butyl at the para position, then the ring that includes Z, Y$^1$, Y$^2$, Y$^3$, and Y$^4$ must be substituted with one or more R$^1$ that is other than hydrogen; and further provided with the proviso that the compound is other than one or more of the following:

-continued

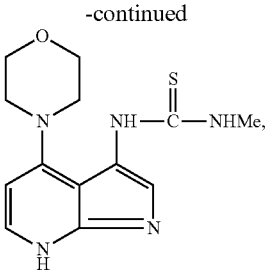

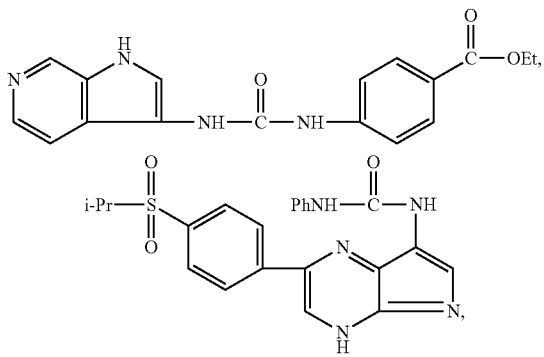

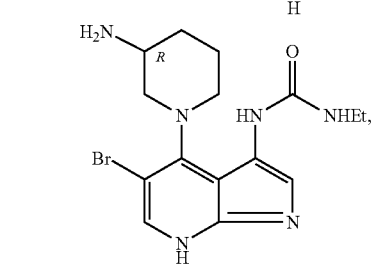

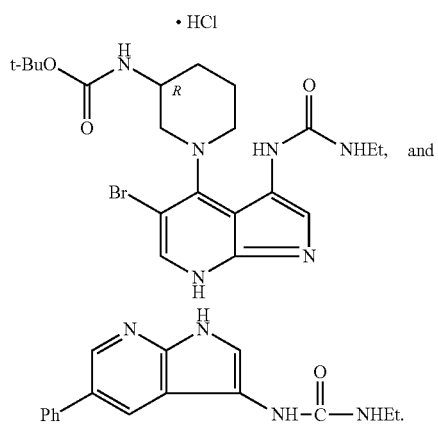

·HCl

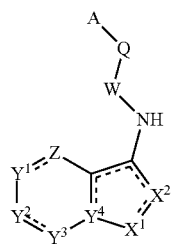

In another aspect, provided herein is a compound of Formula (I), (I)

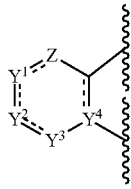

or a pharmaceutically acceptable salt thereof, or an N-oxide thereof,
wherein:
one or more of Z, $Y^1$, $Y^2$, $Y^3$, and $Y^4$ in the ring below is an independently selected heteroatom;
Z is selected from the group consisting of $CR^1$ and N;
each of $Y^1$, $Y^2$, and $Y^3$ is independently selected from the group consisting of $CR^1$ and N;
provided that one or more of Z, $Y^1$, $Y^2$, and $Y^3$ is an independently selected $CR^1$;
$Y^4$ is C;
$X^1$ is NH;
$X^2$ is CH;
each ═ is independently a single bond or a double bond, provided that the five-membered ring comprising $Y^4$, $X^1$, and $X^2$ is heteroaryl; and
the ring that includes Z, $Y^1$, $Y^2$, $Y^3$, and $Y^4$ is aromatic;
W is selected from the group consisting of:
(i) C(═O);
(ii) C(═S);
(iv) C(═$NR^d$); and
(v) C(═NH);
Q-A is defined according to (A) or (B) below:
(A)
Q is NH or N($C_{1-6}$ alkyl) wherein the $C_{1-6}$ alkyl is optionally substituted with 1-2 independently selected $R^a$, and
A is:
(i) —($Y^{41}$)$_n$—$Y^{42}$, wherein:
n is 0 or 1;
$Y^{41}$ is $C_{1-6}$ alkylene, which is optionally substituted with from 1-6 $R^a$; and
$Y^{42}$ is:
(a) $C_{3-20}$ cycloalkyl, which is optionally substituted with from 1-4 $R^b$,
(b) $C_{6-20}$ aryl, which is optionally substituted with from 1-4 $R^c$;
(c) heteroaryl including from 5-20 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
(d) heterocyclyl including from 3-16 ring atoms, wherein from 1-3 ring atoms are heteroatoms, each independently selected from the group consisting of N, N(H), N($R^b$), N($R^d$), and O, and wherein one or more of the heterocyclyl ring carbon atoms are optionally substituted with from 1-4 independently selected $R^b$,
OR
(ii) —$Z^1$—$Z^2$—$Z^3$, wherein:
$Z^1$ is $C_{1-3}$ alkylene, which is optionally substituted with from 1-4 $R^a$;
$Z^2$ is —N(H)—, —N($R^d$)—, —O—, or —S—; and
$Z^3$ is $C_{2-7}$ alkyl, which is optionally substituted with from 1-4 $R^a$;

OR (iii) C$_{1-10}$ alkyl, which is optionally substituted with from 1-6 independently selected R$^a$, or (B) Q and A, taken together, form:

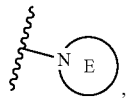

wherein ∤ denotes point of attachment to W; and

E is a ring including from 3-16 ring atoms, wherein aside from the nitrogen atom present, from 0-3 additional ring atoms are heteroatoms, each independently selected from the group consisting of N, N(H), N(R$^d$), and O, and wherein one or more of the heterocyclyl ring carbon atoms are optionally substituted with from 1-4 independently selected R$^b$, each occurrence of R$^1$ is independently selected from the group consisting of H; halo; cyano; C$_{1-6}$ alkyl optionally substituted with 1-2 R$^a$; C$_{2-6}$ alkenyl; C$_{2-6}$ alkynyl; C$_{1-4}$ haloalkyl; C$_{1-4}$ alkoxy; C$_{1-4}$ haloalkoxy; —(C$_{0-3}$ alkylene)-C$_{3-6}$ cycloalkyl optionally substituted with from 1-4 independently selected R$^g$; —(C$_{0-3}$ alkylene)-C$_{6-10}$ aryl optionally substituted with from 1-4 independently selected R$^g$; —(C$_{0-3}$ alkylene)-5-10 membered heteroaryl, wherein from 1-3 ring atoms of the heteroaryl are heteroatoms each independently selected from the group consisting of N, NH, NR$^d$, O, and S, wherein the heteroaryl is optionally substituted with from 1-4 independently selected R$^g$; —(C$_{0-3}$ alkylene)-5-10 membered heterocyclyl, wherein from 1-3 ring atoms of the heterocyclyl are heteroatoms each independently selected from the group consisting of N, NH, NR$^d$, O, and S, wherein the heterocyclyl is optionally substituted with 1-4 independently selected R$^g$; —S(O)$_{1-2}$(C$_{1-4}$ alkyl); —NR$^e$R$^f$; —OH; oxo; —S(O)$_{1-2}$(NR'R''); —C$_{1-4}$ thioalkoxy; —NO$_2$; —C(=O)(C$_{1-4}$ alkyl); —C(=O)O(C$_{1-4}$ alkyl); —C(=O)OH; and —C(=O)N(R')(R'');

each occurrence of R$^a$ is independently selected from the group consisting of: —OH; —F; —Cl; —Br; —NR$^e$R$^f$; C$_{1-4}$ alkoxy; C$_{1-4}$ haloalkoxy; —C(=O)O(C$_{1-4}$ alkyl); —C(=O)(C$_{1-4}$ alkyl); —C(=O)OH; —CON(R')(R''); —S(O)$_{1-2}$(NR'R''); —S(O)$_{1-2}$(C$_{1-4}$ alkyl); cyano; and C$_{3-6}$ cycloalkyl optionally substituted with from 1-4 independently selected C$_{1-4}$ alkyl;

each occurrence of R$^b$ is independently selected from the group consisting of: C$_{1-10}$ alkyl optionally substituted with from 1-6 independently selected R$^a$; C$_{1-4}$ haloalkyl; —OH; oxo; —F; —Cl; —Br; —NR$^e$R$^f$; C$_{1-4}$ alkoxy; C$_{1-4}$ haloalkoxy; —C(=O)(C$_{1-4}$ alkyl); —C(=O)O(C$_{1-4}$ alkyl); —C(=O)OH; —C(=O)N(R')(R''); —S(O)$_{1-2}$(NR'R''); —S(O)$_{1-2}$(C$_{1-4}$ alkyl); cyano; (C$_{0-3}$ alkylene)-C$_{6-10}$ aryl optionally substituted with 1-4 independently selected C$_{1-4}$ alkyl; and (C$_{0-3}$ alkylene)-C$_{3-6}$ cycloalkyl optionally substituted with from 1-4 independently selected C$_{1-4}$ alkyl;

each occurrence of R$^c$ is independently selected from the group consisting of:
(i) halo;
(ii) cyano;
(iii) C$_{1-10}$ alkyl which is optionally substituted with from 1-6 independently selected R$^a$;
(iv) C$_{2-6}$ alkenyl;
(v) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl, wherein the heterocyclyl includes from 3-16 ring atoms, wherein from 1-3 ring atoms are heteroatoms, each independently selected from the group consisting of N, N(H), N(R$^d$), and O;
(xi) —S(O)$_{1-2}$(C$_{1-4}$ alkyl);
(xii) —NR$^e$R$^f$;
(xiii) —OH;
(xiv) —S(O)$_{1-2}$(NR'R'');
(xv) —C$_{1-4}$ thioalkoxy;
(xvi) —NO$_2$;
(xvii) —C(=O)(C$_{1-4}$ alkyl);
(xviii) —C(=O)O(C$_{1-4}$ alkyl);
(xix) —C(=O)OH;
(xx) —C(=O)N(R')(R'');
(xxi) —(C$_{0-3}$ alkylene)-C$_{6-10}$ aryl optionally substituted with from 1-4 independently selected C$_{1-4}$ alkyl; and
(xxii) —(C$_{0-3}$ alkylene)-5-10 membered heteroaryl, wherein from 1-3 ring atoms of the heteroaryl are heteroatoms each independently selected from the group consisting of: N, NH, NR$^d$, O, and S, wherein the heteroaryl is optionally substituted with from 1-4 independently selected C$_{1-4}$ alkyl;

R$^d$ is selected from the group consisting of: C$_{1-6}$ alkyl; C$_{3-6}$ cycloalkyl; —C(O)(C$_{1-4}$ alkyl); —C(O)O(C$_{1-4}$ alkyl); —CON(R')(R''); —S(O)$_{1-2}$(NR'R''); —S(O)$_{1-2}$(C$_{1-4}$ alkyl); —OH; —CN; and C$_{1-4}$ alkoxy;

each occurrence of R$^e$ and R$^f$ is independently selected from the group consisting of: H; C$_{1-6}$ alkyl; C$_{1-6}$ haloalkyl; C$_{3-6}$ cycloalkyl; —C(O)(C$_{1-4}$ alkyl); —C(O)O(C$_{1-4}$ alkyl); —CON(R')(R''); —S(O)$_{1-2}$(NR'R''); —S(O)$_{1-2}$(C$_{1-4}$ alkyl); —OH; and C$_{1-4}$ alkoxy; or R$^e$ and R$^f$ together with the nitrogen atom to which each is attached forms a ring including from 3-8 ring atoms, wherein the ring includes: (a) from 1-7 ring carbon atoms, each of which is substituted with from 1-2 substituents independently selected from H and C$_{1-3}$ alkyl; and (b) from 0-3 ring heteroatoms (in addition to the nitrogen atom attached to R$^e$ and R$^f$), which are each independently selected from the group consisting of N(R$^d$), O, and S;

each occurrence of R$^g$ is independently selected from the group consisting of: halo; cyano; C$_{1-6}$ alkyl optionally substituted with from 1-2 independently selected R$^a$; C$_{1-4}$ haloalkyl; C$_{1-6}$ alkoxy optionally substituted with 1-2 independently selected R$^a$; C$_{1-4}$ haloalkoxy; S(O)$_{1-2}$(C$_{1-4}$ alkyl); —NR$^e$R$^f$; —OH; oxo; —S(O)$_{1-2}$(NR'R''); —C$_{1-4}$ thioalkoxy; —NO$_2$; —C(=O)(C$_{1-4}$ alkyl); —C(=O)O(C$_{1-4}$ alkyl); —C(=O)OH; and —C(=O)N(R')(R''); and each occurrence of R' and R'' is independently selected from the group consisting of: H and C$_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and C$_{1-3}$ alkyl; and (b) from 0-3 ring heteroatoms (in addition to the nitrogen atom attached to R' and R''), which are each independently selected from the group consisting of N(R$^d$), O, and S;

provided that:
(1) when W is C(=O), A is other than unsubstituted ethyl or unsubstituted phenyl;
(2) when W is C(=S), R$^1$ is other than morpholin-4-yl; and (3) when $Y^2$ is N; and each of Z, $Y^1$, and $Y^3$ is CH, then A is other than $C_6$ aryl monosubstituted with $C(O)_2$ ($C_{1-3}$ alkyl) (such as $C(O)_2Et$) at the para position;

provided that when Q-A is defined according to (A); A is $C_6$ aryl mono-substituted with a $C_4$ alkyl such as n-butyl at the para position, then the ring that includes Z, $Y^1$, $Y^2$, $Y^3$, and $Y^4$ must be substituted with one or more $R^1$ that is other than hydrogen.

In another aspect, provided herein is a compound of Formula (I),

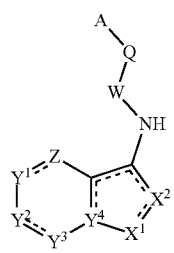

(I)

or a pharmaceutically acceptable salt thereof, or an N-oxide thereof,
wherein:
one or more of Z, $Y^1$, $Y^2$, $Y^3$, and $Y^4$ in the ring below

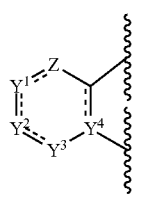

is an independently selected heteroatom;
Z is selected from the group consisting of $CR^1$ and N;
each of $Y^1$, $Y^2$, and $Y^3$ is independently selected from the group consisting of $CR^1$ and N;
provided that one or more of Z, $Y^1$, $Y^2$, and $Y^3$ is an independently selected $CR^1$;
$Y^4$ is C;
$X^1$ is NH;
$X^2$ is CH;
each ═ is independently a single bond or a double bond, provided that the five-membered ring comprising $Y^4$, $X^1$, and $X^2$ is heteroaryl; and
the ring that includes Z, $Y^1$, $Y^2$, $Y^3$, and $Y^4$ is aromatic;
W is selected from the group consisting of:
(i) C(═O);
(ii) C(═S);
(iv) C(═$NR^d$); and
(v) C(═NH);
Q-A is defined according to (A) or (B) below:
(A)
Q is NH or N($C_{1-6}$ alkyl) wherein the $C_{1-6}$ alkyl is optionally substituted with 1-2 independently selected $R^a$, and
A is:
(i) —$(Y^{A1})_n$—$Y^{A2}$, wherein:
n is 0 or 1;
$Y^A1$ is $C_{1-6}$ alkylene, which is optionally substituted with from 1-6 $R^a$; and $Y^{A2}$ is:
(a) $C_{3-20}$ cycloalkyl, which is optionally substituted with from 1-4 $R^b$,
(b) $C_6$ aryl, which is substituted with from 1-4 independently $R^c$, wherein one occurrence of $R^c$ is $R^{c'}$;
(c) $C_{7-20}$ aryl, which is optionally substituted with from 1-4 $R^c$;
(d) heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are substituted with from 1-4 independently selected $R^c$,
(e) heteroaryl including from 7-20 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$; or
(f) heterocyclyl including from 3-16 ring atoms, wherein from 1-3 ring atoms are heteroatoms, each independently selected from the group consisting of N, N(H), N($R^b$), N($R^d$), and O, and wherein one or more of the heterocyclyl ring carbon atoms are optionally substituted with from 1-4 independently selected $R^b$, OR
(ii) —$Z^1$—$Z^2$—$Z^3$, wherein:
$Z^1$ is $C_{1-3}$ alkylene, which is optionally substituted with from 1-4 $R^a$;
$Z^2$ is —N(H)—, —N($R^d$)—, —O—, or —S—; and
$Z^3$ is $C_{2-7}$ alkyl, which is optionally substituted with from 1-4 $R^a$;

OR
(iii) $C_{3-10}$ alkyl (e.g., $C_{5-10}$, $C_{6-10}$, or $C_{7-10}$ alkyl), which is optionally substituted with from 1-6 independently selected $R^a$, or
(B)
Q and A, taken together, form:

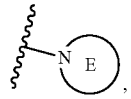

wherein ∫ denotes point of attachment to W; and
E is a ring including from 3-16 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
each occurrence of $R^1$ is independently selected from the group consisting of H; halo; cyano; $C_{1-6}$ alkyl optionally substituted with 1-2 $R^a$; $C_{2-6}$ alkenyl; $C_{2-6}$ alkynyl; $C_{1-4}$ haloalkyl; $C_{1-4}$ alkoxy; $C_{1-4}$ haloalkoxy; —($C_{0-3}$ alkylene)-$C_{3-6}$ cycloalkyl optionally substituted with from 1-4 independently selected $R^g$; —($C_{0-3}$ alkylene)-$C_{6-10}$ aryl optionally substituted with from 1-4 independently selected $R^g$; —($C_{0-3}$ alkylene)-5-10 membered heteroaryl, wherein from 1-3 ring atoms of the heteroaryl are heteroatoms each independently selected from the group consisting of N, NH, $NR^d$, O, and S, wherein the heteroaryl is optionally substituted with from 1-4 independently selected $R^g$; —($C_{0-3}$ alkylene)-5-10 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected $R^g$; —$S(O)_{1-2}$ ($C_{1-4}$ alkyl); —$NR^eR^f$; —OH; oxo; —$S(O)_{1-2}$(NR'R''); —$C_{1-4}$ thioalkoxy; —$NO_2$; —C(=O)($C_{1-4}$ alkyl); —C(=O)O($C_{1-4}$ alkyl); —C(=O)OH; and —C(=O)N(R')(R'');

each occurrence of $R^a$ is independently selected from the group consisting of: —OH; —F; —Cl; —Br; —$NR^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —$S(O)_{1-2}$(NR'R''); —$S(O)_{1-2}$($C_{1-4}$ alkyl); cyano; and $C_{3-6}$ cycloalkyl optionally substituted with from 1-4 independently selected $C_{1-4}$ alkyl;

each occurrence of $R^b$ is independently selected from the group consisting of: $C_{1-10}$ alkyl optionally substituted with from 1-6 independently selected $R^a$; $C_{1-4}$ haloalkyl; —OH; oxo; —F; —Cl; —Br; —$NR^eR^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —$S(O)_{1-2}$(NR'R''); —$S(O)_{1-2}$($C_{1-4}$ alkyl); cyano; ($C_{0-3}$ alkylene)-$C_{6-10}$ aryl optionally substituted with from 1-4 independently selected $C_{1-4}$ alkyl; and ($C_{0-3}$ alkylene)-$C_{3-6}$ cycloalkyl optionally substituted with from 1-4 independently selected $C_{1-4}$ alkyl;

each occurrence of $R^c$ is independently selected from the group consisting of:
(i) halo;
(ii) cyano;
(iii) $C_{1-10}$ alkyl which is optionally substituted with from 1-6 independently selected $R^a$;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O;
(xi) —$S(O)_{1-2}$($C_{1-4}$ alkyl);
(xii) —$NR^eR^f$;
(xiii) —OH;
(xiv) —$S(O)_{1-2}$(NR'R'');
(xv) —$C_{1-4}$ thioalkoxy;
(xvi) —$NO_2$;
(xvii) —C(=O)($C_{1-4}$ alkyl);
(xviii) —C(=O)O($C_{1-4}$ alkyl);
(xix) —C(=O)OH;
(xx) —C(=O)N(R')(R''); and
(xxi) —($C_{0-3}$ alkylene)-$C_{6-10}$ aryl optionally substituted with from 1-4 independently selected $C_{1-4}$ alkyl; and
(xxii) —($C_{0-3}$ alkylene)-5-10 membered heteroaryl, wherein from 1-3 ring atoms of the heteroaryl are heteroatoms each independently selected from the group consisting of N, NH, $NR^d$, O, and S, wherein the heteroaryl is optionally substituted with from 1-4 independently selected $C_{1-4}$ alkyl;

$R^{c'}$ is independently selected from the group consisting of:
(i) halo;
(ii) cyano;
(iii) $C_{1-10}$ alkyl which is optionally substituted with from 1-6 independently selected $R^a$;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O;
(xi) —$S(O)_{1-2}$($C_{1-4}$ alkyl);
(xii) —$NR^eR^f$;
(xiii) —OH;
(xiv) —$S(O)_{1-2}$(NR'R'');
(xv) —$C_{1-4}$ thioalkoxy;
(xvi) —$NO_2$;
(xvii) —C(=O)($C_{1-4}$ alkyl);
(xviii) —C(=O)OMe or —C(=O)O($C_{3-4}$ alkyl);
(xix) —C(=O)OH;
(xx) —C(=O)N(R')(R''); and
(xxi) —($C_{0-3}$ alkylene)-$C_{6-10}$ aryl optionally substituted with from 1-4 independently selected $C_{1-4}$ alkyl; and
(xxii) —($C_{0-3}$ alkylene)-5-10 membered heteroaryl, wherein from 1-3 ring atoms of the heteroaryl are heteroatoms each independently selected from N, NH, $NR^d$, O, and S, wherein the heteroaryl is optionally substituted with from 1-4 independently selected $C_{1-4}$ alkyl;

$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —$S(O)_{1-2}$(NR'R''); —$S(O)_{1-2}$($C_{1-4}$ alkyl); —OH; —CN; and $C_{1-4}$ alkoxy;

each occurrence of $R^e$ and $R^f$ is independently selected from the group consisting of: H; $C_{1-6}$ alkyl; $C_{1-6}$ haloalkyl; $C_{3-6}$ cycloalkyl; —C(O)($C_{1-4}$ alkyl); —C(O)O($C_{1-4}$ alkyl); —CON(R')(R''); —$S(O)_{1-2}$(NR'R''); —$S(O)_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^e$ and $R^f$), which are each independently selected from the group consisting of N($R^d$), O, and S;

each occurrence of $R^g$ is independently selected from the group consisting of: halo; cyano; $C_{1-6}$ alkyl optionally substituted with from 1-2 independently selected $R^a$; $C_{1-4}$ haloalkyl; $C_{1-6}$ alkoxy optionally substituted with 1-2 independently selected $R^a$; $C_{1-4}$ haloalkoxy; $S(O)_{1-2}$($C_{1-4}$ alkyl); —$NR^eR^f$; —OH; oxo; —$S(O)_{1-2}$(NR'R''); —$C_{1-4}$ thioalkoxy; —$NO_2$; —C(=O)($C_{1-4}$ alkyl); —C(=O)O($C_{1-4}$ alkyl); —C(=O)OH; and —C(=O)N(R')(R'');
and each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N($R^d$), O, and S, provided that when Q-A is defined according to (A); A is $C_6$ aryl mono-substituted with a $C_4$ alkyl such as n-butyl at the para position, then the ring that includes Z, $Y^1$, $Y^2$, $Y^3$, and $Y^4$ must be substituted with one or more $R^1$ that is other than hydrogen.

Embodiments can include any one or more of the features delineated below and/or in the claims.

In some embodiments, one or more of Z, $Y^1$, $Y^2$, $Y^3$, and $Y^4$ in the ring below

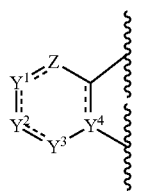

is an independently selected heteroatom.

In some embodiments, the ring that includes Z, $Y^1$, $Y^2$, $Y^3$, and $Y^4$:

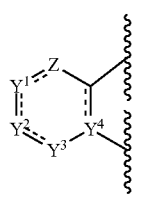

is aromatic.

In certain embodiments, Z is other than a bond.

In certain of these embodiments, from 1-2 of Z, $Y^1$, $Y^2$, $Y^3$, and $Y^4$ is independently N. For examples, the ring that includes Z, $Y^1$, $Y^2$, $Y^3$, and $Y^4$ is selected from:

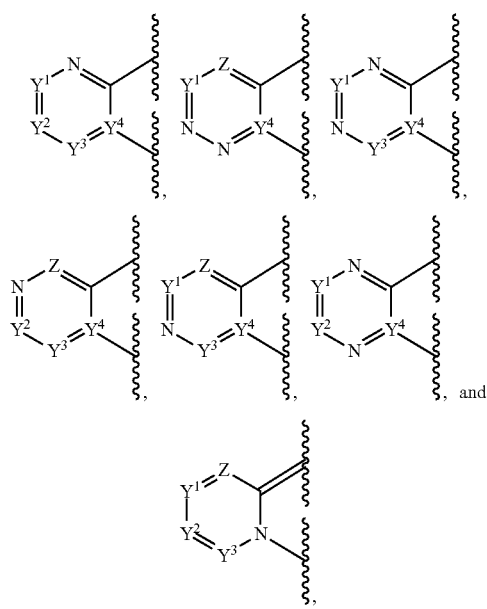

wherein each ∤ denotes points of attachment to the ring comprising $X^1$ and $X^2$, and wherein the bottom ∤ denotes point of attachment to $X^1$.

For example, the ring comprising Z, $Y^1$, $Y^2$, $Y^3$, and $Y^4$ is selected from:

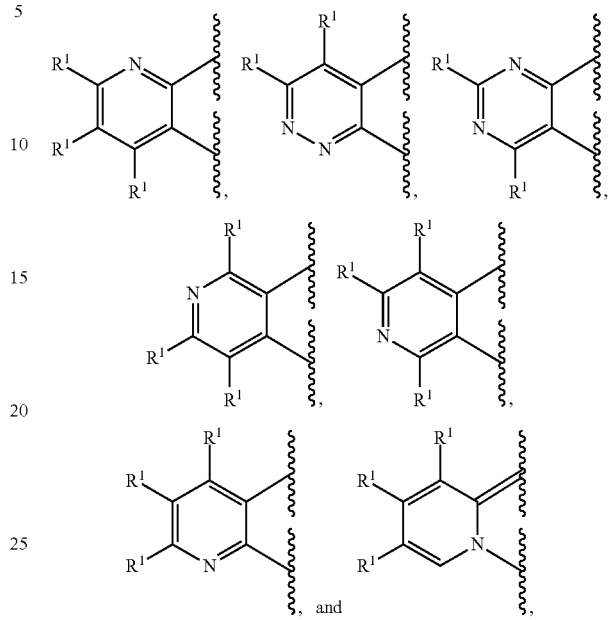

wherein each ∤ denotes points of attachment to the ring comprising $X^1$ and $X^2$, and wherein the bottom ∤ denotes point of attachment to $X^1$.

In other embodiments, Z is a bond.

In certain of these embodiments, $Y^2$ is $CR^1$.

In certain of these embodiments, from 1-2 of $Y^1$ and $Y^3$ is other than $CR^1$.

In certain of these embodiments, from 1-2 of $Y^1$ and $Y^3$ is independently selected from N, $CR^1$, and S.

For example, the ring that includes Z, $Y^1$, $Y^2$, $Y^3$, and $Y^4$ is selected from:

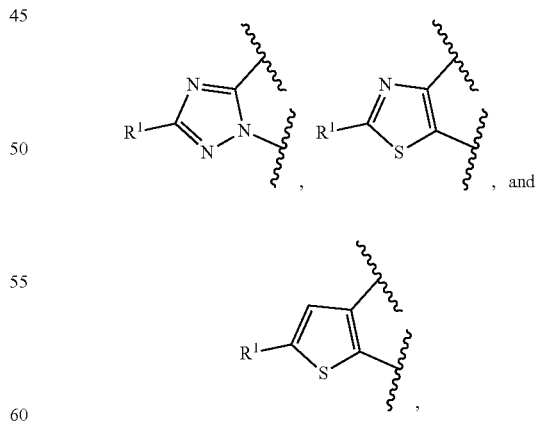

wherein each ∤ denotes points of attachment to the ring comprising $X^1$ and $X^2$, and wherein the bottom ∤ denotes point of attachment to $X^1$.

In some embodiments, the ring that includes Z, $Y^1$, $Y^2$, $Y^3$, and $Y^4$ is partially unsaturated.

In certain of these embodiments, the ring that includes Z, $Y^1$, $Y^2$, $Y^3$, and $Y^4$ is:

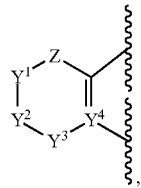

wherein each / denotes points of attachment to the ring comprising $X^1$ and $X^2$, and wherein the bottom / denotes point of attachment to $X^1$.

In other of these embodiments, Z is other than a single bond.

In certain embodiments, $Y^4$ is C.

In certain embodiments, one of Z, $Y^1$, $Y^2$, and $Y^3$ is other than $C(R^3)_2$.

For example, the ring comprising Z, $Y^1$, $Y^2$, $Y^3$, and $Y^4$ is:

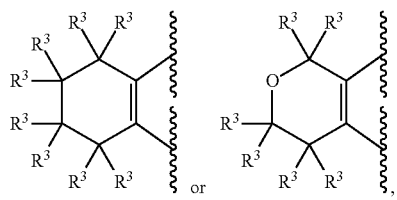

wherein each / denotes points of attachment to the ring comprising $X^1$ and $X^2$, and wherein the bottom / denotes point of attachment to $X^1$.

In some embodiments, $X^2$ is N or $CR^5$ (e.g., $X^2$ is $CR^5$).

In some embodiments, $X^1$ is selected from N and $NR^2$ (e.g., $R^2$ is H).

In certain embodiments, the compound has Formula:

(I-a)
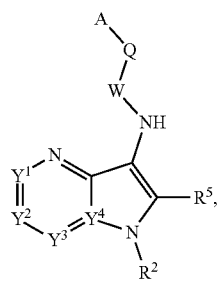

(I-b)
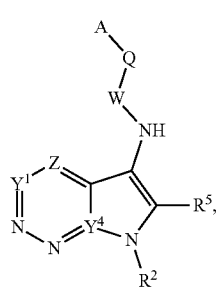

(I-c)
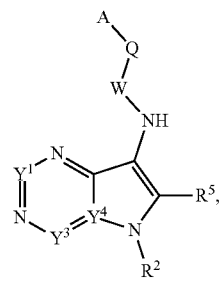

(I-d)
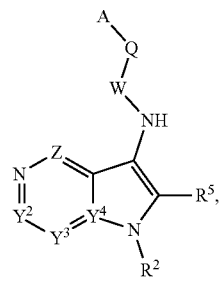

(I-e)
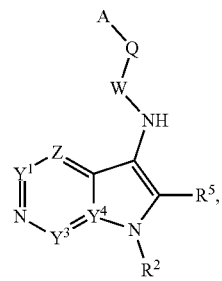

(I-f)
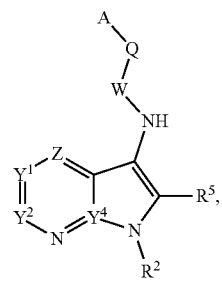

(I-g)
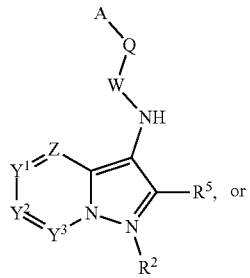

(I-h)
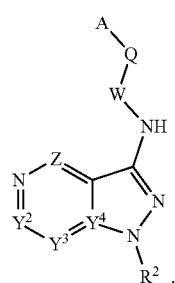
For example, the compound can have Formula:
(I-a1)
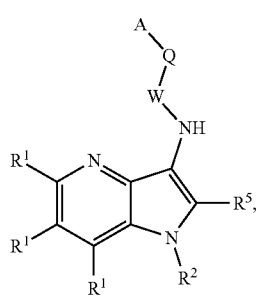
(I-b1)
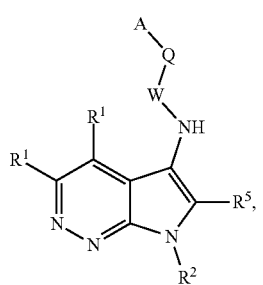
(I-c1)
(I-d1)
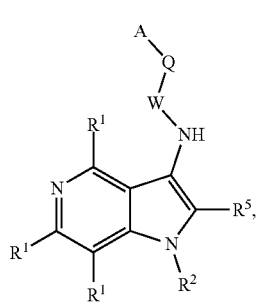
(I-e1)
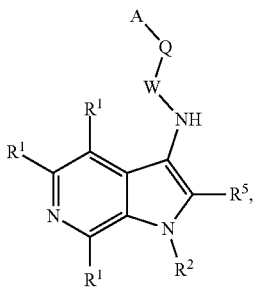
(I-f1)
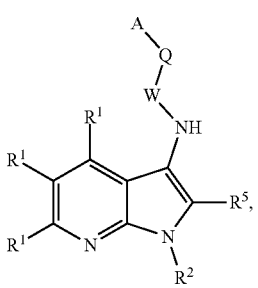
(I-g1)
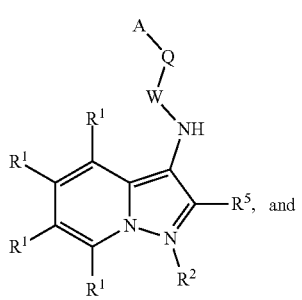
and
(I-h1)
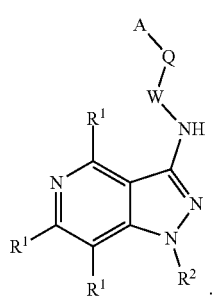
In certain embodiments, the compound has Formula (I-a1); or the compound has Formula (I-b1); or the compound has Formula (I-c1); or the compound has Formula (I-d1); or the compound has Formula (I-e1); or the compound has Formula (I-f1); or the compound has Formula (I-g1); the compound has Formula (I-h1).

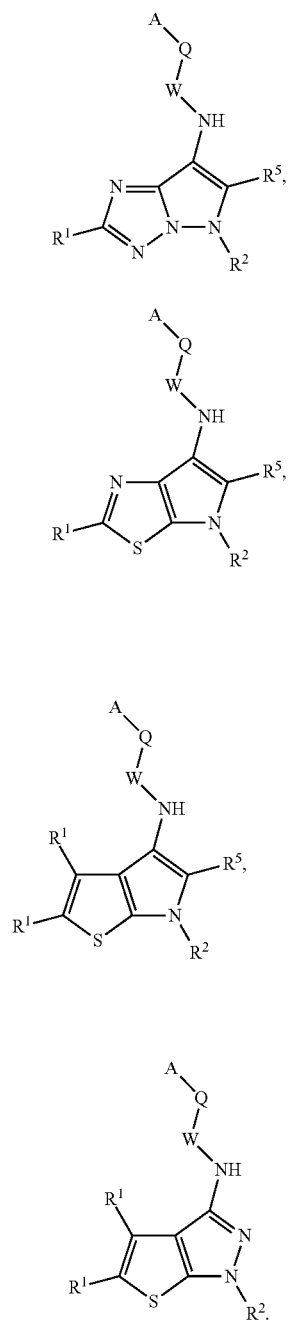
(I-i1)
(I-j1)
(I-k1)
(I-l1)
In certain embodiments, the compound has Formula:
(I-m)
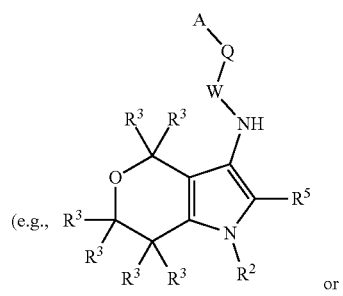
(I-m1)
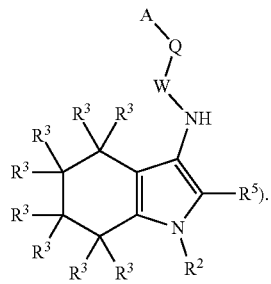
(I-m2)
In some embodiments, the compound has Formula (I-a2):
(I-a2)
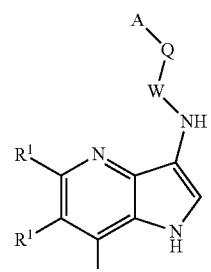
(such as 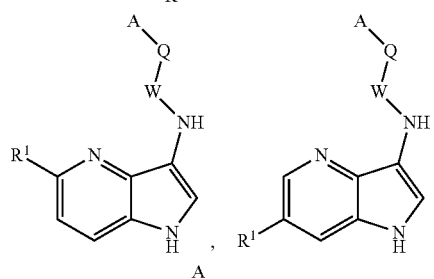, or
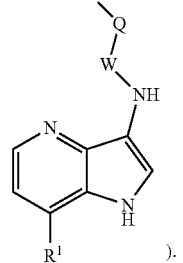).

In some embodiments, the compound has Formula (I-d2):
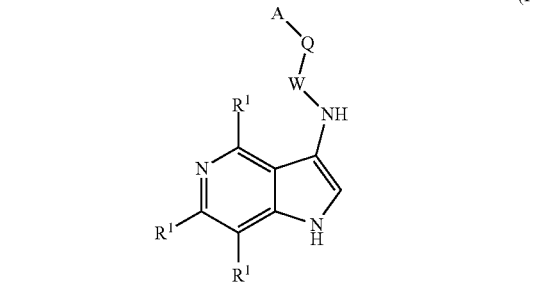
(such as
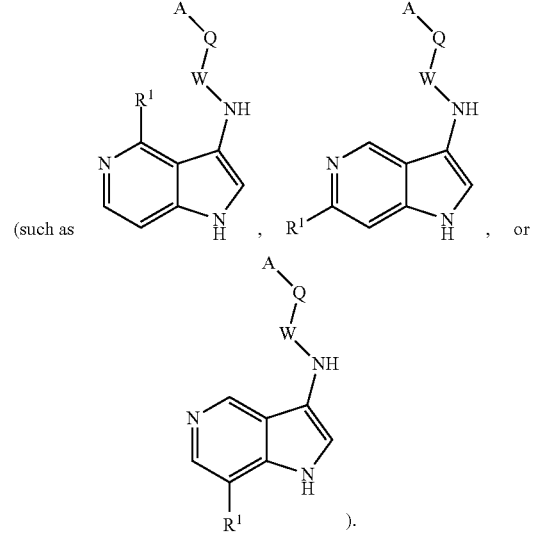
).
In some embodiments, the compound has Formula (I-e2):
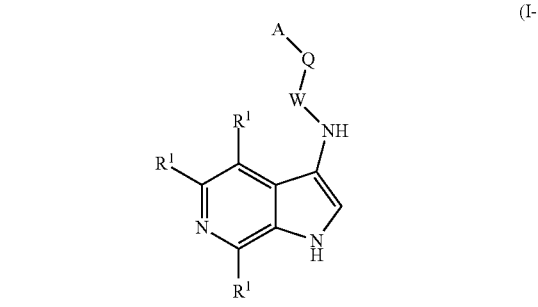
(such as
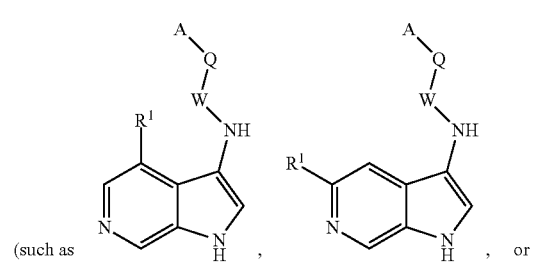
, or
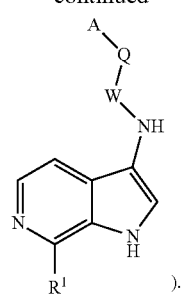
).
In some embodiments, the compound has Formula (I-f2):
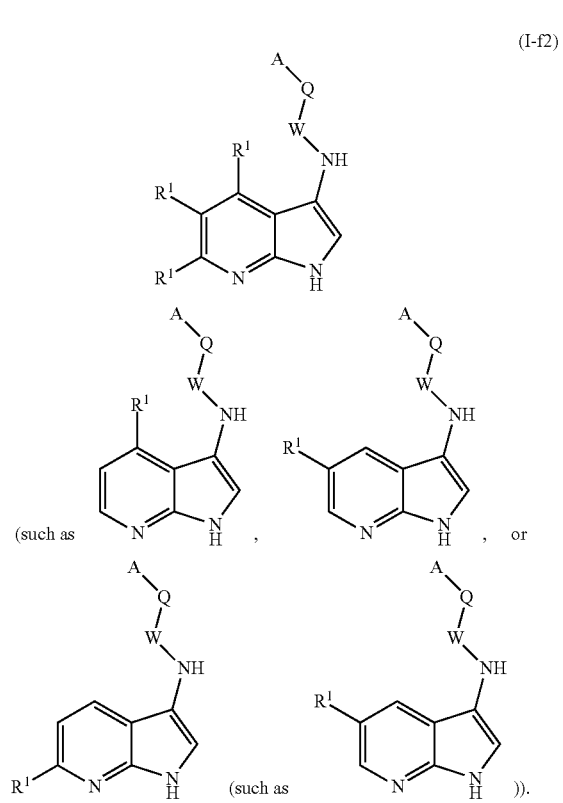
In some embodiments, the compound has Formula (I-c2) or (I-i2):
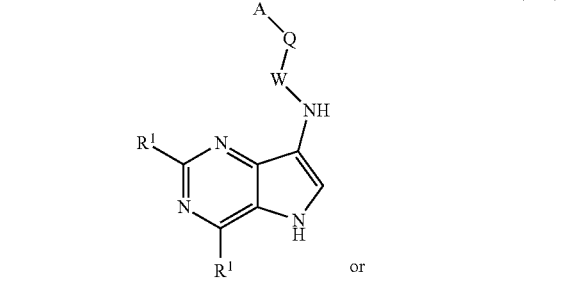
or (I-h2)

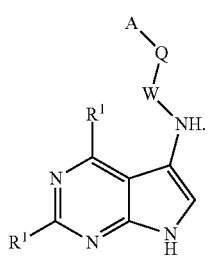

In some embodiments, R¹ independently selected from the group consisting of H, halo, cyano, $C_{1-6}$ alkyl optionally substituted with 1-2 $R^a$, $C_{1-4}$ haloalkyl, $C_{1-4}$ alkoxy, $C_{1-4}$ haloalkoxy, OH, —S(O)$_{1-2}$($C_{1-4}$ alkyl), —S(O)$_{1-2}$(NR'R"), —$C_{1-4}$ thioalkoxy, —NO$_2$, —C(=O)($C_{1-4}$ alkyl), —C(=O)O($C_{1-4}$ alkyl), —C(=O)OH, and —C(=O)N(R')(R").

In certain embodiments, one or more occurrences of R¹ is independently H.

In certain embodiment, each of the remaining occurrences of R¹ is as defined in claim 32 (e.g., other than H). For example, each of the remaining occurrences of R¹ is selected from: methyl, C(O)NHMe, CF$_3$, hydroxy-$C_{1-6}$ alkyl (e.g., 1-hydroxy-eth-1-yl), and methoxy.

In some embodiments, each R¹ independently selected from the group consisting of H; halo; cyano; $C_{1-6}$ alkyl optionally substituted with 1-2 $R^a$; $C_{1-4}$ haloalkyl; $C_{2-6}$ alkenyl (such as vinyl); $C_{2-6}$ alkynyl (such as acetylenyl); $C_{1-4}$ alkoxy; $C_{1-4}$ haloalkoxy; OH; —S(O)$_{1-2}$ ($C_{1-4}$ alkyl); —S(O)$_{1-2}$(NR'R"); —$C_{1-4}$ thioalkoxy; —NO$_2$; —C(=O)($C_{1-4}$ alkyl); —C(=O)O($C_{1-4}$ alkyl); —C(=O)OH; —C(=O)N(R')(R"); —($C_{0-3}$ alkylene)-$C_{3-6}$ cycloalkyl optionally substituted with from 1-4 independently selected $R^g$; —($C_{0-3}$ alkylene)-$C_{6-10}$ aryl optionally substituted with from 1-4 independently selected $R^g$; —($C_{0-3}$ alkylene)-5-10 membered heteroaryl, wherein from 1-3 ring atoms of the heteroaryl are heteroatoms each independently selected from N, NH, $NR^d$, O, and S, wherein the heteroaryl is optionally substituted with 1-4 independently selected $R^g$; and —($C_{0-3}$ alkylene)-5-10 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected $R^g$.

In certain embodiments, from 1-2 (such as 1) occurrences of R¹ is other than H.

In certain embodiments, from 1-2 (such as 1) occurrences of R¹ is independently selected from the group consisting of: halo (such as F), cyano, $C_{1-3}$ alkyl (such as methyl), $C_{1-3}$ haloalkyl, —C(=O)N(R')(R"), hydroxy-$C_{1-6}$ alkyl (such as 1-hydroxy-eth-1-yl), and methoxy (such as, one occurrence of R¹ is independently halo).

In certain of these embodiments, from 1-2 (such as 1) occurrences of R¹ is independently halo (such as F).

In certain embodiments, one occurrence of R¹ is $C_{1-6}$ alkyl optionally substituted with 1-2 $R^a$. In certain of these embodiments, one occurrence of R¹ is $C_{1-6}$ alkyl (such as methyl or ethyl).

In certain embodiments, one occurrence of R¹ is $C_{2-6}$ alkenyl (such as vinyl).

In certain embodiments, one occurrence of R¹ is $C_{2-6}$ alkynyl (such as acetylenyl).

In certain embodiments, one occurrence of R¹ is $C_{1-4}$ alkoxy (such as methoxy).

In certain embodiments, one occurrence of R¹ is cyano.

In certain embodiments, one occurrence of R¹ is selected from the group consisting of:
- $C_{3-6}$ cycloalkyl optionally substituted with from 1-4 independently selected $R^g$;
- $C_{6-10}$ aryl optionally substituted with from 1-4 independently selected $R^g$ (such as phenyl optionally substituted with from 1-4 independently selected $R^g$);
- 5-10 membered heteroaryl (such as 5- or 6-membered heteroaryl), wherein from 1-3 ring atoms of the heteroaryl are heteroatoms each independently selected from the group consisting of N, NH, $NR^d$, O, and S, wherein the heteroaryl is optionally substituted with from 1-4 independently selected $R^g$ (such as pyrimidyl, pyridyl, pyrazolyl, and thienyl (e.g., pyrazolyl) each of which is optionally substituted with 1-3 independently selected $R^g$); and
- 5-10 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected $R^g$ (such as tetrahydropyridyl or tetrahydropyranyl, each of which is optionally substituted with from 1-4 independently selected $R^g$).

In certain of these embodiments, one occurrence of R¹ is independently $C_{6-10}$ aryl optionally substituted with from 1-4 independently selected $R^g$.

In certain embodiments, one occurrence of R¹ is independently phenyl optionally substituted with from 1-4 (e.g., from 1-3) independently selected $R^g$.

In certain embodiments, one occurrence of R¹ is independently 5-10 membered heteroaryl, wherein from 1-3 ring atoms of the heteroaryl are heteroatoms each independently selected from the group consisting of N, NH, $NR^d$, O, and S, wherein the heteroaryl is optionally substituted with from 1-4 independently selected $R^g$.

In certain of these embodiments, one occurrence of R¹ is independently 5-membered heteroaryl, wherein from 1-3 (such as 1 or 2-3) ring atoms of the heteroaryl are heteroatoms each independently selected from the group consisting of N, NH, $NR^d$, O, and S, wherein the heteroaryl is optionally substituted with from 1-4 independently selected $R^g$.

As a non-limiting example of these embodiments, R¹ is pyrazolyl optionally substituted with from 1-3 independently selected $R^g$

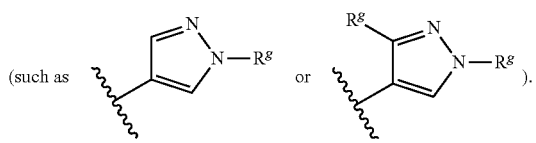

As another non-limiting example, R¹ is thiazolyl optionally substituted with from 1-2 independently selected $R^g$.

As another non-limiting example, R¹ is thiophenyl optionally substituted with from 1-2 independently selected $R^g$.

In certain embodiments, one occurrence of R¹ is independently 6 membered heteroaryl, wherein from 1-2 ring atoms of the heteroaryl are ring nitrogen atoms, wherein the heteroaryl is optionally substituted with from 1-4 independently selected $R^g$.

In certain of these embodiments, one occurrence of R¹ is pyridyl or pyrimidyl, each of which is optionally substituted with from 1-4 independently selected $R^g$ (such as 3-pyridyl

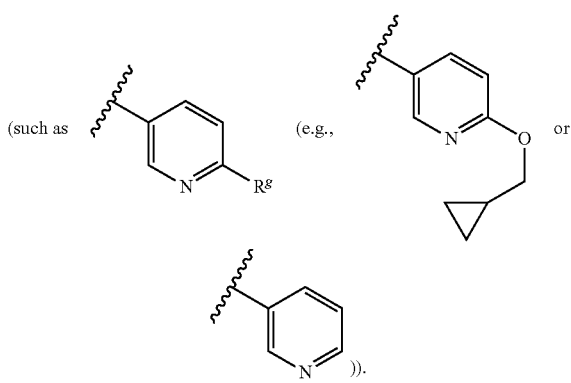

(such as ... (e.g., ... or ... )).

In certain embodiments, one occurrence of $R^1$ is 5-10 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected $R^g$ (such as tetrahydropyridyl or tetrahydropyranyl

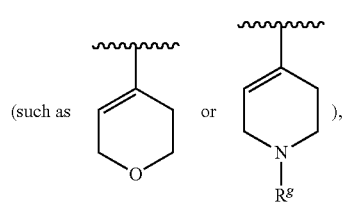

(such as ... or ... ), each of which is optionally substituted with from 1-4 independently selected $R^g$)).

In certain embodiments, one occurrence of $R^1$ is $C_{3-6}$ cycloalkyl optionally substituted with from 1-4 independently selected $R^g$ (such as $C_6$ cycloalkyl (e.g., cyclohexyl or cyclohexenyl)) optionally substituted with from 1-2 independently selected $R^g$.

In one or more of the foregoing embodiments, each $R^g$ is independently selected from the group consisting of: $NR^eR^f$ (such as $NH_2$, 4-methylpiperazin-1-yl, morpholin-4-yl), $C_{1-4}$ alkyl (such as methyl, ethyl, or isopropyl), $C_{1-4}$ haloalkyl (such as $CF_3$), $C_{1-4}$ alkyl substituted with $R^a$ (such as $C_{1-4}$ alkyl substituted with OH, $NR^eR^f$, or $C(O)OC_{1-4}$ alkyl), $C_{1-4}$ alkoxy optionally substituted with $R^a$ (such as methoxy or —OCH$_2$-cyclopropyl), —S(O)$_{1-2}$ (NR'R'') (such as S(O)$_2$NMe$_2$ or S(O)$_2$NH$_2$), and —S(O)$_{1-2}$(C$_{1-4}$ alkyl) (such as S(O)$_2$Me).

In some embodiments, each $R^2$ is independently selected from:
(i) $C_{1-6}$ alkyl, which is optionally substituted with from 1-2 independently selected $R^a$;
(ii) $C_{3-6}$ cycloalkyl;
(iii) heterocyclyl including from 3-10 ring atoms, wherein from 1-3 ring atoms are heteroatoms, each independently selected from the group consisting of N, N(H), N($R^d$), and O; and
(xi) H.

In certain embodiments, each $R^2$ is independently selected from:
(i) $C_{1-6}$ alkyl, which is optionally substituted with from 1-2 independently selected $R^a$; and
(xi) H (e.g., each $R^2$ is independently H).

In some embodiments, each $R^3$ is independently selected from H, $C_{1-6}$ alkyl optionally substituted with from 1-6 independently selected $R^a$; $C_{1-4}$ haloalkyl; —OH; —F; —Cl; —Br; $C_{1-4}$ alkoxy; $C_{1-4}$ haloalkoxy; —C(=O)(C$_{1-4}$ alkyl); —C(=O)O(C$_{1-4}$ alkyl); —C(=O)OH; —C(=O)N(R')(R''); —S(O)$_{1-2}$(NR'R''); —S(O)$_{1-2}$(C$_{1-4}$ alkyl); and cyano; or two $R^3$ on the same carbon combine to form an oxo;

In certain embodiments, each $R^3$ is independently selected from H, $C_{1-6}$ alkyl optionally substituted with from 1-6 independently selected $R^a$; and $C_{1-4}$ haloalkyl; or two $R^3$ on the same carbon combine to form an oxo.

In certain embodiments, each $R^3$ is independently selected from H, $C_{1-6}$ alkyl optionally substituted with from 1-6 independently selected $R^a$; and $C_{1-4}$ haloalkyl.

In certain embodiments, each $R^3$ is H.

In some embodiments, each $R^5$ is independently selected from H, oxo, and hydroxy.

In some embodiments, each $R^5$ is H or $C_{1-3}$ alkyl (e.g., $R^5$ is H).

In some embodiments, W is selected from the group consisting of:
(i) C(=O);
(ii) C(=S);
(iii) S(O)$_{1-2}$;
(iv) C(=$NR^d$);
(v) C(=NH); and
(vi) C(=C—NO$_2$).

In certain embodiments, W is C(=O).
In certain embodiments, W is S(O)$_2$.
In certain embodiments, W is C(=$NR^d$). In certain of these embodiments, W is C(=N—CN).

In some embodiments, Q and A are defined according to (A).

In certain embodiments, Q is NH.
In certain embodiments, Q is N(C$_{1-3}$ alkyl).
In certain embodiments, A is —(Y$^{A1}$)$_n$—Y$^{A2}$.
In certain embodiments, n is 0.
In certain embodiments, n is 1. In certain of these embodiments, $Y^{A1}$ is $C_{1-3}$ alkylene (e.g., Y is CH$_2$ or CH$_2$CH$_2$). In certain other embodiments, $Y^{A1}$ is $C_{1-3}$ alkylene substituted with $R^a$ (such as CHR$^a$CH$_2$ (such as CH(C(=O)NHMe)CH$_2$)).

In certain of the foregoing embodiments, $Y^{A2}$ is $C_{6-20}$ aryl, which is optionally substituted with from 1-4 $R^c$.

For example, $Y^{A2}$ can be $C_{6-10}$ aryl, which is optionally substituted with from 1-3 $R^c$; e.g., $Y^{A2}$ can be phenyl, which is optionally substituted with from 1-3 $R^c$. In certain embodiments, $Y^{A2}$ is phenyl which is substituted with 1 $R^c$ (e.g., at the para position).

As another example, $Y^{A2}$ can be naphthyl, which is optionally substituted with from 1-3 $R^c$.

As a further example, $Y^{A2}$ is tetrahydro-naphthyl, which is optionally substituted with from 1-3 $R^c$.

In certain embodiments, $Y^{A2}$ is $C_6$ aryl, which is substituted with from 1-4 independently $R^c$.

In certain of these embodiments, $Y^{A2}$ is $C_6$ aryl, which is substituted with from 1-3 independently R, wherein one occurrence of $R^c$ is $R^{c'}$.

In certain embodiments, $Y^{A2}$ is phenyl substituted with from 1-3 independently selected $R^c$ (such as phenyl substituted with one $R^c$; or phenyl substituted with one $R^{c'}$), wherein one occurrence of $R^c$ is $R^{c'}$ which is at the para position.

In certain embodiments, $Y^{A2}$ is phenyl substituted with from 1-3 independently selected $R^c$ (such as phenyl substituted with one $R^c$; or phenyl substituted with one $R^{c'}$), wherein one occurrence of $R^c$ is $R^{c'}$ which is at the meta position.

In certain embodiments, $Y^{A2}$ is $C_{7-20}$ aryl, which is optionally substituted with from 1-4 $R^c$.

As non-limiting examples of the foregoing embodiments, $Y^{A2}$ is selected from the group consisting of: naphthyl, tetrahydronaphthyl (such as 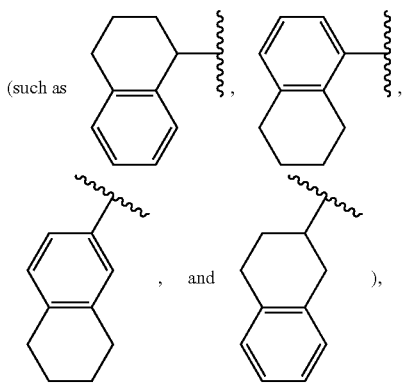, and ), and dihydroindenyl (such as 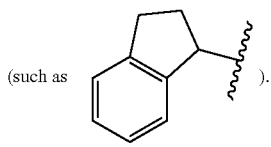 [SMILES: *C1CCc2ccccc21] ).

In other of the foregoing embodiments, $Y^{A2}$ is heteroaryl including from 5-20 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

For example, $Y^{A2}$ can be heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 (e.g., 1-3) independently selected $R^c$.

In certain embodiments, $Y^{A2}$ is heteroaryl including from 5-10 ring atoms, wherein from 1-3 ring atoms are heteroatoms, each independently selected from the group consisting of N, N(H), and N($R^d$), and wherein one or more of the heteroaryl ring carbon atoms are optionally substituted with from 1-3 independently selected $R^c$.

In certain embodiments, $Y^{A2}$ is heteroaryl including from 5-10 ring atoms, wherein from 1-3 ring atoms are heteroatoms, each independently selected from the group consisting of N, N(H), and N($R^d$), and wherein one or more of the heteroaryl ring carbon atoms are optionally substituted with from 1-2 independently selected $R^c$.

In certain embodiments, $Y^{A2}$ is heteroaryl including from 6-10 ring atoms, wherein from 1-2 ring atoms are heteroatoms, each independently selected from the group consisting of N, N(H), and N($R^d$), and wherein one or more of the heteroaryl ring carbon atoms are optionally substituted with from 1-2 independently selected $R^c$.

For example, $Y^{A2}$ is quinolinyl or tetrahydroquinolinyl, which is optionally substituted with 1-2 independently selected $R^c$ (e.g., unsubstituted quinolinyl or tetrahydroquinolinyl).

In certain embodiments, $Y^{A2}$ is heteroaryl including from 5-6 ring atoms, wherein from 1-3 ring atoms are heteroatoms, each independently selected from the group consisting of N, N(H), N($R^d$), O, and S, and wherein one or more of the heteroaryl ring carbon atoms are substituted with from 1-3 independently selected $R^c$.

In certain of these embodiments, $Y^{A2}$ is heteroaryl including 5 ring atoms, wherein from 1-3 (such as 1-2) ring atoms are heteroatoms, each independently selected from the group consisting of N, N(H), N($R^d$), O, and S, and wherein one or more of the heteroaryl ring carbon atoms are substituted with from 1-2 independently selected $R^c$.

As a non-limiting example of the foregoing embodiments, $Y^{A2}$ is thiazolyl or pyrazolyl

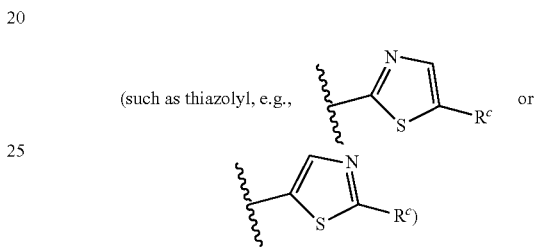

substituted with 1-2 independently selected $R^c$.

In certain embodiments, $Y^{A2}$ is heteroaryl including 6 ring atoms (such as pyridyl or pyrimidyl), wherein from 1-2 ring atoms are ring nitrogen atoms, and wherein one or more of the heteroaryl ring carbon atoms are substituted with from 1-3 independently selected $R^c$.

In certain of these embodiments, one occurrence of $R^c$ is para relative to point of attachment to $Y^{A1}$.

In certain embodiments (when $Y^{A2}$ is heteroaryl including 6 ring atoms (such as pyridyl or pyrimidyl), wherein from 1-2 ring atoms are ring nitrogen atoms, and wherein one or more of the heteroaryl ring carbon atoms are substituted with from 1-3 independently selected $R^c$), one occurrence of $R^c$ is meta relative to point of attachment to $Y^{A1}$.

In certain other embodiments, $Y^{A2}$ is heteroaryl including from 7-12 (such as 8-10) ring atoms, wherein from 1-3 ring atoms are heteroatoms, each independently selected from the group consisting of N, N(H), N($R^d$), O, and S, and wherein one or more of the heteroaryl ring carbon atoms are optionally substituted with from 1-3 independently selected $R^c$.

As non-limiting examples, $Y^{A2}$ is isoquinolinyl, quinolinyl, tetrahydro-quinolinyl, or tetrahydroisoquinolinyl optionally substituted with from 1-2 independently selected R (such as unsubstituted quinolinyl or tetrahydroquinolinyl).

As another non-limiting example, $Y^{A2}$ is benzothiazolyl (such as 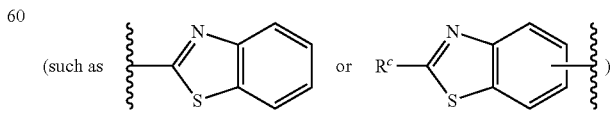 )

which is optionally substituted with from 1-2 independently selected $R^c$.

In certain of the foregoing embodiments, each occurrence $R^c$ is independently selected from:

(iii) $C_{1-10}$ alkyl which is optionally substituted with from 1-6 independently selected $R^a$;

(ix) —($C_{0-3}$ alkylene)-$C_{3-6}$ cycloalkyl optionally substituted with from 1-4 independently selected $C_{1-4}$ alkyl; and (x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O.

In certain embodiments, each occurrence of $R^c$ is independently $C_{1-6}$ alkyl which is optionally substituted with from 1-6 independently selected $R^a$.

In certain embodiments, $R^c$ is independently selected from $C_{1-6}$ alkyl which is optionally substituted with halo (e.g., F), $C_{1-4}$ alkoxy, and/or $NR^eR^f$.

For example, R can be independently unsubstituted $C_{1-6}$ alkyl (e.g., n-butyl), ethoxymethyl, $CH_2NHCH_2CF_3$, and $CH_2CF_2CH_2CH_3$.

Non-limiting examples of A can be selected from:

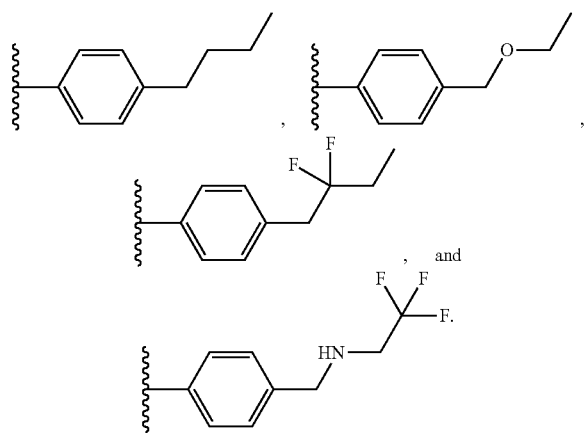

In certain embodiments, each occurrence of R is independently selected from:

(ix) —($C_{0-3}$ alkylene)-$C_{3-6}$ cycloalkyl optionally substituted with from 1-4 independently selected $C_{1-4}$ alkyl; and (x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O.

In certain embodiments, each occurrence of $R^c$ is independently selected from:

(ix) —($C_1$ alkylene)-$C_{3-6}$ cycloalkyl optionally substituted with one independently selected $C_{1-4}$ alkyl; and (x) -heterocyclyl, wherein the heterocyclyl includes from 6 ring atoms, wherein from 1 ring atoms are heteroatoms, each independently selected from the group consisting of N, N(H), N($R^d$), and O.

For example, each occurrence of $R^c$ is independently selected from:

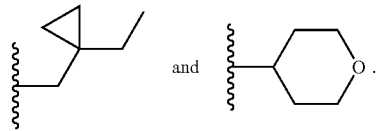

In certain of the foregoing embodiments, one occurrence of $R^c$ or $R^{c'}$ is independently $C_{1-10}$ (such as $C_{1-2}$, $C_3$, $C_4$, $C_5$, $C_6$, or $C_{7-10}$) alkyl which is optionally substituted with from 1-6 independently selected $R^a$.

In certain of these embodiments, one occurrence of $R^c$ or $R^{c'}$ is unsubstituted $C_{1-10}$ (such as $C_{1-2}$, $C_3$, $C_4$, $C_5$, $C_6$, or $C_{7-10}$) alkyl (such as butyl).

In certain other embodiments, one occurrence of $R^c$ or $R^{c'}$ is independently $C_{1-10}$ (such as $C_3$, $C_4$, $C_5$, $C_6$, or $C_{7-10}$) alkyl which is substituted with from 1-6 independently selected $R^a$.

In certain of these embodiments, each occurrence of $R^a$ is independently selected from the group consisting of: halo (such as F), $C_{1-4}$ alkoxy (such as methoxy or ethoxy), and $NR^eR^f$.

As non-limiting examples of the foregoing embodiments, one occurrence of $R^c$ or $R^{c'}$ is selected from the group consisting of: $CF_3$, ethoxymethyl, $CH_2NHCH_2CF_3$, and $CH_2CF_2CH_2CH_3$ (e.g., one occurrence of $R^c$ or $R^{c'}$ is $CF_3$).

In certain embodiments, one occurrence of $R^c$ or $R^{c'}$ is independently $C_{1-4}$ haloalkyl.

As a non-limiting example, one occurrence of $R^c$ or $R^{c'}$ is $CF_3$.

In certain embodiments, one occurrence of $R^c$ or $R^{c'}$ is independently selected from the group consisting of:

(ix) —($C_{0-3}$ alkylene)-$C_{3-6}$ cycloalkyl optionally substituted with from 1-4 independently selected $C_{1-4}$ alkyl;

(x) —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O;

(xxi) —($C_{0-3}$ alkylene)-$C_{6-10}$ aryl optionally substituted with from 1-4 independently selected $C_{1-4}$ alkyl; and (xxii) —($C_{0-3}$ alkylene)-5-10 membered heteroaryl, wherein from 1-3 ring atoms of the heteroaryl are heteroatoms each independently selected from the group consisting of N, NH, $NR^d$, O, and S, wherein the heteroaryl is optionally substituted with from 1-4 independently selected $C_{1-4}$ alkyl.

In certain embodiments, one occurrence of $R^c$ or $R^{c'}$ is independently selected from the group consisting of —($C_{1-3}$ alkylene)-$C_{3-6}$ cycloalkyl optionally substituted with from 1-4 independently selected $C_{1-4}$ alkyl. For example, one occurrence of $R^c$ or $R^{c'}$ is cyclohexyl. As another example, one occurrence of $R^c$ or $R^{c'}$ is cyclobutyl. As an additional example, one occurrence of $R^c$ or $R^{c'}$ is

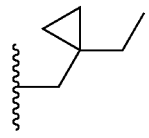

In certain embodiments, one occurrence of $R^c$ or $R^{c'}$ is —($C_{0-3}$ alkylene)-heterocyclyl, wherein the heterocyclyl includes from 3-16 ring atoms, wherein from 1-3 ring atoms are heteroatoms, each independently selected from the group consisting of N, N(H), N($R^d$), and O.

In certain of these embodiments, one occurrence of $R^c$ or $R^{c'}$ is —($C_{0-3}$ alkylene)-heterocyclyl, wherein the heterocyclyl includes from 3-10 ring atoms, wherein from 1-3 ring atoms are heteroatoms, each independently selected from the group consisting of N, N(H), N($R^d$), and O.

In certain embodiments, one occurrence of $R^c$ or $R^{c'}$ is —($C_{0-3}$ alkylene)-heterocyclyl, wherein the heterocyclyl includes from 5-6 ring atoms, wherein from 1-3 ring atoms are heteroatoms, each independently selected from the group consisting of N, N(H), N(R$^d$), and O.

In certain embodiments, one occurrence of R$^c$ or R$^{c'}$ is selected from the group consisting of:

(xxi) —(C$_{0-3}$ alkylene)-C$_{6-10}$ aryl optionally substituted with from 1-4 independently selected C$_{1-4}$ alkyl (such as C$_{6-10}$ aryl such as phenyl); and (xxii) —(C$_{0-3}$ alkylene)-5-10 membered heteroaryl, wherein from 1-3 ring atoms of the heteroaryl are heteroatoms each independently selected from N, NH, NR$^d$, O, and S, wherein the heteroaryl is optionally substituted with from 1-4 independently selected C$_{1-4}$ alkyl.

In certain embodiments, one occurrence of R$^c$ or R$^{c'}$ is C$_{2-6}$ alkenyl (e.g., vinyl) or C$_{2-6}$ alkynyl (e.g., acetylenyl).

As a non-limiting example, one occurrence of R$^c$ or R$^{c'}$ is C$_{2-6}$ alkynyl (e.g., acetylenyl).

Non-limiting examples of A can be selected from:

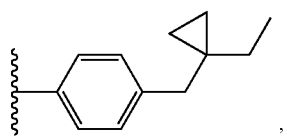

,

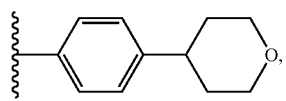

,

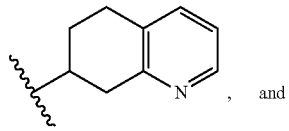

, and

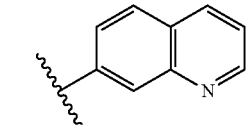

.

In still other of the foregoing embodiments, Y$^{A2}$ is C$_{3-10}$ cycloalkyl, which is optionally substituted with from 1-4 R$^b$.

In certain embodiments, Y$^{A2}$ is C$_{3-8}$ monocyclic cycloalkyl (such as cyclobutyl and cyclohexyl), which is optionally substituted with from 1-4 R$^b$.

As a non-limiting example of the foregoing embodiments, Y$^{A2}$ is C$_6$ cycloalkyl (such as cyclohexyl), which is optionally substituted with from 1-3 R$^b$, wherein one occurrence of R$^b$ is at the para position.

As another non-limiting example, Y$^{A2}$ is C$_5$ cycloalkyl (such as cyclopentyl (e.g., 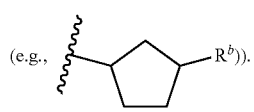)).

As yet another non-limiting example, Y$^{A2}$ is C$_4$ cycloalkyl (e.g. 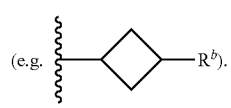).

In certain other embodiments, Y$^{A2}$ is C$_{7-13}$ bicyclic cycloalkyl, which is optionally substituted with from 1-4 independently selected R$^b$, such as

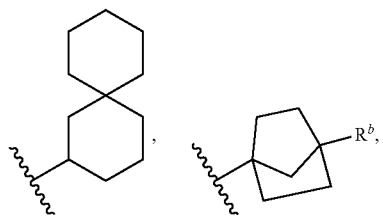

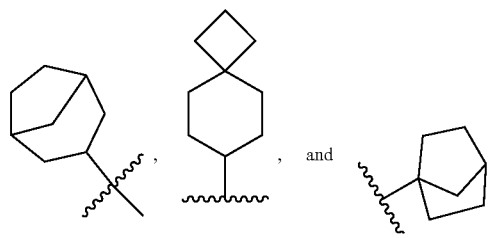

In certain embodiments, Y$^{A2}$ is C$_{7-13}$ bicyclic (e.g., spirocyclic bicylcic) cycloalkyl, which is optionally substituted with from 1-4 independently selected R$^b$, such as

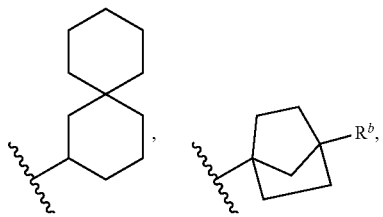

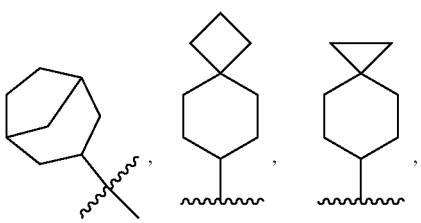

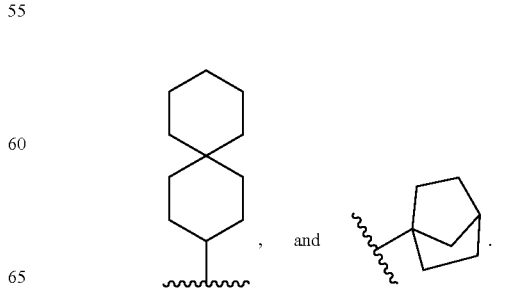

As non-limiting examples of the foregoing embodiments, $Y^{A2}$ is

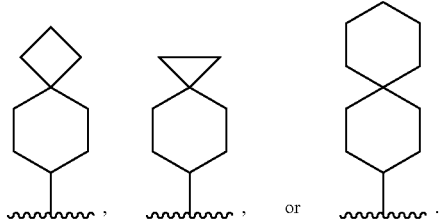 [SMILES: *C1CCC2(CCC2)CC1 ; *C1CCC2(CC1)CC2 ; *C1CCC2(CCCCC2)CC1]

In another of the foregoing embodiments, $Y^{A2}$ is heterocyclyl including from 3-12 ring atoms, wherein from 1-3 ring atoms are heteroatoms, each independently selected from the group consisting of N, N(H), N(R$^d$), and O, and wherein one or more of the heterocyclyl ring carbon atoms are optionally substituted with from 1-4 independently selected $R^b$.

In certain embodiments, each occurrence of $R^b$ is selected from the group consisting of: $C_{1-10}$ alkyl optionally substituted with from 1-6 independently selected $R^a$; $C_{1-4}$ haloalkyl; —OH; oxo; —F; —Cl; —Br; $C_{1-4}$ alkoxy; $C_{1-4}$ haloalkoxy; $C_{6-10}$ aryl optionally substituted with 1-4 independently selected $C_{1-4}$ alkyl; and $C_{3-6}$ cycloalkyl optionally substituted with from 1-4 independently selected $C_{1-4}$ alkyl.

In certain of these embodiments, each occurrence of $R^b$ is selected from $C_{1-10}$ alkyl optionally substituted with from 1-6 independently selected $R^a$; $C_{1-4}$ haloalkyl; —OH; oxo; —F; —Cl; —Br; $C_{1-4}$ alkoxy; $C_{1-4}$ haloalkoxy; and $C_{3-6}$ cycloalkyl optionally substituted with from 1-4 independently selected $C_{1-4}$ alkyl.

In certain of these embodiments, each occurrence of $R^b$ is selected from $C_{1-10}$ alkyl optionally substituted with from 1-6 independently selected $R^a$ and $C_{1-4}$ haloalkyl.

In certain of these embodiments, each occurrence of $R^b$ is selected from $C_{1-6}$ alkyl optionally substituted with from 1-2 independently selected $R^a$.

For example, each occurrence of $R^b$ can be selected from unsubstituted $C_{1-6}$ alkyl (e.g., butyl such as n-butyl).

In certain embodiments, one occurrence of $R^b$ is independently $C_{1-10}$ (such as $C_{1-2}$, $C_3$, $C_4$, $C_5$, $C_6$, or $C_{7-10}$) alkyl which is optionally substituted with from 1-6 independently selected $R^a$.

In certain of these embodiments, one occurrence of $R^b$ is unsubstituted $C_{1-10}$ (such as $C_{1-2}$, $C_3$, $C_4$, $C_5$, $C_6$, or $C_{7-10}$) alkyl (such as butyl).

In certain other embodiments, one occurrence of $R^b$ is independently $C_{1-10}$ (such as $C_3$, $C_4$, $C_5$, $C_6$, or $C_{7-10}$) alkyl which is substituted with from 1-6 independently selected $R^a$.

In certain of these embodiments, each occurrence of $R^a$ is independently selected from the group consisting of: halo (such as F), $C_{1-4}$ alkoxy, and $NR^eR^f$.

In certain other embodiments, one occurrence of $R^b$ is selected from the group consisting of: ($C_{0-1}$ alkylene)-$C_{6-10}$ aryl optionally substituted with 1-4 independently selected $C_{1-4}$ alkyl; and ($C_{0-1}$ alkylene)-$C_{3-6}$ cycloalkyl optionally substituted with from 1-4 independently selected $C_{1-4}$ alkyl (such as unsubstituted phenyl).

As non-limiting examples of the foregoing embodiments, $R^b$ is unsubstituted phenyl or unsubstituted benzyl.

In certain embodiments, $Y^{A2}$ is

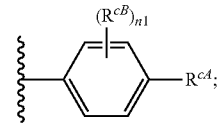

n1 is 0, 1, or 2; $R^{cA}$ is an independently selected $R^c$ or $R^{c'}$; and $R^{cB}$ is an independently selected $R^c$.

In certain embodiments, $Y^{A2}$ is

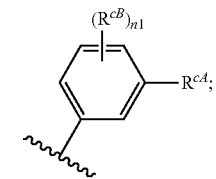

n1 is 0, 1, or 2; $R^{cA}$ is an independently selected $R^c$ or $R^{c'}$; and $R^{cB}$ is an independently selected $R^c$.

In certain embodiments, $Y^{A2}$ is

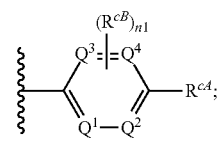

from 1-2 of $Q^1$, $Q^2$, $Q^3$, and $Q^4$ is N; each of the remaining of $Q^1$, $Q^2$, $Q^3$, and $Q^4$ is CH; n1 is 0, 1, or 2; and each of $R^{cA}$ and $R^{cB}$ is an independently selected $R^c$.

In certain embodiments, $Y^{A2}$ is

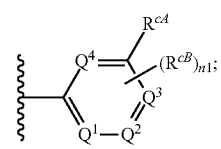

from 1-2 of $Q^1$, $Q^2$, $Q^3$, and $Q^4$ is N; each of the remaining of $Q^1$, $Q^2$, $Q^3$, and $Q^4$ is CH; n1 is 0, 1, or 2; and each of $R^{cA}$ and $R^{cB}$ is an independently selected $R^c$.

In certain embodiments

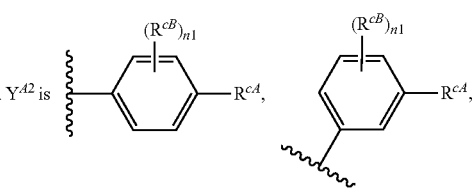

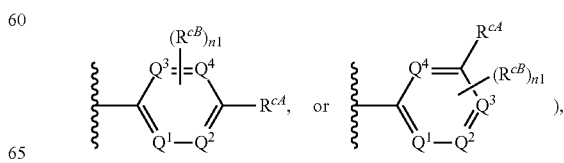

$R^{cA}$ is as defined for $R^c$ or $R^{c'}$ in any one of claims 174-178.

In certain embodiments

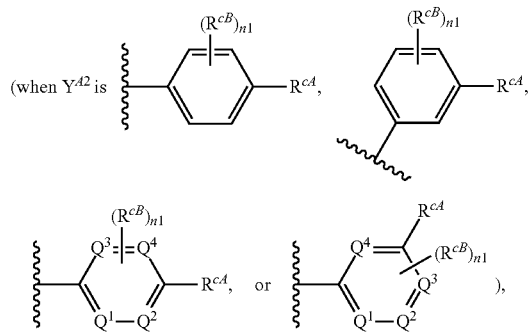

(when $Y^{A2}$ is ... , or ), $R^{cA}$ is as defined for $R^c$ or $R^{c'}$ in any one of claims 179-185.

In certain embodiments

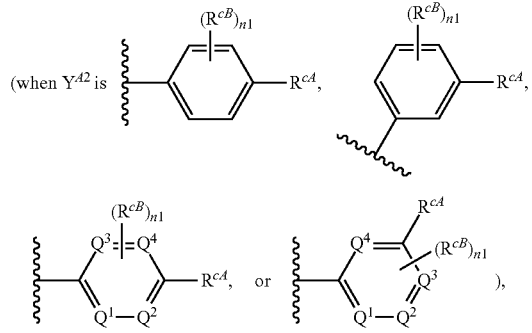

(when $Y^{A2}$ is ... , or ), n1 is 0.

In certain other embodiments, n1 is 1 or 2. In certain of these embodiments, each $R^{cB}$ is independently halo, $C_{1-3}$ alkyl, or $C_{1-3}$ haloalkyl.

In certain embodiments, $Y^{A2}$ is

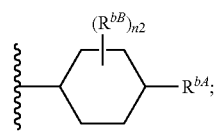

n2 is 0, 1, or 2; and each of $R^{bA}$ and $R^{bB}$ is an independently selected $R^b$.

In certain embodiments, $Y^{A2}$ is

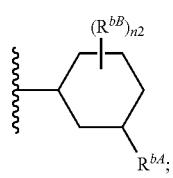

n2 is 0, 1, or 2; and each of $R^{bA}$ and $R^{bB}$ is an independently selected $R^b$.

In certain embodiments

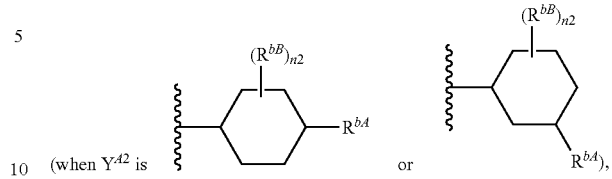

(when $Y^{A2}$ is ... or ), $R^{bA}$ is as defined for $R^b$ in any one of claims 192-196.

In certain embodiments

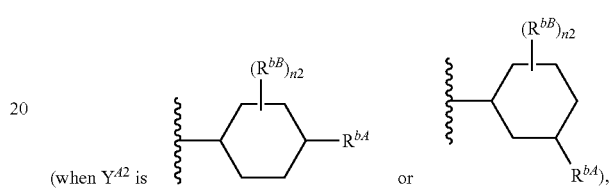

(when $Y^{A2}$ is ... or ), $R^{bA}$ is as defined for $R^b$ in claim 197.

In certain embodiments

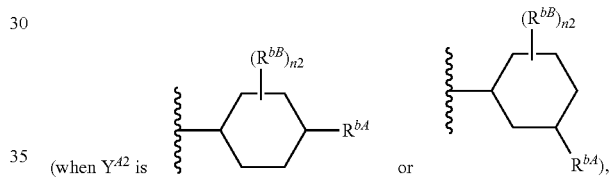

(when $Y^{A2}$ is ... or ), $R^{bA}$ is as defined for $R^b$ in claim 191.

In certain embodiments

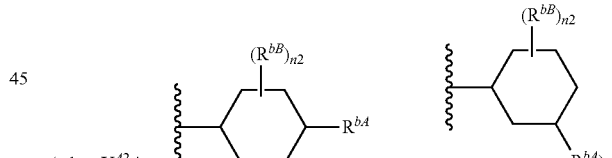

(when $Y^{A2}$ is ... or ), n2 is 0.

In certain other embodiments, n2 is 1 or 2. In certain of these embodiments, each $R^{bB}$ is independently halo, $C_{1-3}$ alkyl, or $C_{1-3}$ haloalkyl.

Other non-limiting examples of A can be selected from:

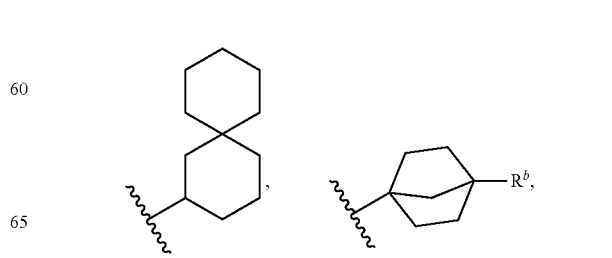

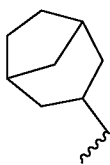 and 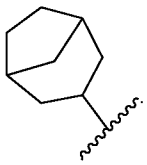 ; e.g.:

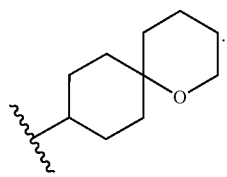 [SMILES: *C1CCC2(CCCCO2)CC1]

Other non-limiting examples of A can include:

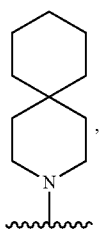

In some embodiments, Q and A are defined according to (B).

In certain embodiments, E is heterocyclyl including from 3-12 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-2 independently selected $R^b$.

In certain embodiments, E is heterocyclyl including from 6-12 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-2 independently selected $R^b$.

In certain embodiments, E is heterocyclyl (e.g., spirocyclic heterocyclyl) including from 6-12 ring atoms, wherein aside from the nitrogen atom present, from 0-2 additional ring atoms are heteroatoms, each independently selected from the group consisting of N, N(H), N($R^d$), and O, and wherein one or more of the heterocyclyl ring carbon atoms are optionally substituted with 1 independently selected $R^b$.

Non-limiting examples of E can be selected from:

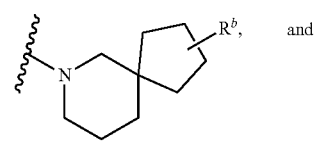 and

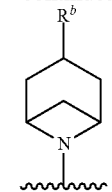

(e.g., $R^b$ is unsubstituted $C_{1-6}$ alkyl such as n-butyl and ethyl); e.g.:

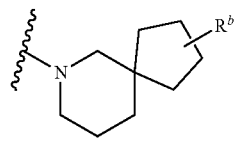

(e.g., $R^b$ is unsubstituted $C_{1-6}$ alkyl such as ethyl).

In certain embodiments (when Q-A is defined according to (B)), Q and A, taken together, form:

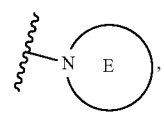

wherein ∫ denotes point of attachment to W; and

E is a ring (e.g., monocyclic ring or bicyclic ring) including from 5-12 ring atoms, wherein aside from the nitrogen atom present, from 0-3 additional ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

In certain embodiments, E is heterocyclyl including from 5-10 (such as 5-6) ring atoms, wherein aside from the nitrogen atom present, from 0-1 additional ring atoms are heteroatoms, each independently selected from the group consisting of N, N(H), N($R^d$), and O, and wherein one or more of the heterocyclyl ring carbon atoms are substituted with from 1-2 independently selected $R^b$.

As a non-limiting example, E is piperidinyl

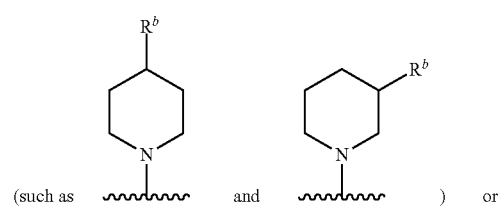 or

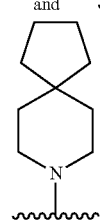

In certain embodiments, one occurrence of $R^b$ substituent of E is independently selected from the group consisting of: $C_{1-4}$ alkoxy (such as propoxy); $C_{1-4}$ haloalkoxy; $C_{1-10}$ alkyl optionally substituted with from 1-6 independently selected $R^a$ (such as butyl); and $C_{1-4}$ haloalkyl.

Other non-limiting examples of E can include:

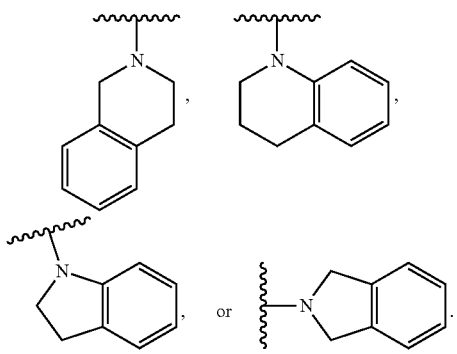

Non-Limiting Combinations

In certain embodiments, Q is NH; W is C(=O); and A is $Y^{A2}$, wherein $Y^{A2}$ is as defined in claims 51-55 and 62-65.

In certain embodiments, Q is NH; W is C(=O); and A is $Y^{A2}$, wherein $Y^{A2}$ is as defined in claims 51-55 and 67-70.

In certain embodiments, Q is NH; W is C(=O); and A is $Y^{A2}$, wherein $Y^{A2}$ is as defined in claims 56-61 and 62-65.

In certain embodiments, Q is NH; W is C(=O); and A is $Y^{A2}$, wherein $Y^{A2}$ is as defined in claims 56-61 and 67-70.

In certain embodiments, Q is NH; W is C(=O); and A is $Y^{A2}$, wherein $Y^{A2}$ is as defined in claims 71 and 73-78.

In certain embodiments, Q is NH; W is C(=O); and A is $Y^{A2}$, wherein $Y^{A2}$ is as defined in claims 72, 73-76, and 79.

In certain embodiments, Q is NH; W is C(=S); and A is $Y^{A2}$, wherein $Y^{A2}$ is as defined in claims 51-55 and 62-65.

In certain embodiments, Q is NH; W is C(=S); and A is $Y^{A2}$, wherein $Y^{A2}$ is as defined in claims 51-55 and 67-70.

In certain embodiments, Q is NH; W is C(=S); and A is $Y^{A2}$, wherein $Y^{A2}$ is as defined in claims 56-61 and 62-65.

In certain embodiments, Q is NH; W is C(=S); and A is $Y^{A2}$, wherein $Y^{A2}$ is as defined in claims 56-61 and 67-70.

In certain embodiments, Q is NH; W is C(=S); and A is $Y^{A2}$, wherein $Y^{A2}$ is as defined in claims 71 and 73-78.

In certain embodiments, Q is NH; W is C(=S); and A is $Y^{A2}$, wherein $Y^{A2}$ is as defined in claims 72, 73-76, and 79.

In certain embodiments, Q is NH; W is C(=$NR^d$) (e.g., C(=N(Boc)); and A is $Y^{A2}$, wherein $Y^{A2}$ is as defined in claims 51-55 and 62-65.

In certain embodiments, Q is NH; W is C(=$NR^d$) (e.g., C(=N(Boc)); and A is $Y^{A2}$, wherein $Y^{A2}$ is as defined in claims 51-55 and 67-70.

In certain embodiments, Q is NH; W is C(=$NR^d$) (e.g., C(=N(Boc)); and A is $Y^{A2}$, wherein $Y^{A2}$ is as defined in claims 56-61 and 62-65.

In certain embodiments, Q is NH; W is C(=$NR^d$) (e.g., C(=N(Boc)); and A is $Y^{A2}$, wherein $Y^{A2}$ is as defined in claims 56-61 and 67-70.

In certain embodiments, Q is NH; W is C(=$NR^d$) (e.g., C(=N(Boc)); and A is $Y^{A2}$, wherein $Y^{A2}$ is as defined in claims 71 and 73-78.

In certain embodiments, Q is NH; W is C(=$NR^d$) (e.g., C(=N(Boc)); and A is $Y^{A2}$, wherein $Y^{A2}$ is as defined in claims 72, 73-76, and 79.

In certain embodiments, Q is NH; W is C(=NH); and A is $Y^{A2}$, wherein $Y^{A2}$ is as defined in claims 51-55 and 62-65.

In certain embodiments, Q is NH; W is C(=NH); and A is $Y^{A2}$, wherein $Y^{A2}$ is as defined in claims 51-55 and 67-70.

In certain embodiments, Q is NH; W is C(=NH); and A is $Y^{A2}$, wherein $Y^{A2}$ is as defined in claims 56-61 and 62-65.

In certain embodiments, Q is NH; W is C(=NH); and A is $Y^{A2}$, wherein $Y^{A2}$ is as defined in claims 56-61 and 67-70.

In certain embodiments, Q is NH; W is C(=NH); and A is $Y^{A2}$, wherein $Y^{A2}$ is as defined in claims 71 and 73-78.

In certain embodiments, Q is NH; W is C(=NH); and A is $Y^{A2}$, wherein $Y^{A2}$ is as defined in claims 72, 73-76, and 79.

Any of the foregoing non-limiting combinations can include one or more of the following features.

W can be C(=O); and Q-A is as defined in claims 80-85.

W can be C(=S); and Q-A is as defined in claims 80-85.

W can be C(=$NR^d$) (e.g., C(=NBoc)); and Q-A is as defined in claims 80-85.

W can be C(=NH); and Q-A is as defined in claims 80-85.

The compound can have Formula (I-a1) or the compound can have Formula (I-b1); or the compound can have (I-c1); or the compound can have (I-d1); or the compound can have (I-e1); or the compound can have (I-f1); or the compound can have (I-g1); or the compound can have (I-h1); or the compound can have (I-i1); or the compound can have (I-j1); or the compound can have (I-k1); or the compound can have (I-l1); or the compound can have (I-m1).

$R^1$ can be as defined in claims 32-35.
$R^2$ can be as defined in claims 36-37.
$R^3$ can be as defined in claims 38-41.
$R^5$ can as defined in claim 43.

In some embodiments, the compound has the following formula:

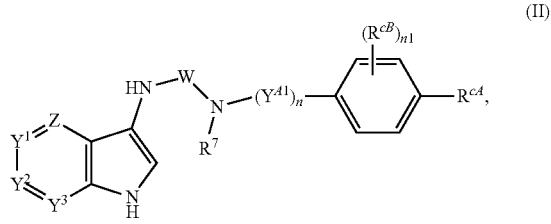

(II)

wherein each of Z, $Y^1$, $Y^2$, and $Y^3$ is independently N or $CR^1$, provided that one or more of Z, $Y^1$, $Y^2$, and $Y^3$ is N; $R^7$ is H or $C_{1-3}$ alkyl; n1 is 0, 1, or 2; $R^{cA}$ is an independently selected $R^c$ or $R^{c'}$; and each $R^{cB}$ is an independently selected $R^c$.

In some embodiments, the compound has the following formula:

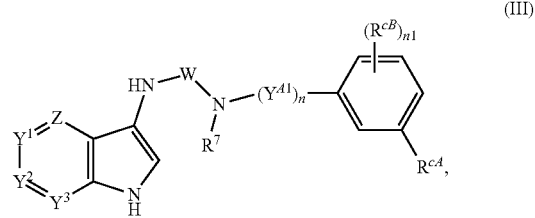

(III)

wherein each of Z, $Y^1$, $Y^2$, and $Y^3$ is independently N or $CR^1$, provided that one or more of Z, $Y^1$, $Y^2$, and $Y^3$ is N; $R^7$ is H or $C_{1-3}$ alkyl; n1 is 0, 1, or 2; $R^{cA}$ is an independently selected $R^c$ or $R^{c'}$; and each $R^{cB}$ is an independently selected $R^c$.

In some embodiments, the compound has the following formula:

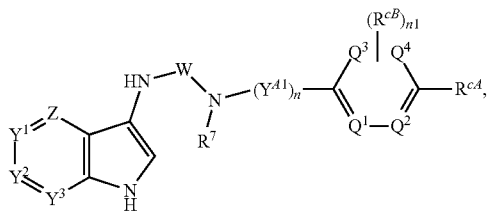

(IV)

wherein each of Z, $Y^1$, $Y^2$, and $Y^3$ is independently N or $CR^1$, provided that one or more of Z, $Y^1$, $Y^2$, and $Y^3$ is N; $R^7$ is H or $C_{1-3}$ alkyl; from 1-2 of $Q^1$, $Q^2$, $Q^3$, and $Q^4$ is N; each of the remaining of $Q^1$, $Q^2$, $Q^3$, and $Q^4$ is CH; n1 is 0, 1, or 2; and each of $R^{cA}$ and $R^{cB}$ is an independently selected $R^c$.

In some embodiments, the compound has the following formula:

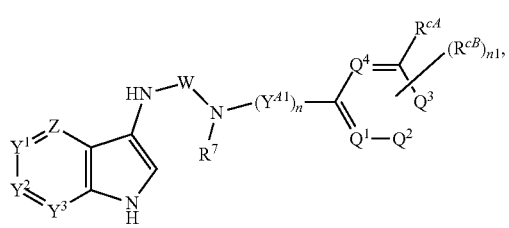

(V)

wherein each of Z, $Y^1$, $Y^2$, and $Y^3$ is independently N or $CR^1$, provided that one or more of Z, $Y^1$, $Y^2$, and $Y^3$ is N; $R^7$ is H or $C_{1-3}$ alkyl; from 1-2 of $Q^1$, $Q^2$, $Q^3$, and $Q^4$ is N; each of the remaining of $Q^1$, $Q^2$, $Q^3$, and $Q^4$ is CH; n1 is 0, 1, or 2; and each of $R^{cA}$ and $R^{cB}$ is an independently selected $R^c$.

In certain embodiments of Formula (II), (III), (IV), and/or (V), $R^{cA}$ is as defined for $R^c$ or $R^{c'}$ in any one of claims 174-178.

In certain embodiments of Formula (II), (III), (IV), and/or (V), $R^{cA}$ is as defined for $R^c$ or $R^{c'}$ in any one of claims 179-185.

In certain embodiments of Formula (II), (III), (IV), and/or (V), n1 is 0.

In certain other embodiments of Formula (II), (III), (IV), and/or (V), n1 is 1 or 2.

In certain of these embodiments, each $R^{cB}$ is halo, $C_{1-3}$ alkyl, or $C_{1-3}$ haloalkyl.

In some embodiments, the compound has the following formula:

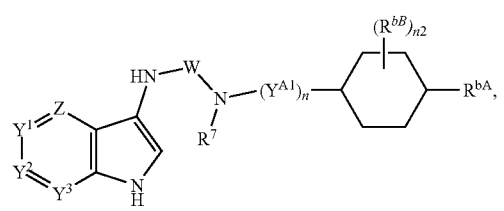

(VI)

wherein each of Z, $Y^1$, $Y^2$, and $Y^3$ is independently N or $CR^1$, provided that one or more of Z, $Y^1$, $Y^2$, and $Y^3$ is N; $R^7$ is H or $C_{1-3}$ alkyl; n2 is 0, 1, or 2; and each of $R^{bA}$ and $R^{bB}$ is an independently selected $R^b$.

In some embodiments, the compound has the following formula:

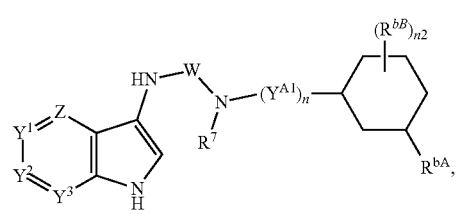

(VII)

wherein each of Z, $Y^1$, $Y^2$, and $Y^3$ is independently N or $CR^1$, provided that one or more of Z, $Y^1$, $Y^2$, and $Y^3$ is N; $R^7$ is H or $C_{1-3}$ alkyl; n2 is 0, 1, or 2; and each of $R^{bA}$ and $R^{bB}$ is an independently selected $R^b$.

In certain embodiments of Formula (VI) and/or (VII), $R^{bA}$ is as defined for $R^b$ in any one of claims 192-196.

In certain embodiments of Formula (VI) and/or (VII), $R^{bA}$ is as defined for $R^b$ in any one of claim 197.

In certain embodiments of Formula (VI) and/or (VII), n2 is 0.

In certain other embodiments, n2 is 1 or 2. In certain of these embodiments, each $R^{bB}$ is independently halo, $C_{1-3}$ alkyl or $C_{1-3}$ haloalkyl.

In some embodiments the compound has the following formula:

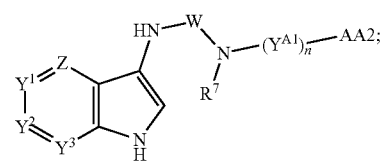

(VIII)

wherein each of Z, $Y^1$, $Y^2$, and $Y^3$ is independently N or $CR^1$, provided that one or more of Z, $Y^1$, $Y^2$, and $Y^3$ is N;

$R^7$ is H or $C_{1-3}$ alkyl; and

AA2 is selected from the group consisting of:

(a) heteroaryl including from 9-10 ring atoms, wherein from 1-3 ring atoms are heteroatoms, each independently selected from the group consisting of N, N(H), N($R^d$), O, and S (such as quinolinyl, isoquinolinyl, tetrahydro-quinolinyl, and benzothiazolyl (such as 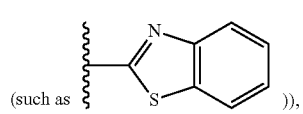 )), and wherein one or more of the heteroaryl ring carbon atoms are optionally substituted with from 1-3 independently selected $R^e$; and (b) C$_{7-11}$ aryl (such as naphthyl, tetrahydronaphthyl

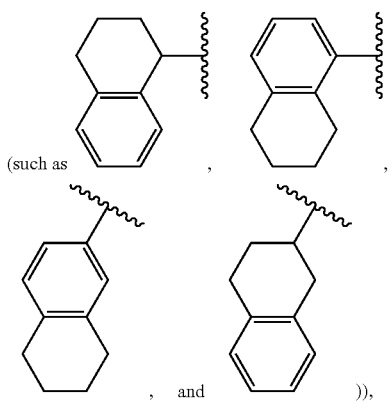

which is optionally substituted with from 1-4 R$^c$.

In certain embodiments, AA2 is heteroaryl including from 9-10 ring atoms, wherein from 1-3 ring atoms are heteroatoms, each independently selected from the group consisting of N, N(H), N(R$^d$), O, and S (such as quinolinyl, isoquinolinyl, tetrahydro-quinolinyl, and benzothiazolyl

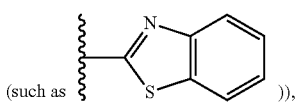

and wherein one or more of the heteroaryl ring carbon atoms are optionally substituted with from 1-3 independently selected R$^c$.

In certain embodiments, AA2 is (b) C$_{7-11}$ aryl (such as naphthyl, tetrahydronaphthyl

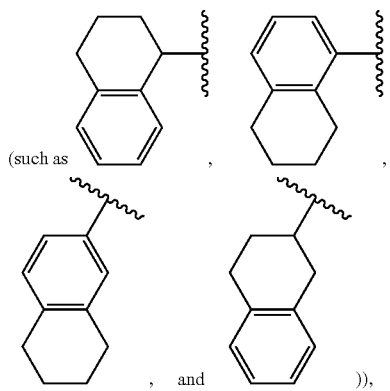

which is optionally substituted with from 1-4 R$^c$.

As a non-limiting example, AA2 is

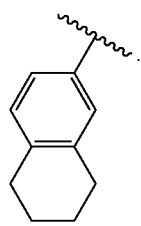 [SMILES: *c1ccc2c(c1)CCCC2]

In some embodiments, the compound has the following formula:

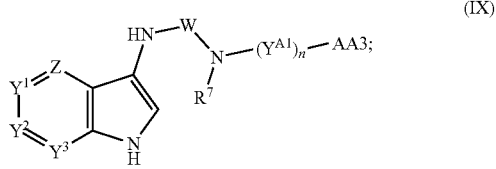

(IX)

wherein each of Z, Y$^1$, Y$^2$, and Y$^3$ is independently N or CR$^1$, provided that one or more of Z, Y$^1$, Y$^2$, and Y$^3$ is N;

R$^7$ is H or C$_{1-3}$ alkyl; and

AA3 is heteroaryl including 5 ring atoms, wherein from 1-3 (such as 1-2) ring atoms are heteroatoms, each independently selected from the group consisting of N, N(H), N(R$^d$), O, and S (such as thiazolyl

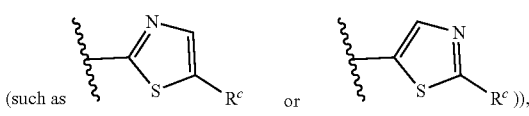

and wherein one or more of the heteroaryl ring carbon atoms are substituted with from 1-2 independently selected R$^c$.

In certain of these embodiments, AA3 is thiazolyl

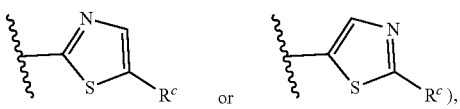

which is optionally substituted with from 1-2 independently selected R$^c$.

In certain of these embodiments, R$^c$ is selected from the group consisting of:

(xxi) —(C$_{0-3}$ alkylene)-C$_{6-10}$ aryl optionally substituted with from 1-4 independently selected C$_{1-4}$ alkyl; and (xxii) —(C$_{0-3}$ alkylene)-5-10 membered heteroaryl, wherein from 1-3 ring atoms of the heteroaryl are heteroatoms each independently selected from N, NH, NR$^d$, O, and S, wherein the heteroaryl is optionally substituted with from 1-4 independently selected C$_{1-4}$ alkyl.

In certain of these embodiments, R$^c$ is selected from the group consisting of:

(xxi) C$_{6-10}$ aryl optionally substituted with from 1-4 independently selected C$_{1-4}$ alkyl; and (xxii) 5-10 membered heteroaryl, wherein from 1-3 ring atoms of the heteroaryl are heteroatoms each independently selected from N, NH, NR$^d$, O, and S, wherein the heteroaryl is optionally substituted with from 1-4 independently selected C$_{1-4}$ alkyl.

As a non-limiting example of the foregoing embodiments, R$^c$ is unsubstituted phenyl.

In some embodiments, the compound has the following formula:

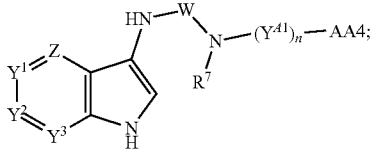
(X)

wherein each of Z, Y$^1$, Y$^2$, and Y$^3$ is independently N or CR$^1$, provided that one or more of Z, Y$^1$, Y$^2$, and Y$^3$ is N; R$^7$ is H or C$_{1-3}$ alkyl; and
AA4 is C$_{7-13}$ bicyclic cycloalkyl (such as

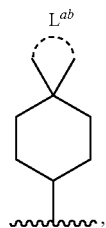

wherein L$^{ab}$ is a bond or a C$_{1-3}$ alkylene), which is optionally substituted with from 1-4 independently selected R$^b$.

In certain of these embodiments, AA4 is

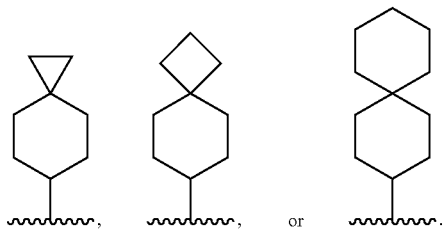 [SMILES: *C1CCC2(CC1)CC2 ; *C1CCC2(CCC2)CC1 ; *C1CCC2(CCCCC2)CC1]

In certain embodiments of Formulae (II)-(X), n in —(Y$^{A1}$)$_n$ is 0.

In some embodiments, the compound has the following formula:

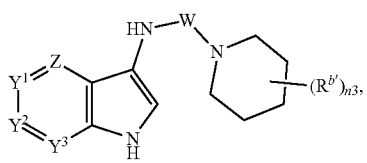
(XI)

wherein each of Z, Y$^1$, Y$^2$, and Y$^3$ is independently N or CR$^1$, provided that one or more of Z, Y$^1$, Y$^2$, and Y$^3$ is N; n3 is 1 or 2; and each R$^{b'}$ is an independently selected R$^b$; or a pair of R$^{b'}$, attached to the same carbon atom or different carbon atoms, taken together with the atom to which each is attached forms a ring including 3-8 ring atoms.

In certain of these embodiments, n3 is 1. In certain of these embodiments, R$^{b'}$ is selected from the group consisting of: C$_{1-4}$ alkoxy (such as propoxy); C$_{1-4}$ haloalkoxy; C$_{1-10}$ alkyl optionally substituted with from 1-6 independently selected R$^a$ (such as butyl); and C$_{1-4}$ haloalkyl.

In certain other embodiments, n3 is 2; and a pair of R$^{b'}$ attached to the same carbon atom or different carbon atoms taken together with the atom to which each is attached forms a ring including 3-8 ring atoms (such as 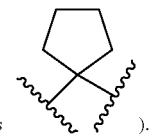).

In certain embodiments of Formulae (II)-(XI), Z is N; and each of Y$^1$, Y$^2$, and Y$^3$ is independently CR$^1$. For example, Z is N; Y$^1$ is CR$^1$; and each of Y$^2$ and Y$^3$ is CH; or Z is N; Y$^2$ is CR$^1$; and each of Y$^1$ and Y$^3$ is CH; or Z is N; Y$^3$ is CR$^1$; and each of Y$^2$ and Y$^1$ is CH.

In certain embodiments of Formulae (II)-(XI), Y$^1$ is N; and each of Z, Y$^2$, and Y$^3$ is independently CR$^1$. For example Y$^1$ is N; Z is CR$^1$; and each of Y$^2$ and Y$^3$ is CH; or Y$^1$ is N; Y$^2$ is CR$^1$; and each of Z and Y$^3$ is CH; or Y$^1$ is N; Y$^3$ is CR$^1$; and each of Z and Y$^2$ is CH.

In certain embodiments of Formulae (II)-(XI), Y$^2$ is N; and each of Z, Y$^1$, and Y$^3$ is independently CR$^1$. For example, Y$^2$ is N; Z is CR$^1$; and each of Y$^1$ and Y$^3$ is CH; or Y$^2$ is N; Y$^1$ is CR$^1$; and each of Z and Y$^3$ is CH; or Y$^2$ is N; Y$^3$ is CR$^1$; and each of Z and Y$^1$ is CH;

In certain embodiments of Formulae (II)-(XI), Y$^3$ is N; and each of Z, Y$^1$, and Y$^2$ is independently CR$^1$. For example, Y$^3$ is N; Z is CR$^1$; and each of Y$^1$ and Y$^2$ is CH; or Y$^3$ is N; Y$^1$ is CR$^1$; and each of Z and Y$^2$ is CH; or Y$^3$ is N; Y$^2$ is CR$^1$; and each of Z and Y$^1$ is CH.

In certain embodiments of Formulae (II)-(XI), one occurrence of R$^1$ is selected from the group consisting of: one occurrence of R$^1$ is selected from the group consisting of:
- —(C$_{0-3}$ alkylene)-C$_{3-6}$ cycloalkyl optionally substituted with from 1-4 independently selected R$^g$;
- —(C$_{0-3}$ alkylene)-C$_{6-10}$ aryl optionally substituted with from 1-4 independently selected R$^g$; —(C$_{0-3}$ alkylene)-5-10 membered heteroaryl, wherein from 1-3 ring atoms of the heteroaryl are heteroatoms each independently selected from N, NH, NR$^d$, O, and S, wherein the heteroaryl is optionally substituted with from 1-4 independently selected R$^g$; and
- —(C$_{0-3}$ alkylene)-5-10 membered heterocyclyl, wherein from 1-3 ring atoms of the heterocyclyl are heteroatoms each independently selected from the group consisting of N, NH, NR$^d$, O, and S, wherein the heterocyclyl is optionally substituted with 1-4 independently selected R$^g$.

In certain of these embodiments, one occurrence of R$^1$ is selected from the group consisting of:
- C$_{3-6}$ cycloalkyl optionally substituted with from 1-4 independently selected R$^g$;
- C$_{6-10}$ aryl optionally substituted with from 1-4 independently selected R$^g$ (such as phenyl optionally substituted with from 1-4 independently selected R$^g$);
- 5-10 membered heteroaryl (such as 5- or 6-membered heteroaryl), wherein from 1-3 ring atoms of the heteroaryl are heteroatoms each independently selected from N, NH, NR$^d$, O, and S, wherein the heteroaryl is optionally substituted with from 1-4 independently selected R$^g$ (such as pyrimidyl, pyridyl, pyrazolyl, and thienyl (e.g., pyrazolyl) each of which is optionally substituted with 1-3 independently selected $R^g$); and 5-10 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected $R^g$ (such as tetrahydropyridyl or tetrahydropyranyl, each of which is optionally substituted with from 1-4 independently selected $R^g$).

In certain embodiments of Formulae (II)-(XI), one occurrence of $R^1$ is selected from the group consisting of:

$C_{3-6}$ cycloalkyl optionally substituted with from 1-4 independently selected $R^g$;

$C_6$ aryl optionally substituted with from 1-4 independently selected $R^g$ (such as phenyl optionally substituted with from 1-4 independently selected $R^g$);

5-6 membered heteroaryl (such as 5- or 6-membered heteroaryl), wherein from 1-3 ring atoms of the heteroaryl are heteroatoms each independently selected from N, NH, $NR^d$, O, and S, wherein the heteroaryl is optionally substituted with from 1-4 independently selected $R^g$ (such as pyrimidyl, pyridyl, pyrazolyl, and thienyl (e.g., pyrazolyl) each of which is optionally substituted with 1-3 independently selected $R^E$); and 5-6 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected $R^g$ (such as tetrahydropyridyl or tetrahydropyranyl, each of which is optionally substituted with from 1-4 independently selected $R^g$).

In certain embodiments of Formulae (II)-(XI), one occurrence of $R^1$ is as defined as in any one of claims 144-145.

In certain embodiments of Formulae (II)-(XI), one occurrence of $R^1$ is as defined as in any one of claims 146-148.

In certain embodiments of Formulae (II)-(XI), one occurrence of $R^1$ is as defined as in any one of claims 149-150.

In certain embodiments of Formulae (II)-(XI), one occurrence of $R^1$ is as defined as in claim 151.

In certain embodiments of Formulae (II)-(XI), one occurrence of $R^1$ is as defined as in claim 141-142.

In one or more of the foregoing embodiments, each $R^g$ is independently selected from the group consisting of: $NR^eR^f$ (such as $NH_2$, 4-methylpiperazin-1-yl, morpholin-4-yl), $C_{1-4}$ alkyl (such as methyl, ethyl, or isopropyl), $C_{1-4}$ haloalkyl (such as $CF_3$), $C_{1-4}$ alkyl substituted with $R^a$ (such as $C_{1-4}$ alkyl substituted with OH, $NR^eR^f$, or $C(O)OC_{1-4}$ alkyl), $C_{1-4}$ alkoxy optionally substituted with $R^a$ (such as methoxy or —OCH$_2$-cyclopropyl), —S(O)$_{1-2}$ (NR'R") (such as S(O)$_2$NMe$_2$ or S(O)$_2$NH$_2$), and —S(O)$_{1-2}$(C$_{1-4}$ alkyl) (such as S(O)$_2$Me).

In certain embodiments of Formulae (II)-(XI), one occurrence of $R^1$ is halo (e.g., F, Cl, or Br).

In certain embodiments of Formulae (II)-(XI), one occurrence of $R^1$ is cyano.

In certain embodiments of Formulae (II)-(XI), one occurrence of $R^1$ is $C_{1-6}$ alkyl (e.g., ethyl).

In certain embodiments of Formulae (II)-(XI), one occurrence of $R^1$ is $C_{2-6}$ alkenyl (e.g., vinyl).

In certain embodiments of Formulae (II)-(XI), one occurrence of $R^1$ is $C_{2-6}$ alkynyl (e.g., acetylenyl).

In certain of the foregoing embodiments of Formulae (II)-(XI), each of the remaining occurrences of $R^1$ is H.

In certain embodiments of Formulae (II)-(XI), W is $C(=O)$.

In certain embodiments of Formulae (II)-(XI), $R^7$ is H.

In some embodiments, the compound is selected from the following:

| Compound # | Structure |
|---|---|
| 100 | 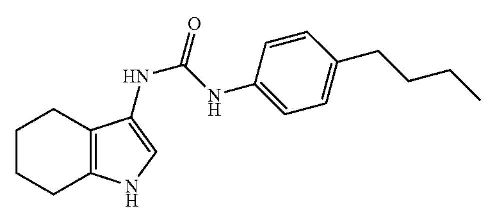 [SMILES: CCCCc1ccc(NC(=O)Nc2c[nH]c3c2CCCC3)cc1] |
| 102 | 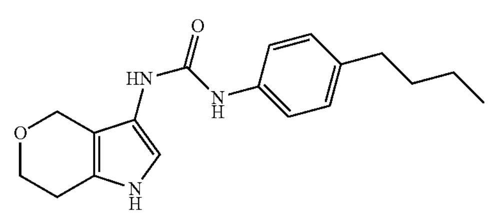 [SMILES: CCCCc1ccc(NC(=O)Nc2c[nH]c3c2COCC3)cc1] |
| 103 | 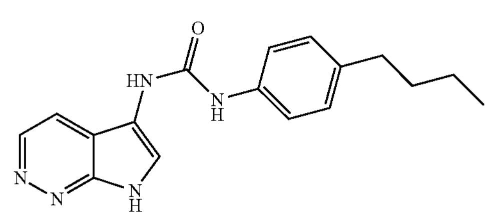 [SMILES: CCCCc1ccc(NC(=O)Nc2c[nH]c3nnccc23)cc1] |

-continued

| Compound # | Structure |
|---|---|
| 104 | 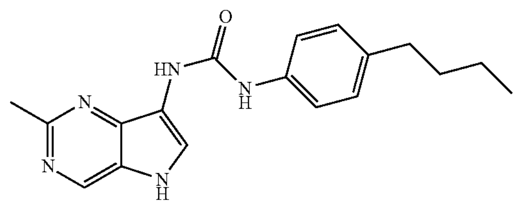 [SMILES: CCCCc1ccc(NC(=O)Nc2c[nH]c3cnc(C)nc23)cc1] |
| 105 | 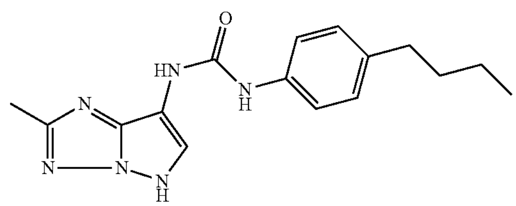 [SMILES: CCCCc1ccc(NC(=O)Nc2c[nH]n3nc(C)nc23)cc1] |
| 106 | 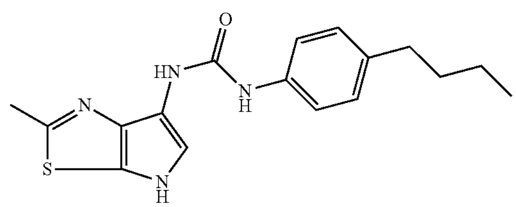 [SMILES: CCCCc1ccc(NC(=O)Nc2c[nH]c3sc(C)nc23)cc1] |
| 107 | 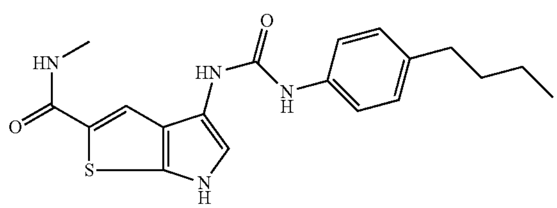 [SMILES: CCCCc1ccc(NC(=O)Nc2c[nH]c3sc(C(=O)NC)cc23)cc1] |
| 108 | 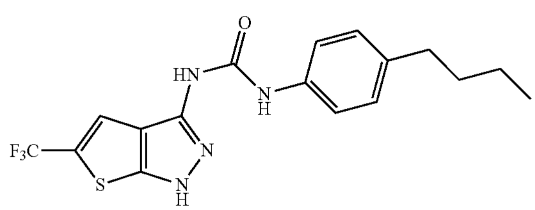 [SMILES: CCCCc1ccc(NC(=O)Nc2n[nH]c3sc(C(F)(F)F)cc23)cc1] |
| 109 | 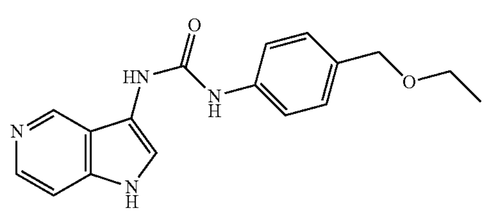 |
| 110 | 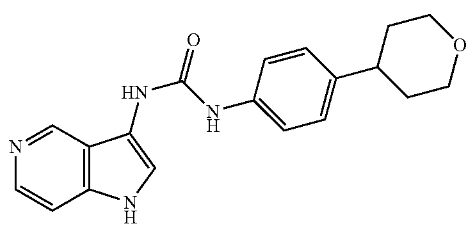 [SMILES: O=C(Nc1ccc(C2CCOCC2)cc1)Nc1c[nH]c2ccncc12] |

-continued

| Compound # | Structure |
|---|---|
| 111 | 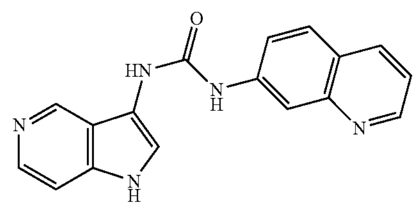 [SMILES: O=C(Nc1ccc2cccnc2c1)Nc1c[nH]c2ccncc12] |
| 112 | 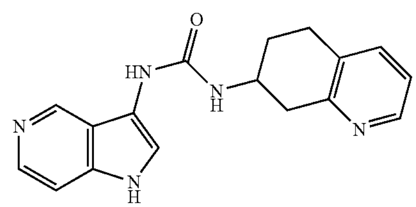 [SMILES: O=C(Nc1c[nH]c2ccncc12)NC1CCc2cccnc2C1] |
| 113 | 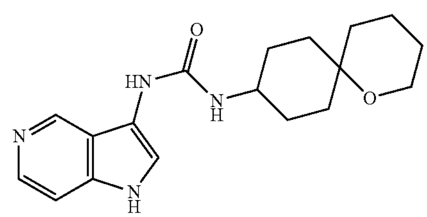 [SMILES: O=C(Nc1c[nH]c2ccncc12)NC1CCC2(CCCCO2)CC1] |
| 114 | 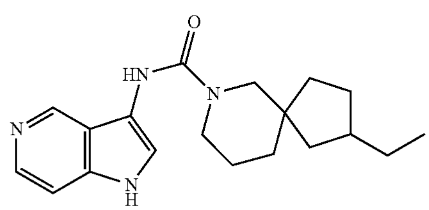 [SMILES: CCC1CCC2(CCCN(C(=O)Nc3c[nH]c4ccncc34)C2)C1] |
| 115 | 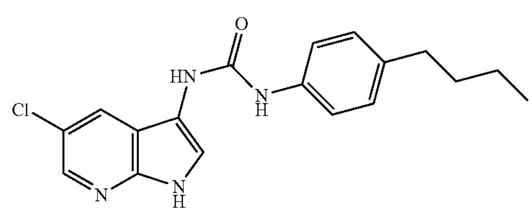 [SMILES: CCCCc1ccc(NC(=O)Nc2c[nH]c3ncc(Cl)cc23)cc1] |
| 116 | 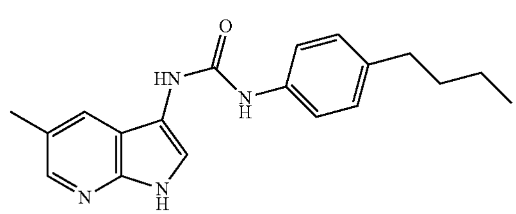 [SMILES: CCCCc1ccc(NC(=O)Nc2c[nH]c3ncc(C)cc23)cc1] |
| 117 | 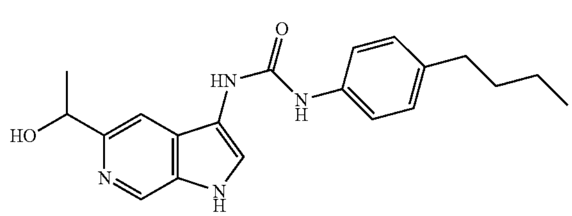 [SMILES: CCCCc1ccc(NC(=O)Nc2c[nH]c3cnc(C(C)O)cc23)cc1] |

| Compound # | Structure |
|---|---|
| 118 | 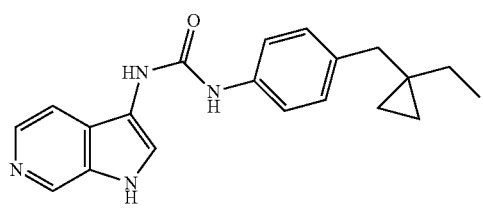 [SMILES: CCC1(Cc2ccc(NC(=O)Nc3c[nH]c4cnccc34)cc2)CC1] |
| 119 | 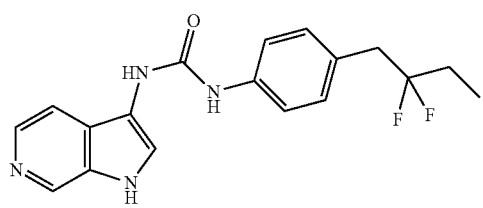 [SMILES: CCC(F)(F)Cc1ccc(NC(=O)Nc2c[nH]c3cnccc23)cc1] |
| 120 | 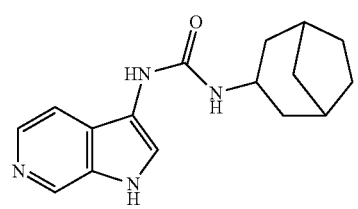 [SMILES: O=C(Nc1c[nH]c2cnccc12)NC1CC2CCC(C2)C1] |
| 121 | 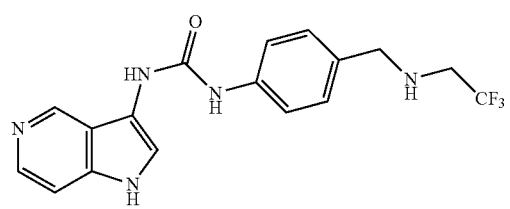 [SMILES: O=C(Nc1ccc(CNCC(F)(F)F)cc1)Nc1c[nH]c2ccncc12] |
| 122 | 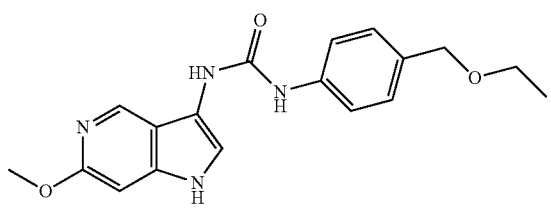 [SMILES: CCOCc1ccc(NC(=O)Nc2c[nH]c3cc(OC)ncc23)cc1] |
| 123 | 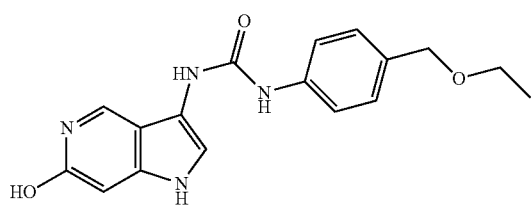 [SMILES: CCOCc1ccc(NC(=O)Nc2c[nH]c3cc(O)ncc23)cc1] |
| 124 | 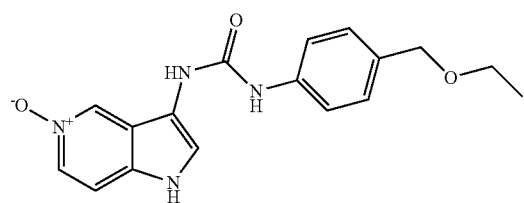 |

-continued
| Compound # | Structure |
|---|---|
| 125 | 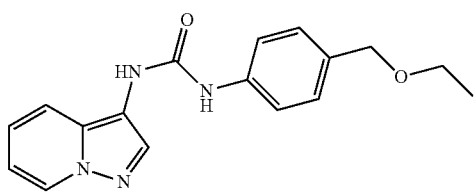 [SMILES: CCOCc1ccc(NC(=O)Nc2cnn3ccccc23)cc1] |
| 126 | 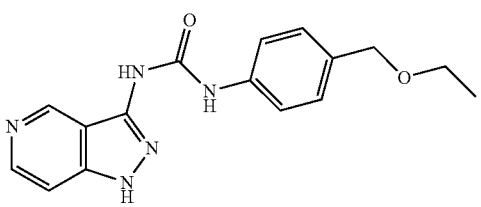 [SMILES: CCOCc1ccc(NC(=O)Nc2n[nH]c3ccncc23)cc1] |
| 127 | 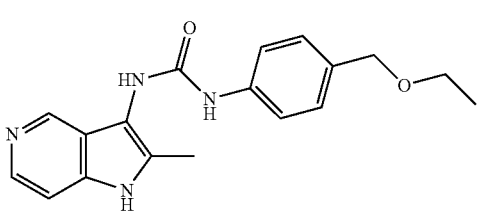 [SMILES: CCOCc1ccc(NC(=O)Nc2c(C)[nH]c3ccncc23)cc1] |
| 129 | 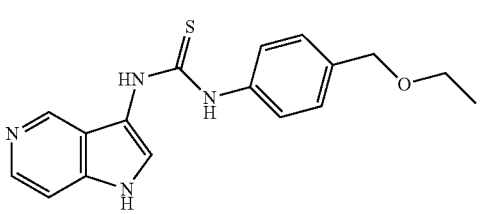 |
| 130 | 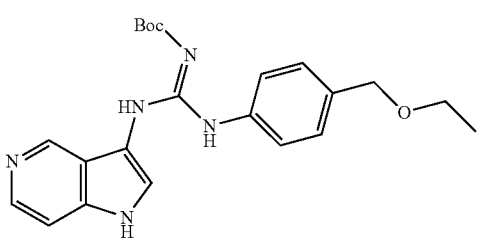 [SMILES: CCOCc1ccc(N/C(=N/C(=O)OC(C)(C)C)Nc2c[nH]c3ccncc23)cc1] |
| 131 | 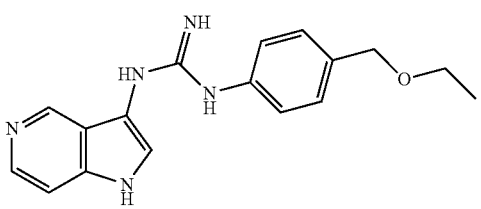 [SMILES: CCOCc1ccc(NC(=N)Nc2c[nH]c3ccncc23)cc1] |
| 132 | 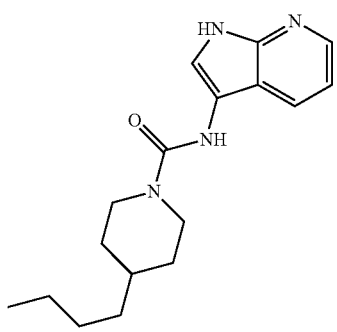 [SMILES: CCCCC1CCN(C(=O)Nc2c[nH]c3ncccc23)CC1] |

-continued
| Compound # | Structure |
|---|---|
| 133 | 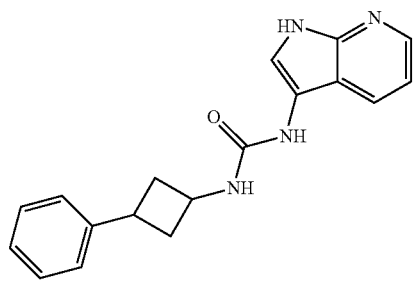 [SMILES: O=C(Nc1c[nH]c2ncccc12)NC1CC(c2ccccc2)C1] |
| 134 | 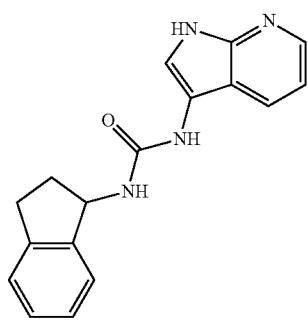 [SMILES: O=C(Nc1c[nH]c2ncccc12)NC1CCc2ccccc21] |
| 135 | 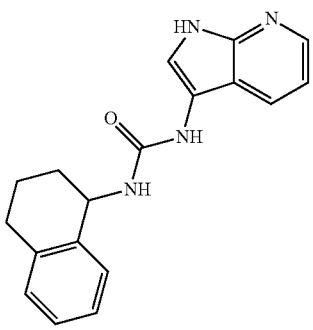 [SMILES: O=C(Nc1c[nH]c2ncccc12)NC1CCCc2ccccc21] |
| 136 | 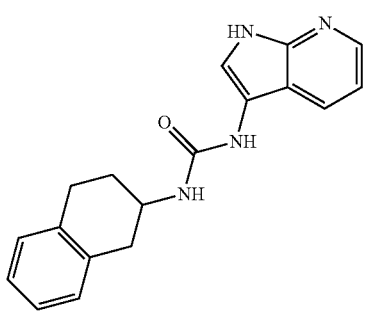 [SMILES: O=C(Nc1c[nH]c2ncccc12)NC1CCc2ccccc2C1] |
| 137 | 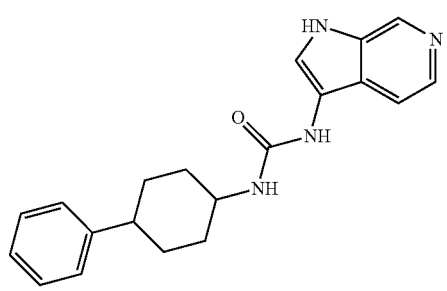 [SMILES: O=C(Nc1c[nH]c2cnccc12)NC1CCC(c2ccccc2)CC1] |

-continued

| Compound # | Structure |
|---|---|
| 138 | 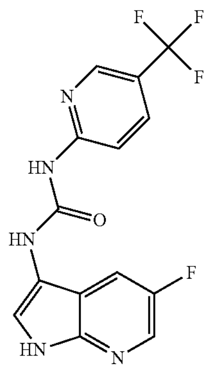 [SMILES: O=C(Nc1ccc(C(F)(F)F)cn1)Nc1c[nH]c2ncc(F)cc12] |
| 139 | 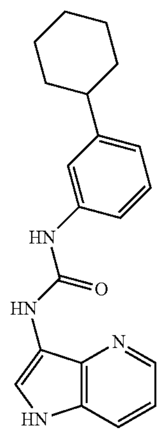 [SMILES: O=C(Nc1cccc(C2CCCCC2)c1)Nc1c[nH]c2cccnc12] |
| 140 | 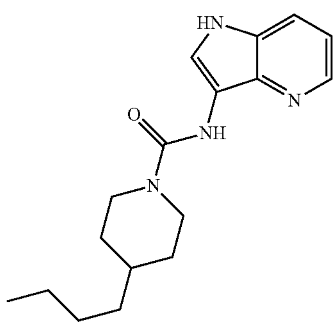 [SMILES: CCCCC1CCN(C(=O)Nc2c[nH]c3cccnc23)CC1] |
| 141 | 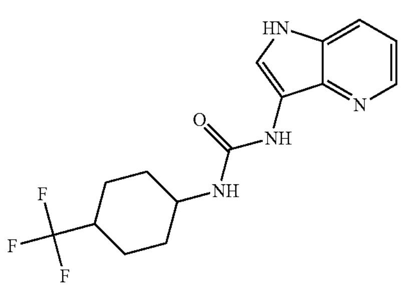 [SMILES: O=C(Nc1c[nH]c2cccnc12)NC1CCC(C(F)(F)F)CC1] |

-continued
| Compound # | Structure |
|---|---|
| 142 | 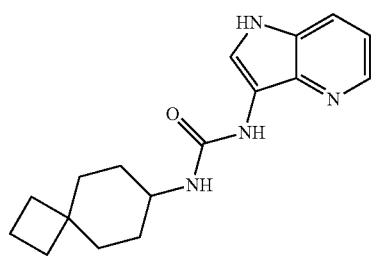 [SMILES: O=C(Nc1c[nH]c2cccnc12)NC1CCC2(CCC2)CC1] |
| 143 | 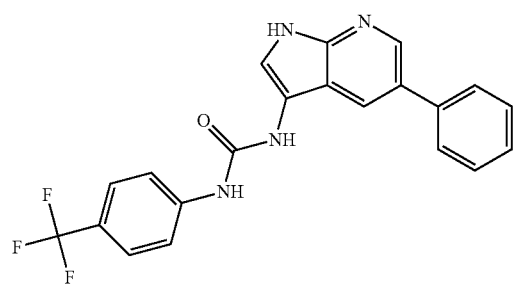 [SMILES: O=C(Nc1ccc(C(F)(F)F)cc1)Nc1c[nH]c2ncc(-c3ccccc3)cc12] |
| 144 | 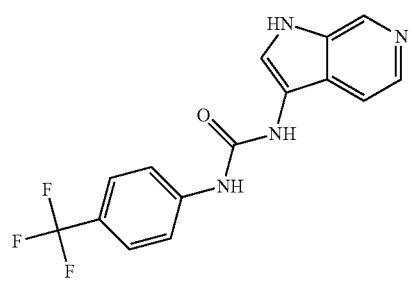 [SMILES: O=C(Nc1ccc(C(F)(F)F)cc1)Nc1c[nH]c2cnccc12] |
| 145 | 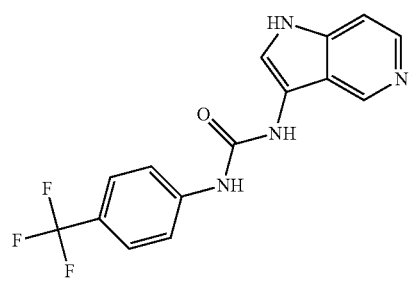 |
| 146 | 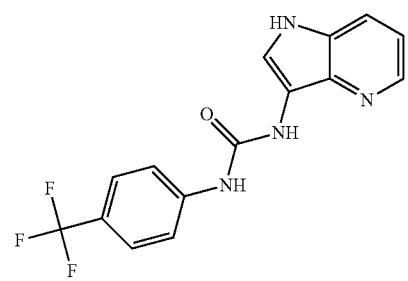 [SMILES: O=C(Nc1ccc(C(F)(F)F)cc1)Nc1c[nH]c2cccnc12] |

-continued
| Compound # | Structure |
|---|---|
| 147 | 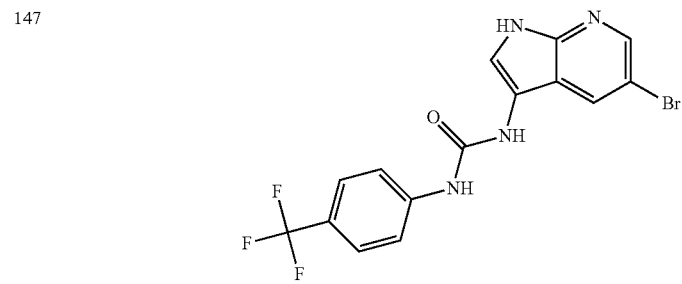 |
| 148 | 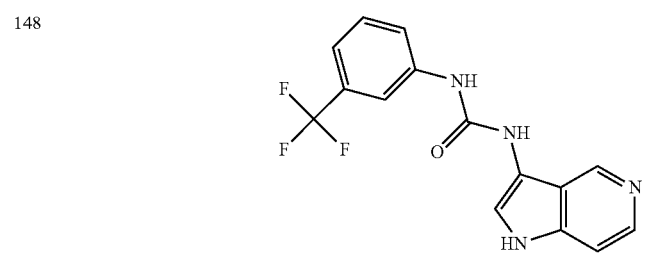 |
| 149 | 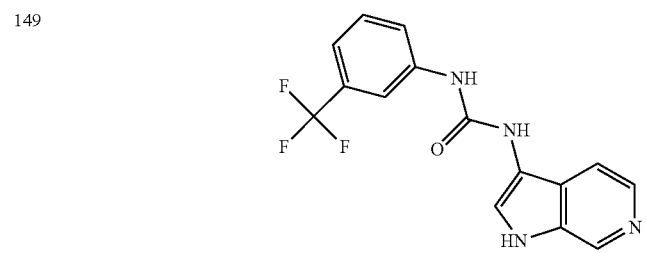 |
| 150 | 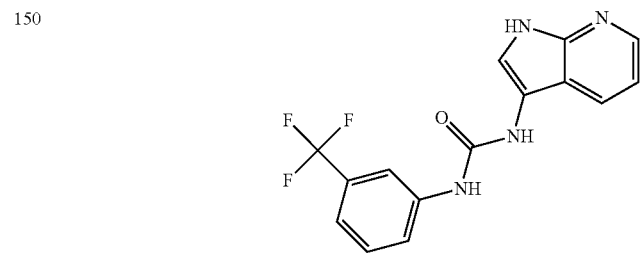 |
| 151 | 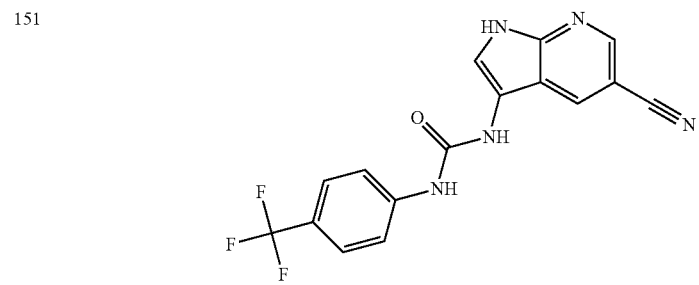 |

-continued

| Compound # | Structure |
|---|---|
| 152 | 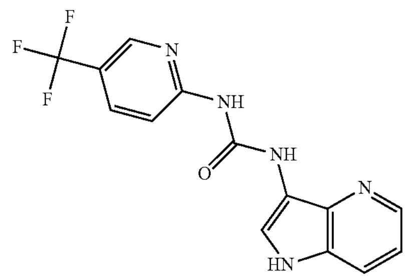 [SMILES: O=C(Nc1ccc(C(F)(F)F)cn1)Nc1c[nH]c2cccnc12] |
| 153 | 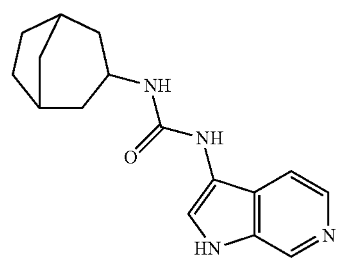 [SMILES: O=C(Nc1c[nH]c2cnccc12)NC1CC2CCC(C2)C1] |
| 154 | 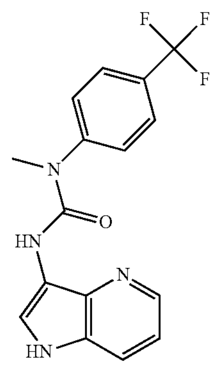 [SMILES: CN(C(=O)Nc1c[nH]c2cccnc12)c1ccc(C(F)(F)F)cc1] |
| 155 | 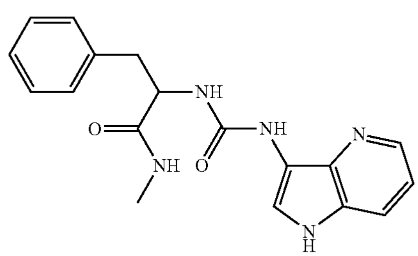 [SMILES: CNC(=O)C(Cc1ccccc1)NC(=O)Nc1c[nH]c2cccnc12] |
| 156 | 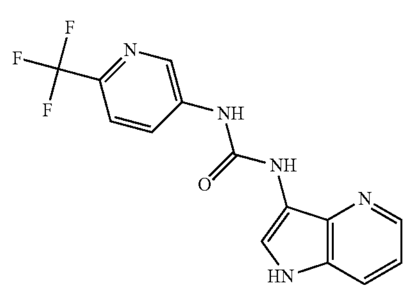 [SMILES: O=C(Nc1ccc(C(F)(F)F)nc1)Nc1c[nH]c2cccnc12] |

| Compound # | Structure |
|---|---|
| 157 | 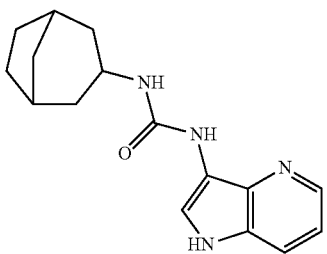 [SMILES: O=C(Nc1c[nH]c2cccnc12)NC1CC2CCC(C2)C1] |
| 158 | 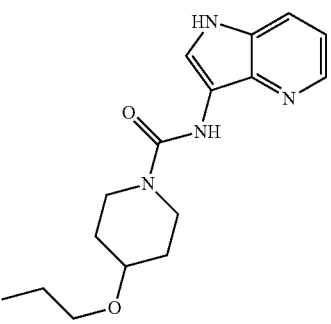 [SMILES: CCCOC1CCN(C(=O)Nc2c[nH]c3cccnc23)CC1] |
| 159 | 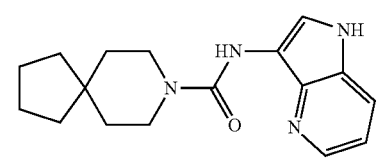 [SMILES: O=C(Nc1c[nH]c2cccnc12)N1CCC2(CCCC2)CC1] |
| 160 | 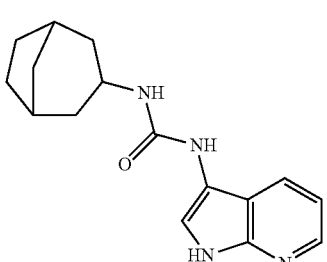 |
| 161 | 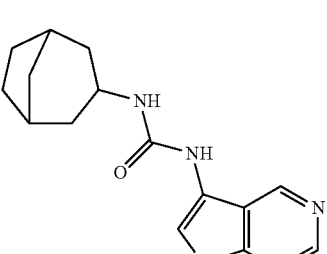 |
| 162 | 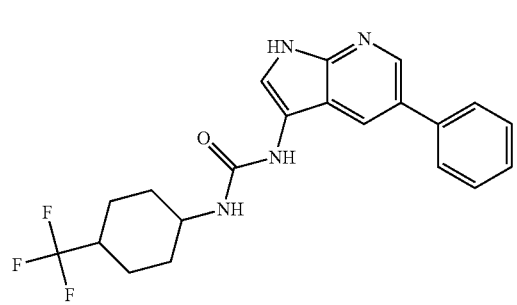 [SMILES: O=C(Nc1c[nH]c2ncc(-c3ccccc3)cc12)NC1CCC(C(F)(F)F)CC1] |

-continued
| Compound # | Structure |
|---|---|
| 163 | 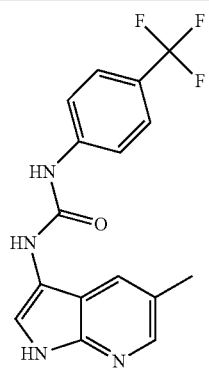 [SMILES: Cc1cnc2[nH]cc(NC(=O)Nc3ccc(C(F)(F)F)cc3)c2c1] |
| 164 | 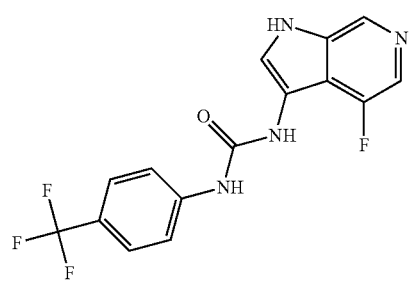 [SMILES: O=C(Nc1ccc(C(F)(F)F)cc1)Nc1c[nH]c2cncc(F)c12] |
| 165 | 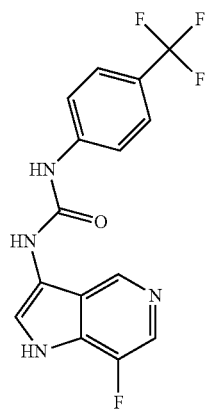 [SMILES: O=C(Nc1ccc(C(F)(F)F)cc1)Nc1c[nH]c2c(F)cncc12] |
| 166 | 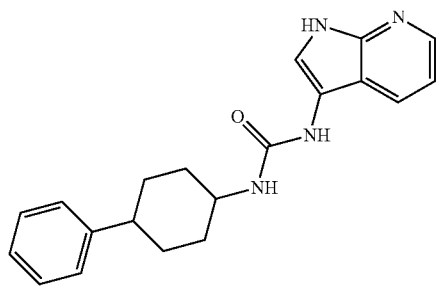 [SMILES: O=C(Nc1c[nH]c2ncccc12)NC1CCC(c2ccccc2)CC1] |
| 167 | 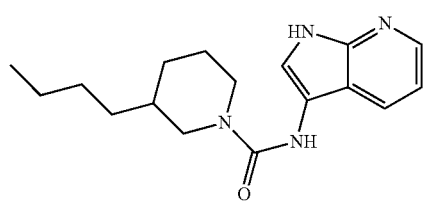 [SMILES: CCCCC1CCCN(C(=O)Nc2c[nH]c3ncccc23)C1] |

| Compound # | Structure |
|---|---|
| 168 | 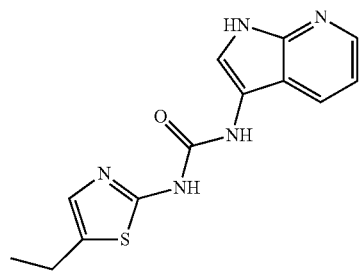 [SMILES: CCc1cnc(NC(=O)Nc2c[nH]c3ncccc23)s1] |
| 169 | 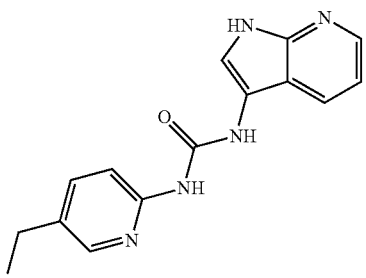 [SMILES: CCc1ccc(NC(=O)Nc2c[nH]c3ncccc23)nc1] |
| 170 | 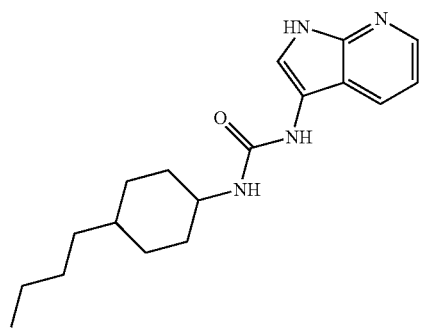 [SMILES: CCCCC1CCC(NC(=O)Nc2c[nH]c3ncccc23)CC1] |
| 171 | 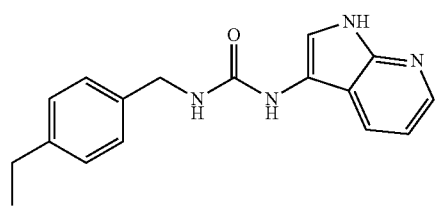 [SMILES: CCc1ccc(CNC(=O)Nc2c[nH]c3ncccc23)cc1] |
| 172 | 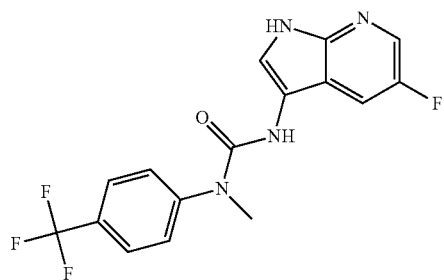 [SMILES: CN(C(=O)Nc1c[nH]c2ncc(F)cc12)c1ccc(C(F)(F)F)cc1] |

-continued
| Compound # | Structure |
|---|---|
| 173 | 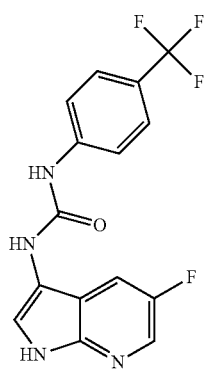 |
| 174 | 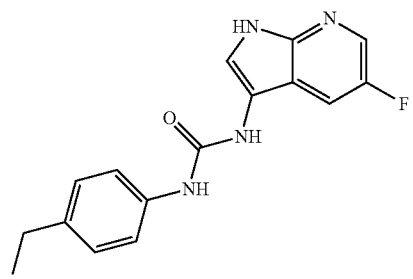 [SMILES: CCc1ccc(NC(=O)Nc2c[nH]c3ncc(F)cc23)cc1] |
| 179 | 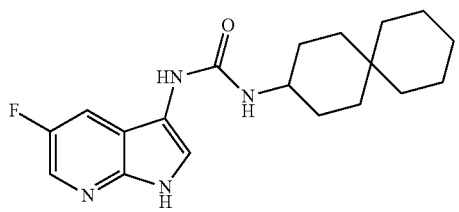 [SMILES: O=C(Nc1c[nH]c2ncc(F)cc12)NC1CCC2(CCCCC2)CC1] |
| 180 | 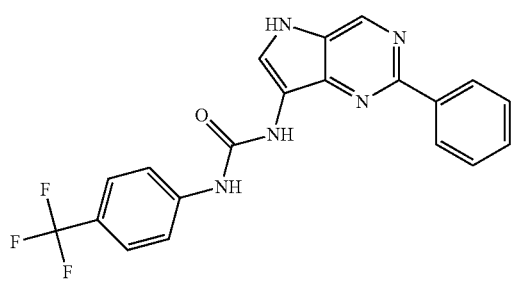 |
| 181 | 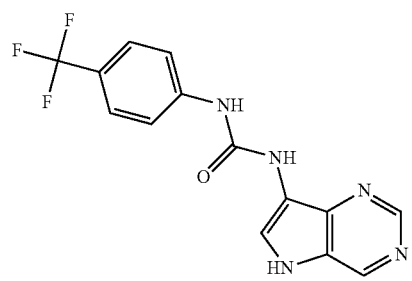 [SMILES: O=C(Nc1ccc(C(F)(F)F)cc1)Nc1c[nH]c2cncnc12] |

-continued
| Compound # | Structure |
|---|---|
| 182 | 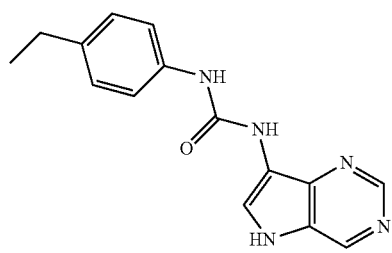 [SMILES: CCc1ccc(NC(=O)Nc2c[nH]c3cncnc23)cc1] |
| 183 | 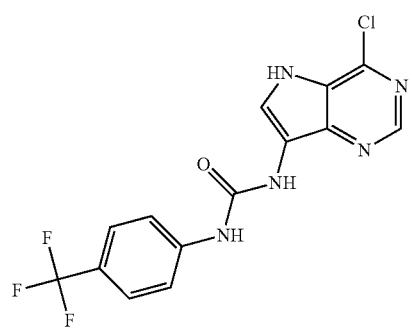 [SMILES: O=C(Nc1ccc(C(F)(F)F)cc1)Nc1c[nH]c2c(Cl)ncnc12] |
| 183b | 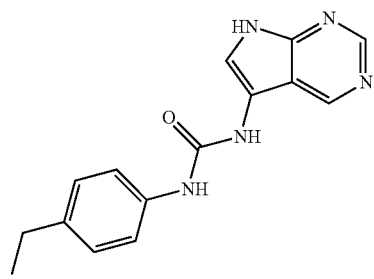 [SMILES: CCc1ccc(NC(=O)Nc2c[nH]c3ncncc23)cc1] |
| 184 | 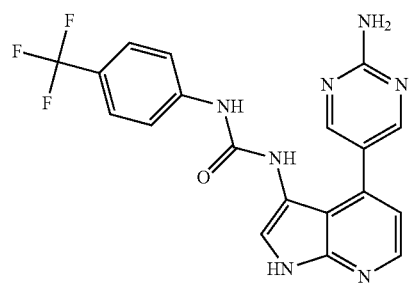 [SMILES: Nc1ncc(-c2ccnc3[nH]cc(NC(=O)Nc4ccc(C(F)(F)F)cc4)c23)cn1] |
| 185 | 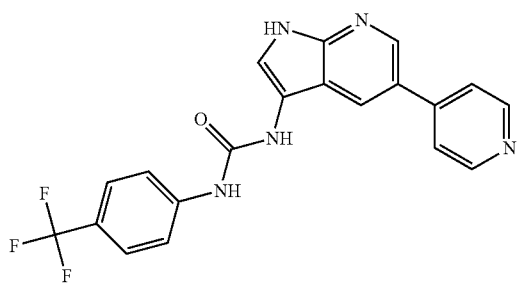 [SMILES: O=C(Nc1ccc(C(F)(F)F)cc1)Nc1c[nH]c2ncc(-c3ccncc3)cc12] |

-continued
| Compound # | Structure |
|---|---|
| 186 | 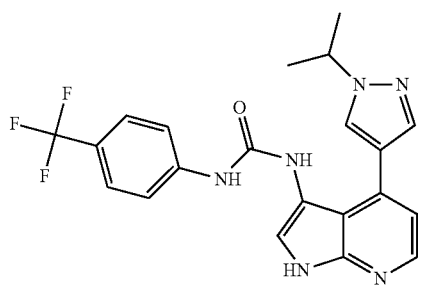 [SMILES: CC(C)n1cc(-c2ccnc3[nH]cc(NC(=O)Nc4ccc(C(F)(F)F)cc4)c23)cn1] |
| 187 | 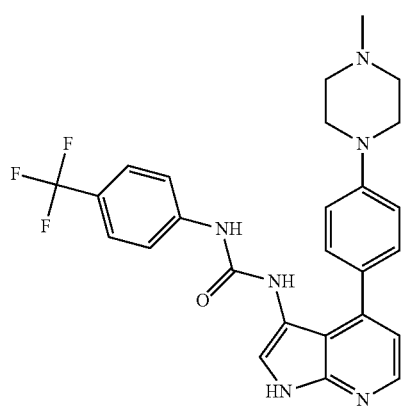 [SMILES: CN1CCN(c2ccc(-c3ccnc4[nH]cc(NC(=O)Nc5ccc(C(F)(F)F)cc5)c34)cc2)CC1] |
| 188 | 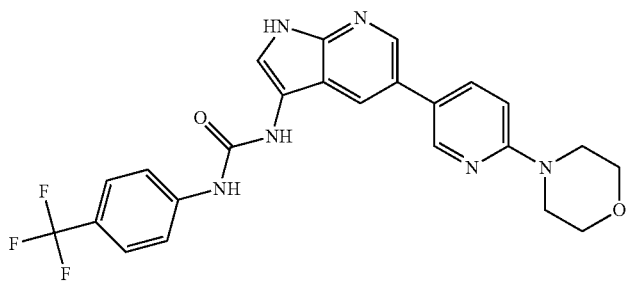 [SMILES: O=C(Nc1ccc(C(F)(F)F)cc1)Nc1c[nH]c2ncc(-c3ccc(N4CCOCC4)nc3)cc12] |
| 189 | 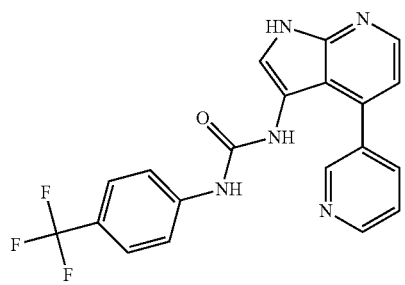 [SMILES: O=C(Nc1ccc(C(F)(F)F)cc1)Nc1c[nH]c2nccc(-c3cccnc3)c12] |
| 190 | 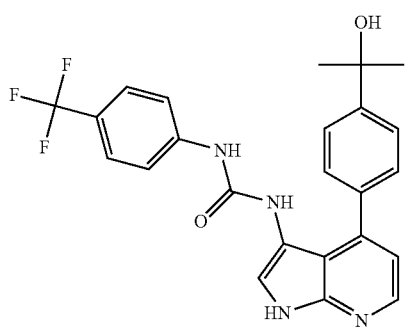 [SMILES: CC(C)(O)c1ccc(-c2ccnc3[nH]cc(NC(=O)Nc4ccc(C(F)(F)F)cc4)c23)cc1] |

-continued
| Compound # | Structure |
|---|---|
| 191 | 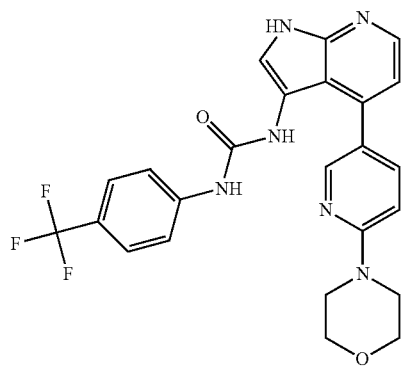 [SMILES: O=C(Nc1ccc(C(F)(F)F)cc1)Nc1c[nH]c2nccc(-c3ccc(N4CCOCC4)nc3)c12] |
| 192 | 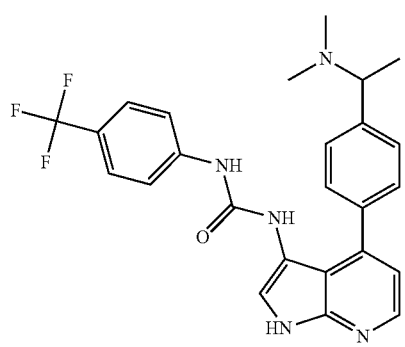 [SMILES: CC(c1ccc(-c2ccnc3[nH]cc(NC(=O)Nc4ccc(C(F)(F)F)cc4)c23)cc1)N(C)C] |
| 193 | 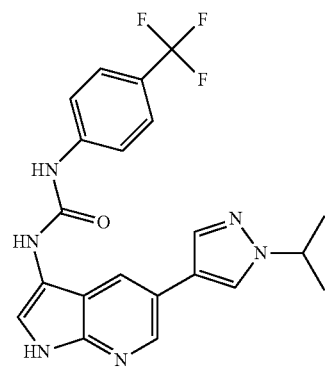 [SMILES: CC(C)n1cc(-c2cnc3[nH]cc(NC(=O)Nc4ccc(C(F)(F)F)cc4)c3c2)cn1] |
| 194 | 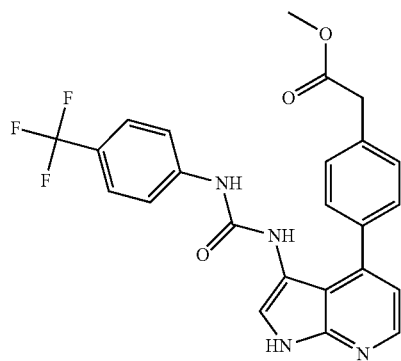 [SMILES: COC(=O)Cc1ccc(-c2ccnc3[nH]cc(NC(=O)Nc4ccc(C(F)(F)F)cc4)c23)cc1] |

-continued
| Compound # | Structure |
|---|---|
| 195 | 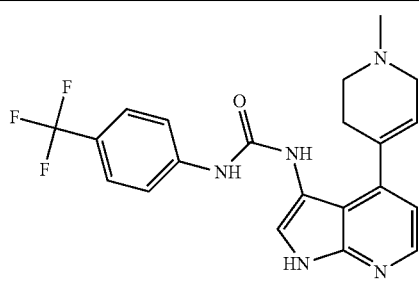 |
| 196 | 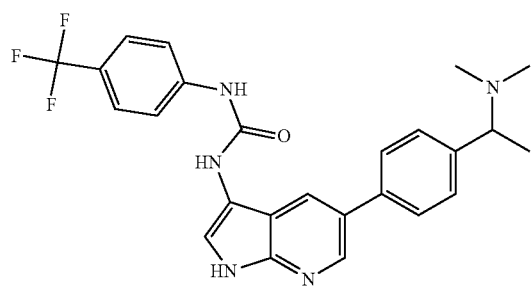 [SMILES: CC(c1ccc(-c2cnc3[nH]cc(NC(=O)Nc4ccc(C(F)(F)F)cc4)c3c2)cc1)N(C)C] |
| 197 | 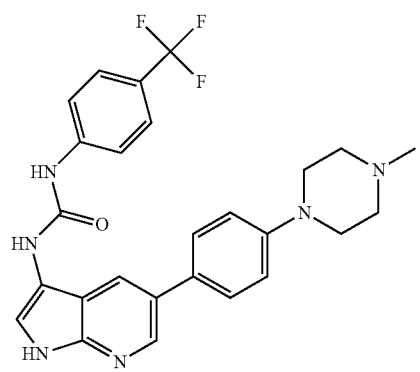 [SMILES: CN1CCN(c2ccc(-c3cnc4[nH]cc(NC(=O)Nc5ccc(C(F)(F)F)cc5)c4c3)cc2)CC1] |
| 198 | 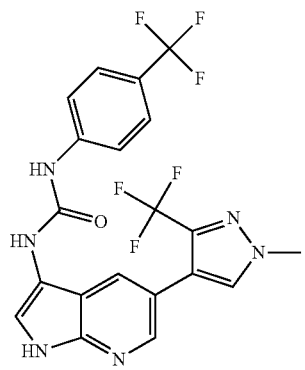 [SMILES: Cn1cc(-c2cnc3[nH]cc(NC(=O)Nc4ccc(C(F)(F)F)cc4)c3c2)c(C(F)(F)F)n1] |
| 199 | 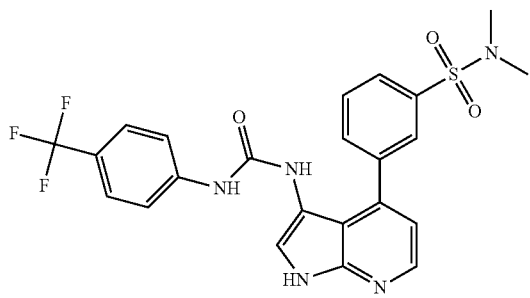 [SMILES: CN(C)S(=O)(=O)c1cccc(-c2ccnc3[nH]cc(NC(=O)Nc4ccc(C(F)(F)F)cc4)c23)c1] |

-continued

| Compound # | Structure |
| --- | --- |
| 200 | 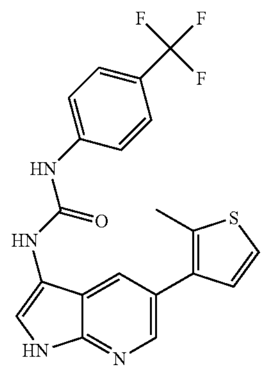 [SMILES: Cc1sccc1-c1cnc2[nH]cc(NC(=O)Nc3ccc(C(F)(F)F)cc3)c2c1] |
| 201 | 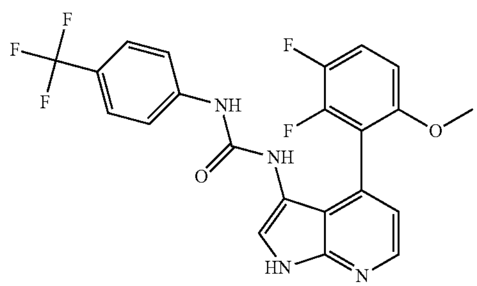 [SMILES: COc1ccc(F)c(F)c1-c1ccnc2[nH]cc(NC(=O)Nc3ccc(C(F)(F)F)cc3)c12] |
| 202 | 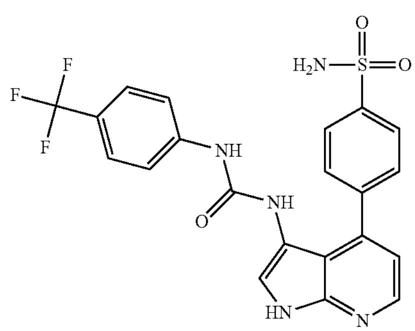 [SMILES: NS(=O)(=O)c1ccc(-c2ccnc3[nH]cc(NC(=O)Nc4ccc(C(F)(F)F)cc4)c23)cc1] |
| 203 | 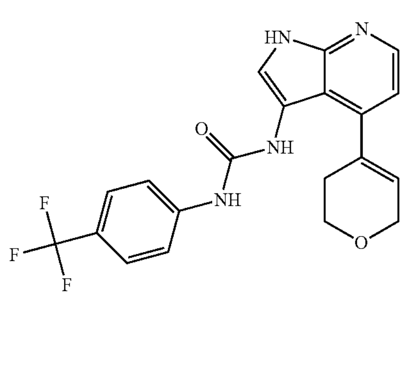 [SMILES: O=C(Nc1ccc(C(F)(F)F)cc1)Nc1c[nH]c2nccc(C3=CCOCC3)c12] |

-continued

| Compound # | Structure |
|---|---|
| 204 | 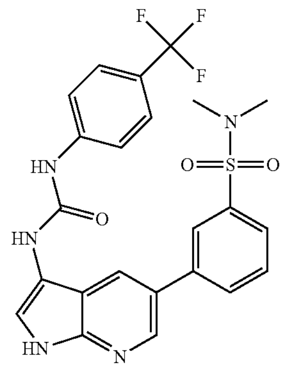 [SMILES: CN(C)S(=O)(=O)c1cccc(-c2cnc3[nH]cc(NC(=O)Nc4ccc(C(F)(F)F)cc4)c3c2)c1] |
| 205 | 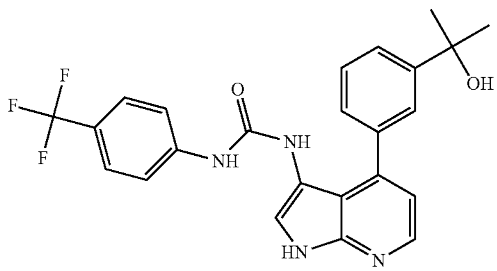 [SMILES: CC(C)(O)c1cccc(-c2ccnc3[nH]cc(NC(=O)Nc4ccc(C(F)(F)F)cc4)c23)c1] |
| 206 | 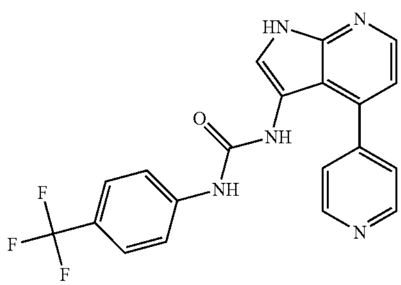 [SMILES: O=C(Nc1ccc(C(F)(F)F)cc1)Nc1c[nH]c2nccc(-c3ccncc3)c12] |
| 207 | 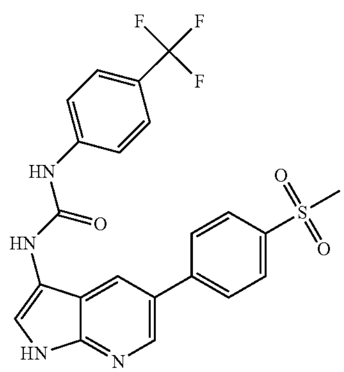 [SMILES: CS(=O)(=O)c1ccc(-c2cnc3[nH]cc(NC(=O)Nc4ccc(C(F)(F)F)cc4)c3c2)cc1] |
| 208 | 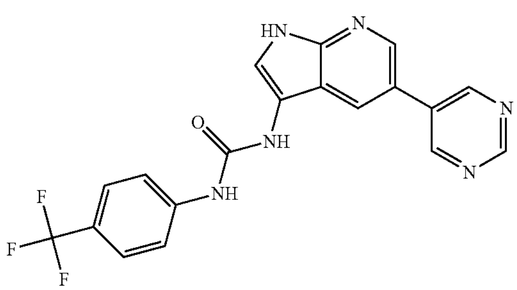 [SMILES: O=C(Nc1ccc(C(F)(F)F)cc1)Nc1c[nH]c2ncc(-c3cncnc3)cc12] |

| Compound # | Structure |
|---|---|
| 209 | 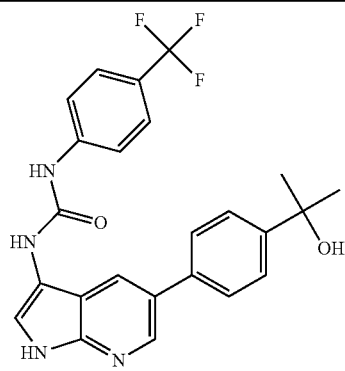 |
| 210 | 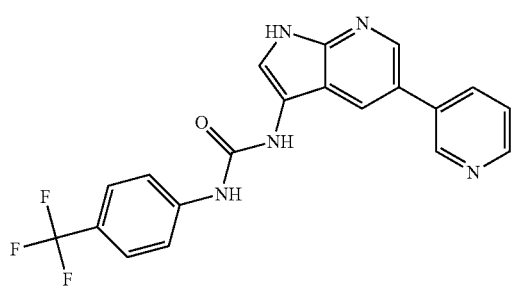 [SMILES: O=C(Nc1ccc(C(F)(F)F)cc1)Nc1c[nH]c2ncc(-c3cccnc3)cc12] |
| 211 | 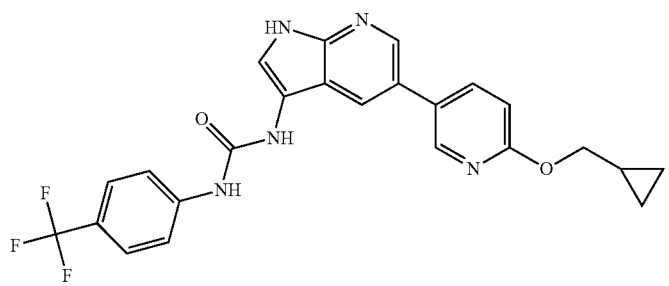 [SMILES: O=C(Nc1ccc(C(F)(F)F)cc1)Nc1c[nH]c2ncc(-c3ccc(OCC4CC4)nc3)cc12] |
| 212 | 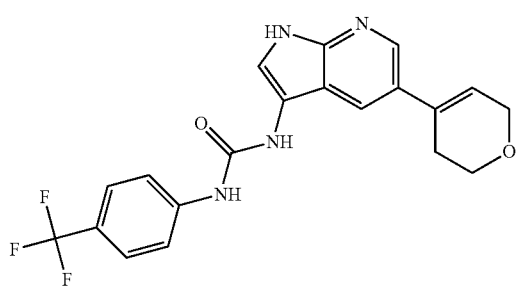 [SMILES: O=C(Nc1ccc(C(F)(F)F)cc1)Nc1c[nH]c2ncc(C3=CCOCC3)cc12] |
| 213 | 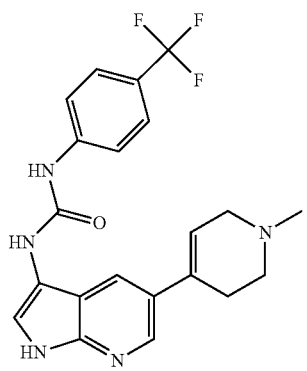 [SMILES: CN1CC=C(c2cnc3[nH]cc(NC(=O)Nc4ccc(C(F)(F)F)cc4)c3c2)CC1] |

-continued
| Compound # | Structure |
|---|---|
| 214 | 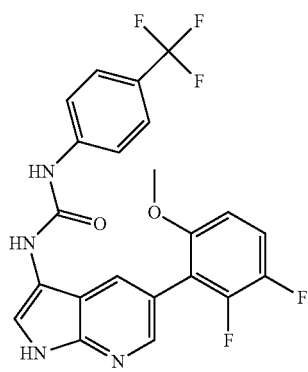 [SMILES: COc1ccc(F)c(F)c1-c1cnc2[nH]cc(NC(=O)Nc3ccc(C(F)(F)F)cc3)c2c1] |
| 215 | 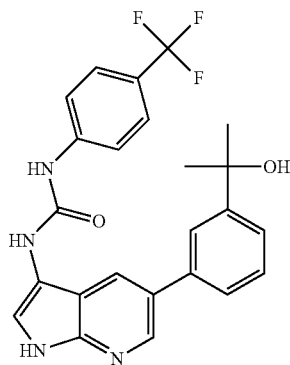 [SMILES: CC(C)(O)c1cccc(-c2cnc3[nH]cc(NC(=O)Nc4ccc(C(F)(F)F)cc4)c3c2)c1] |
| 216 | 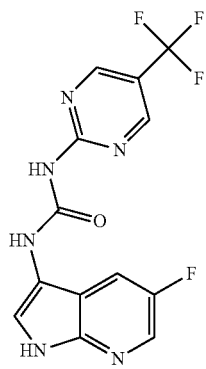 [SMILES: O=C(Nc1ncc(C(F)(F)F)cn1)Nc1c[nH]c2ncc(F)cc12] |
| 217 | 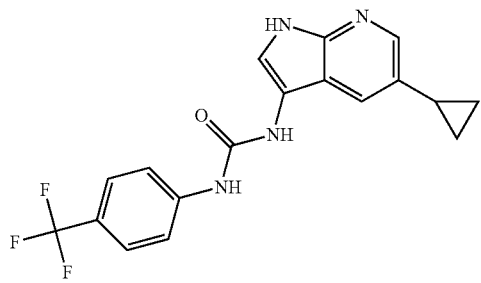 [SMILES: O=C(Nc1ccc(C(F)(F)F)cc1)Nc1c[nH]c2ncc(C3CC3)cc12] |

| Compound # | Structure |
|---|---|
| 218 | 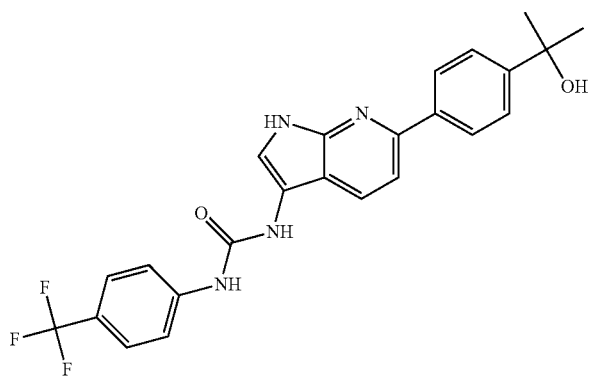 [SMILES: CC(C)(O)c1ccc(-c2ccc3c(NC(=O)Nc4ccc(C(F)(F)F)cc4)c[nH]c3n2)cc1] |
| 219 | 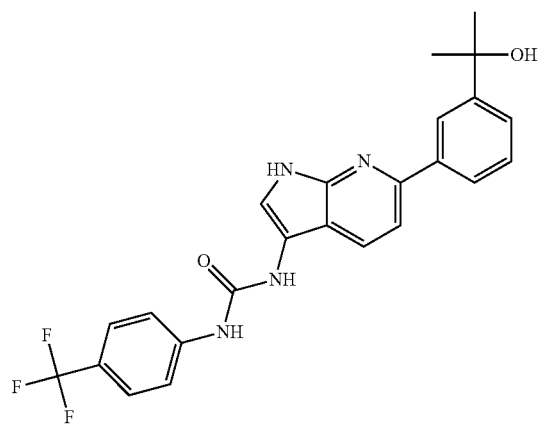 [SMILES: CC(C)(O)c1cccc(-c2ccc3c(NC(=O)Nc4ccc(C(F)(F)F)cc4)c[nH]c3n2)c1] |
| 220 | 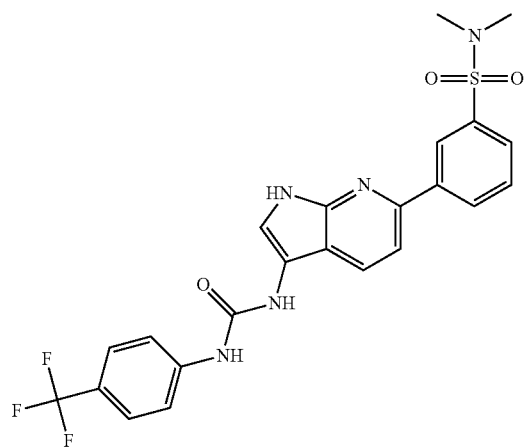 [SMILES: CN(C)S(=O)(=O)c1cccc(-c2ccc3c(NC(=O)Nc4ccc(C(F)(F)F)cc4)c[nH]c3n2)c1] |

| Compound # | Structure |
|---|---|
| 221 | 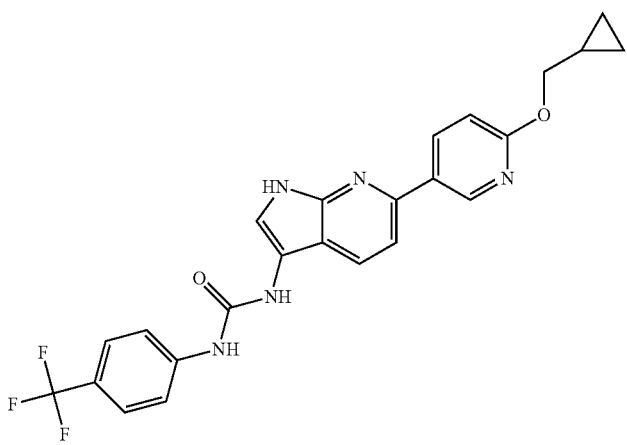 [SMILES: O=C(Nc1ccc(C(F)(F)F)cc1)Nc1c[nH]c2nc(-c3ccc(OCC4CC4)nc3)ccc12] |
| 222 | 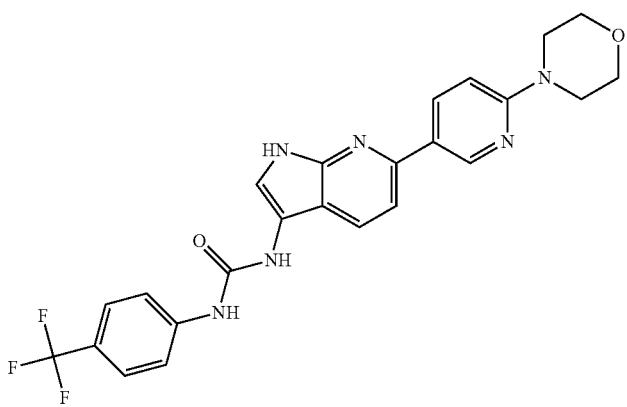 [SMILES: O=C(Nc1ccc(C(F)(F)F)cc1)Nc1c[nH]c2nc(-c3ccc(N4CCOCC4)nc3)ccc12] |
| 223 | 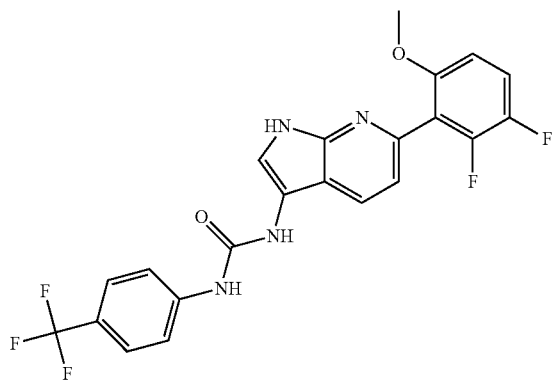 [SMILES: COc1ccc(F)c(F)c1-c1ccc2c(NC(=O)Nc3ccc(C(F)(F)F)cc3)c[nH]c2n1] |
| 224 | 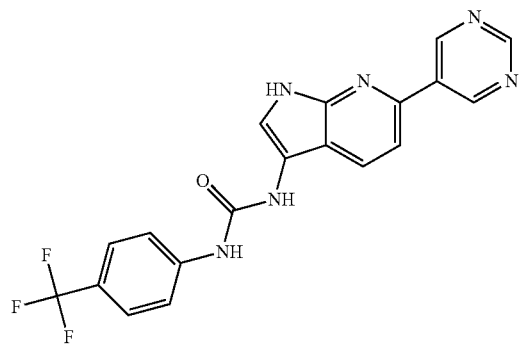 [SMILES: O=C(Nc1ccc(C(F)(F)F)cc1)Nc1c[nH]c2nc(-c3cncnc3)ccc12] |

| Compound # | Structure |
|---|---|
| 225 | 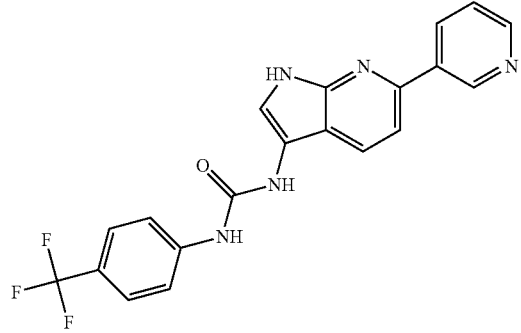 [SMILES: O=C(Nc1ccc(C(F)(F)F)cc1)Nc1c[nH]c2nc(-c3cccnc3)ccc12] |
| 226 | 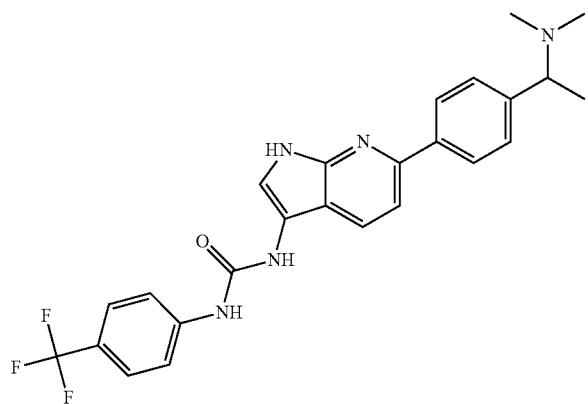 [SMILES: CC(c1ccc(-c2ccc3c(NC(=O)Nc4ccc(C(F)(F)F)cc4)c[nH]c3n2)cc1)N(C)C] |
| 227 | 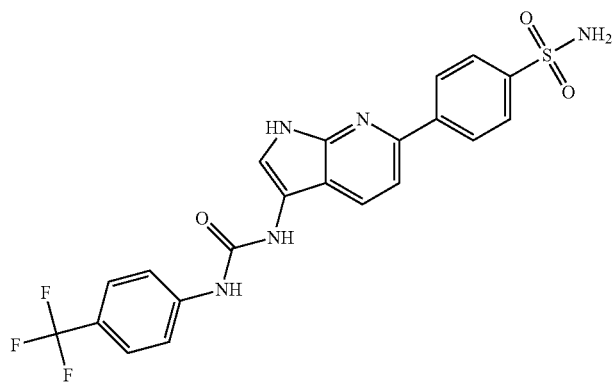 [SMILES: NS(=O)(=O)c1ccc(-c2ccc3c(NC(=O)Nc4ccc(C(F)(F)F)cc4)c[nH]c3n2)cc1] |
| 228 | 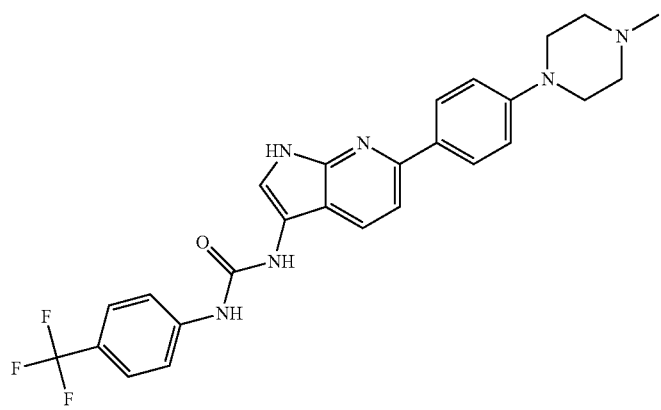 [SMILES: CN1CCN(c2ccc(-c3ccc4c(NC(=O)Nc5ccc(C(F)(F)F)cc5)c[nH]c4n3)cc2)CC1] |

-continued
| Compound # | Structure |
|---|---|
| 229 | 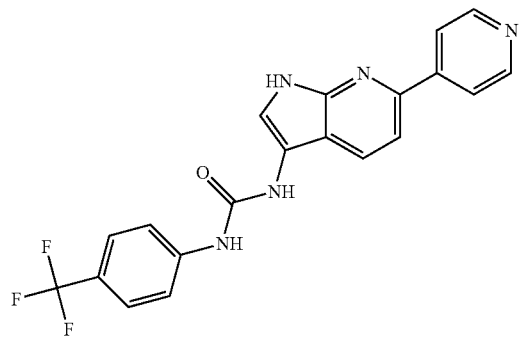 [SMILES: O=C(Nc1ccc(C(F)(F)F)cc1)Nc1c[nH]c2nc(-c3ccncc3)ccc12] |
| 230 | 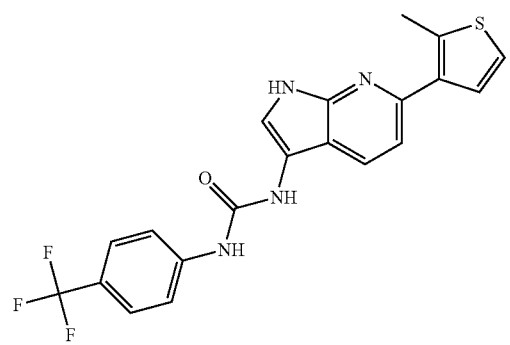 [SMILES: Cc1sccc1-c1ccc2c(NC(=O)Nc3ccc(C(F)(F)F)cc3)c[nH]c2n1] |
| 231 | 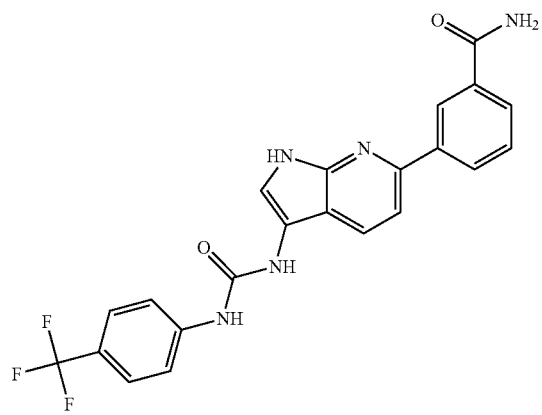 [SMILES: NC(=O)c1cccc(-c2ccc3c(NC(=O)Nc4ccc(C(F)(F)F)cc4)c[nH]c3n2)c1] |
| 232 | 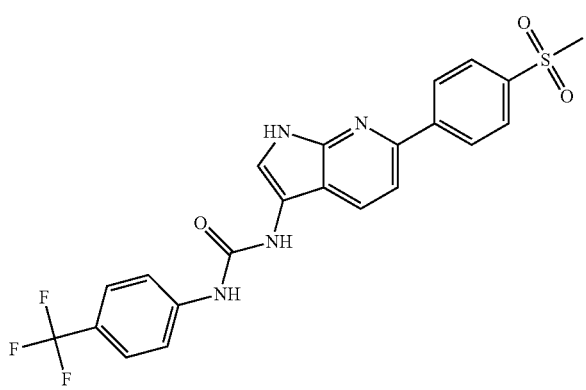 [SMILES: CS(=O)(=O)c1ccc(-c2ccc3c(NC(=O)Nc4ccc(C(F)(F)F)cc4)c[nH]c3n2)cc1] |

-continued
| Compound # | Structure |
|---|---|
| 233 | 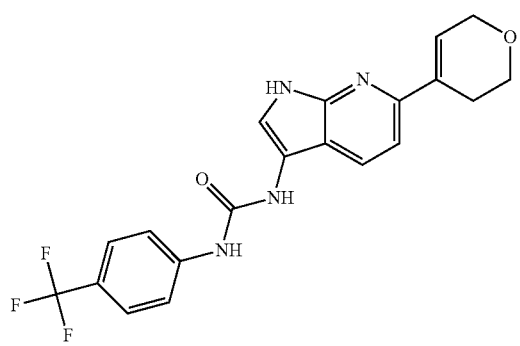 [SMILES: O=C(Nc1ccc(C(F)(F)F)cc1)Nc1c[nH]c2nc(C3=CCOCC3)ccc12] |
| 234 | 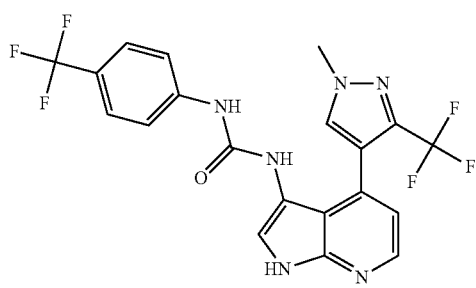 [SMILES: Cn1cc(-c2ccnc3[nH]cc(NC(=O)Nc4ccc(C(F)(F)F)cc4)c23)c(C(F)(F)F)n1] |
| 235 | 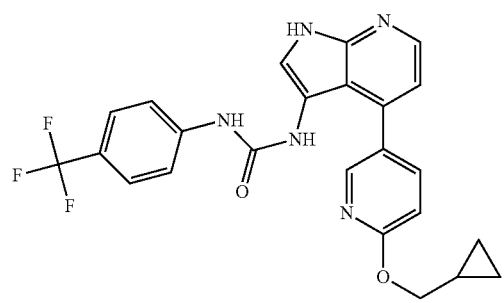 [SMILES: O=C(Nc1ccc(C(F)(F)F)cc1)Nc1c[nH]c2nccc(-c3ccc(OCC4CC4)nc3)c12] |
| 236 | 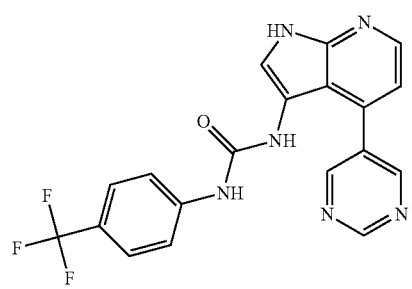 [SMILES: O=C(Nc1ccc(C(F)(F)F)cc1)Nc1c[nH]c2nccc(-c3cncnc3)c12] |
| 237 | 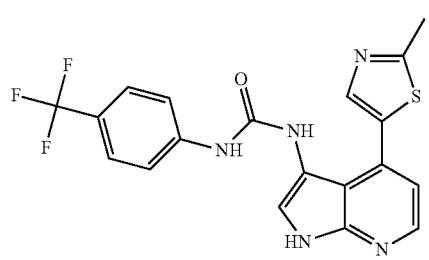 [SMILES: Cc1ncc(-c2ccnc3[nH]cc(NC(=O)Nc4ccc(C(F)(F)F)cc4)c23)s1] |

| Compound # | Structure |
|---|---|
| 238 | 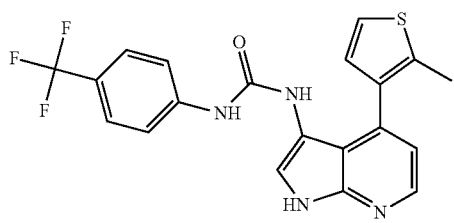 [SMILES: Cc1sccc1-c1ccnc2[nH]cc(NC(=O)Nc3ccc(C(F)(F)F)cc3)c12] |
| 239 | 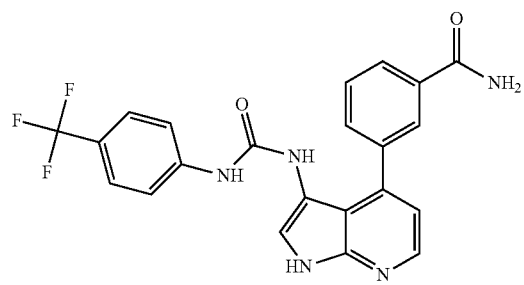 [SMILES: NC(=O)c1cccc(-c2ccnc3[nH]cc(NC(=O)Nc4ccc(C(F)(F)F)cc4)c23)c1] |
| 240 | 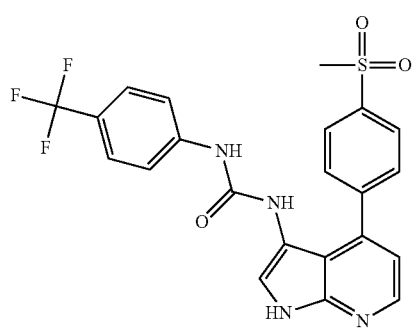 [SMILES: CS(=O)(=O)c1ccc(-c2ccnc3[nH]cc(NC(=O)Nc4ccc(C(F)(F)F)cc4)c23)cc1] |
| 241 | 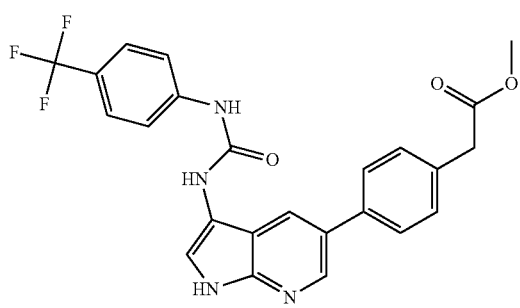 [SMILES: COC(=O)Cc1ccc(-c2cnc3[nH]cc(NC(=O)Nc4ccc(C(F)(F)F)cc4)c3c2)cc1] |
| 242 | 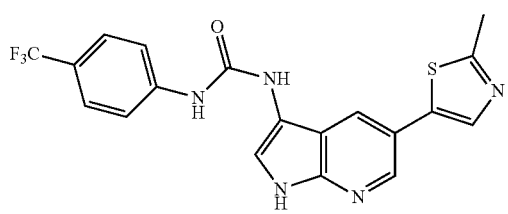 [SMILES: Cc1ncc(-c2cnc3[nH]cc(NC(=O)Nc4ccc(C(F)(F)F)cc4)c3c2)s1] |

-continued
| Compound # | Structure |
|---|---|
| 243 | 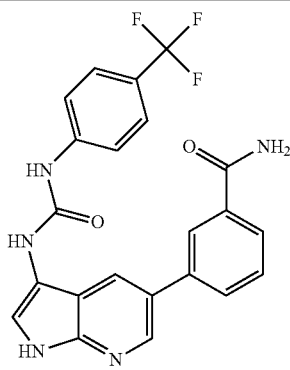 [SMILES: NC(=O)c1cccc(-c2cnc3[nH]cc(NC(=O)Nc4ccc(C(F)(F)F)cc4)c3c2)c1] |
| 244 | 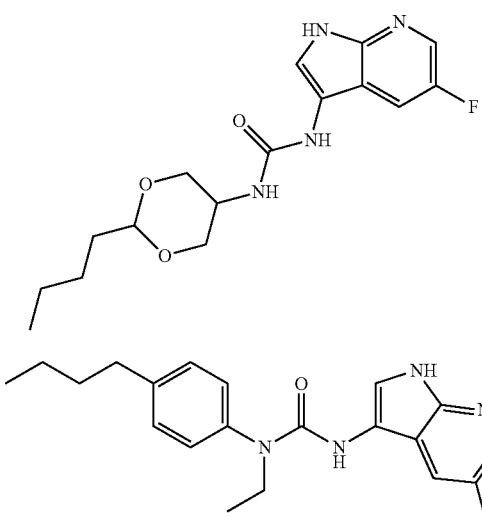 |
| 245 | 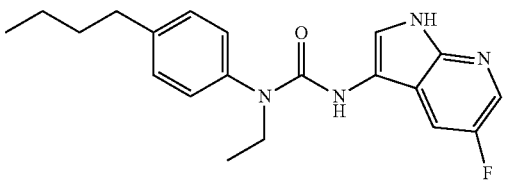 [SMILES: CCCCc1ccc(N(CC)C(=O)Nc2c[nH]c3ncc(F)cc23)cc1] |
| 246 | 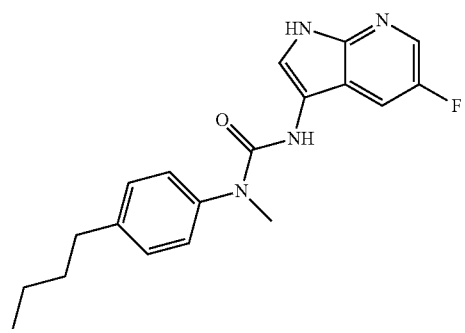 [SMILES: CCCCc1ccc(N(C)C(=O)Nc2c[nH]c3ncc(F)cc23)cc1] |
| 247 | 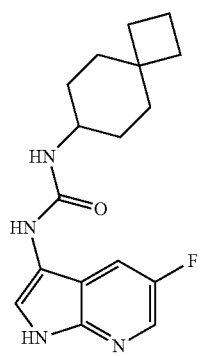 [SMILES: O=C(Nc1c[nH]c2ncc(F)cc12)NC1CCC2(CCC2)CC1] |

| Compound # | Structure |
|---|---|
| 248 | 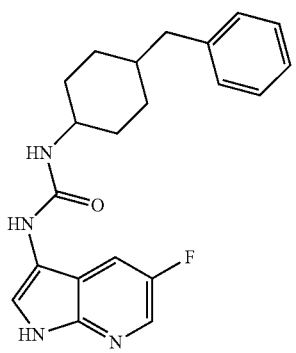 [SMILES: O=C(Nc1c[nH]c2ncc(F)cc12)NC1CCC(Cc2ccccc2)CC1] |
| 249 | 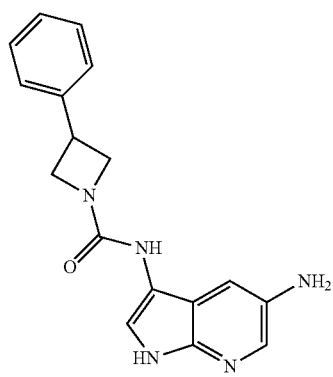 [SMILES: Nc1cnc2[nH]cc(NC(=O)N3CC(c4ccccc4)C3)c2c1] |
| 250 | 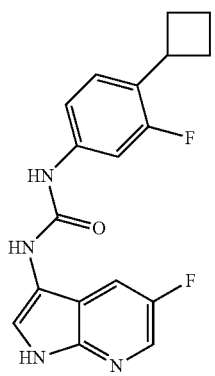 [SMILES: O=C(Nc1ccc(C2CCC2)c(F)c1)Nc1c[nH]c2ncc(F)cc12] |
| 251 | 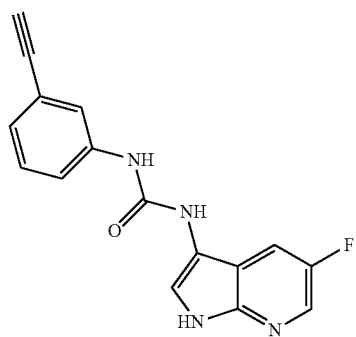 [SMILES: C#Cc1cccc(NC(=O)Nc2c[nH]c3ncc(F)cc23)c1] |

| Compound # | Structure |
|---|---|
| 252 | 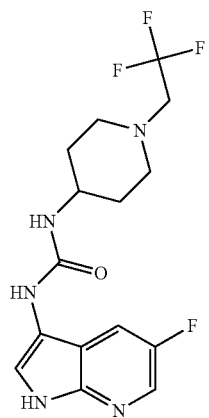 [SMILES: O=C(Nc1c[nH]c2ncc(F)cc12)NC1CCN(CC(F)(F)F)CC1] |
| 253 | 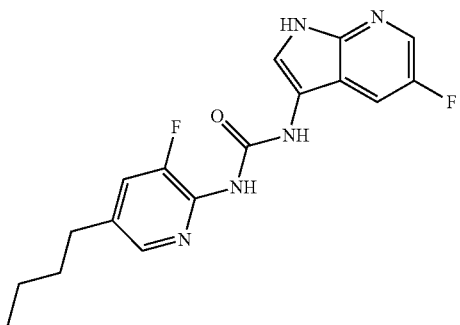 [SMILES: CCCCc1cnc(NC(=O)Nc2c[nH]c3ncc(F)cc23)c(F)c1] |
| 254 | 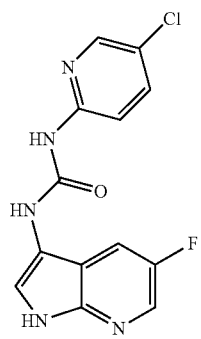 [SMILES: O=C(Nc1ccc(Cl)cn1)Nc1c[nH]c2ncc(F)cc12] |
| 255 | 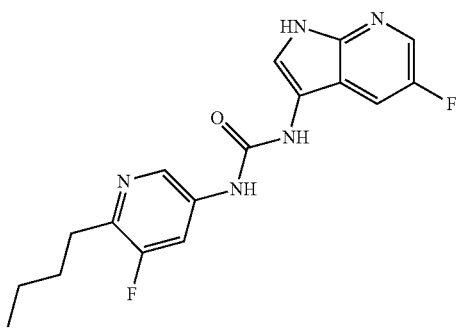 [SMILES: CCCCc1ncc(NC(=O)Nc2c[nH]c3ncc(F)cc23)cc1F] |

US 11,618,749 B2
131                                                                      132
-continued
| Compound # | Structure |
|---|---|
| 256 | 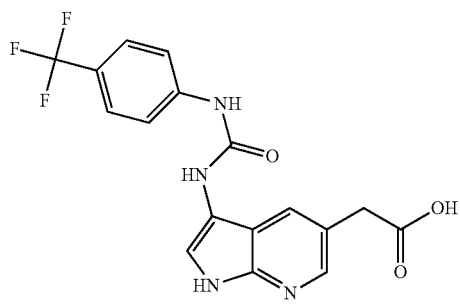 [SMILES: O=C(O)Cc1cnc2[nH]cc(NC(=O)Nc3ccc(C(F)(F)F)cc3)c2c1] |
| 257 | 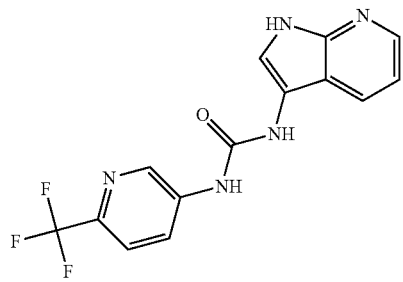 [SMILES: O=C(Nc1ccc(C(F)(F)F)nc1)Nc1c[nH]c2ncccc12] |
| 258 | 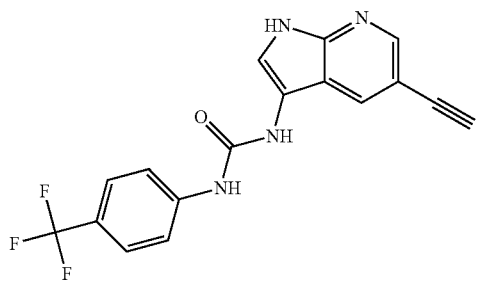 [SMILES: C#Cc1cnc2[nH]cc(NC(=O)Nc3ccc(C(F)(F)F)cc3)c2c1] |
| 259 | 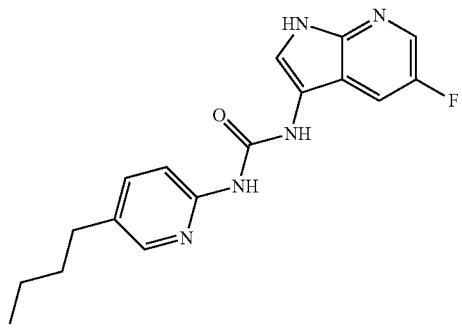 [SMILES: CCCCc1ccc(NC(=O)Nc2c[nH]c3ncc(F)cc23)nc1] |
| 260 | 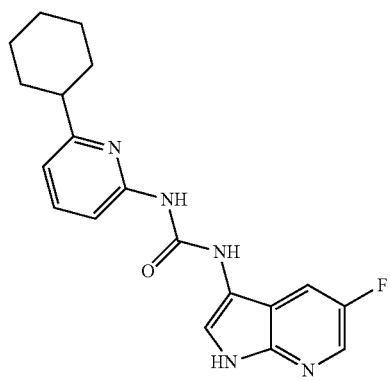 [SMILES: O=C(Nc1cccc(C2CCCCC2)n1)Nc1c[nH]c2ncc(F)cc12] |

| Compound # | Structure |
|---|---|
| 261 | 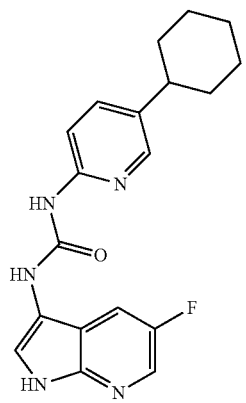 [SMILES: O=C(Nc1ccc(C2CCCCC2)cn1)Nc1c[nH]c2ncc(F)cc12] |
| 262 | 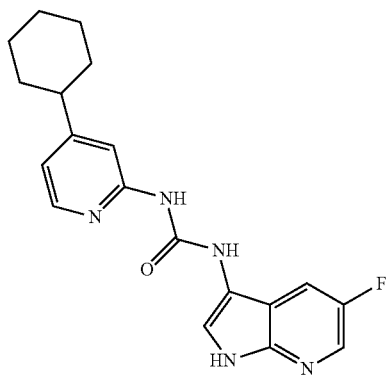 [SMILES: O=C(Nc1cc(C2CCCCC2)ccn1)Nc1c[nH]c2ncc(F)cc12] |
| 263 | 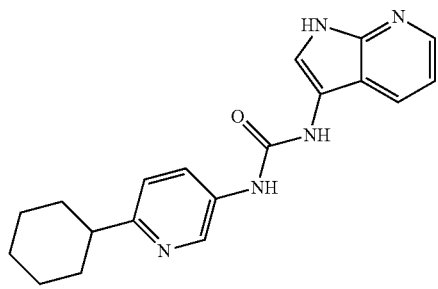 [SMILES: O=C(Nc1ccc(C2CCCCC2)nc1)Nc1c[nH]c2ncccc12] |
| 264 | 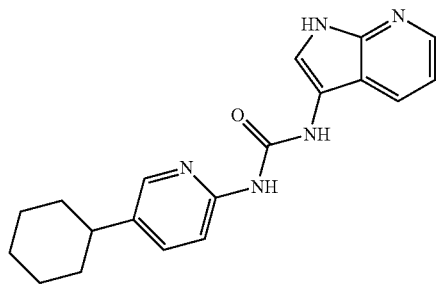 [SMILES: O=C(Nc1ccc(C2CCCCC2)cn1)Nc1c[nH]c2ncccc12] |

-continued

| Compound # | Structure |
|---|---|
| 265 | 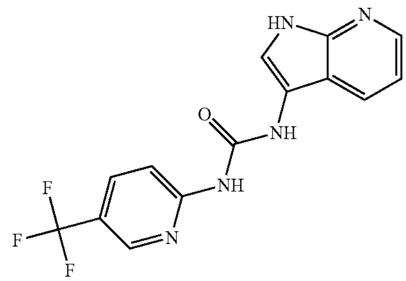 [SMILES: O=C(Nc1ccc(C(F)(F)F)cn1)Nc1c[nH]c2ncccc12] |
| 266 | 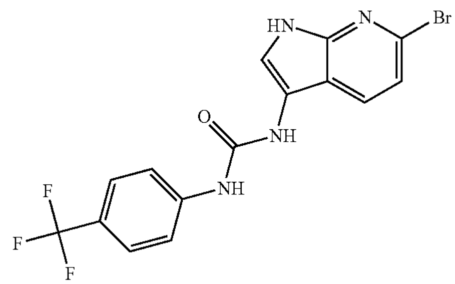 [SMILES: O=C(Nc1ccc(C(F)(F)F)cc1)Nc1c[nH]c2nc(Br)ccc12] |
| 267 | 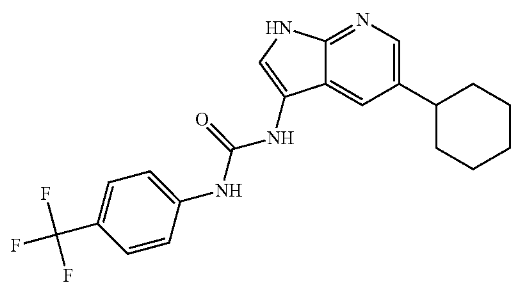 [SMILES: O=C(Nc1ccc(C(F)(F)F)cc1)Nc1c[nH]c2ncc(C3CCCCC3)cc12] |
| 268 | 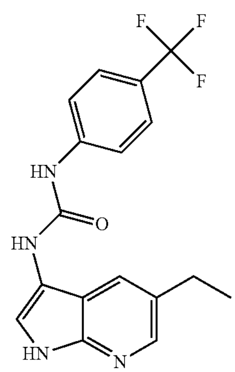 [SMILES: CCc1cnc2[nH]cc(NC(=O)Nc3ccc(C(F)(F)F)cc3)c2c1] |
| 269 | 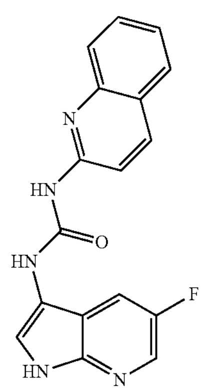 [SMILES: O=C(Nc1ccc2ccccc2n1)Nc1c[nH]c2ncc(F)cc12] |

| Compound # | Structure |
|---|---|
| 270 | 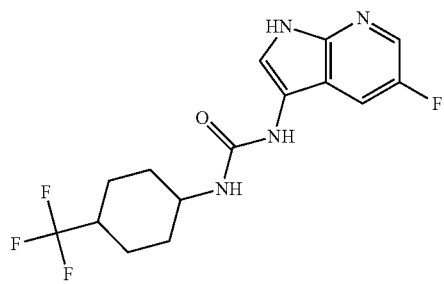 [SMILES: O=C(Nc1c[nH]c2ncc(F)cc12)NC1CCC(C(F)(F)F)CC1] |
| 271 | 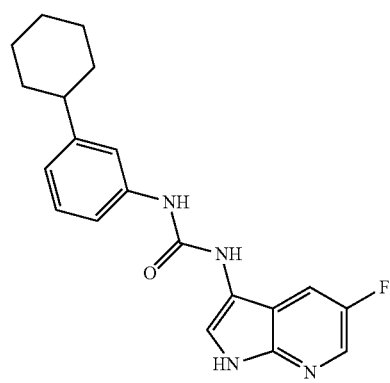 |
| 272 | 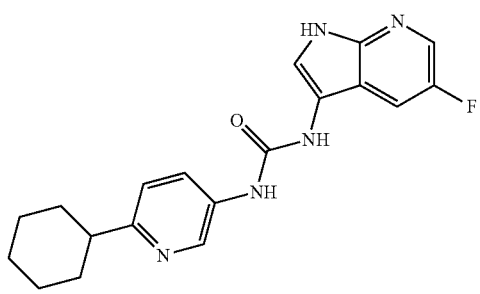 [SMILES: O=C(Nc1ccc(C2CCCCC2)nc1)Nc1c[nH]c2ncc(F)cc12] |
| 273 | 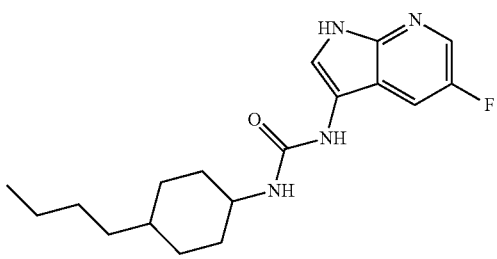 [SMILES: CCCCC1CCC(NC(=O)Nc2c[nH]c3ncc(F)cc23)CC1] |
| 274 | 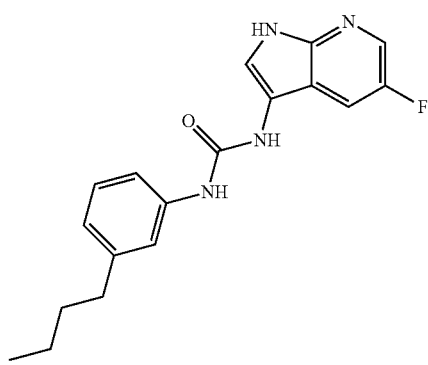 [SMILES: CCCCc1cccc(NC(=O)Nc2c[nH]c3ncc(F)cc23)c1] |

| Compound # | Structure |
|---|---|
| 275 | 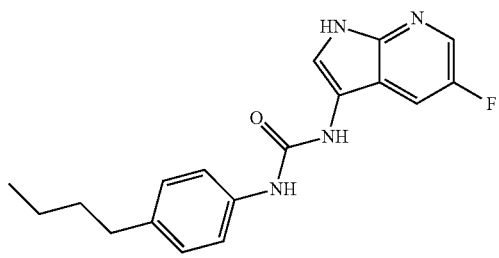 [SMILES: CCCCc1ccc(NC(=O)Nc2c[nH]c3ncc(F)cc23)cc1] |
| 276 | 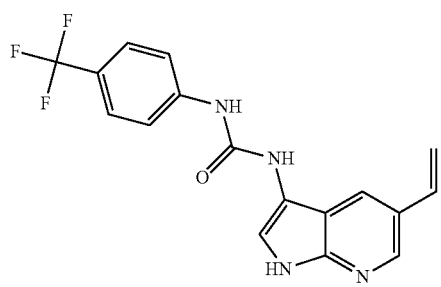 [SMILES: C=Cc1cnc2[nH]cc(NC(=O)Nc3ccc(C(F)(F)F)cc3)c2c1] |
| 277 | 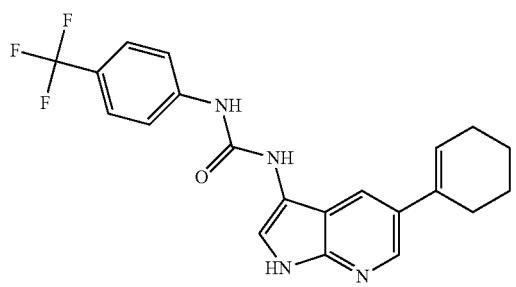 [SMILES: O=C(Nc1ccc(C(F)(F)F)cc1)Nc1c[nH]c2ncc(C3=CCCCC3)cc12] |
| 278 | 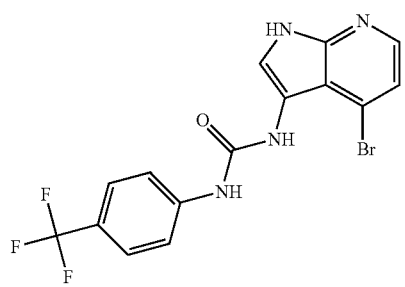 [SMILES: O=C(Nc1ccc(C(F)(F)F)cc1)Nc1c[nH]c2nccc(Br)c12] |
| 279 | 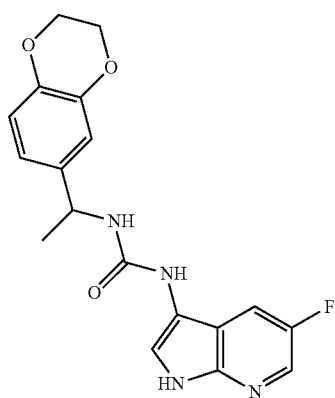 [SMILES: CC(NC(=O)Nc1c[nH]c2ncc(F)cc12)c1ccc2c(c1)OCCO2] |

| Compound # | Structure |
|---|---|
| 280 | 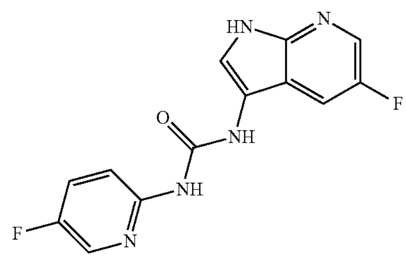 [SMILES: O=C(Nc1ccc(F)cn1)Nc1c[nH]c2ncc(F)cc12] |
| 281 | 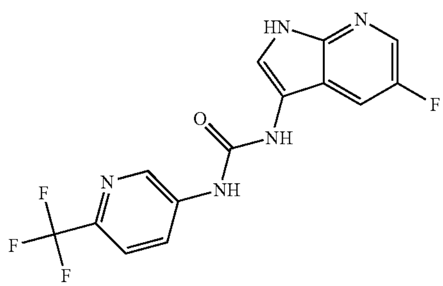 [SMILES: O=C(Nc1ccc(C(F)(F)F)nc1)Nc1c[nH]c2ncc(F)cc12] |
| 282 | 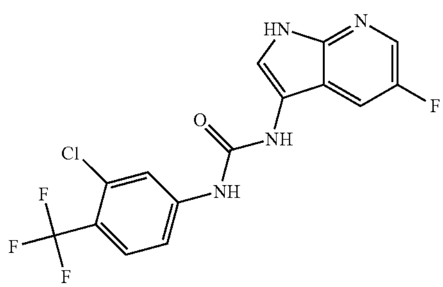 [SMILES: O=C(Nc1ccc(C(F)(F)F)c(Cl)c1)Nc1c[nH]c2ncc(F)cc12] |
| 283 | 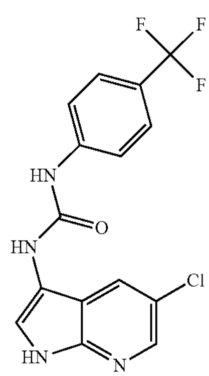 [SMILES: O=C(Nc1ccc(C(F)(F)F)cc1)Nc1c[nH]c2ncc(Cl)cc12] |
| 284 | 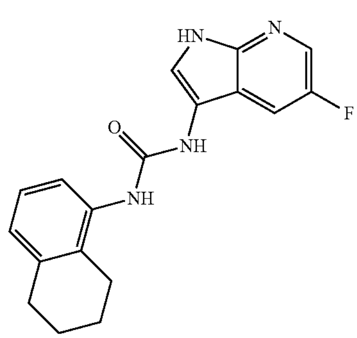 [SMILES: O=C(Nc1cccc2c1CCCC2)Nc1c[nH]c2ncc(F)cc12] |

-continued
| Compound # | Structure |
|---|---|
| 285 | 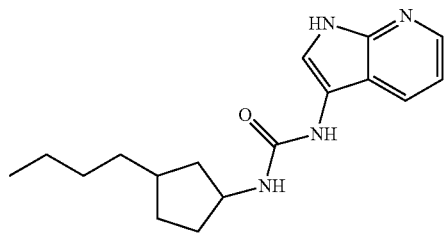 [SMILES: CCCCC1CCC(NC(=O)Nc2c[nH]c3ncccc23)C1] |
| 286 | 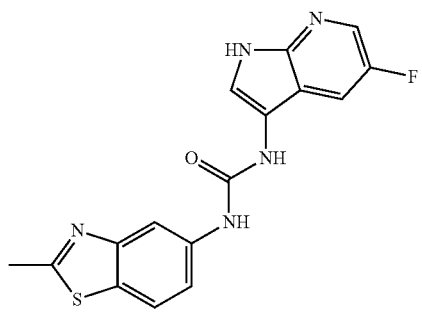 [SMILES: Cc1nc2cc(NC(=O)Nc3c[nH]c4ncc(F)cc34)ccc2s1] |
| 287 | 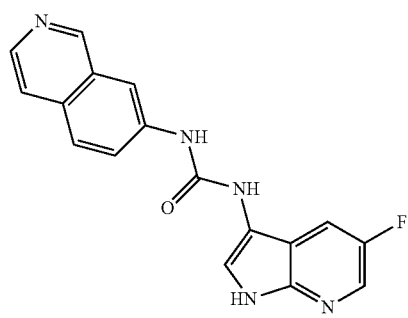 [SMILES: O=C(Nc1ccc2ccncc2c1)Nc1c[nH]c2ncc(F)cc12] |
| 288 | 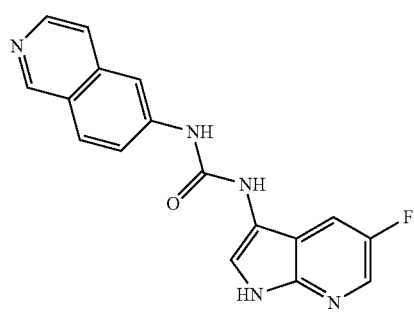 [SMILES: O=C(Nc1ccc2cnccc2c1)Nc1c[nH]c2ncc(F)cc12] |
| 289 | 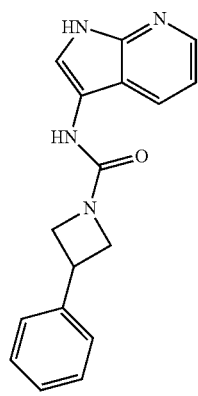 [SMILES: O=C(Nc1c[nH]c2ncccc12)N1CC(c2ccccc2)C1] |

-continued
| Compound # | Structure |
|---|---|
| 290 | 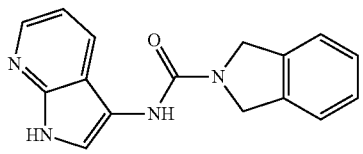 [SMILES: O=C(Nc1c[nH]c2ncccc12)N1Cc2ccccc2C1] |
| 291 | 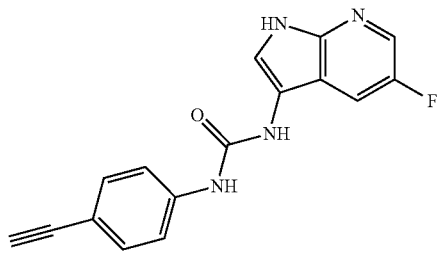 [SMILES: C#Cc1ccc(NC(=O)Nc2c[nH]c3ncc(F)cc23)cc1] |
| 292 | 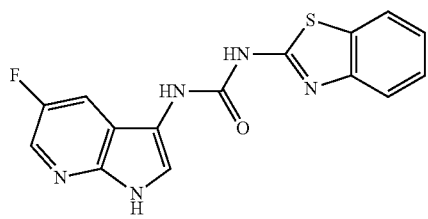 [SMILES: O=C(Nc1nc2ccccc2s1)Nc1c[nH]c2ncc(F)cc12] |
| 293 | 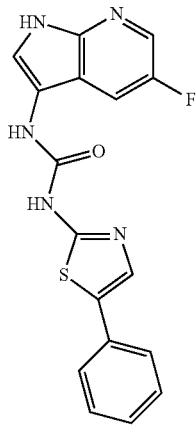 [SMILES: O=C(Nc1ncc(-c2ccccc2)s1)Nc1c[nH]c2ncc(F)cc12] |
| 294 | 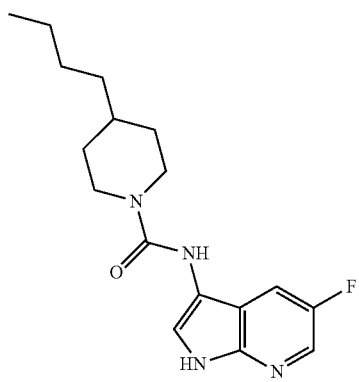 [SMILES: CCCCC1CCN(C(=O)Nc2c[nH]c3ncc(F)cc23)CC1] |

-continued
| Compound # | Structure |
|---|---|
| 295 | 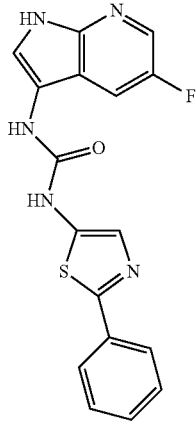 [SMILES: O=C(Nc1cnc(-c2ccccc2)s1)Nc1c[nH]c2ncc(F)cc12] |
| 296 | 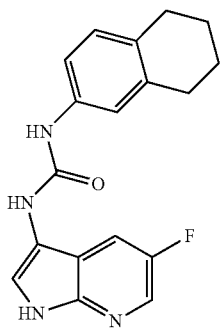 [SMILES: O=C(Nc1ccc2c(c1)CCCC2)Nc1c[nH]c2ncc(F)cc12] |
| 297 | 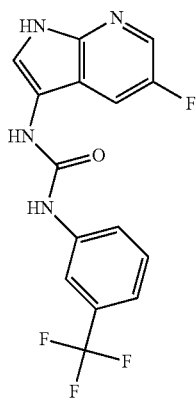 [SMILES: O=C(Nc1cccc(C(F)(F)F)c1)Nc1c[nH]c2ncc(F)cc12] |
| 298 | 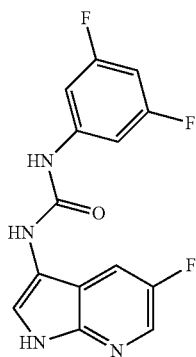 [SMILES: O=C(Nc1cc(F)cc(F)c1)Nc1c[nH]c2ncc(F)cc12] |

-continued
| Compound # | Structure |
|---|---|
| 299 | 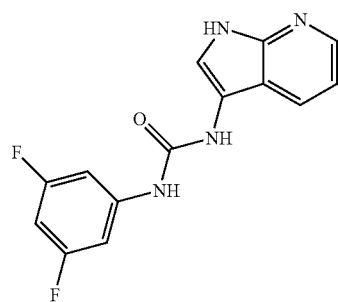 [SMILES: O=C(Nc1cc(F)cc(F)c1)Nc1c[nH]c2ncccc12] |
| 300 | 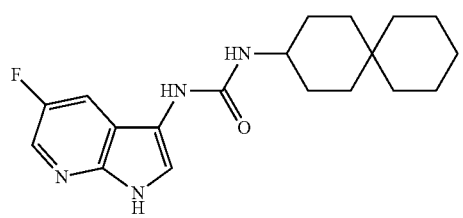 [SMILES: O=C(Nc1c[nH]c2ncc(F)cc12)NC1CCC2(CCCCC2)CC1] |
| 301 | 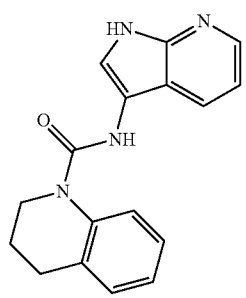 [SMILES: O=C(Nc1c[nH]c2ncccc12)N1CCCc2ccccc21] |
| 302 | 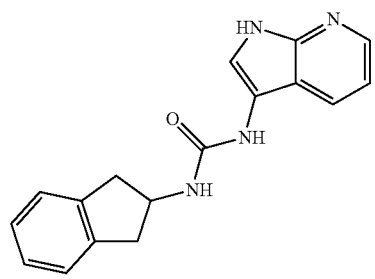 [SMILES: O=C(Nc1c[nH]c2ncccc12)NC1Cc2ccccc2C1] |
| 303 | 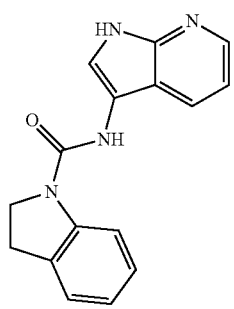 [SMILES: O=C(Nc1c[nH]c2ncccc12)N1CCc2ccccc21] |

| Compound # | Structure |
|---|---|
| 304 | 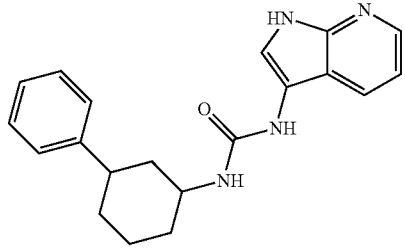 [SMILES: O=C(Nc1c[nH]c2ncccc12)NC1CCCC(c2ccccc2)C1] |
| 305 | 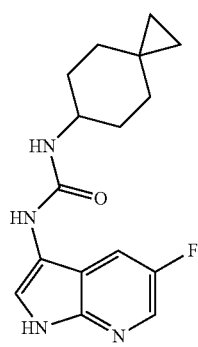 [SMILES: O=C(Nc1c[nH]c2ncc(F)cc12)NC1CCC2(CC1)CC2] |
| 306 | 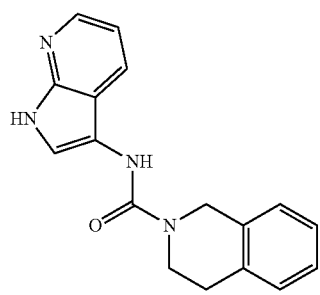 [SMILES: O=C(Nc1c[nH]c2ncccc12)N1CCc2ccccc2C1] |
| 307 | 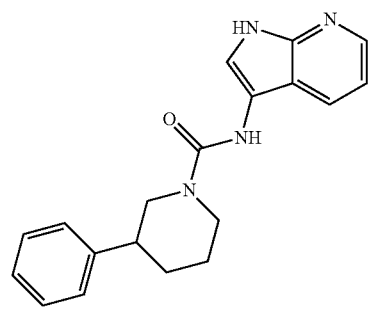 [SMILES: O=C(Nc1c[nH]c2ncccc12)N1CCCC(c2ccccc2)C1] |

| Compound # | Structure |
|---|---|
| 308 | *(structure: 7-azaindole-3-yl NH-C(O)-N-piperidine-4-phenyl)* |
| 309 | *(structure: 5-phenyl-6-azaindol-3-yl NH-C(O)-NH-(4-trifluoromethylphenyl))* |
| 310 | *(structure: 6-azaindol-3-yl NH-C(O)-NH-(6-trifluoromethylpyridin-3-yl))* |
| 311 | *(structure: 6-azaindol-3-yl NH-C(O)-NH-(5-trifluoromethylpyridin-2-yl))* |
| 312 | *(structure: 6-azaindol-3-yl NH-C(O)-NH-(6-cyclohexylpyridin-3-yl))* |

-continued
| Compound # | Structure |
|---|---|
| 313 | 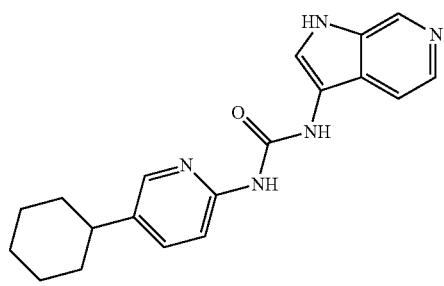 [SMILES: O=C(Nc1ccc(C2CCCCC2)cn1)Nc1c[nH]c2cnccc12] |
| 314 | 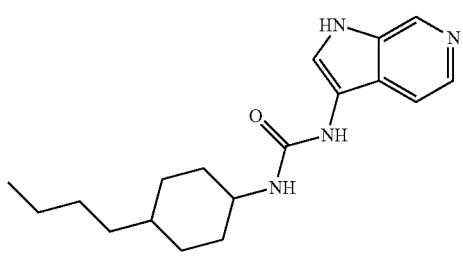 [SMILES: CCCCC1CCC(NC(=O)Nc2c[nH]c3cnccc23)CC1] |
| 315 | 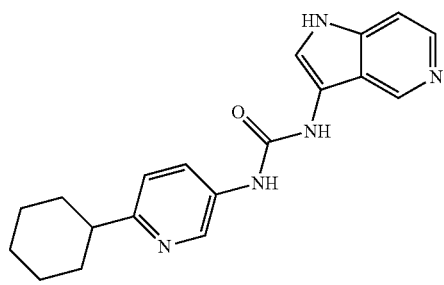 [SMILES: O=C(Nc1ccc(C2CCCCC2)nc1)Nc1c[nH]c2ccncc12] |
| 316 | 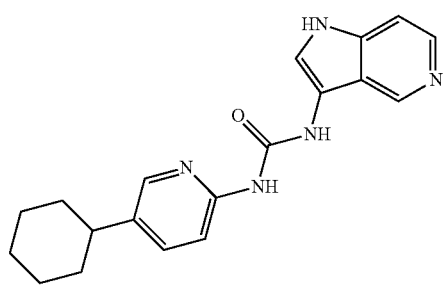 [SMILES: O=C(Nc1ccc(C2CCCCC2)cn1)Nc1c[nH]c2ccncc12] |
| 317 | 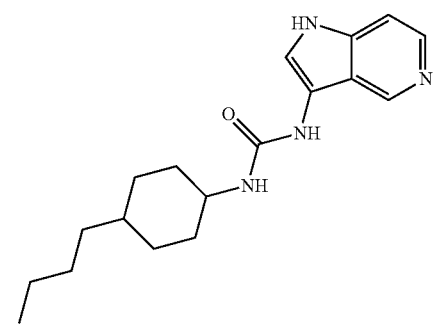 [SMILES: CCCCC1CCC(NC(=O)Nc2c[nH]c3ccncc23)CC1] |

-continued
| Compound # | Structure |
|---|---|
| 318 | 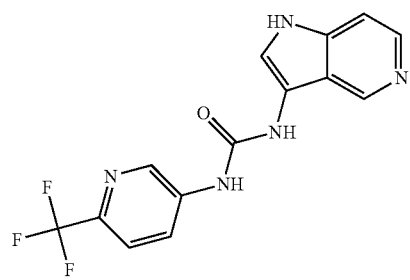 [SMILES: O=C(Nc1ccc(C(F)(F)F)nc1)Nc1c[nH]c2ccncc12] |
| 319 | 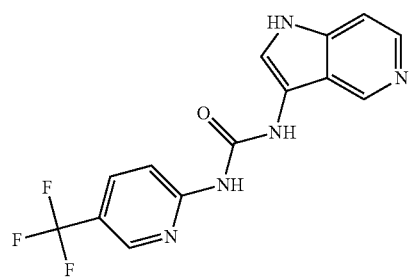 [SMILES: O=C(Nc1ccc(C(F)(F)F)cn1)Nc1c[nH]c2ccncc12] |
| 320 | 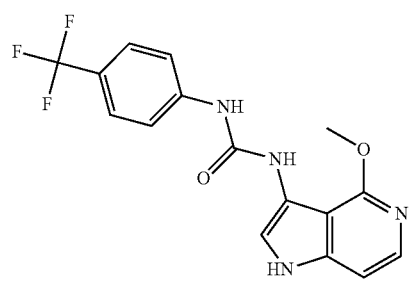 [SMILES: COc1nccc2[nH]cc(NC(=O)Nc3ccc(C(F)(F)F)cc3)c12] |
| 321 | 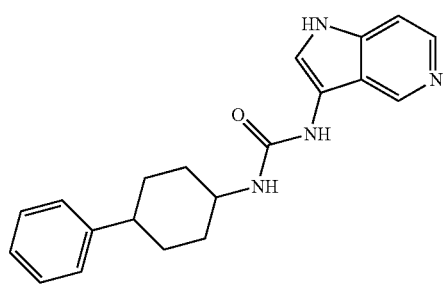 |
| 322 | 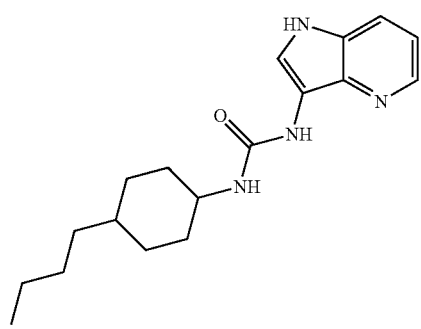 [SMILES: CCCCC1CCC(NC(=O)Nc2c[nH]c3cccnc23)CC1] |

| Compound # | Structure |
|---|---|
| 323 | 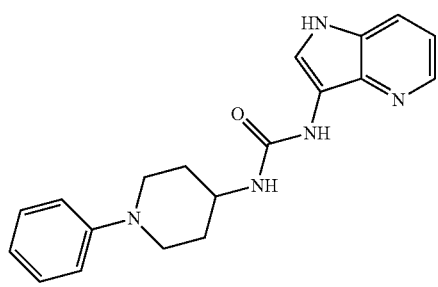 [SMILES: O=C(Nc1c[nH]c2cccnc12)NC1CCN(c2ccccc2)CC1] |
| 324 | 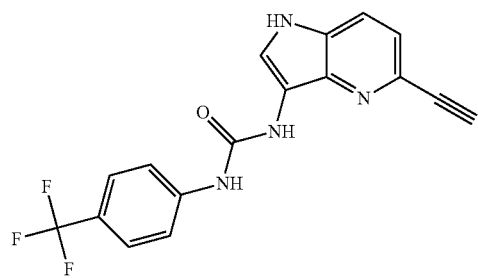 [SMILES: C#Cc1ccc2[nH]cc(NC(=O)Nc3ccc(C(F)(F)F)cc3)c2n1] |
| 325 | 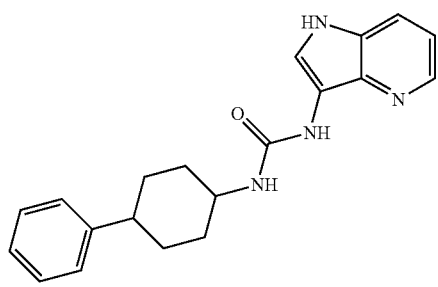 [SMILES: O=C(Nc1c[nH]c2cccnc12)NC1CCC(c2ccccc2)CC1] |
| 326 | 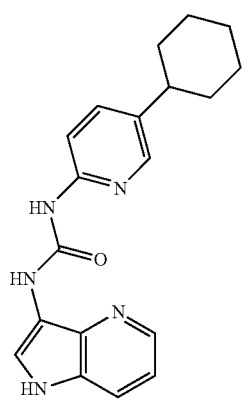 [SMILES: O=C(Nc1ccc(C2CCCCC2)cn1)Nc1c[nH]c2cccnc12] |

-continued
| Compound # | Structure |
|---|---|
| 327 | 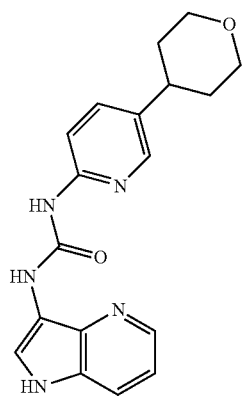 [SMILES: O=C(Nc1ccc(C2CCOCC2)cn1)Nc1c[nH]c2cccnc12] |
| 328 | 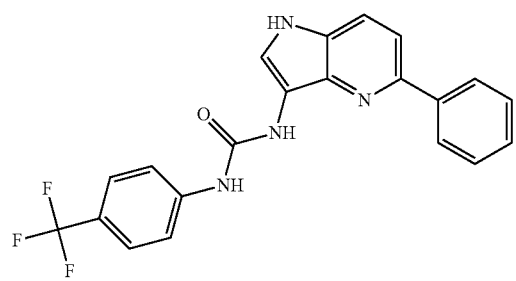 [SMILES: O=C(Nc1ccc(C(F)(F)F)cc1)Nc1c[nH]c2ccc(-c3ccccc3)nc12] |
| 329 | 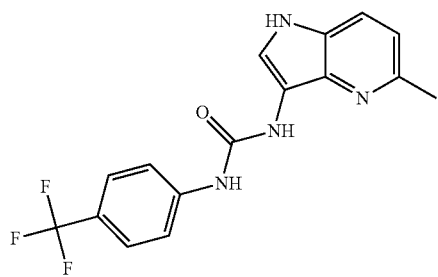 [SMILES: Cc1ccc2[nH]cc(NC(=O)Nc3ccc(C(F)(F)F)cc3)c2n1] |
| 330 | 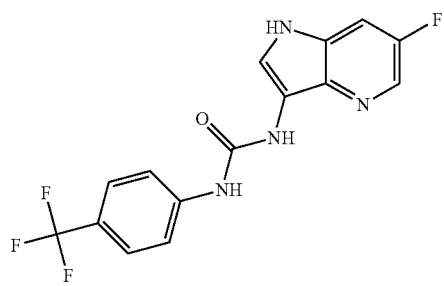 [SMILES: O=C(Nc1ccc(C(F)(F)F)cc1)Nc1c[nH]c2cc(F)cnc12] |

| Compound # | Structure |
|---|---|
| 331 | 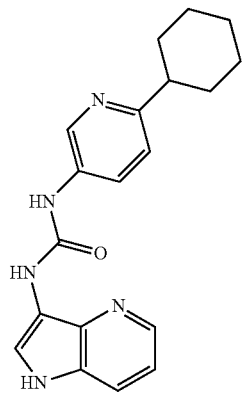 [SMILES: O=C(Nc1ccc(C2CCCCC2)nc1)Nc1c[nH]c2cccnc12] |
| 332 | 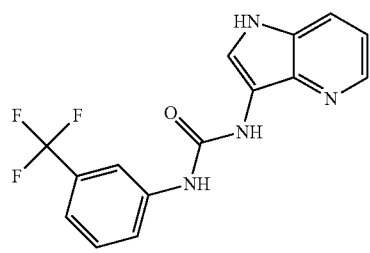 [SMILES: O=C(Nc1cccc(C(F)(F)F)c1)Nc1c[nH]c2cccnc12] |
| 333 | 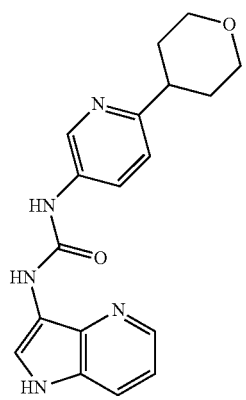 [SMILES: O=C(Nc1ccc(C2CCOCC2)nc1)Nc1c[nH]c2cccnc12] |
| 334 | 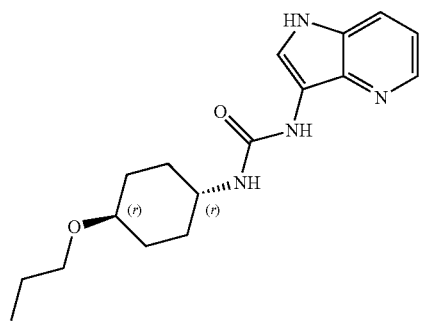 [SMILES: CCCO[C@H]1CC[C@H](NC(=O)Nc2c[nH]c3cccnc23)CC1] |

-continued
| Compound # | Structure |
|---|---|
| 335 | 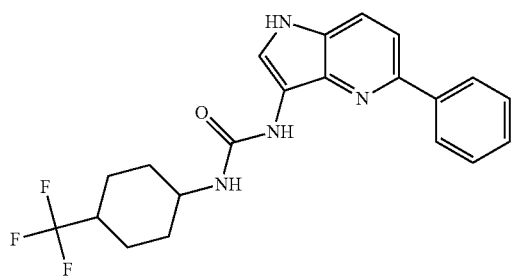 [SMILES: O=C(Nc1c[nH]c2ccc(-c3ccccc3)nc12)NC1CCC(C(F)(F)F)CC1] |
| 336 | 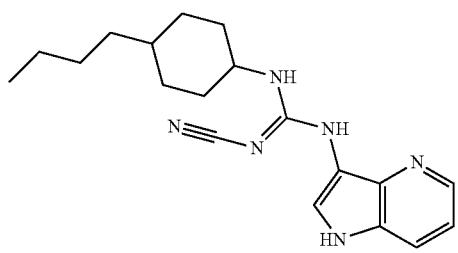 [SMILES: CCCCC1CCC(N/C(=N\C#N)Nc2c[nH]c3cccnc23)CC1] |
| 337 | 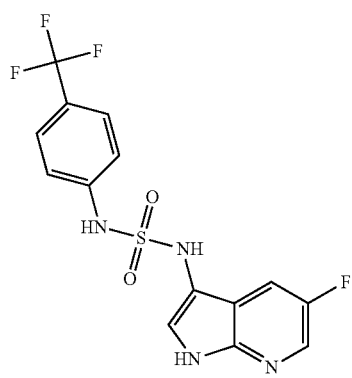 [SMILES: O=S(=O)(Nc1ccc(C(F)(F)F)cc1)Nc1c[nH]c2ncc(F)cc12] |
| 338 | 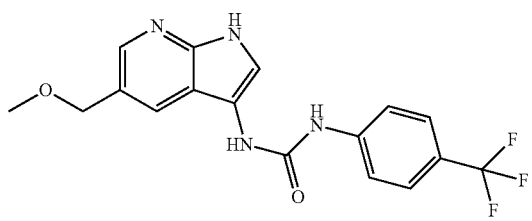 [SMILES: COCc1cnc2[nH]cc(NC(=O)Nc3ccc(C(F)(F)F)cc3)c2c1] |
| 339 | 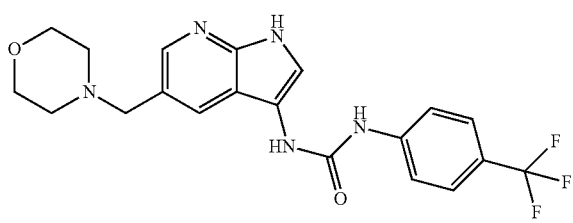 [SMILES: O=C(Nc1ccc(C(F)(F)F)cc1)Nc1c[nH]c2ncc(CN3CCOCC3)cc12] |
| 340 | 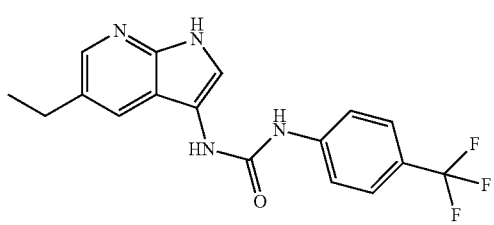 [SMILES: CCc1cnc2[nH]cc(NC(=O)Nc3ccc(C(F)(F)F)cc3)c2c1] |

| Compound # | Structure |
|---|---|
| 341 | 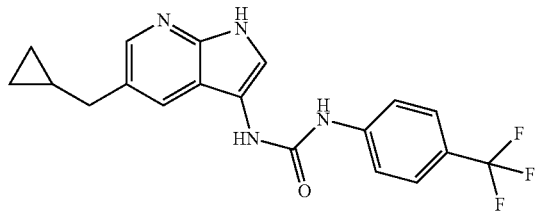 [SMILES: O=C(Nc1ccc(C(F)(F)F)cc1)Nc1c[nH]c2ncc(CC3CC3)cc12] |
| 342 | 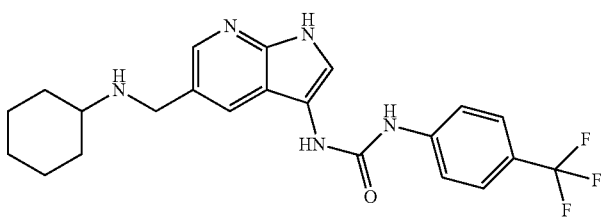 [SMILES: O=C(Nc1ccc(C(F)(F)F)cc1)Nc1c[nH]c2ncc(CNC3CCCCC3)cc12] |
| 343 | 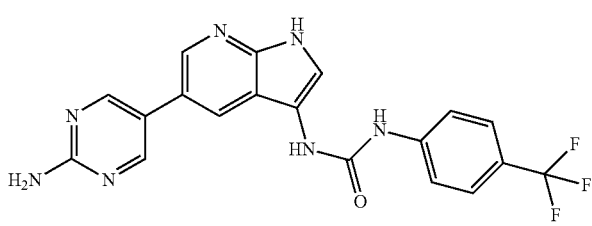 [SMILES: Nc1ncc(-c2cnc3[nH]cc(NC(=O)Nc4ccc(C(F)(F)F)cc4)c3c2)cn1] |
| 344 | 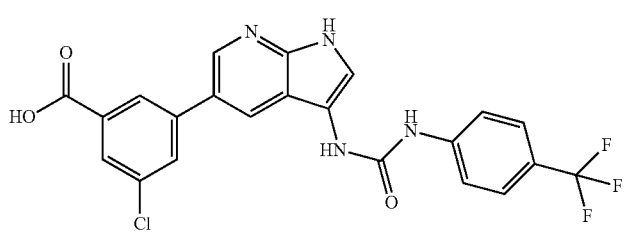 [SMILES: O=C(Nc1ccc(C(F)(F)F)cc1)Nc1c[nH]c2ncc(-c3cc(Cl)cc(C(=O)O)c3)cc12] |
| 345 | 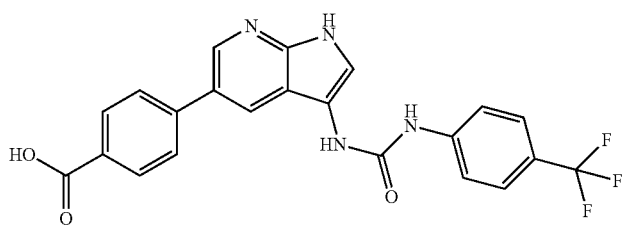 [SMILES: O=C(Nc1ccc(C(F)(F)F)cc1)Nc1c[nH]c2ncc(-c3ccc(C(=O)O)cc3)cc12] |
| 346 | 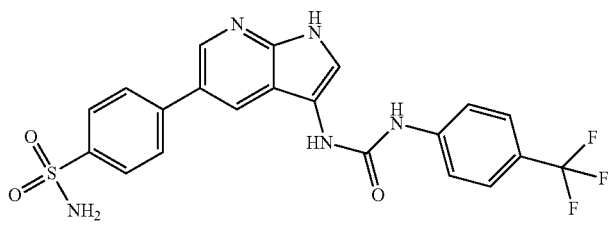 [SMILES: NS(=O)(=O)c1ccc(-c2cnc3[nH]cc(NC(=O)Nc4ccc(C(F)(F)F)cc4)c3c2)cc1] |
| 347 | 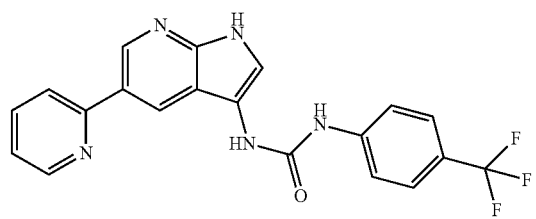 [SMILES: O=C(Nc1ccc(C(F)(F)F)cc1)Nc1c[nH]c2ncc(-c3ccccn3)cc12] |

-continued
| Compound # | Structure |
|---|---|
| 348 | 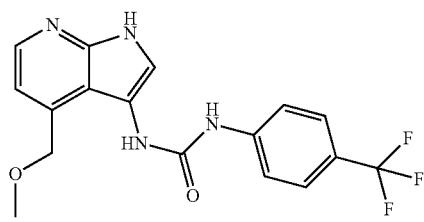 [SMILES: COCc1ccnc2[nH]cc(NC(=O)Nc3ccc(C(F)(F)F)cc3)c12] |
| 349 | 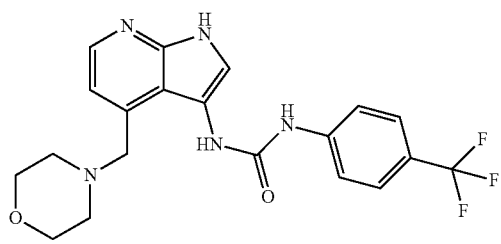 [SMILES: O=C(Nc1ccc(C(F)(F)F)cc1)Nc1c[nH]c2nccc(CN3CCOCC3)c12] |
| 350 | 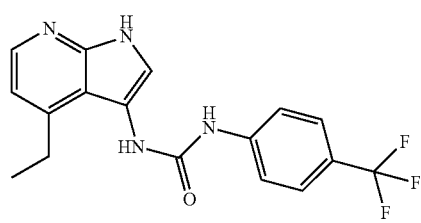 [SMILES: CCc1ccnc2[nH]cc(NC(=O)Nc3ccc(C(F)(F)F)cc3)c12] |
| 351 | 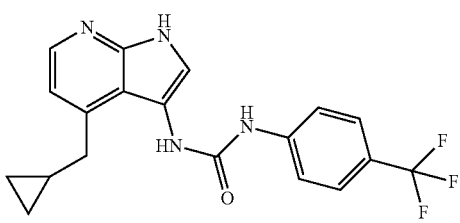 [SMILES: O=C(Nc1ccc(C(F)(F)F)cc1)Nc1c[nH]c2nccc(CC3CC3)c12] |
| 352 | 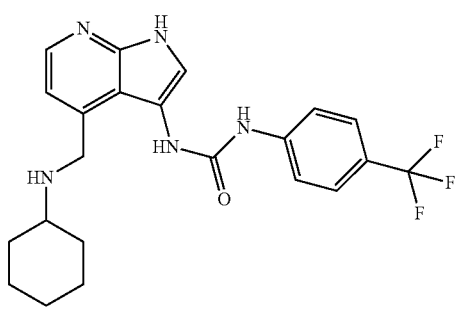 [SMILES: O=C(Nc1ccc(C(F)(F)F)cc1)Nc1c[nH]c2nccc(CNC3CCCCC3)c12] |
| 353 | 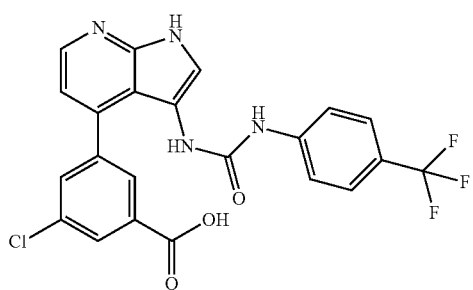 [SMILES: O=C(Nc1ccc(C(F)(F)F)cc1)Nc1c[nH]c2nccc(-c3cc(Cl)cc(C(=O)O)c3)c12] |

US 11,618,749 B2
171                                        172
-continued
| Compound # | Structure |
|---|---|
| 354 | 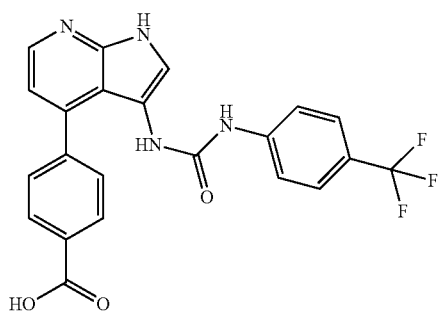 [SMILES: O=C(Nc1ccc(C(F)(F)F)cc1)Nc1c[nH]c2nccc(-c3ccc(C(=O)O)cc3)c12] |
| 355 | 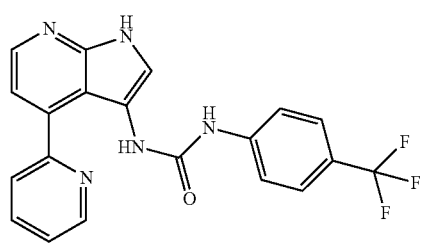 [SMILES: O=C(Nc1ccc(C(F)(F)F)cc1)Nc1c[nH]c2nccc(-c3ccccn3)c12] |
| 356 | 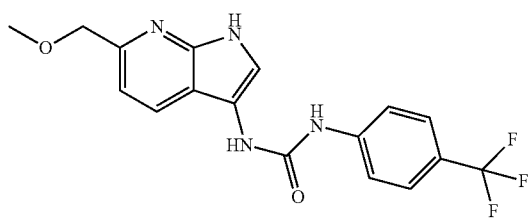 [SMILES: COCc1ccc2c(NC(=O)Nc3ccc(C(F)(F)F)cc3)c[nH]c2n1] |
| 357 | 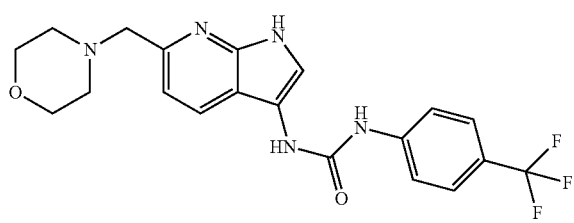 [SMILES: O=C(Nc1ccc(C(F)(F)F)cc1)Nc1c[nH]c2nc(CN3CCOCC3)ccc12] |
| 358 | 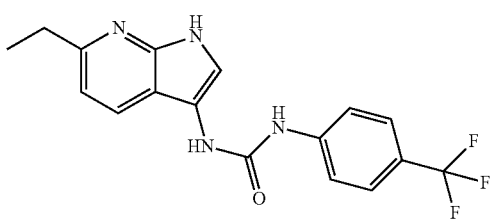 [SMILES: CCc1ccc2c(NC(=O)Nc3ccc(C(F)(F)F)cc3)c[nH]c2n1] |
| 359 | 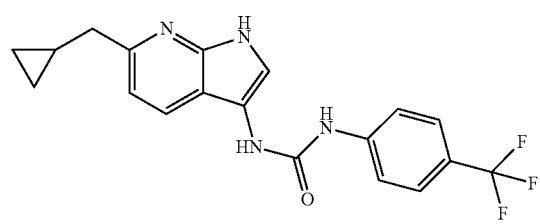 [SMILES: O=C(Nc1ccc(C(F)(F)F)cc1)Nc1c[nH]c2nc(CC3CC3)ccc12] |

-continued
| Compound # | Structure |
|---|---|
| 360 | 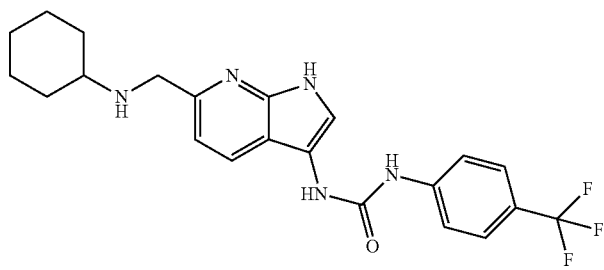 [SMILES: O=C(Nc1ccc(C(F)(F)F)cc1)Nc1c[nH]c2nc(CNC3CCCCC3)ccc12] |
| 361 | 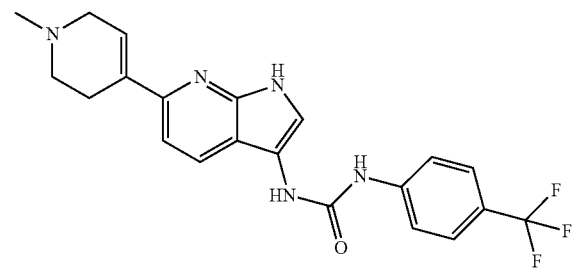 [SMILES: CN1CC=C(c2ccc3c(NC(=O)Nc4ccc(C(F)(F)F)cc4)c[nH]c3n2)CC1] |
| 362 | 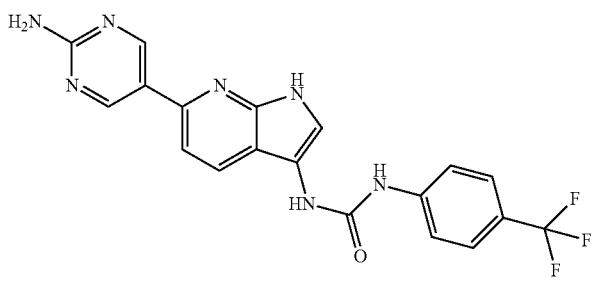 [SMILES: Nc1ncc(-c2ccc3c(NC(=O)Nc4ccc(C(F)(F)F)cc4)c[nH]c3n2)cn1] |
| 363 | 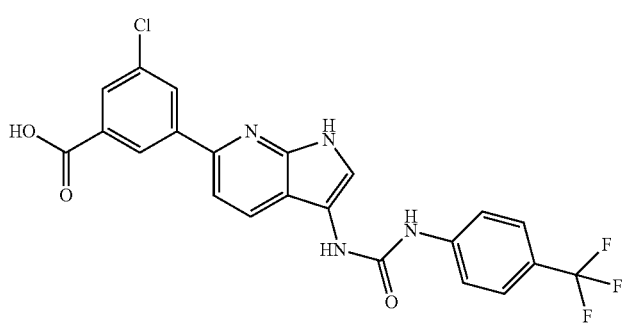 [SMILES: O=C(Nc1ccc(C(F)(F)F)cc1)Nc1c[nH]c2nc(-c3cc(Cl)cc(C(=O)O)c3)ccc12] |
| 364 | 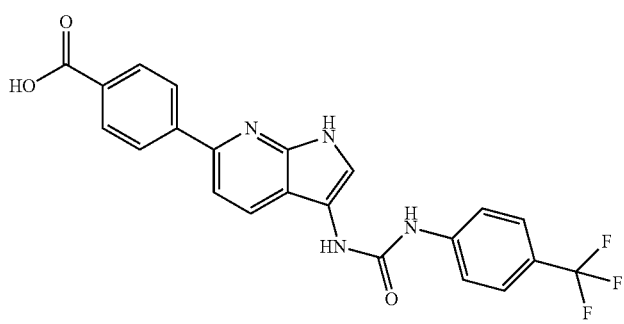 [SMILES: O=C(Nc1ccc(C(F)(F)F)cc1)Nc1c[nH]c2nc(-c3ccc(C(=O)O)cc3)ccc12] |

| Compound # | Structure |
|---|---|
| 365 | 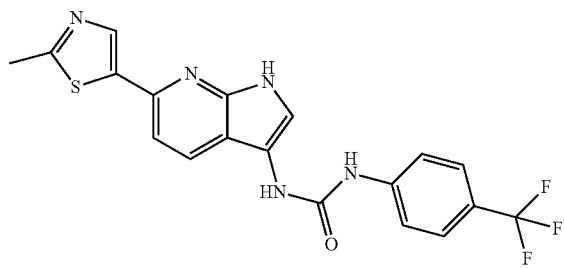 [SMILES: Cc1ncc(-c2ccc3c(NC(=O)Nc4ccc(C(F)(F)F)cc4)c[nH]c3n2)s1] |
| 366 | 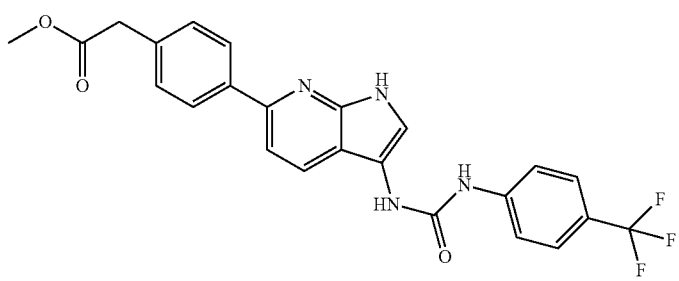 [SMILES: COC(=O)Cc1ccc(-c2ccc3c(NC(=O)Nc4ccc(C(F)(F)F)cc4)c[nH]c3n2)cc1] |
| 367 | 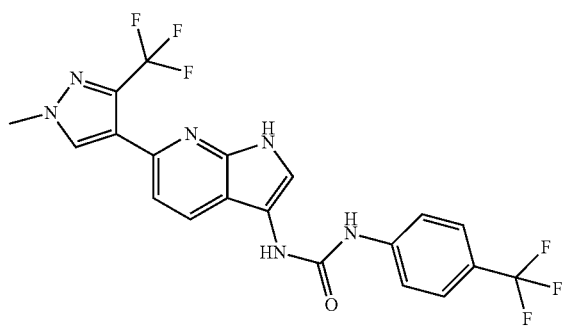 [SMILES: Cn1cc(-c2ccc3c(NC(=O)Nc4ccc(C(F)(F)F)cc4)c[nH]c3n2)c(C(F)(F)F)n1] |
| 368 | 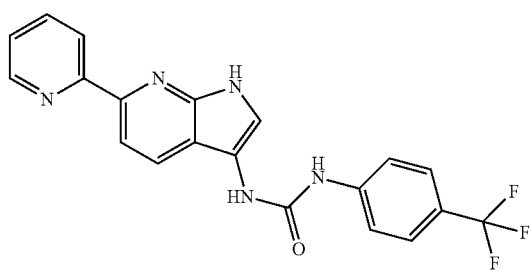 [SMILES: O=C(Nc1ccc(C(F)(F)F)cc1)Nc1c[nH]c2nc(-c3ccccn3)ccc12] |
| 369 | 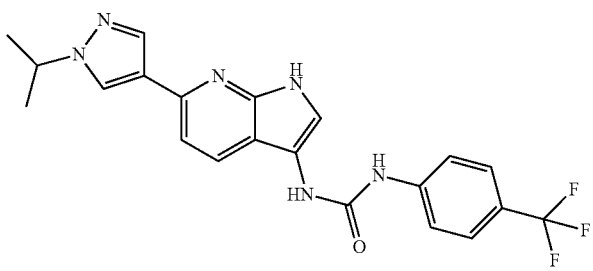 [SMILES: CC(C)n1cc(-c2ccc3c(NC(=O)Nc4ccc(C(F)(F)F)cc4)c[nH]c3n2)cn1] |

| Compound # | Structure |
|---|---|
| 370 | ![Structure of compound 370] |
| 371 | ![Structure of compound 371] |
| 372 | ![Structure of compound 372] |
| 373 | ![Structure of compound 373] |
| 374 | ![Structure of compound 374] |
| 375 | ![Structure of compound 375] |
| 376 | ![Structure of compound 376] |

| Compound # | Structure |
|---|---|
| 377 | 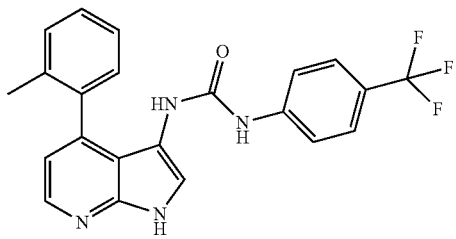 [SMILES: Cc1ccccc1-c1ccnc2[nH]cc(NC(=O)Nc3ccc(C(F)(F)F)cc3)c12] |
| 378 | 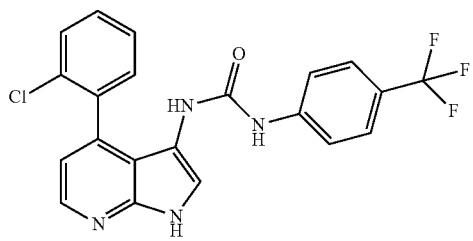 [SMILES: O=C(Nc1ccc(C(F)(F)F)cc1)Nc1c[nH]c2nccc(-c3ccccc3Cl)c12] |
| 379 | 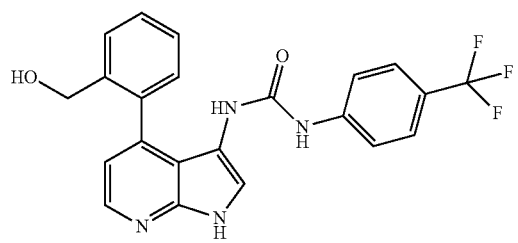 [SMILES: O=C(Nc1ccc(C(F)(F)F)cc1)Nc1c[nH]c2nccc(-c3ccccc3CO)c12] |
| 380 | 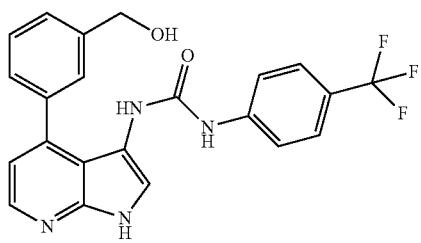 [SMILES: O=C(Nc1ccc(C(F)(F)F)cc1)Nc1c[nH]c2nccc(-c3cccc(CO)c3)c12] |
| 381 | 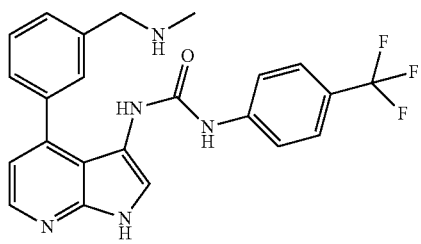 [SMILES: CNCc1cccc(-c2ccnc3[nH]cc(NC(=O)Nc4ccc(C(F)(F)F)cc4)c23)c1] |
| 382 | 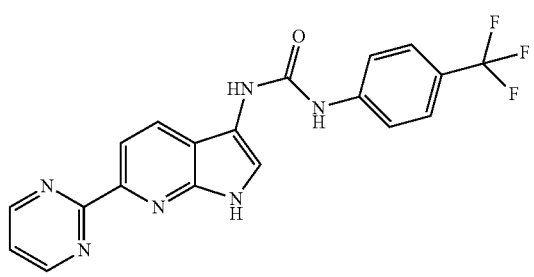 [SMILES: O=C(Nc1ccc(C(F)(F)F)cc1)Nc1c[nH]c2nc(-c3ncccn3)ccc12] |

-continued

| Compound # | Structure |
|---|---|
| 383 | 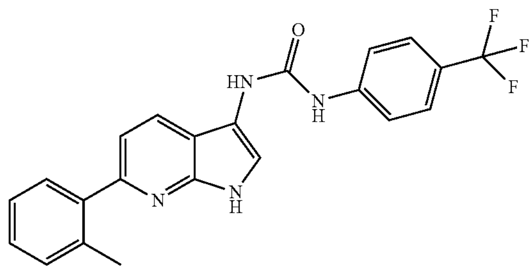 [SMILES: Cc1ccccc1-c1ccc2c(NC(=O)Nc3ccc(C(F)(F)F)cc3)c[nH]c2n1] |
| 384 | 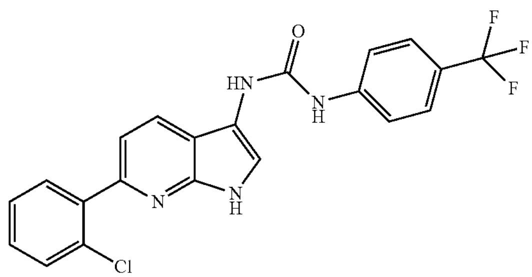 [SMILES: O=C(Nc1ccc(C(F)(F)F)cc1)Nc1c[nH]c2nc(-c3ccccc3Cl)ccc12] |
| 385 | 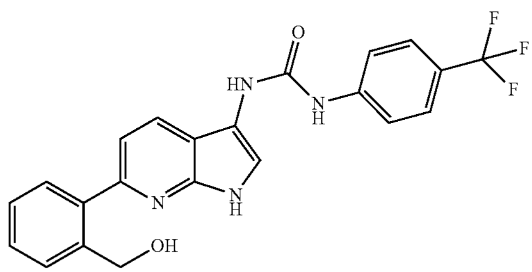 [SMILES: O=C(Nc1ccc(C(F)(F)F)cc1)Nc1c[nH]c2nc(-c3ccccc3CO)ccc12] |
| 386 | 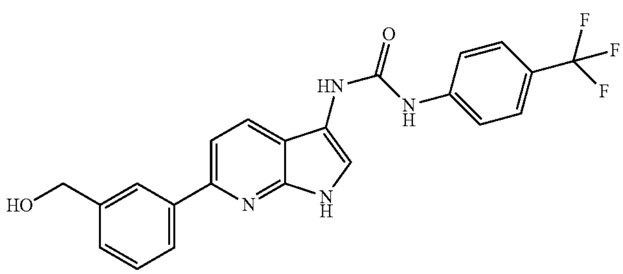 [SMILES: O=C(Nc1ccc(C(F)(F)F)cc1)Nc1c[nH]c2nc(-c3cccc(CO)c3)ccc12] |
| 387 | 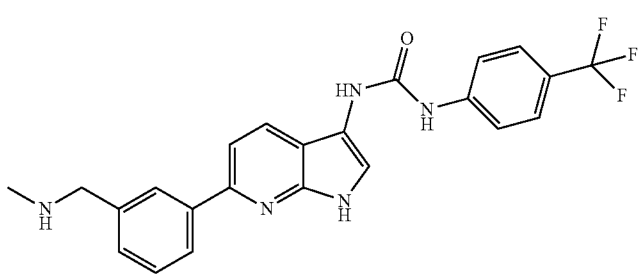 [SMILES: CNCc1cccc(-c2ccc3c(NC(=O)Nc4ccc(C(F)(F)F)cc4)c[nH]c3n2)c1] |
| 388 | 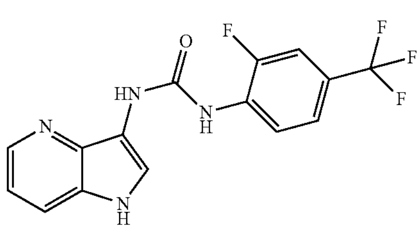 [SMILES: O=C(Nc1ccc(C(F)(F)F)cc1F)Nc1c[nH]c2cccnc12] |

| Compound # | Structure |
|---|---|
| 389 | 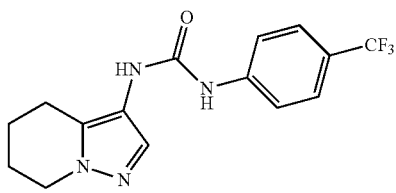 [SMILES: O=C(Nc1ccc(C(F)(F)F)cc1)Nc1cnn2c1CCCC2] | and pharmaceutically acceptable salts thereof.

Pharmaceutical Compositions and Administration

General

In some embodiments, a chemical entity (e.g., a compound that inhibits (e.g., antagonizes) STING, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization.

Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which increased (e.g., excessive) STING activity (e.g., e.g., STING signaling) contributes to the pathology and/or symptoms and/or progression of the condition, disease or disorder (e.g., immune disorders, cancer) are provided.

Indications

In some embodiments, the condition, disease or disorder is cancer. Non-limiting examples of cancer include melanoma, carcinoma, lymphoma, blastoma, sarcoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some cases, the cancer is melanoma.

In some embodiments, the condition, disease or disorder is a neurological disorder, which includes disorders that involve the central nervous system (brain, brainstem and cerebellum), the peripheral nervous system (including cranial nerves), and the autonomic nervous system (parts of which are located in both central and peripheral nervous system). Non-limiting examples of cancer include acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; amyotrophe lateral sclerosis and Zellweger syndrome.

In some embodiments, the condition, disease or disorder is STING-associated conditions, e.g., type I interferonopathies (e.g., STING-associated vasculopathy with onset in infancy (SAVI)), Aicardi-Goutieres Syndrome (AGS), genetic forms of lupus, and inflammation-associated disorders such as systemic lupus erythematosus, and rheumatoid arthritis. In certain embodiments, the condition, disease or disorder is an autoimmune disease (e.g., a cytosolic DNA-triggered autoinflammatory disease). Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, modulation of the immune system by STING provides for the treatment of diseases, including diseases caused by foreign agents. Exemplary infections by foreign agents which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant *enterococcus*), or sepsis. In another embodiment, the infection is a fungal infection (e.g. infection by a mould, a yeast, or a higher fungus). In still another embodiment, the infection is a parasitic infection (e.g., infection by a single-celled or multicellular parasite, including *Giardia duodenalis, Cryptosporidium parvum, Cyclospora cayetanensis*, and *Toxoplasma gondiz*). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus)).

In some embodiments, the condition, disease or disorder is hepatitis B (see, e.g., WO 2015/061294).

In some embodiments, the condition, disease or disorder is selected from cardiovascular diseases (including e.g., myocardial infarction).

In some embodiments, the condition, disease or disorder is age-related macular degeneration.

In some embodiments, the condition, disease or disorder is mucositis, also known as stomatitits, which can occur as a result of chemotherapy or radiation therapy, either alone or in combination as well as damage caused by exposure to radiation outside of the context of radiation therapy.

In some embodiments, the condition, disease or disorder is uveitis, which is inflammation of the uvea (e.g., anterior uveitis, e.g., iridocyclitis or iritis; intermediate uveitis (also known as pars planitis); posterior uveitis; or chorioretinitis, e.g., pan-uveitis).

In some embodiments, the condition, disease or disorder is selected from the group consisting of a cancer, a neurological disorder, an autoimmune disease, hepatitis B, uveitis, a cardiovascular disease, age-related macular degeneration, and mucositis.

Still other examples can include those indications discussed herein and below in contemplated combination therapy regimens.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional chemotherapeutic agent is an immunomodulatory moiety, e.g., an immune checkpoint inhibitor. In certain of these embodiments, the immune checkpoint inhibitor targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155; e.g., CTLA-4 or PD1 or PD-L1). See, e.g., Postow, M. *J. Clin. Oncol.* 2015, 33, 1.

In certain of these embodiments, the immune checkpoint inhibitor is selected from the group consisting of: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736

(PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, Bevacizumab, and MNRP1685A, and MGA271.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a *vinca* alkaloid, a podophyllotoxin and/or a taxane. *Vinca* alkaloids, in general, bind to specific sites on tubulin, inhibiting the assembly of tubulin into microtubules, generally during the M phase of the cell cycle. In an embodiment, a *vinca* alkaloid is derived, without limitation, from the Madagascar periwinkle, Catharanthus *roseus* (formerly known as *Vinca rosea*). In an embodiment, a *vinca* alkaloid includes, without limitation, Vincristine, Vinblastine, Vinorelbine and/or Vindesine. In an embodiment, a taxane includes, but is not limited to, Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. [021] In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613, which is incorporated herein by reference in its entirety.

In some embodiments, the additional therapeutic agent and/or regimen are those that can be used for treating other STING-associated conditions, e.g., type I interferonopathies (e.g., STING-associated vasculopathy with onset in infancy (SAVI)), Aicardi-Goutieres Syndrome (AGS), genetic forms of lupus, and inflammation-associated disorders such as systemic lupus erythematosus, and rheumatoid arthritis and the like.

Non-limiting examples of additional therapeutic agents and/or regimens for treating rheumatoid arthritis include non-steroidal anti-inflammatory drugs (NSAIDs; e.g., ibuprofen and naproxen), corticosteroids (e.g., prednisone), disease-modifying antirheumatic drugs (DMARDs; e.g., methotrexate (Trexall®, Otrexup®, Rasuvo®, Rheumatrex®), leflunomide (Arava®), hydroxychloroquine (Plaquenil), PF-06650833, iguratimod, tofacitinib (Xeljanz®), ABBV-599, evobrutinib, and sulfasalazine (Azulfidine®)), and biologics (e.g., abatacept (Orencia®), adalimumab (Humira®), anakinra (Kineret®), certolizumab (Cimzia®), etanercept (Enbrel®), golimumab (Simponi®), infliximab (Remicade®), rituximab (Rituxan®), tocilizumab (Actemra®), vobarilizumab, sarilumab (Kevzara®), secukinumab, ABP 501, CHS-0214, ABC-3373, and tocilizumab (ACTEMRA®)).

Non-limiting examples of additional therapeutic agents and/or regimens for treating lupus include steroids, topical immunomodulators (e.g., tacrolimus ointment (Protopic®) and pimecrolimus cream (Elidel®)), thalidomide (Thalomid®), non-steroidal anti-inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., evobrutinib, iberdomide, voclosporin, cenerimod, azathioprine (Imuran®), cyclophosphamide (Cytoxan®, Neosar®, Endoxan®), and cyclosporine (Neoral, Sandimmune®, Gengraf®), and mycophenolate mofetil) baricitinb, iguratimod, filogotinib, GS-9876, rapamycin, and PF-06650833), and biologics (e.g., belimumab (Benlysta®), anifrolumab, prezalumab, MEDI0700, obinutuzumab, vobarilizumab, lulizumab, atacicept, PF-06823859, and lupizor, rituximab, BT063, BI655064, BIIB059, aldesleukin (Proleukin®), dapirolizumab, edratide, IFN-α-kinoid, OMS721, RC18, RSLV-132, theralizumab, XmAb5871, and ustekinumab (Stelara®)). For example, non-limiting treatments for systemic lupus erythematosus include non-steroidal anti-inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., iberdomide, voclosporin, azathioprine (Imuran®), cyclophosphamide (Cytoxan®, Neosar®, Endoxan®), and cyclosporine (Neoral, Sandimmune®, Gengraf®), and mycophenolate mofetil, baricitinb, filogotinib, and PF-06650833), and biologics (e.g., belimumab (Benlysta®), anifrolumab, prezalumab, MEDI0700, vobarilizumab, lulizumab, atacicept, PF-06823859, lupizor, rituximab, BT063, BI655064, BIIB059, aldesleukin (Proleukin®), dapirolizumab, edratide, IFN-α-kinoid, RC18, RSLV-132, theralizumab, XmAb5871, and ustekinumab (Stelara®)). As another example, non-limiting examples of treatments for cutaneous lupus include steroids, immunomodulators (e.g., tacrolimus ointment (Protopic®) and pimecrolimus cream (Elidel®)), GS-9876, filogotinib, and thalidomide (Thalomid®). Agents and regimens for treating drug-induced and/or neonatal lupus can also be administered.

Non-limiting examples of additional therapeutic agents and/or regimens for treating STING-associated vasculopathy with onset in infancy (SAVI) include JAK inhibitors (e.g., tofacitinib, ruxolitinib, filgotinib, and baricitinib).

Non-limiting examples of additional therapeutic agents and/or regimens for treating Aicardi-Goutieres Syndrome (AGS) include physiotherapy, treatment for respiratory complications, anticonvulsant therapies for seizures, tube-feeding, nucleoside reverse transcriptase inhibitors (e.g., emtricitabine (e.g., Emtriva®), tenofovir (e.g., Viread®), emtricitabine/tenofovir (e.g., Truvada®), zidovudine, lamivudine, and abacavir), and JAK inhibitors (e.g., tofacitinib, ruxolitinib, filgotinib, and baricitinib).

Non-limiting examples of additional therapeutic agents and/or regimens for treating IBDs include 6-mercaptopurine, AbGn-168H, ABX464, ABT-494, adalimumab, AJM300, alicaforsen, AMG139, anrukinzumab, apremilast, ATR-107 (PF0530900), autologous CD34-selected peripheral blood stem cells transplant, azathioprine, bertilimumab, BI 655066, BMS-936557, certolizumab pegol (Cimzia®), cobitolimod, corticosteroids (e.g., prednisone, Methylprednisolone, prednisone), CP-690,550, CT-P13, cyclosporine, DIMS0150, E6007, E6011, etrasimod, etrolizumab, fecal microbial transplantation, figlotinib, fingolimod, firategrast (SB-683699) (formerly T-0047), GED0301, GLPG0634, GLPG0974, guselkumab, golimumab, GSK1399686, HMPL-004 (Andrographis paniculata extract), IMU-838, infliximab, Interleukin 2 (IL-2), Janus kinase (JAK) inhibitors, laquinimod, masitinib (AB 1010), matrix metalloproteinase 9 (MMP 9) inhibitors (e.g., GS-5745), MEDI2070, mesalamine, methotrexate, mirikizumab (LY3074828), natalizumab, NNC 0142-0000-0002, NNC0114-0006, ozanimod, peficitinib (JNJ-54781532), PF-00547659, PF-04236921, PF-06687234, QAX576, RHB-104, rifaximin, risankizumab, RPC1063, SB012, SHP647, sulfasalazine, TD-1473, thalidomide, tildrakizumab (MK 3222), TJ301, TNF-Kinoid®, tofacitinib, tralokinumab, TRK-170, upadacitinib, ustekinumab, UTTR1147A, V565, vatelizumab, VB-201, vedolizumab, and vidofludimus.

Non-limiting examples of additional therapeutic agents and/or regimens for treating irritable bowel syndrome include alosetron, bile acid sequesterants (e.g., cholestyramine, colestipol, colesevelam), chloride channel activators (e.g., lubiprostone), coated peppermint oil capsules, desipramine, dicyclomine, ebastine, eluxadoline, farnesoid X receptor agonist (e.g., obeticholic acid), fecal microbiota transplantation, fluoxetine, gabapentin, guanylate cyclase-C agonists (e.g., linaclotide, plecanatide), ibodutant, imipramine, JCM-16021, loperamide, lubiprostone, nortriptyline, ondansetron, opioids, paroxetine, pinaverium, polyethylene glycol, pregabalin, probiotics, ramosetron, rifaximin, and tanpanor.

Non-limiting examples of additional therapeutic agents and/or regimens for treating scleroderma include non-steroidal anti-inflammatory drugs (NSAIDs; e.g., ibuprofen and naproxen), corticosteroids (e.g, prednisone), immunomodulators (e.g., azathioprine, methotrexate (Trexall®, Otrexup®, Rasuvo®, Rheumatrex®), cyclophosphamide (Cytoxan®, Neosar®, Endoxan®), and cyclosporine (Neoral®, Sandimmune®, Gengraf®), antithymocyte globulin, mycophenolate mofetil, intravenous immunoglobulin, rituximab, sirolimus, and alefacept), calcium channel blockers (e.g., nifedipine), alpha blockers, serotonin receptor antagonists, angiotensin II receptor inhibitors, statins, local nitrates, iloprost, phosphodiesterase 5 inhibitors (e.g., sildenafil), bosentan, tetracycline antibiotics, endothelin receptor antagonists, prostanoids, and tyrosine kinase inhibitors (e.g., imatinib, nilotinib and dasatinib).

Non-limiting examples of additional therapeutic agents and/or regimens for treating Crohn's Disease (CD) include adalimumab, autologous CD34-selected peripheral blood stem cells transplant, 6-mercaptopurine, azathioprine, certolizumab pegol (Cimzia®), corticosteroids (e.g., prednisone), etrolizumab, E6011, fecal microbial transplantation, figlotinib, guselkumab, infliximab, IL-2, JAK inhibitors, matrix metalloproteinase 9 (MMP 9) inhibitors (e.g., GS-5745), MEDI2070, mesalamine, methotrexate, natalizumab, ozanimod, RHB-104, rifaximin, risankizumab, SHP647, sulfasalazine, thalidomide, upadacitinib, V565, and vedolizumab.

Non-limiting examples of additional therapeutic agents and/or regimens for treating UC include AbGn-168H, ABT-494, ABX464, apremilast, PF-00547659, PF-06687234, 6-mercaptopurine, adalimumab, azathioprine, bertilimumab, brazikumab (MEDI2070), cobitolimod, certolizumab pegol (Cimzia®), CP-690,550, corticosteroids (e.g., multimax budesonide, Methylprednisolone), cyclosporine, E6007, etrasimod, etrolizumab, fecal microbial transplantation, figlotinib, guselkumab, golimumab, IL-2, IMU-838, infliximab, matrix metalloproteinase 9 (MMP9) inhibitors (e.g., GS-5745), mesalamine, mesalamine, mirikizumab (LY3074828), RPC1063, risankizumab (BI 6555066), SHP647, sulfasalazine, TD-1473, TJ301, tildrakizumab (MK 3222), tofacitinib, tofacitinib, ustekinumab, UTTR1147A, and vedolizumab.

Non-limiting examples of additional therapeutic agents and/or regimens for treating autoimmune colitis include corticosteroids (e.g., budesonide, prednisone, prednisolone, Beclometasone dipropionate), diphenoxylate/atropine, infliximab, loperamide, mesalamine, TIP60 inhibitors (see, e.g., U.S. Patent Application Publication No. 2012/0202848), and vedolizumab.

Non-limiting examples of additional therapeutic agents and/or regimens for treating iatrogenic autoimmune colitis include corticosteroids (e.g., budesonide, prednisone, prednisolone, Beclometasone dipropionate), diphenoxylate/atropine, infliximab, loperamide, TIP60 inhibitors (see, e.g., U.S. Patent Application Publication No. 2012/0202848), and vedolizumab.

Non-limiting examples of additional therapeutic agents and/or regimens for treating colitis induced by one or more chemotherapeutics agents include corticosteroids (e.g., budesonide, prednisone, prednisolone, beclometasone dipropionate), diphenoxylate/atropine, infliximab, loperamide, mesalamine, TIP60 inhibitors (see, e.g., U.S. Patent Application Publication No. 2012/0202848), and vedolizumab.

Non-limiting examples of additional therapeutic agents and/or regimens for treating colitis induced by treatment with adoptive cell therapy include corticosteroids (e.g., budesonide, prednisone, prednisolone, beclometasone dipropionate), diphenoxylate/atropine, infliximab, loperamide, TIP60 inhibitors (see, e.g., U.S. Patent Application Publication No. 2012/0202848), and vedolizumab.

Non-limiting examples of additional therapeutic agents and/or regimens for treating colitis associated with one or more alloimmune diseases include corticosteroids (e.g., budesonide, prednisone, prednisolone, beclometasone dipropionate), sulfasalazine, and eicopentaenoic acid.

Non-limiting examples of additional therapeutic agents and/or regimens for treating radaiation enteritis include teduglutide, amifostine, angiotensin-converting enzyme (ACE) inhibitors (e.g., benazepril, captopril, enalapril, fosinopril, lisinopril, moexipril, perindopril, quinapril, ramipril, and trandolapril), probiotics, selenium supplementation, statins (e.g., atorvastatin, fluvastatin, lovastatin, pravastatin, rosuvastatin, simvastatin, and pitavastatin), sucralfate, and vitamin E.

Non-limiting examples of additional therapeutic agents and/or regimens for treating collagenous colitis include 6-mercaptopurine, azathaioprine, bismuth subsalicate, *Boswellia serrata* extract, cholestyramine, colestipol, corticosteroids (e.g., budesonide, prednisone, prednisolone, beclometasone dipropionate), loperamide, mesalamine, methotrexate, probiotics, and sulfasalazine.

Non-limiting examples of additional therapeutic agents and/or regimens for treating lyphocytic colitis include 6-mercaptopurine, azathioprine, bismuth subsalicylate, cholestyramine, colestipol, corticosteroids (e.g., budesonide, prednisone, prednisolone, beclometasone dipropionate), loperamide, mesalamine, methotrexate, and sulfasalazine.

Non-limiting examples of additional therapeutic agents and/or regimens for treating microscopic colitis include 6-mercaptopurine, azathioprine, bismuth subsalicylate, *Boswellia serrata* extract, cholestyramine, colestipol, corticosteroids (e.g., budesonide, prednisone, prednisolone, beclometasone dipropionate), fecal microbial transplantation, loperamide, mesalamine, methotrexate, probiotics, and sulfasalazine.

Non-limiting examples of additional therapeutic agents and/or regimens for treating alloimmune disease include intrauterine platelet transfusions, intravenous immunoglobin, maternal steroids, abatacept, alemtuzumab, alpha1-antitrypsin, AMG592, antithymocyte globulin, barcitinib, basiliximab, bortezomib, brentuximab, cannabidiol, corticosteroids (e.g., methylprednisone, prednisone), cyclosporine, dacilzumab, defribrotide, denileukin diftitox, glasdegib, ibrutinib, IL-2, infliximab, itacitinib, LBH589, maraviroc, mycophenolate mofetil, natalizumab, neihulizumab, pentostatin, pevonedistat, photobiomodulation, photopheresis, ruxolitinib, sirolimus, sonidegib, tacrolimus, tocilizumab, and vismodegib.

Non-limiting examples of additional therapeutic agents and/or regimens for treating multiple sclerosis (MS) include alemtuzumab (Lemtrada®), ALKS 8700, amiloride, ATX-MS-1467, azathioprine, baclofen (Lioresal®), beta interferons (e.g., IFN-β-1a, IFN-β-1b), cladribine, corticosteroids (e.g., methylprednisolone), daclizumab, dimethyl fumarate (Tecfidera®), fingolimod (Gilenya®), fluoxetine, glatiramer acetate (Copaxone®), hydroxychloroquine, ibudilast, idebenone, laquinimod, lipoic acid, losartan, masitinib, MD1003 (biotin), mitoxantrone, montelukast, natalizumab (Tysabri®), NeuroVax™, ocrelizumab, ofatumumab, pioglitazone, and RPC1063.

Non-limiting examples of additional therapeutic agents and/or regimens for treating graft-vs-host disease include abatacept, alemtuzumab, alpha1-antitrypsin, AMG592, antithymocyte globulin, barcitinib, basiliximab, bortezomib, brentuximab, cannabidiol, corticosteroids (e.g., methylprednisone, prednisone), cyclosporine, dacilzumab, defribrotide, denileukin diftitox, glasdegib, ibrutinib, IL-2, imatinib, infliximab, itacitinib, LBH589, maraviroc, mycophenolate mofetil, natalizumab, neihulizumab, pentostatin, pevonedistat, photobiomodulation, photopheresis, ruxolitinib, sirolimus, sonidegib, tacrolimus, tocilizumab, and vismodegib.

Non-limiting examples of additional therapeutic agents and/or regimens for treating acute graft-vs-host disease include alemtuzumab, alpha-1 antitrypsin, antithymocyte globulin, basiliximab, brentuximab, corticosteroids (e.g., methylprednisone, prednisone), cyclosporine, dacilzumab, defribrotide, denileukin diftitox, ibrutinib, infliximab, itacitinib, LBH589, mycophenolate mofetil, natalizumab, neihulizumab, pentostatin, photopheresis, ruxolitinib, sirolimus, tacrolimus, and tocilizumab.

Non-limiting examples of additional therapeutic agents and/or regimens for treating chronic graft vs. host disease include abatacept, alemtuzumab, AMG592, antithymocyte globulin, basiliximab, bortezomib, corticosteroids (e.g., methylprednisone, prednisone), cyclosporine, dacilzumab, denileukin diftitox, glasdegib, ibrutinib, IL-2, imatinib, infliximab, mycophenolate mofetil, pentostatin, photobiomodulation, photopheresis, ruxolitinib, sirolimus, sonidegib, tacrolimus, tocilizumab, and vismodegib.

Non-limiting examples of additional therapeutic agents and/or regimens for treating celiac disease include AMG 714, AMY01, *Aspergillus niger* prolyl endoprotease, BL-7010, CALY-002, GBR 830, Hu-Mik-Beta-1, IMGX003, KumaMax, Larazotide Acetate, Nexvan2®, pancrelipase, TIMP-GLIA, vedolizumab, and ZED1227.

Non-limiting examples of additional therapeutic agents and/or regimens for treating psoriasis include topical corticosteroids, topical crisaborole/AN2728, topical SNA-120, topical SAN021, topical tapinarof, topical tocafinib, topical IDP-118, topical M518101, topical calcipotriene and betamethasone dipropionate (e.g., MC2-01 cream and Taclonex®), topical P-3073, topical LEO 90100 (Enstilar®), topical betamethasone dipropriate (Sernivo®), halobetasol propionate (Ultravate®), vitamin D analogues (e.g., calcipotriene (Dovonex®) and calcitriol (Vectical®)), anthralin (e.g., Dritho-Scalp® and Dritho-Creme®), topical retinoids (e.g., tazarotene (e.g., Tazorac® and Avage®)), calcineurin inhibitors (e.g., tacrolimus (Prograf®) and pimecrolimus (Elidel®)), salicylic acid, coal tar, moisturizers, phototherapy (e.g., exposure to sunlight, UVB phototherapy, narrow band UVB phototherapy, Goeckerman therapy, psoralen plus ultraviolet A (PUVA) therapy, and excimer laser), retinoids (e.g., acitretin (Soriatane®)), methotrexate (Trexall®, Otrexup®, Rasuvo®, Rheumatrex®), Apo805K1, baricitinib, FP187, KD025, prurisol, VTP-43742, XP23829, ZPL-389, CF101 (piclidenoson), LAS41008, VPD-737 (serlopitant), upadacitinib (ABT-494), aprmilast, tofacitibin, cyclosporine (Neoral®, Sandimmune®, Gengraf®), biologics (e.g., etanercept (Enbrel®), entanercept-szzs (Elrezi®), infliximab (Remicade®), adalimumab (Humira®), adalimumab-adbm (Cyltezo®), ustekinumab (Stelara®), golimumab (Simponi®), apremilast (Otezla®), secukinumab (Cosentyx®), certolixumab pegol, secukinumab, tildrakizumab-asmn, infliximab-dyyb, abatacept, ixekizumab (Taltz®), ABP 710, BCD-057, BI695501, bimekizumab (UCB4940), CHS-1420, GP2017, guselkumab (CNTO 1959), HD203, M923, MSB11022, Mirikizumab (LY3074828), PF-06410293, PF-06438179, risankizumab (BI655066), SB2, SB4, SB5, siliq (brodalumab), namilumab (MT203, tildrakizumab (MK-3222), and ixekizumab (Taltz®)), thioguanine, and hydroxyurea (e.g., Droxia® and Hydrea®).

Non-limiting examples of additional therapeutic agents and/or regimens for treating cutaneous T-cell lymphoma include phototherapy (e.g., exposure to sunlight, UVB phototherapy, narrow band UVB phototherapy, Goeckerman therapy, psoralen plus ultraviolet A (PUVA) therapy, and excimer laser), extracorporeal photopheresis, radiation therapy (e.g., spot radiation and total skin body electron beam therapy), stem cell transplant, corticosteroids, imiquimod, bexarotene gel, topical bis-chloroethyl-nitrourea, mechlorethamine gel, vorinostat (Zolinza®), romidepsin (Istodax®), pralatrexate (Folotyn®) biologics (e.g., alemtuzumab (Campath®), brentuximab vedotin (SGN-35), mogamulizumab, and IPH4102).

Non-limiting examples of additional therapeutic agents and/or regimens for treating uveitis include corticosteroids (e.g., intravitreal triamcinolone acetonide injectable suspensions), antibiotics, antivirals (e.g., acyclovir), dexamethasone, immunomodulators (e.g., tacrolimus, leflunomide, cyclophosphamide (Cytoxan®, Neosar®, Endoxan®), and cyclosporine (Neoral®, Sandimmune®, Gengraf®), chlorambucil, azathioprine, methotrexate, and mycophenolate mofetil), biologics (e.g., infliximab (Remicade®), adalimumab (Humira®), etanercept (Enbrel®), golimumab (Simponi®), certolizumab (Cimzia®), rituximab (Rituxan®), abatacept (Orencia®), basiliximab (Simulect®), anakinra (Kineret®), canakinumab (Ilaris®), gevokixumab (XOMA052), tocilizumab (Actemra®), alemtuzumab (Campath®), efalizumab (Raptiva®), LFG316, sirolimus (Santen®), abatacept, sarilumab (Kevzara®), and daclizumab (Zenapax®)), cytotoxic drugs, surgical implant (e.g., fluocinolone insert), and vitrectomy.

Non-limiting examples of additional therapeutic agents and/or regimens for treating mucositis include AG013, SGX942 (dusquetide), amifostine (Ethyol®), cryotherapy, cepacol lonzenges, capsaicin lozenges, mucoadhesives (e.g., MuGard®) oral diphenhydramine (e.g., Benadry® elixir), oral bioadherents (e.g., polyvinylpyrrolidone-sodium hyaluronate gel (Gelclair®)), oral lubricants (e.g., Oral Balance®), caphosol, *chamomilla recutita* mouthwash, edible grape plant exosome, antiseptic mouthwash (e.g., chlorhexidine gluconate (e.g., Peridex® or Periogard®), topical pain relievers (e.g., lidocaine, benzocaine, dyclonine hydrochloride, xylocaine (e.g., viscous xylocaine 2%), and Ulcerease® (0.6% phenol)), corticosteroids (e.g., prednisone), pain killers (e.g., ibuprofen, naproxen, acetaminophen, and opioids), GC4419, palifermin (keratinocyte growth factor; Kepivance®), ATL-104, clonidine lauriad, IZN-6N4, SGX942, rebamipide, nepidermin, soluble β-1,3/1,6 glucan, P276, LP-0004-09, CR-3294, ALD-518, IZN-6N4, quercetin, granules comprising *vaccinium myrtillus* extract, macleaya *cordata* alkaloids and *echinacea angustifolia* extract (e.g., SAMITAL®), and gastrointestinal cocktail (an acid reducer such aluminum hydroxide and magnesium hydroxide (e.g., Maalox), an antifungal (e.g., nystatin), and an analgesic (e.g., hurricane liquid)). For example, non-limiting examples of treatments for oral mucositis include AG013, amifostine (Ethyol®), cryotherapy, cepacol lonzenges, mucoadhesives (e.g., MuGard®) oral diphenhydramine (e.g., Benadry® elixir), oral bioadherents (e.g., polyvinylpyrrolidone-sodium hyaluronate gel (Gelclair®)), oral lubricants (e.g., Oral Balance®), caphosol, *chamomilla recutita* mouthwash, edible grape plant exosome, antiseptic mouthwash (e.g., chlorhexidine gluconate (e.g., Peridex® or Periogard®), topical pain relievers (e.g., lidocaine, benzocaine, dyclonine hydrochloride, xylocaine (e.g., viscous xylocaine 2%), and Ulcerease® (0.6% phenol)), corticosteroids (e.g., prednisone), pain killers (e.g., ibuprofen, naproxen, acetaminophen, and opioids), GC4419, palifermin (keratinocyte growth factor; Kepivance®), ATL-104, clonidine lauriad, IZN-6N4, SGX942, rebamipide, nepidermin, soluble β-1,3/1,6 glucan, P276, LP-0004-09, CR-3294, ALD-518, IZN-6N4, quercetin, and gastrointestinal cocktail (an acid reducer such aluminum hydroxide and magnesium hydroxide (e.g., Maalox), an antifungal (e.g., nystatin), and an analgesic (e.g., hurricane liquid)). As another example, non-limiting examples of treatments for esophageal mucositis include xylocaine (e.g., gel viscous Xylocaine 2%). As another example, treatments for intestinal mucositis, treatments to modify intestinal mucositis, and treatments for intestinal mucositis signs and symptoms include gastrointestinal cocktail (an acid reducer such aluminum hydroxide and magnesium hydroxide (e.g., Maalox), an antifungal (e.g., nystatin), and an analgesic (e.g., hurricane liquid)).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the STING protein can serve as a biomarker for certain types of cancer, e.g., colon cancer and prostate cancer. In other embodiments, identifying a subject can include assaying the patient's tumor microenvironment for the absence of T-cells and/or presence of exhausted T-cells, e.g., patients having one or more cold tumors. Such patients can include those that are resistant to treatment with checkpoint inhibitors. In certain embodiments, such patients can be treated with a chemical entity herein, e.g., to recruit T-cells into the tumor, and in some cases, further treated with one or more checkpoint inhibitors, e.g., once the T-cells become exhausted.

In some embodiments, the chemical entities, methods, and compositions described herein can be administered to certain treatment-resistant patient populations (e.g., patients resistant to checkpoint inhibitors; e.g., patients having one or more cold tumors, e.g., tumors lacking T-cells or exhausted T-cells).

Compound Preparation

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224, the contents of each of which are hereby incorporated by reference in their entirety. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^{1}$H NMR, heteronuclear NMR, mass spectrometry, liquid chromatography, and infrared spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

EXAMPLES

Synthesis of Compound 100

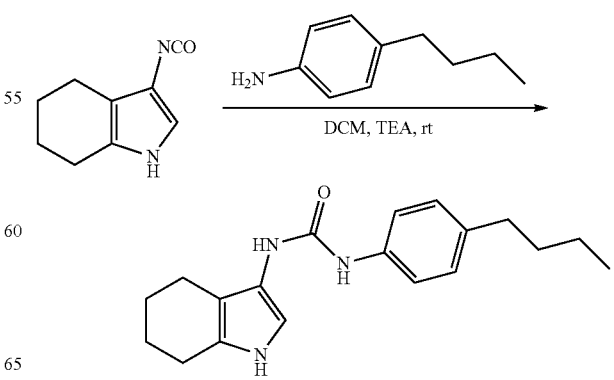

4-Butylaniline (1 mmol) and TEA (1 mmol) is dissolved in DCM, and the solution cooled to 0° C. 3-Isocyanato-4,5,6,7-tetrahydro-1H-indole (1 mmol) is added dropwise over 10 minutes and the mixture allowed to stir at room temperature overnight. Water is added, and the organic layer is separated. The organic layer is dried over anhydrous MgSO₄, and solvent is removed under reduced pressure. The crude product is purified by flash chromatography on silica gel using hexane/EtOAc as an eluent.

The following examples are synthesized by the method described above from the corresponding isocyanate and amine

| Compound # | Isocyanate | Amine | Final Structure | Mol. Wt |
|---|---|---|---|---|
| 102 | 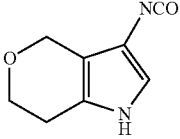 | 4-butyl-aniline |  | 313.1790 |
| 103 | 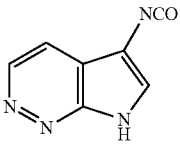 | 4-butyl-aniline | 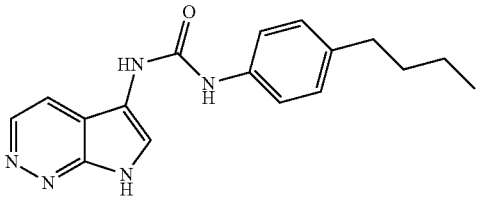 [SMILES: CCCCc1ccc(NC(=O)Nc2c[nH]c3nnccc23)cc1] | 309.1590 |
| 104 | 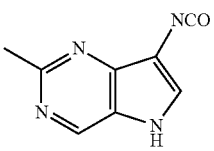 | 4-butyl-aniline | 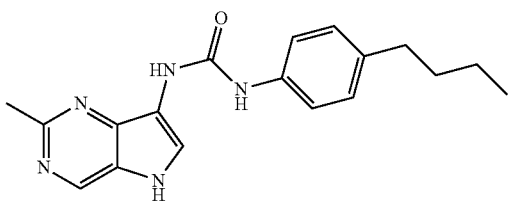 [SMILES: CCCCc1ccc(NC(=O)Nc2c[nH]c3cnc(C)nc23)cc1] | 323.1746 |
| 105 | 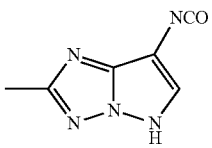 | 4-butyl-aniline | 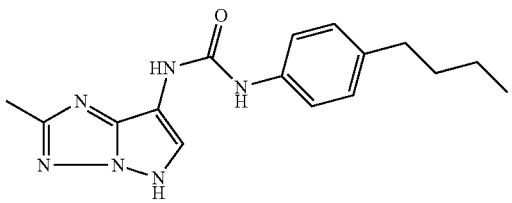 [SMILES: CCCCc1ccc(NC(=O)Nc2c[nH]n3nc(C)nc23)cc1] | 312.17 |
| 106 | 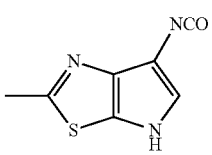 | 4-butyl-aniline | 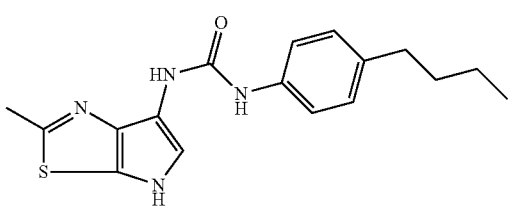 [SMILES: CCCCc1ccc(NC(=O)Nc2c[nH]c3sc(C)nc23)cc1] | 328.13 |
| 107 | 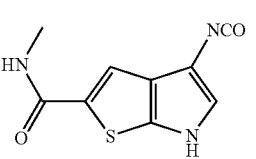 | 4-butyl-aniline | 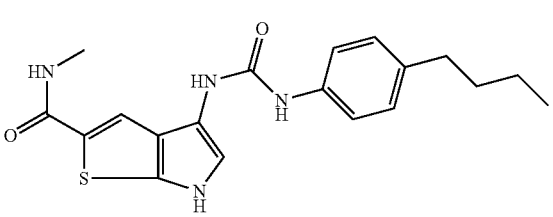 [SMILES: CCCCc1ccc(NC(=O)Nc2c[nH]c3sc(C(=O)NC)cc23)cc1] | 370.14 |

-continued

| Compound # | Isocyanate | Amine | Final Structure | Mol. Wt |
|---|---|---|---|---|
| 108 | (structure with F₃C, S, N, NH, NCO) | 4-butyl-aniline | (urea structure with F₃C-thienopyrazole and 4-butylphenyl) | 382.1 |
| 109 | (5-azaindole-3-NCO) | 4-(ethoxymethyl)aniline | (urea with 5-azaindole and 4-(ethoxymethyl)phenyl) | 310.1 |
| 110 | (5-azaindole-3-NCO) | 4-(tetrahydro-2H-pyran-4-yl)aniline | (urea with 5-azaindole and 4-(tetrahydropyran-4-yl)phenyl) | 336.2 |
| 111 | (5-azaindole-3-NCO) | quinolin-7-amine | (urea with 5-azaindole and quinolin-7-yl) | 303.1 |
| 112 | (5-azaindole-3-NCO) | 5,6,7,8-tetrahydro-quinolin-7-amine | (urea with 5-azaindole and tetrahydroquinolin-7-yl) | 307.1 |
| 113 | (5-azaindole-3-NCO) | 1-oxaspiro[5.5]undecan-9-amine | (urea with 5-azaindole and 1-oxaspiro[5.5]undecan-9-yl) | 328.2 |
| 114 | (5-azaindole-3-NCO) | 2-ethyl-7-azaspiro[4,5]decane | (amide with 5-azaindole and 2-ethyl-7-azaspiro[4,5]decan-7-yl) | |

| Compound # | Isocyanate | Amine | Final Structure | Mol. Wt |
|---|---|---|---|---|
| 115 | 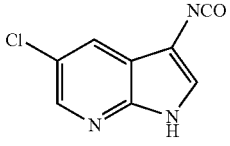 | 4-butyl-aniline | 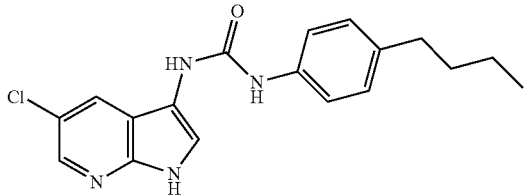 [SMILES: CCCCc1ccc(NC(=O)Nc2c[nH]c3ncc(Cl)cc23)cc1] | 342.2 |
| 116 |  | 4-butyl-aniline | 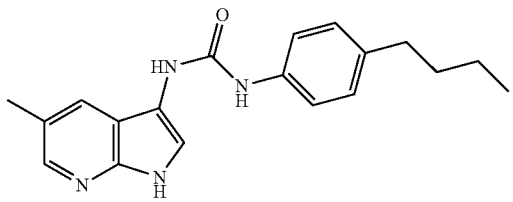 [SMILES: CCCCc1ccc(NC(=O)Nc2c[nH]c3ncc(C)cc23)cc1] | 322.2 |
| 117 | 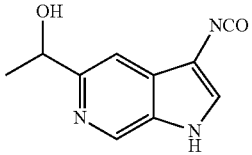 | 4-butyl-aniline | 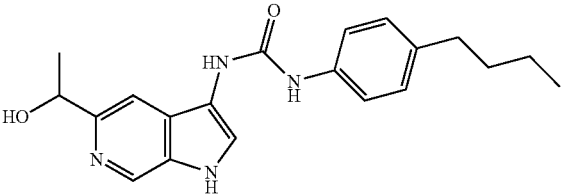 [SMILES: CCCCc1ccc(NC(=O)Nc2c[nH]c3cnc(C(C)O)cc23)cc1] | 352.2 |
| 118 | 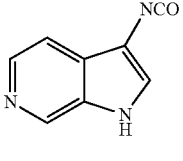 | 4-((1-ethylcyclo-propyl)meth-yl)aniline | 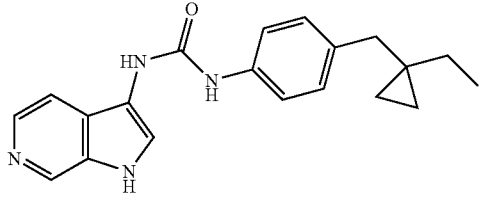 [SMILES: CCC1(Cc2ccc(NC(=O)Nc3c[nH]c4cnccc34)cc2)CC1] | 334.2 |
| 119 |  | 4-(2,2-difluorobutyl)aniline | 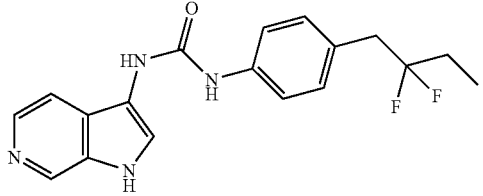 [SMILES: CCC(F)(F)Cc1ccc(NC(=O)Nc2c[nH]c3cnccc23)cc1] | 344.2 |
| 120 | 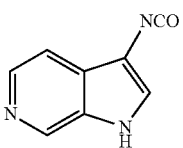 | bicyclo[3.2.1]octan-3-amine | 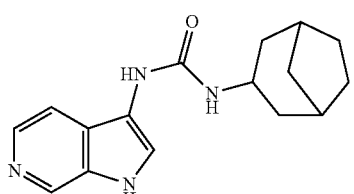 | 284.2 |
| 121 | 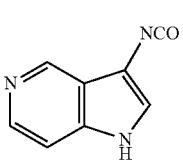 | 4-(((2,2,2-trifluoroeth-yl)amino)methyl)ani-line | 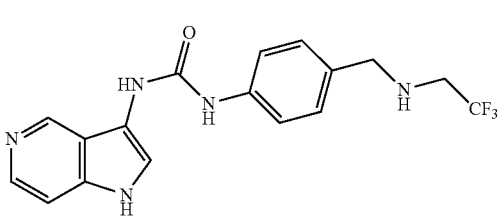 [SMILES: O=C(Nc1ccc(CNCC(F)(F)F)cc1)Nc1c[nH]c2ccncc12] | 363.2 |

-continued
| Compound # | Isocyanate | Amine | Final Structure | Mol. Wt |
|---|---|---|---|---|
| 122 | 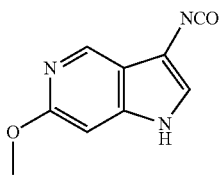 | 4-(ethoxymethyl)aniline | 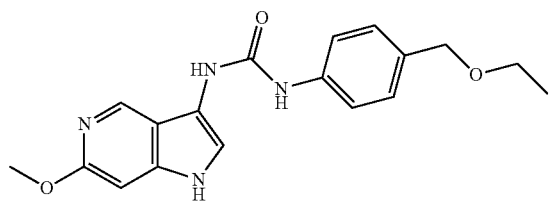 [SMILES: CCOCc1ccc(NC(=O)Nc2c[nH]c3cc(OC)ncc23)cc1] | 340.2 |
| 123 | 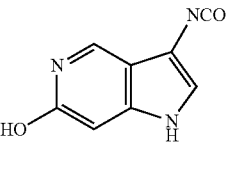 | 4-(ethoxymethyl)aniline | 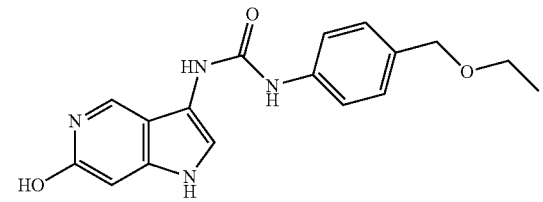 [SMILES: CCOCc1ccc(NC(=O)Nc2c[nH]c3cc(O)ncc23)cc1] | 326.2 |
| 124 | 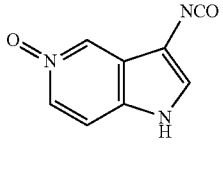 | 4-(ethoxymethyl)aniline | 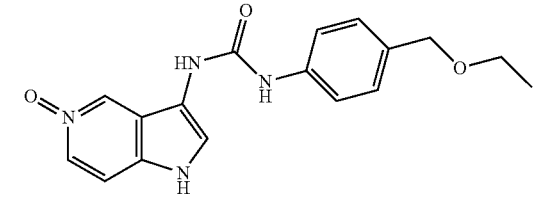 [SMILES: CCOCc1ccc(NC(=O)Nc2c[nH]c3cc[n+]([O-])cc23)cc1] | 326.2 |
| 125 | 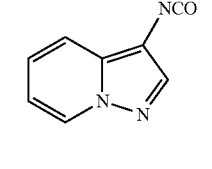 | 4-(ethoxymethyl)aniline | 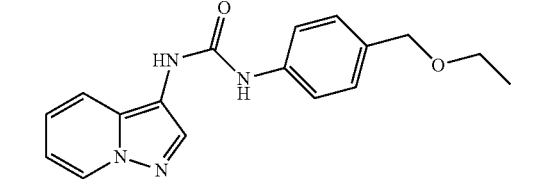 [SMILES: CCOCc1ccc(NC(=O)Nc2cnn3ccccc23)cc1] | 310.2 |
| 126 | 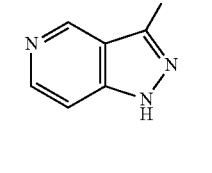 | 4-(ethoxymethyl)aniline | 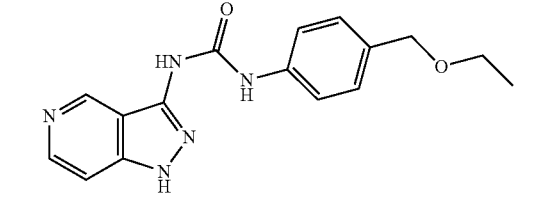 | 311.2 |
| 127 | 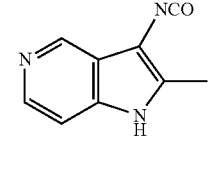 | 4-(ethoxymethyl)aniline | 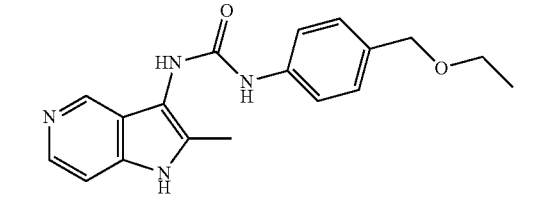 [SMILES: CCOCc1ccc(NC(=O)Nc2c(C)[nH]c3ccncc23)cc1] | 324.2 |

Compounds 132-183b are synthesized using the methods described above.
| Compound # | |
|---|---|
| 132 | 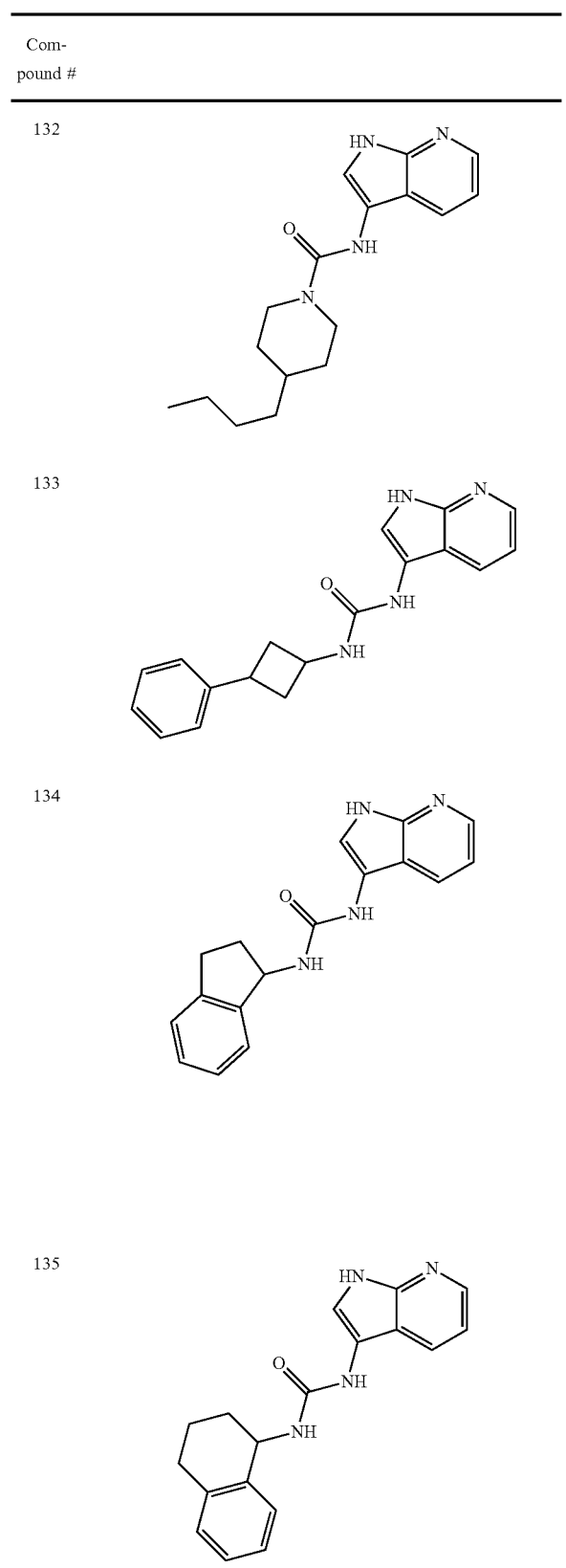 |
| 133 | |
| 134 | |
| 135 | |
| Compound # | |
|---|---|
| 136 | 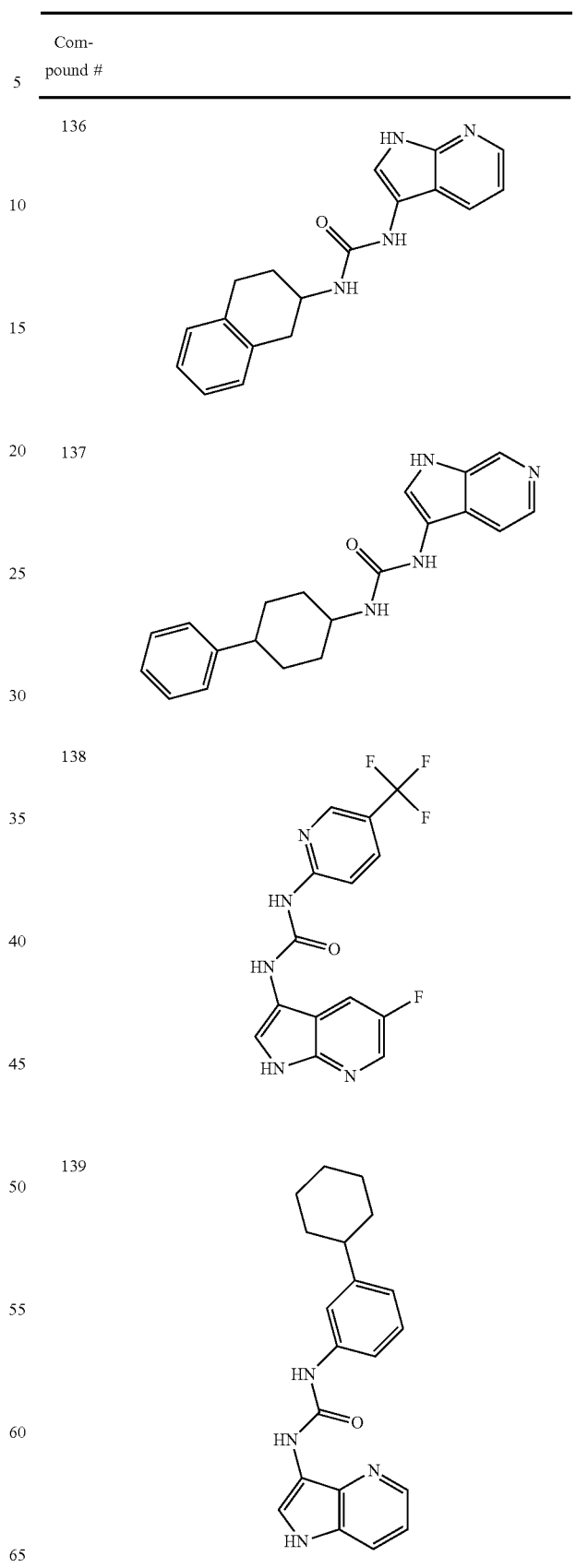 |
| 137 | |
| 138 | |
| 139 | |

| Compound # | | Compound # | |
|---|---|---|---|
| 140 | 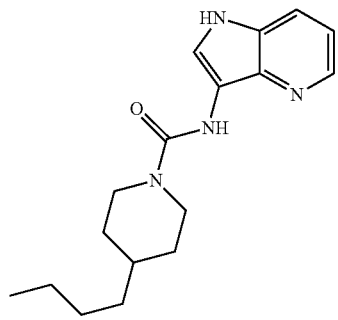 [SMILES: CCCCC1CCN(C(=O)Nc2c[nH]c3cccnc23)CC1] | 145 | 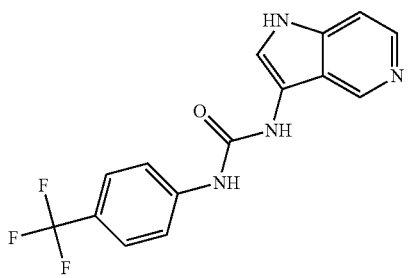 |
| 141 | 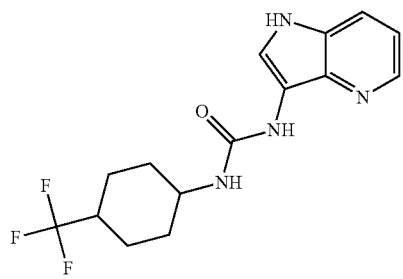 [SMILES: O=C(Nc1c[nH]c2cccnc12)NC1CCC(C(F)(F)F)CC1] | 146 | 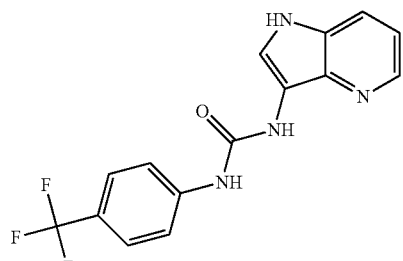 |
| 142 | 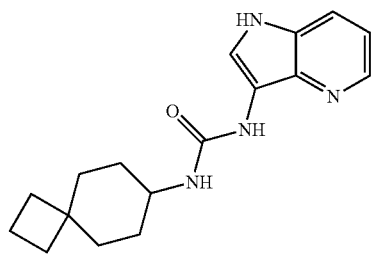 [SMILES: O=C(Nc1c[nH]c2cccnc12)NC1CCC2(CCC2)CC1] | 147 | 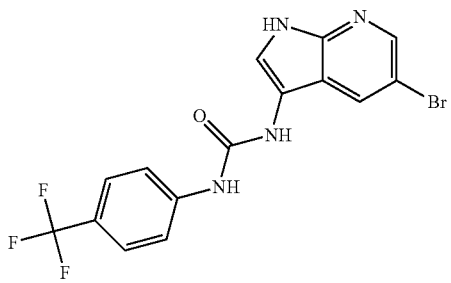 |
| 143 | 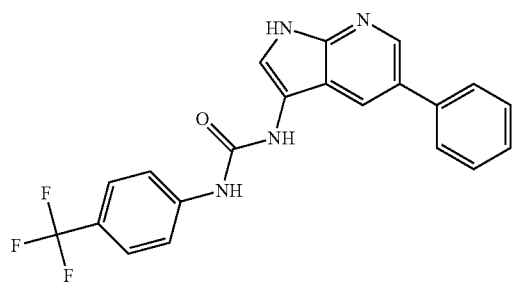 [SMILES: O=C(Nc1ccc(C(F)(F)F)cc1)Nc1c[nH]c2ncc(-c3ccccc3)cc12] | 148 | 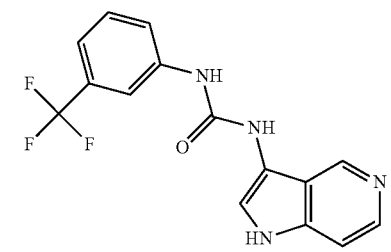 |
| 144 | 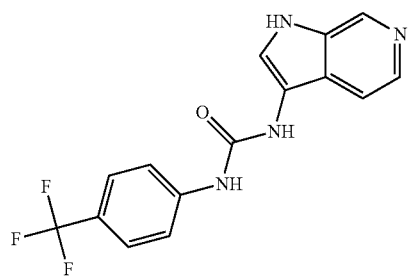 | 149 | 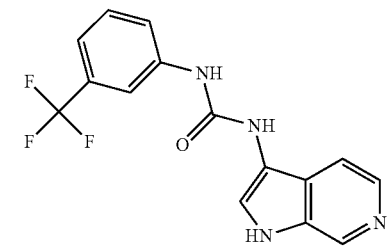 [SMILES: O=C(Nc1cccc(C(F)(F)F)c1)Nc1c[nH]c2cnccc12] |

-continued
| Compound # | |
|---|---|
| 150 | 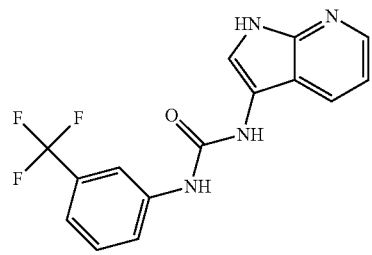 [SMILES: O=C(Nc1cccc(C(F)(F)F)c1)Nc1c[nH]c2ncccc12] |
| 151 | 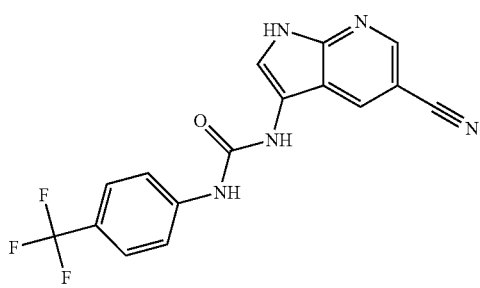 [SMILES: N#Cc1cnc2[nH]cc(NC(=O)Nc3ccc(C(F)(F)F)cc3)c2c1] |
| 152 | 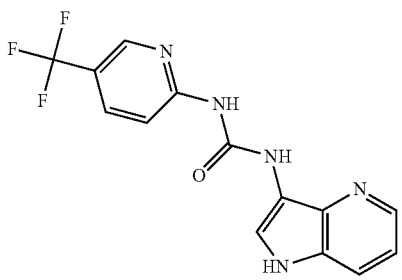 [SMILES: O=C(Nc1ccc(C(F)(F)F)cn1)Nc1c[nH]c2cccnc12] |
| 153 | 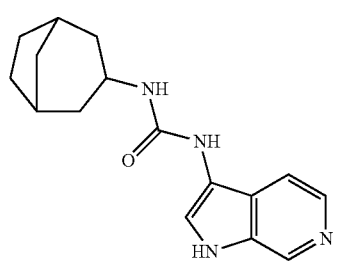 [SMILES: O=C(Nc1c[nH]c2cnccc12)NC1CC2CCC(C2)C1] |
| 154 | 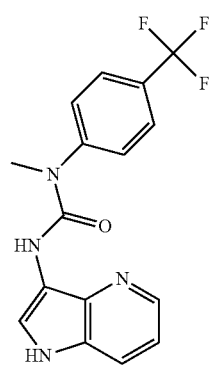 [SMILES: CN(C(=O)Nc1c[nH]c2cccnc12)c1ccc(C(F)(F)F)cc1] |
-continued
| Compound # | |
|---|---|
| 155 | 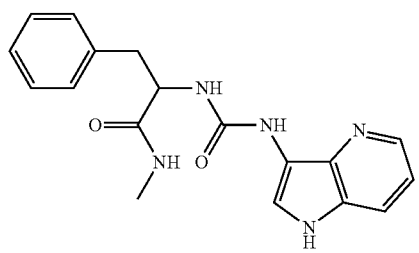 [SMILES: CNC(=O)C(Cc1ccccc1)NC(=O)Nc1c[nH]c2cccnc12] |
| 156 | 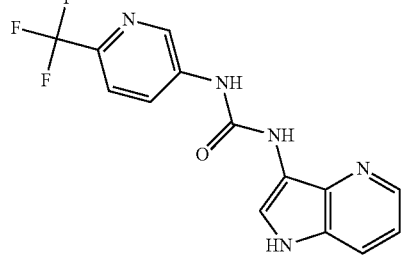 |
| 157 | 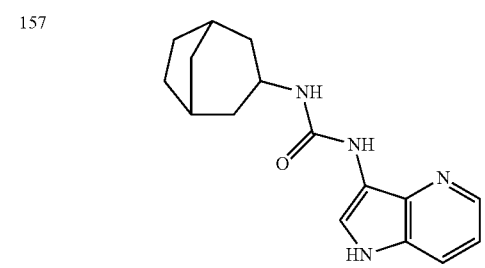 |
| 158 | 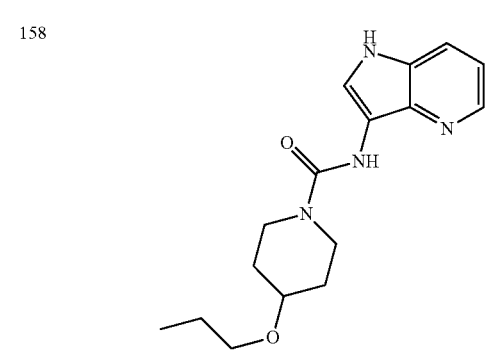 |
| 159 | 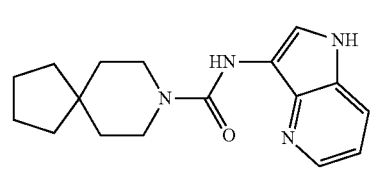 [SMILES: O=C(Nc1c[nH]c2cccnc12)N1CCC2(CCCC2)CC1] |

| Compound # | | Compound # | |
|---|---|---|---|
| 160 | 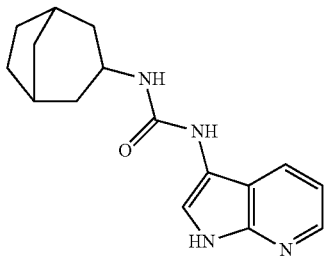 [SMILES: O=C(Nc1c[nH]c2ncccc12)NC1CC2CCC(C2)C1] | 165 | 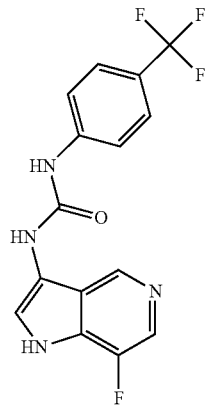 |
| 161 | 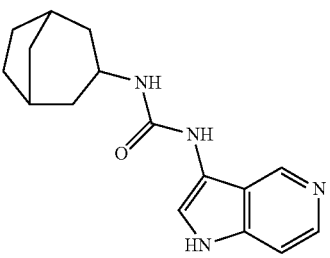 [SMILES: O=C(Nc1c[nH]c2ccncc12)NC1CC2CCC(C2)C1] | 166 | 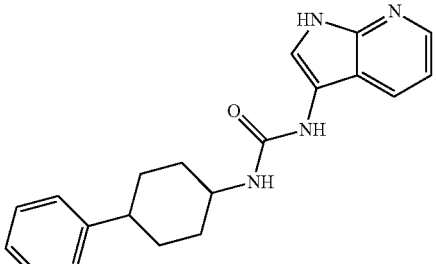 |
| 162 | 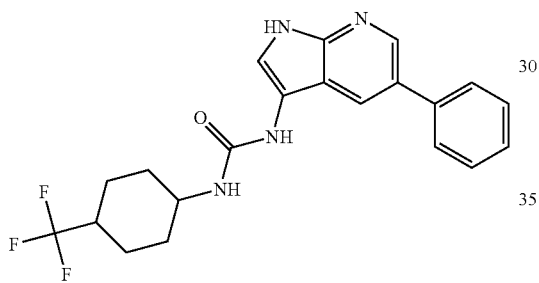 | 167 | 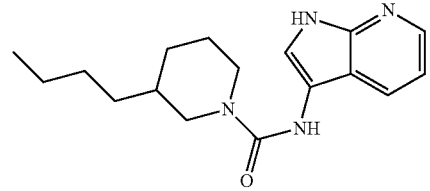 |
| 163 | 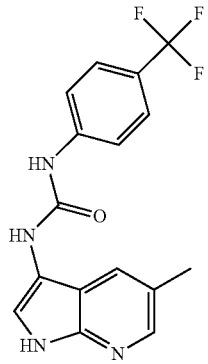 [SMILES: Cc1cnc2[nH]cc(NC(=O)Nc3ccc(C(F)(F)F)cc3)c2c1] | 168 | 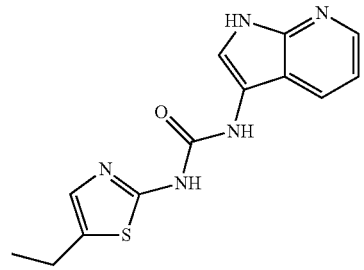 |
| 164 | 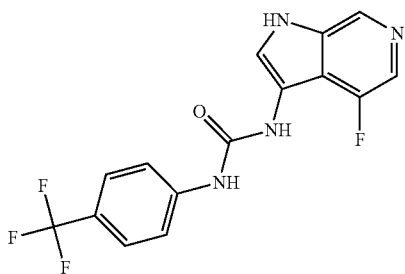 [SMILES: O=C(Nc1ccc(C(F)(F)F)cc1)Nc1c[nH]c2cncc(F)c12] | 169 | 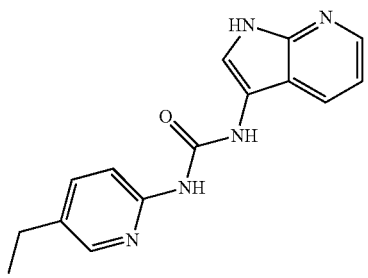 [SMILES: CCc1ccc(NC(=O)Nc2c[nH]c3ncccc23)nc1] |

| Compound # |
|---|
| 170 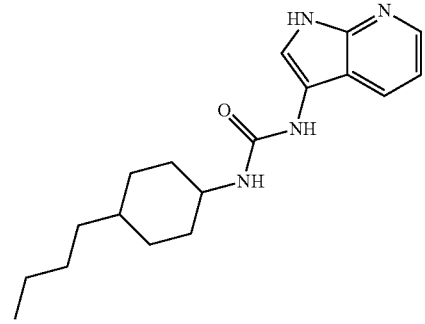 [SMILES: CCCCC1CCC(NC(=O)Nc2c[nH]c3ncccc23)CC1] |
| 171 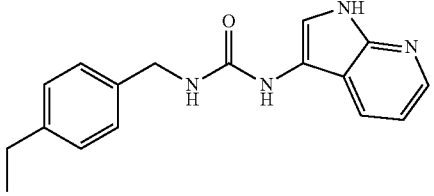 [SMILES: CCc1ccc(CNC(=O)Nc2c[nH]c3ncccc23)cc1] |
| 172 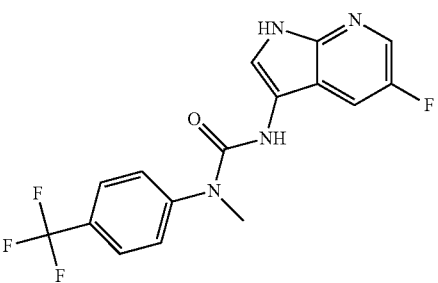 [SMILES: CN(C(=O)Nc1c[nH]c2ncc(F)cc12)c1ccc(C(F)(F)F)cc1] |
| 173 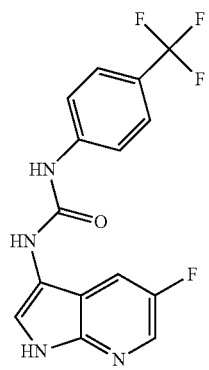 |
| 174 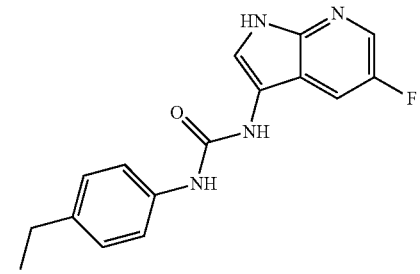 [SMILES: CCc1ccc(NC(=O)Nc2c[nH]c3ncc(F)cc23)cc1] |
| Compound # |
|---|
| 179 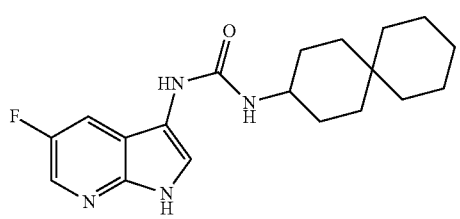 [SMILES: O=C(Nc1c[nH]c2ncc(F)cc12)NC1CCC2(CCCCC2)CC1] |
| 180 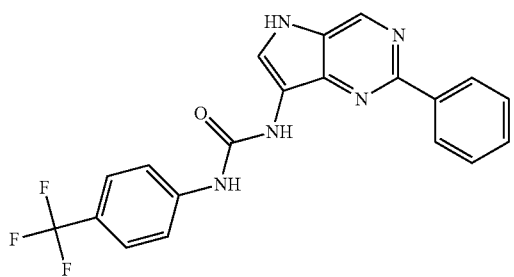 [SMILES: O=C(Nc1ccc(C(F)(F)F)cc1)Nc1c[nH]c2cnc(-c3ccccc3)nc12] |
| 181 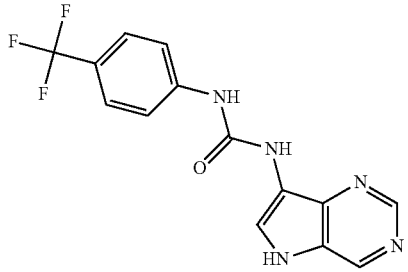 [SMILES: O=C(Nc1ccc(C(F)(F)F)cc1)Nc1c[nH]c2cncnc12] |
| 182 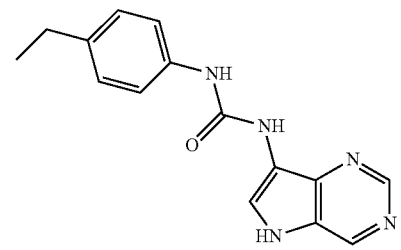 [SMILES: CCc1ccc(NC(=O)Nc2c[nH]c3cncnc23)cc1] |
| 183 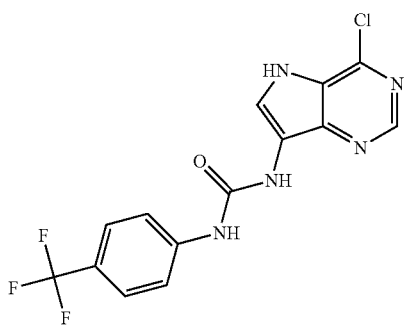 [SMILES: O=C(Nc1ccc(C(F)(F)F)cc1)Nc1c[nH]c2c(Cl)ncnc12] |

| Compound # | Structure | |
|---|---|---|
| 183b | 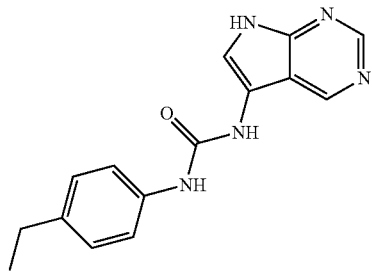 [SMILES: CCc1ccc(NC(=O)Nc2c[nH]c3ncncc23)cc1] | |

Compound 29 is synthesized from Compound 9 via thiolation. Compound 30 is synthesized from Compound 29. Compound 31 is obtained from deprotection of Compound 30 (e.g., under acidic conditions such as TFA).

| Compound # | Structure | Mol. Weight |
|---|---|---|
| 129 | 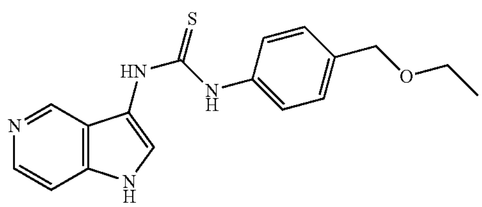 | 270.3 |
| 130 | 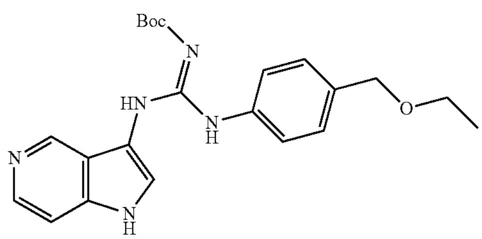 [SMILES: CCOCc1ccc(N/C(=N/C(=O)OC(C)(C)C)Nc2c[nH]c3ccncc23)cc1] | 409.2 |
| 131 | 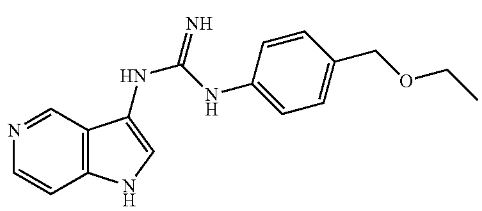 [SMILES: CCOCc1ccc(NC(=N)Nc2c[nH]c3ccncc23)cc1] | 309.2 |

Abbreviation of Chemical Terms

ACN=acetonitrile
AcOH=acetic acid
BTC=trichloromethyl chloroformate
DBU=1,8-diazabicycloundec-7-ene
DCM=dichloromethane
Dess-Martin=(1,1,1-triacetoxy)-1,1-dihydro-1,2-benziodoxol-3(1H)-one
DMEDA=N,N'-dimethylethylenediamine
DMF=N,N-dimethylformamide
DMSO=dimethyl sulfoxide
Et=ethyl
EtOH=ethanol
LC-MS=liquid chromatography-mass spectrometry
LDA=lithium diisopropylamide
Me=methyl
MeOH=methanol
n-Bu=n-butyl
NBS=N-bromosuccinimide
NCS=N-chlorosuccinimide
NIS=N-iodosuccinimide
NMR=nuclear magnetic resonance
Pd(dppf)Cl$_2$=dichloro[1,1'-bis(diphenylphosphino)ferrocene]palladium
Pd(PPh3)$_4$=tetrakis(triphenylphosphine)Palladium(0)
Ph=phenyl
PE=petroleum ether
HPLC=high performance liquid chromatography
PTSA=p-toluenesulfonic acid
Py=pyridine
RT=room temperature
TBAF=tetrabutylammonium fluoride
TBDPSCl=t-Budiphenylsilyl chloride
t-Bu=tert-butyl
TEA=triethylamine
TFA=trifluoro acetic acid
THF=tetrahydrofuran
Ti(i-PrO)$_4$=tetraisopropyl titanate
TLC=thin layer chromatography
SEM-Cl=(2-(chloromethoxy)ethyl)trimethylsilane
CDI=N,N'-Carbonyldiimidazole Materials and Methods The progress of reactions was often monitored by TLC or LC-MS. The identity of the products was often confirmed by LC-MS. The LC-MS was recorded using one of the following methods.

Method A:

Shim-pack XR-ODS, C18, 3×50 mm, 2.5 um column, 1.0 uL injection, 1.5 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B:
Kinetex EVO, C18, 3×50 mm, 2.2 um column, 1.0 uL injection, 1.5 mL/min flow rate, 90-900 amu scan range, 190-400 nm UV range, 10-95% (1.1 min), 95% (0.6 min) gradient with ACN and water (0.5% NH4HCO3), 2 minute total run time.

Method C:
Shim-pack XR-ODS, C18, 3×50 mm, 2.5 um column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D:
Kinetex EVO, C18, 3×50 mm, 2.2 um column, 1.0 uL injection, 1.5 mL/min flow rate, 90-900 amu scan range, 190-400 nm UV range, 10-95% (2.1 min), 95% (0.6 min) gradient with ACN and water (0.5% NH4HCO3), 3 minute total run time.

Method E:
YMC Triart-C18, 50*3.0 mm, 1.0 uL injection, 1.0 mL/min flowrate, 90-900 amu scan range, 254 nm UV detection. Mobile phase A: Water (5 mmoL/L NH4HCO3) and Mobile Phase B: MeCN. 10% MPB to 95.0% in 1.1 min, hold at 95% MPB for 0.5 min, 95% MPB to 10% in 0.1 min, then equilibration to 10% MPB for 0.1 min, 1.8 minute total run time Method F:
Poroshell HPH-C18, 50*3.0 mm, 2.7 um, 0.3 uL injection, 1.5 mL/min flowrate, 90-900 amu scan range, 254 nm UV detection. Mobile phase A: Water (5 mmoL/L NH4HCO3) and Mobile Phase B: MeCN. 10% MPB to 95.0% in 2.0 min, hold at 95% MPB for 0.6 min, 95% MPB to 10% in 0.15 min, then equilibration to 10% MPB for 0.15 min.

Method G:
Kinetex EVO, C18, 3×50 mm, 2.2 um column, 0.3 uL injection, 1.5 mL/min flow rate, 90-900 amu scan range, 190-400 nm UV range, Mobile phase A: Water (5 mmoL/L NH4HCO3) and Mobile Phase B: MeCN. 10% MPB to 95.0% in 1.1 min, hold at 95% MPB for 0.5 min, 95% MPB to 10% in 0.1 min, then equilibration to 10% MPB for 0.1 min, 1.8 minute total run time Method H:
XBridge C18, 50*3.0 mm, 0.5 uL injection, 1.2 mL/min flowrate, 90-900 amu scan range, 254 nm UV detection. Mobile phase A: Water/5 Mm NH4HCO3 and Mobile Phase B: MeCN. 10% MPB to 95.0% in 1.99 min, hold at 95% MPB for 0.60 min, 95% MPB to 10% in 0.20 min, then equilibration to 10% MPB for 0.20 min.

Method I:
XBridge BEH C18, 50*3.0 mm, 2.5 um injection, 1.2 mL/min flowrate, 90-900 amu scan range, 254 nm UV detection. Mobile phase A: Water (5 mmoL/L NH4HCO3) and Mobile Phase B: MeCN. 10% MPB to 95.0% in 2.0 min, hold at 95% MPB for 0.6 min, 95% MPB to 10% in 0.15 min, then equilibration to 10% MPB for 0.15 min.

Method J: Poroshell HPH-C18, 50*3.0 mm 2.7 um, 1.0 mL/min flowrate, 90-900 amu scan range, 254 nm UV detection. Mobile Phase A: Water/5mMNH4HCO3; Mobile Phase B: ACN; 30% Water/5mMNH4HCO3 to 95% in 3.1 min, hold at 95% ACN for 0.6 min, 100% MPB to 10% in 0.1 min, then equilibration to 10% ACN for 0.2 min.

Method K:
Shim-pack XR-ODS, 50*3.0 mm, 2.2 uL injection, 1.2 mL/min flowrate, 90-900 amu scan range, 254 nm UV detection. Mobile phase A: Water (0.05% TFA) and Mobile Phase B: MeCN. 5% MPB to 80.0% in 3 min, 80% MPB to 95% in 0.2 min. hold at 95% MPB for 0.5 min, 95% MPB to 5% in 0.1 min, then equilibration to 5% MPB for 0.2 min.

Method L:
Titank C18, 50*3.0 mm, 0.5 uL injection, 1.0 mL/min flowrate, 90-900 amu scan range, 210 nm UV detection. Mobile phase A:Water/5 mM NH4HCO3 and Mobile Phase B: ACN. 50 MPB to 95% in 2.89 min, hold at 95% MPB for 0.80 min, 95% MPB to 10% in 0.10 min, then equilibration to 10% MPB for 0.20 min.

Method M: Column: XSelect HSS T3, 100*4.5 mm, 3.5 um injection, 1.5 mL/min flowrate, 90-900 amu scan range, 254 nm UV detection. Mobile phase A: Water/0.05% TFA and Mobile Phase B: ACN/0.05% TFA. 5% MPB to 100% in 2.0 min, hold at 100% MPB for 0.7 min, 100% MPB to 5% in 0.05 min, then equilibration to 5% MPB for 0.25 min.

Method N:
Kinetex XB-C18 100A, 2.7×50 mm, 1.7 um column, 2.0 uL injection, 1.0 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method O:
Column: HALO, 3*30 mm, 0.5 uL injection, 1.5 mL/min flowrate, 90-900 amu scan range, 254 nm UV detection. Mobile phase A: Water/0.1% FA; Mobile Phase B: ACN/0.05% FA; Gradient: 10% B to 100% B in 1.29 min, hold 0.5 min, then equilibration to 10% MPB for 0.03 min.

Method P:
Pre-HPLC, Column, XBridge Shield RP18 OBD (19×250 mm, 10 um); mobile phase, Water (10 mmol/L NH4HCO3) and ACN, UV detection 254/210 nm.

Method Q:
Pre-HPLC, Column, Xselect CSH OBD Column 30*150 mm 5 um; Mobile Phase, Water (0.05% FA) and ACN, UV detection 254/210 nm.

Method R: Pre-HPLC, Column, XBridge Shield RP18 OBD Column, 30*150 mm, 5 um; Mobile Phase, Water (10 mmol/L NH4HCO3+0.1% NH3.H2O) and CAN, UV detection 254/210 nm.

NMR was recorded on BRUKER NMR 300.03 Mz, DUL-C-H, ULTRASHIELD™ 300, AVANCE II 300 B-ACS™ 120 or BRUKER NMR 400.13 Mz, BBFO, ULTRASHIELD™ 400, AVANCE III 400, B-ACS™ 120.

PREPARATIVE EXAMPLES

Scheme for the Preparation of Key Intermediates:
Schemes below illustrate the preparation of key intermediates.

Scheme 1
Synthesis of intermediate 1 (N-(1H-pyrrolo[3,2-b]pyridin-3-yl)-1H-imidazole-1-carboxamide

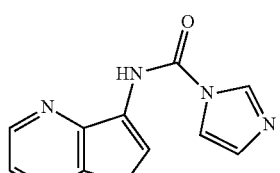

intermediate 1

-continued

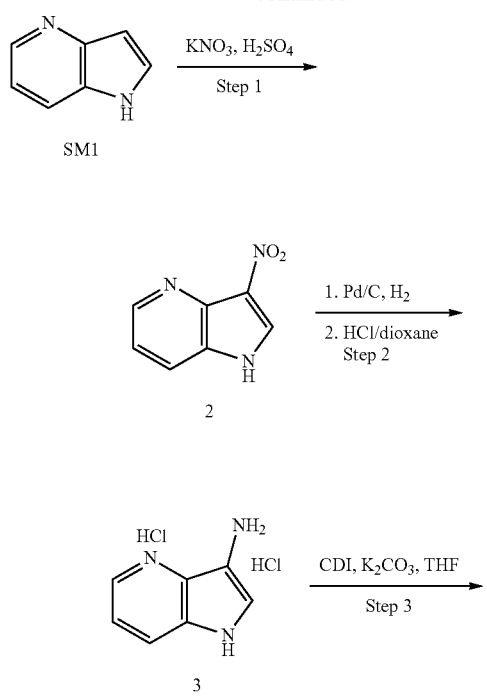

1. Synthesis of 3-nitro-1H-pyrrolo[3,2-b]pyridine

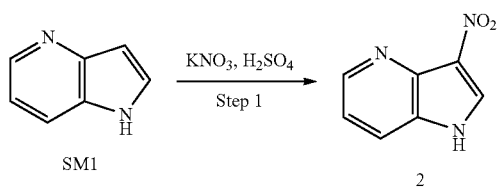 [SMILES: c1cnc2cc[nH]c2c1 ; O=[N+]([O-])c1c[nH]c2cccnc12]

1H-pyrrolo[3,2-b]pyridine (10 g, 84.7 mmol, 1.0 equiv) was dissolved in conc. H₂SO₄ (40 mL). KNO₃ (10.3 g, 101.6 mmol, 1.2 equiv) was added in several portions at 0° C. and stirred for 4 hours at 0° C. After completion of the reaction, pH of the resulting solution was adjusted to 8.0 by dropwise addition of NaOH (1 mol/L) solution. The solid was collected by filtration and washed with water (200 mL×5). 3-Nitro-1H-pyrrolo[3,2-b]pyridine (11 g, 80%) was obtained as a dark solid. LCMS: Method A, MS-ESI, 164.1 [M+H⁺].

2. Synthesis of 1H-pyrrolo[3,2-b]pyridin-3-amine dihydrochloride

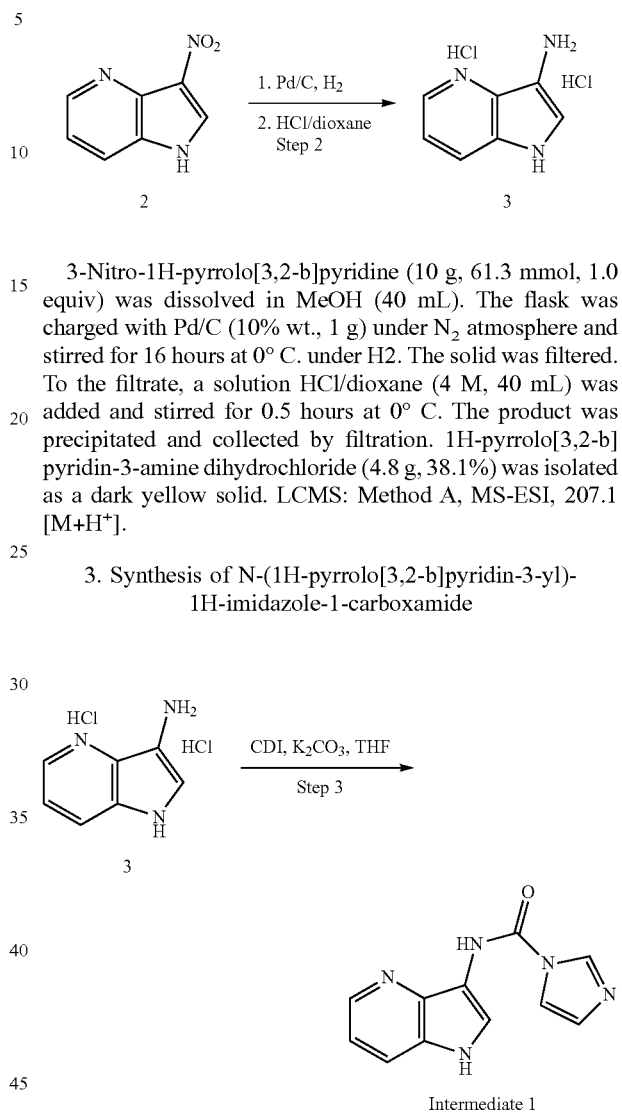

3-Nitro-1H-pyrrolo[3,2-b]pyridine (10 g, 61.3 mmol, 1.0 equiv) was dissolved in MeOH (40 mL). The flask was charged with Pd/C (10% wt., 1 g) under N₂ atmosphere and stirred for 16 hours at 0° C. under H2. The solid was filtered. To the filtrate, a solution HCl/dioxane (4 M, 40 mL) was added and stirred for 0.5 hours at 0° C. The product was precipitated and collected by filtration. 1H-pyrrolo[3,2-b]pyridin-3-amine dihydrochloride (4.8 g, 38.1%) was isolated as a dark yellow solid. LCMS: Method A, MS-ESI, 207.1 [M+H⁺].

3. Synthesis of N-(1H-pyrrolo[3,2-b]pyridin-3-yl)-1H-imidazole-1-carboxamide 1H-pyrrolo[3,2-b]pyridin-3-amine (100.0 mg, 0.8 mmol, 1.0 equiv) was dissolved in THF (10.0 mL). K₂CO₃ (207.6 mg, 1.5 mmol, 2.0 equiv) and CDI (121.8 mg, 0.8 mmol, 1.0 equiv) were added at RT and stirred for 1 h at RT under N₂ atmosphere. The resulting mixture was used directly in the next step without further purification.

Scheme 2
Synthesis of intermediate
2(5-fluoro-1H-pyrrolo[2,3-b]pyridine-3-carbonyl azide)

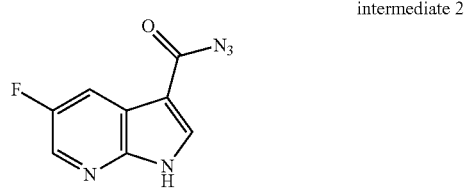

intermediate 2

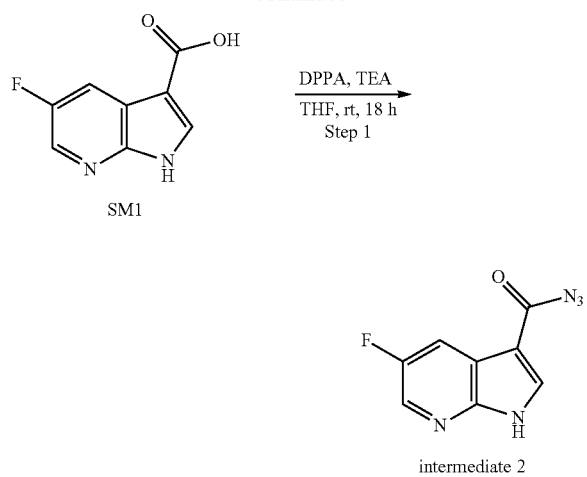

1. Synthesis of 5-fluoro-1H-pyrrolo[2,3-b]pyridine-3-carbonyl azide

5-Fluoro-1H-pyrrolo[2,3-b]pyridine-3-carboxylic acid (10.0 g, 55.6 mmol, 1.0 equiv) was dissolved in THF (100 mL). DPPA (22.9 g, 83.3 mmol, 1.5 equiv) and TEA (11.2 g, 111.1 mmol, 2.0 equiv) were added and stirred for 18 hours at RT and after evaporation of most solvent under vacuum, the crude product was precipitated and collected by filtration, followed by subsequent washing with EtOAc (200 mL×3). 5-Fluoro-1H-pyrrolo[2,3-b]pyridine-3-carbonyl azide (6.3 g, 55.3%) was isolated as a light yellow solid. LCMS: Method L, MS-ESI, 206.2 [M+H$^+$].

The following intermediates were synthesized by method described above from the corresponding acids

Intermediate 2a: 1H-pyrrolo[2,3-c]pyridine-3-carbonyl azide

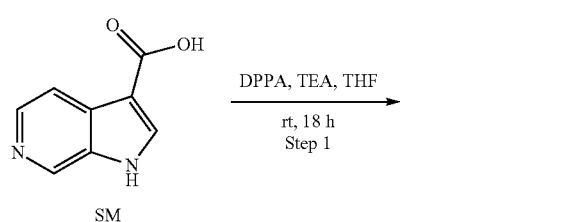

LCMS: Method L, MS-ESI, 188.2 [M+H$^+$].

Intermediate 3a: (1H-pyrrolo[2,3-b]pyridine-3-carbonyl azide)

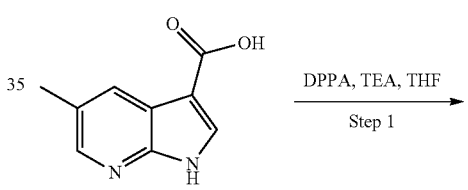

LCMS: Method L, MS-ESI, 188.2 [M+H$^+$].

Intermediate 3b: (5-Methyl-1H-pyrrolo[2,3-b]pyridine-3-carbonyl azide)

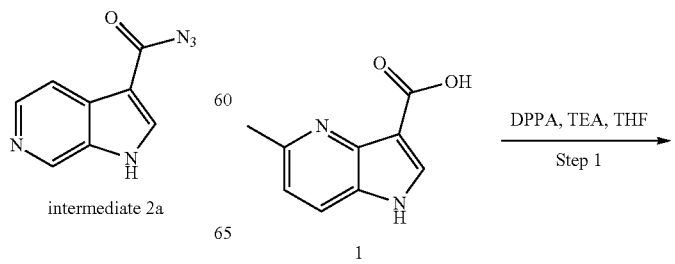

LCMS: Method A, MS-ESI, 202.2 [M+H$^+$].

Intermediate 3c: (5-Methyl-1H-pyrrolo[3,2-b]pyridine-3-carbonyl azide)

-continued

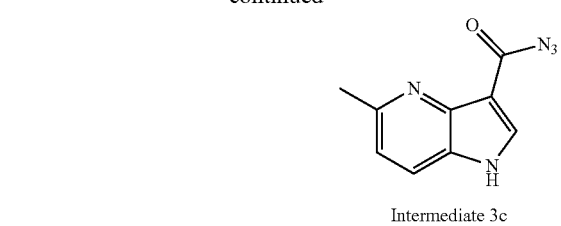

Intermediate 3c

LCMS: Method A, MS-ESI, 202.1 [M+H⁺].

Intermediate 3d:
(1H-pyrrolo[3,2-b]pyridine-3-carbonyl azide)

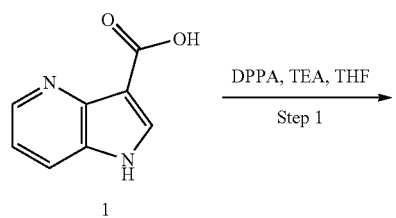

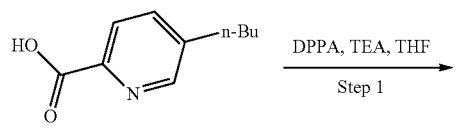

intermediate 3d

LCMS: Method L, MS-ESI, 188.0 [M+H⁺].

Intermediate 3e: (5-butylpicolinoyl azide)

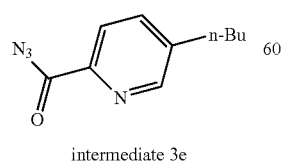

intermediate 3e

LCMS: Method A, MS-ESI, 205.1 [M+H⁺].

Intermediate 3f
(1H-pyrrolo[3,2-c]pyridine-3-carbonyl azide)

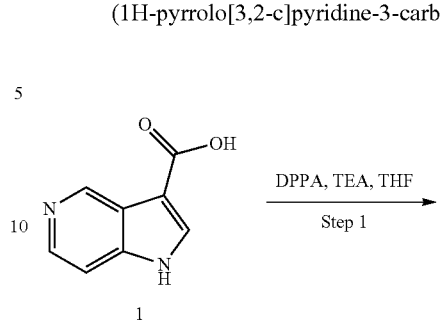

intermediate 3f

LCMS: Method L, MS-ESI, 188.2 [M+H⁺].

Intermediate 3g (6-fluoro-1H-pyrrolo[3,2-b]pyridine-3-carbonyl azide)

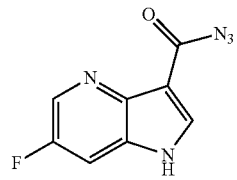

intermediate 3g

LCMS: Method L, MS-ESI, 206.0 [M+H⁺].

Scheme 3
Synthesis of intermediate 4 (1-(5-bromo-(1H-pyrrolo[2,3-b]pyridin-3-yl)-3-(4-(trifluoromethyl)phenyl)urea) (Compound 147)

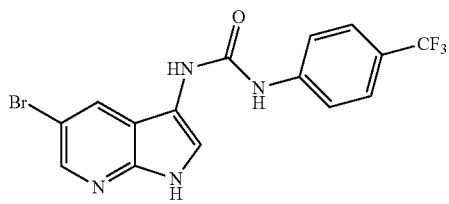

intermediate 4
Compound 147

-continued

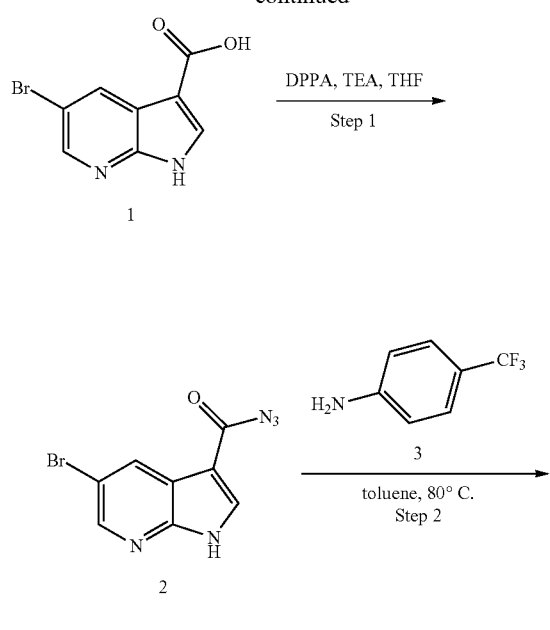

1. Synthesis of 5-bromo-1H-pyrrolo[2,3-b]pyridine-3-carbonyl azide

Synthesized using the method as described for Scheme 2.
LCMS: Method L, MS-ESI 266.0 [M+H⁺].

2. Synthesis of 1-(5-bromo-1H-pyrrolo[2,3-b]pyridin-3-yl)-3-(4-(trifluoromethyl)phenyl) urea

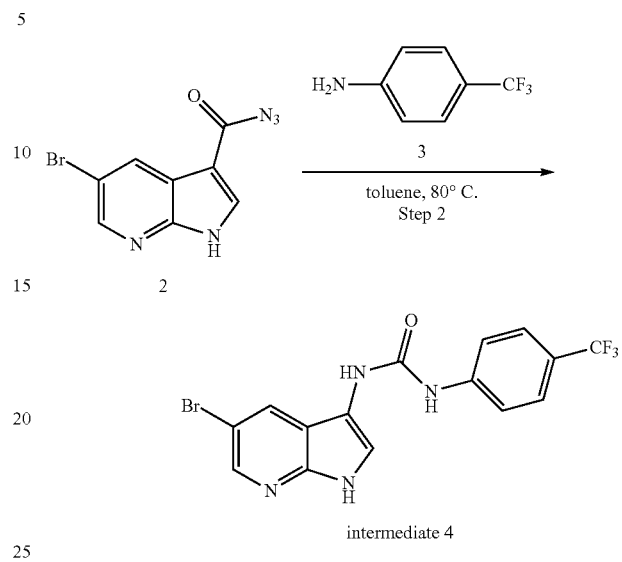

5-Bromo-1H-pyrrolo[2,3-b]pyridine-3-carboxylic acid (9.0 g, 33.8 mmol, 1.0 equiv) was dissolved in toluene (300.0 mL). 4-(trifluoromethyl)aniline (16.4 g, 101 mmol, 3.0 equiv) was added and stirred for 16 hours at 80° C. The resulting mixture was cooled to RT. Then the solids were collected by filtration and washed with MeOH (100 mL×3). The resulting 1-(5-bromo-1H-pyrrolo[2,3-b]pyridin-3-yl)-3-(4-(trifluoromethyl)phenyl)urea (5.3 g, 39.3%) was isolated as an off-white solid. LCMS: Method L, MS-ESI, 399.0 [M+H⁺].

The following intermediates were synthesized by method described above

Intermediate 4a (1-(5-bromo-1H-pyrrolo[3,2-b]pyridin-3-yl)-3-(4-(trifluoromethyl)phenyl)urea)

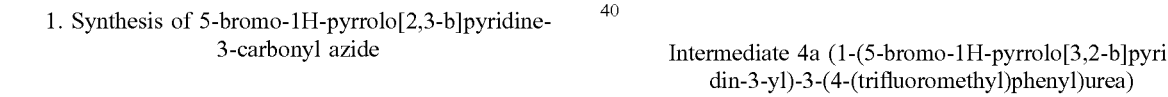

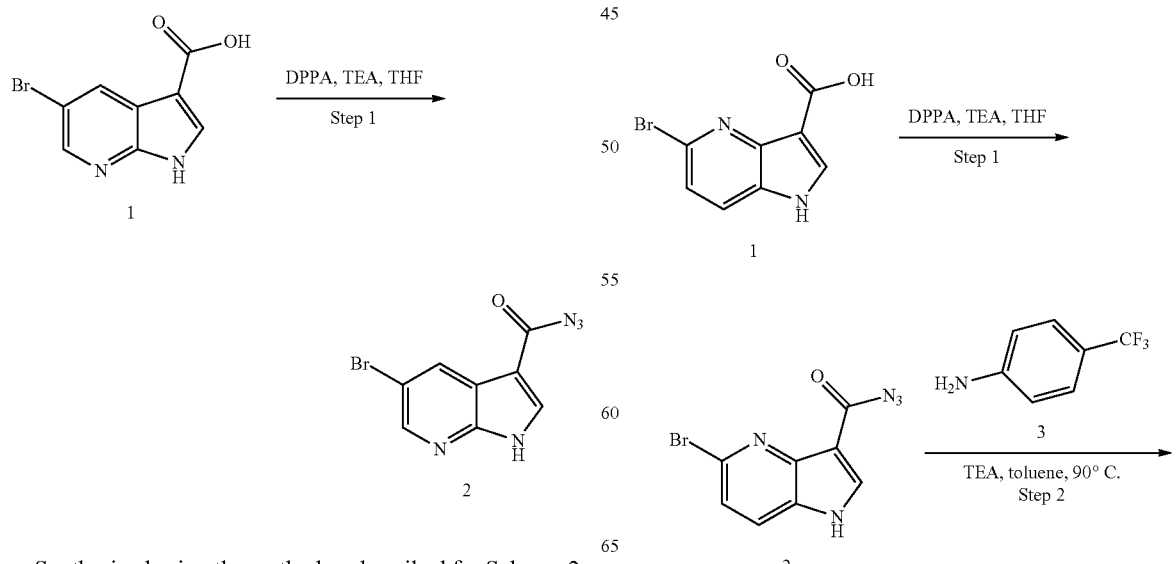

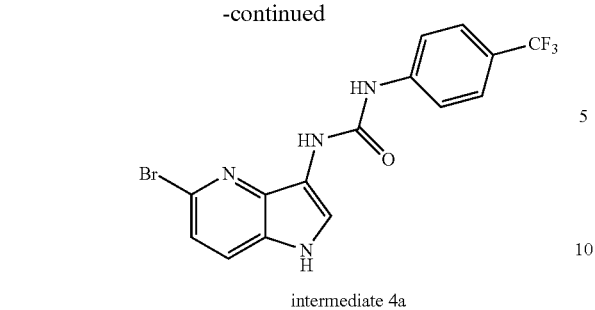

intermediate 4a

LCMS: Method A, MS-ESI, 399.0[M+H⁺].

Intermediate 4b (1-(5-bromo-1H-pyrrolo[2,3-b]pyridin-3-yl)-3-(4-(trifluoromethyl)cyclohexyl)urea)

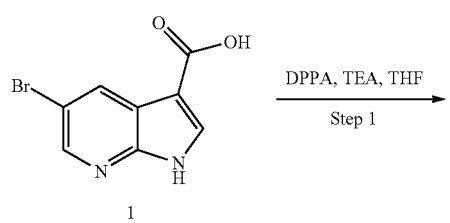

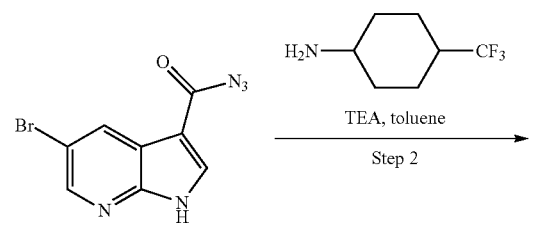

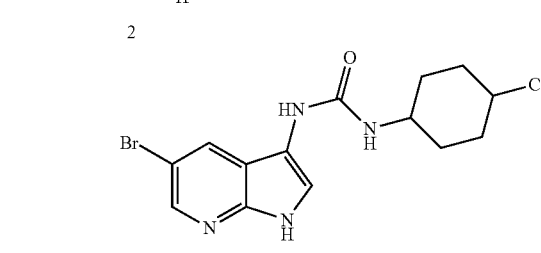

intermediate 4b

LCMS: Method A, MS-ESI, 405.0[M+H⁺].

Scheme 4
Synthesis of intermediate 6 (7-fluoro-1H-pyrrolo[3,2-c]pyridin-3-amine hydrochloride)

1. Synthesis of 7-fluoro-1H-pyrrolo[3,2-c]pyridine-3-carbonyl azide

Same synthetic method as in scheme 2. LCMS: Method L, MS-ESI, 206.2 [M+H⁺].

2. Synthesis of t-butyl (7-fluoro-1H-pyrrolo[3,2-c]pyridin-3-yl)carbamate

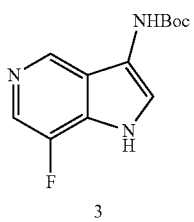

7-Fluoro-1H-pyrrolo[3,2-c]pyridine-3-carbonyl azide (1.0 g, 4.9 mmol, 1.0 equiv) was dissolved in t-BuOH (50 mL) and stirred for 12 hours at 80° C. The resulting mixture was concentrated under vacuum and purified on silical-gel column with EtOAc/PE (1:8) as an eluent. t-Butyl (7-fluoro-1H-pyrrolo[3,2-c]pyridin-3-yl)carbamate (430.0 mg, 17.6%) was isolated as a brown solid. LCMS: Method L, MS-ESI, 252.3 [M+H$^+$].

3. Synthesis of 7-fluoro-1H-pyrrolo[3,2-c]pyridin-3-amine hydrochloride

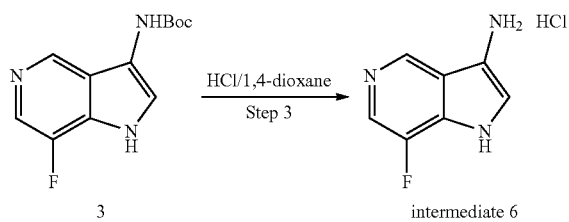 [SMILES: CC(C)(C)OC(=O)Nc1c[nH]c2c(F)cncc12 ; Nc1c[nH]c2c(F)cncc12 ; Cl]

t-Butyl (7-fluoro-1H-pyrrolo[3,2-c]pyridin-3-yl)carbamate (430.0 mg, 1.7 mmol, 1.0 equiv) was dissolved in 1,4-dioxane (10.0 mL). Then HCl in 1,4-dioxane (4 M, 10 mL) was added dropwise. The resulting mixture was stirred for 3 hours at RT and was concentrated under vacuum. 7-Fluoro-1H-pyrrolo[3,2-c]pyridin-3-amine hydrochloride (400 mg, crude) was obtained as a yellow solid. LCMS: Method L, MS-ESI, 188.6 [M+H$^+$].

The following intermediates were synthesized by method described above

Intermediate 6a: 3-amino-1H-pyrrolo[2,3-b]pyridine-5-carbonitrile

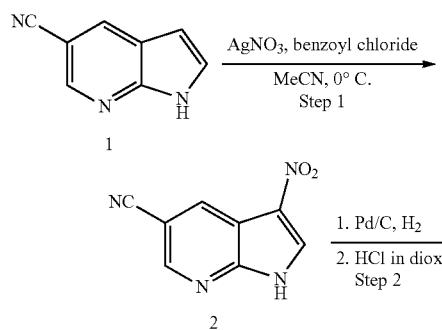

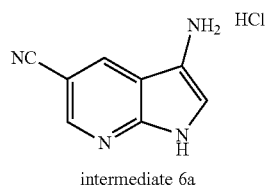

LCMS: Method A, MS-ESI, 195.6 [M+H$^+$].

Intermediate 6b: (5-chloro-1H-pyrrolo[2,3-b]pyridin-3-amine)

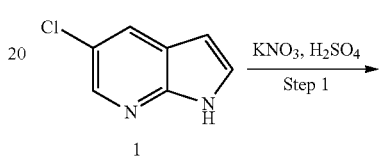

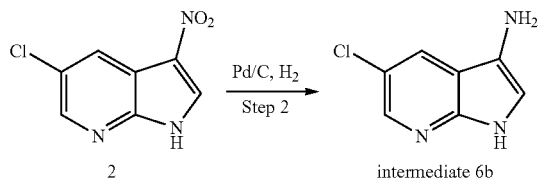

Method L, MS-ESI, 168.6 [M+H$^+$].

Intermediate 6c: (4-bromo-1H-pyrrolo[2,3-b]pyridin-3-amine)

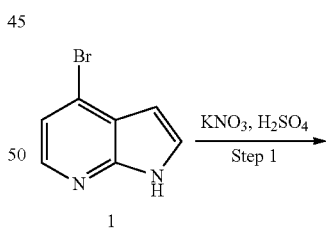

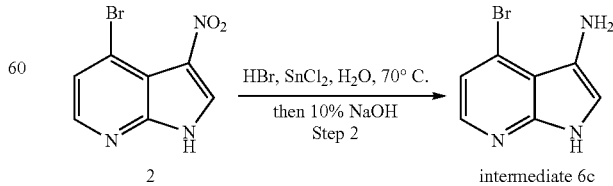

LCMS: Method A, MS-ESI, 212.0 [M+H$^+$].

Intermediate 6d: (4-fluoro-1H-pyrrolo[2,3-c]pyridin-3-amine)

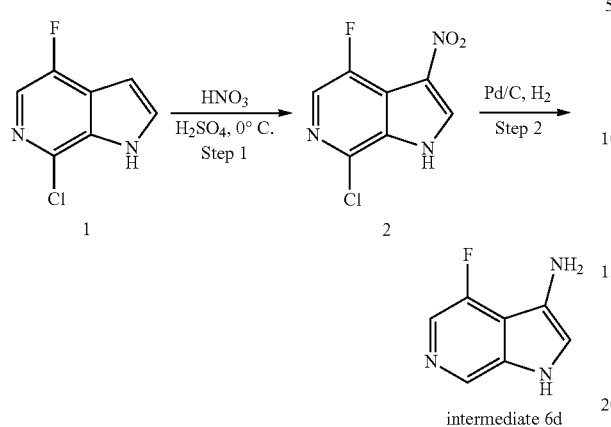

intermediate 6d

LCMS: Method A, MS-ESI, 152.1 [M+H⁺].

Intermediate 6e (1H-pyrrolo[2,3-b]pyridin-3-amine dihydrochloride)

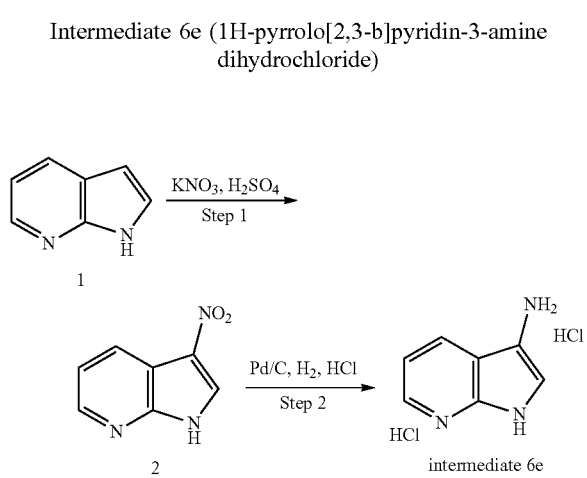

intermediate 6e

LCMS: Method A, MS-ESI, 206.0 [M+H⁺].

Intermediate 6f. (1H-pyrrolo[3,2-b]pyridin-3-amine dihydrochloride)

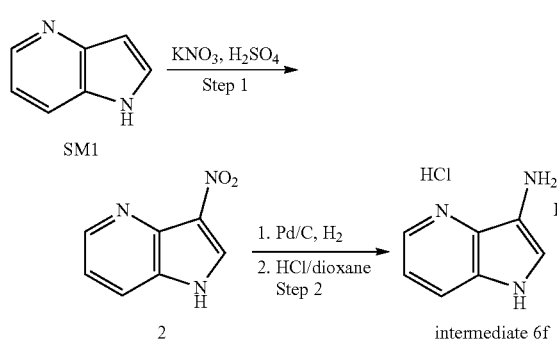

intermediate 6f

LCMS: Method A, MS-ESI, 206.0 [M+H⁺].

Intermediate 6g (6-fluoro-1H-pyrrolo[3,2-b]pyridin-3-amine)

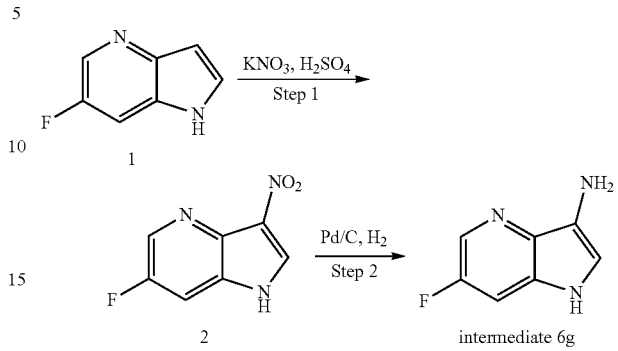

intermediate 6g

1. Synthesis of 6-fluoro-3-nitro-1H-pyrrolo[3,2-b]pyridine

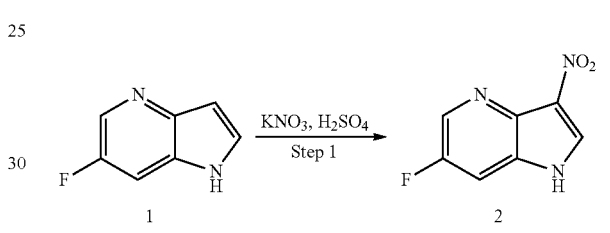

Synthesized using the method as described for Scheme 1.
LCMS: Method A, MS-ESI, 182.0 [M+H⁺].

2. Synthesis of 6-fluoro-1H-pyrrolo[3,2-b]pyridin-3-amine

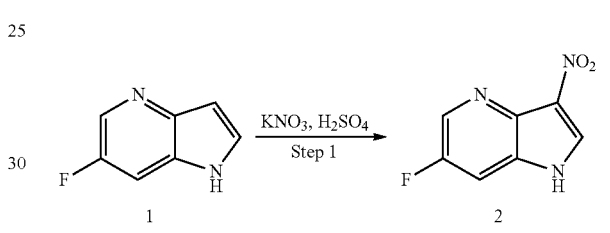

intermediate 6g

Synthesized using the method as described for Scheme 1.
LCMS: Method A, MS-ESI, 152.1 [M+H⁺].

Scheme 10
Synthesis of intermediate 13:
(4-methoxy-1H-pyrrolo[3,2-c]pyridine-3-carboxylic acid)

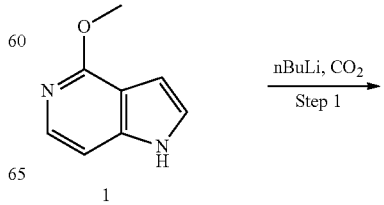

239

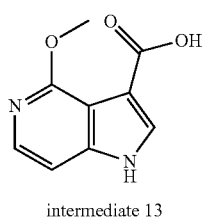

intermediate 13

1. Synthesis of 4-methoxy-1H-pyrrolo[3,2-c]pyridine-3-carboxylic acid

To a stirred solution of 4-methoxy-1H-pyrrolo[3,2-c]pyridine (300.0 mg, 2.0 mmol, 1.0 equiv) in THF (10 mL) under N$_2$ was added n-BuLi in hexanes (2.5 M, 4.1 mL, 10.3 mmol, 5.1 equiv) dropwise with stirring at −20° C. over 2 min. The resulting solution was stirred for 30 min at −20° C. Dry ice (10.0 g, 227.2 mmol, 112.0 equiv) was added in portions at −20° C. and stirred for 2 hours at RT. The reaction was then quenched with MeOH (10 mL). The solids were filtered out and resulting mixture was concentrated under vacuum. The crude product was purified by Method P. This resulted in 100 mg (25.7%) of 4-methoxy-1H-pyrrolo[3,2-c]pyridine-3-carboxylic acid as a white solid.

LCMS: Method A, MS-ESI, 193.1 [M+H$^+$].

Scheme 11
Synthesis of intermediate 14 (5-Phenyl-1H-pyrrolo[2,3-c]pyridin-3-amine)

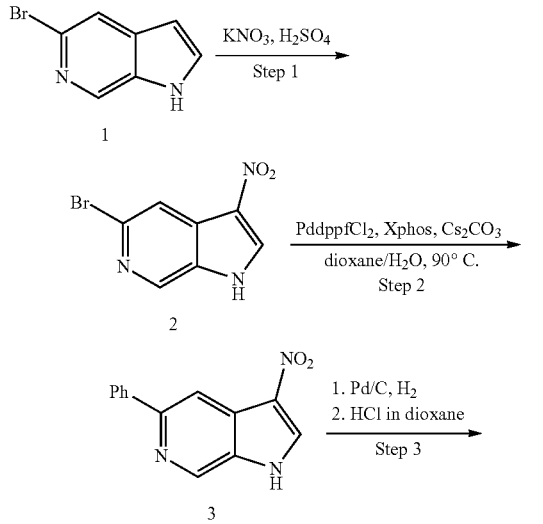

240

1. Synthesis of 5-bromo-3-nitro-1H-pyrrolo[2,3-c]pyridine

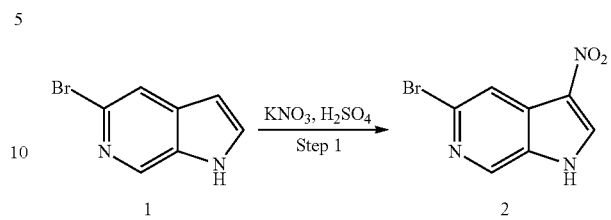

Synthesized using the method as described for Scheme 1. LCMS: Method L, MS-ESI, 241.9 [M+H$^+$].

2. Synthesis of 3-nitro-5-phenyl-1H-pyrrolo[2,3-c]pyridine

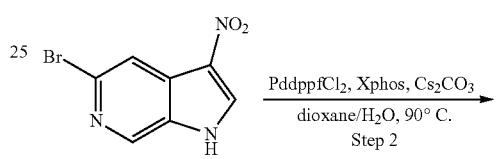

5-Bromo-3-nitro-1H-pyrrolo[2,3-c]pyridine (100.0 mg, 0.4 mmol, 1.0 equiv) was dissolved in dioxane (3.0 mL) and H$_2$O (0.3 mL). Phenylboronic acid (50.4 mg, 0.4 mmol, 1.0 equiv), Cs$_2$CO$_3$ (269.2 mg, 0.8 mmol, 2.0 equiv), Pd(dppf)Cl$_2$ (30.2 mg, 0.04 mmol, 0.1 equiv) and XPhos (19.7 mg, 0.04 mmol, 0.1 equiv) were added and stirred for 12 hr at 90° C. under N$_2$. The resulting mixture was concentrated under vacuum. The crude product was purified by column chromatography with EtOAc/PE (1/1) as an eluent. This resulted in 300 mg (75.9%) of 3-nitro-5-phenyl-1H-pyrrolo[2,3-c]pyridine as a yellow solid. LCMS: Method L, MS-ESI, 240.1 [M+H$^+$].

3. Synthesis of 5-Phenyl-1H-pyrrolo[2,3-c]pyridin-3-amine hydrochloride

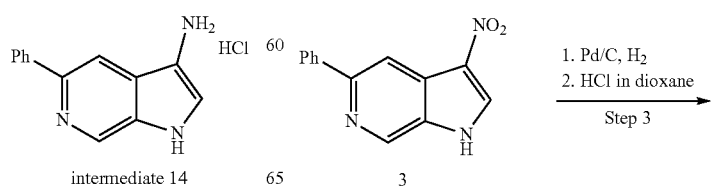

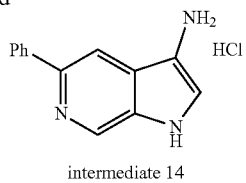

intermediate 14

Synthesized using method as described for Scheme 1. LCMS: Method L, MS-ESI, 246.1 [M+H⁺].

Scheme 13
Synthesis of intermediate 17
(3-isocyanato-1H-pyrrolo[3,2-b]pyridine)

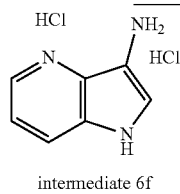

intermediate 6f

BTC, K₂CO₃, THF
────────────→
Step 3

intermediate 17

1H-pyrrolo[3,2-b]pyridin-3-amine (100.0 mg, 0.8 mmol, 1.0 equiv) was dissolved in THF (10.0 mL). K₂CO₃ (207.6 mg, 1.5 mmol, 2.0 equiv) and BTC (77.2 mg, 0.3 mmol, 0.3 equiv) were added at RT and stirred for 1 h at RT under N₂ atmosphere. The resulting mixture was used directly in the next step without further purification.

Scheme 15
Synthesis of intermediate 20 (1-(5-bromo-1H-pyrrolo[3,2-b]pyridin-3-yl)-3-(4-(trifluoromethyl)cyclohexyl)urea)

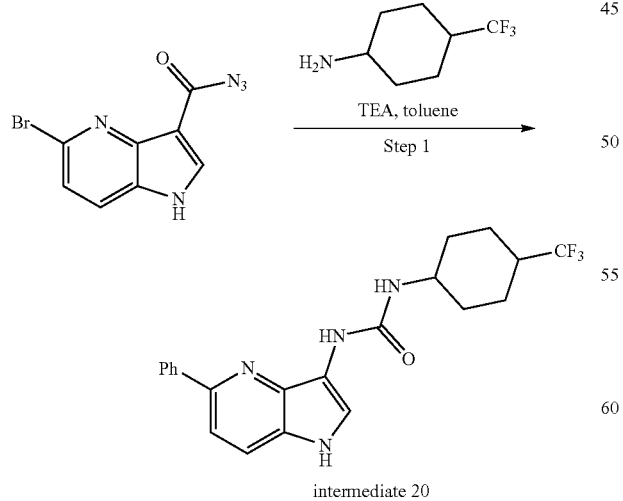

intermediate 20

Synthesized using the method as described for Scheme 3.
LCMS: Method L, MS-ESI, 405.0[M+H⁺].

Scheme 16
Synthesis of intermediate 21 (3-isocyanato-5-phenyl-1H-pyrrolo[2,3-c]pyridine)

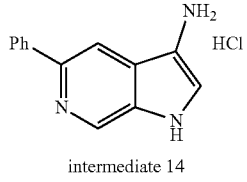

intermediate 14

BTC, K₂CO₃, THF
────────────→
Step 1

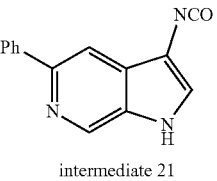

intermediate 21

Synthesized using the method as described for Scheme 13.

Scheme 17
Synthesis of Intermediate 23
(5-fluoro-1H-pyrrolo[2,3-b]pyridin-3-amine hydrochloride)

intermediate 23

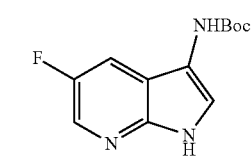

intermediate 2 t-BuOH
─────→
Step 1

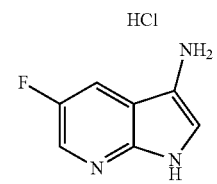

1

HCl in dioxane
──────────→
Step 2 intermediate 23

1. Synthesis of t-butyl (5-fluoro-1H-pyrrolo[2,3-b]pyridin-3-yl)carbamate

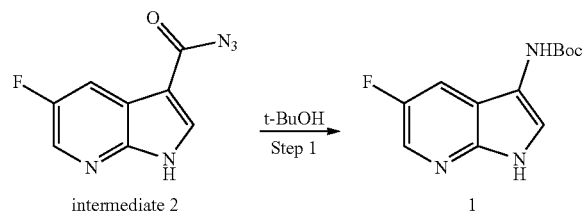 [SMILES: "t-BuOH" ; [N-]=[N+]=NC(=O)c1c[nH]c2ncc(F)cc12 ; CC(C)(C)OC(=O)Nc1c[nH]c2ncc(F)cc12]

Synthesized using the method as described for Scheme 4. LCMS: Method L, MS-ESI, 252.1 [M+H$^+$].

2. Synthesis of 5-fluoro-1H-pyrrolo[2,3-b]pyridin-3-amine hydrochloride

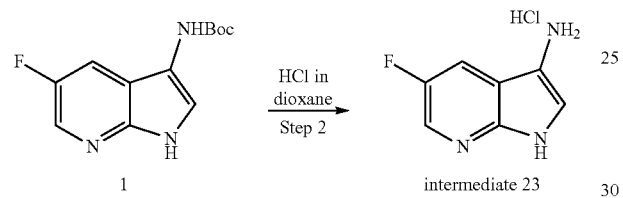

Synthesized using the method as described for Scheme 4. LCMS: Method A, MS-ESI, 188.0 [M+H$^+$].

Scheme 18
Synthesis of intermediate 24
(N-(1H-pyrrolo[2,3-b]pyridin-3-yl)-1H-imidazole-1-carboxamide)

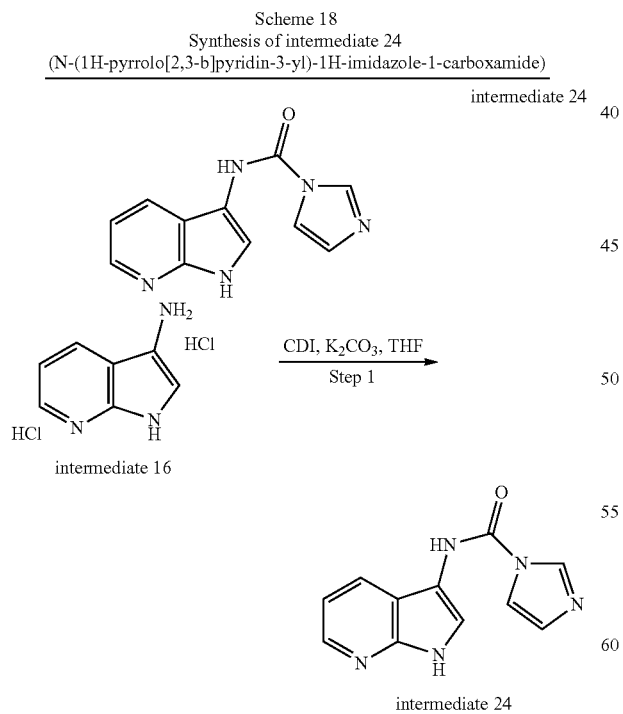

Synthesized using the method as described for Scheme 1. The resulting mixture was used directly in the next step without further purification.

Scheme 28
Synthesis of intermediate 28 (6-cyclohexylpyridin-3-amine)

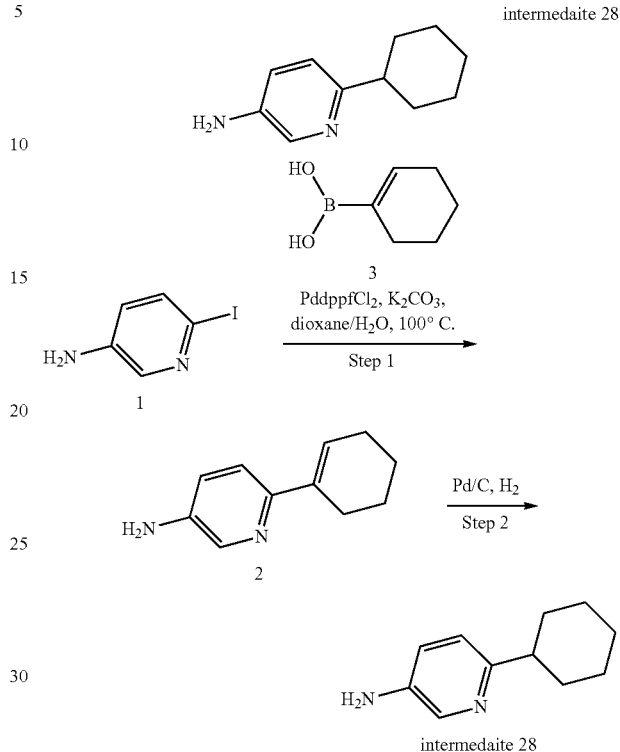

1. Synthesis of 6-(cyclohex-1-en-1-yl)pyridin-3-amine

6-Iodopyridin-3-amine (2.0 g, 9.1 mmol, 1.0 equiv) was dissolved in 1,4-dioxane (20.0 mL). Cyclohex-1-en-1-ylboronic acid (1.7 g, 13.7 mmol, 1.5 equiv), Pd(dppf)Cl$_2$ (971.9 mg, 1.4 mmol, 0.15 equiv), K$_2$CO$_3$ (2.5 g, 18.2 mmol, 2.0 equiv) and H$_2$O (4.0 mL) were added and stirred for 16 hours at 100° C. under N$_2$ atmosphere. The resulting mixture was cooled to RT and concentrated under vacuum. Then remaining residue was purified on silica-gel column with- EtOAc/PE (1:2) as an eluent. 6-(Cyclohex-1-en-1-yl)pyridin-3-amine (800.0 mg, 50.0%) was isolated as a yellow solid.

LCMS: Method L, MS-ESI, 175.1 [M+H⁺].

2. Synthesis of 6-cyclohexylpyridin-3-amine

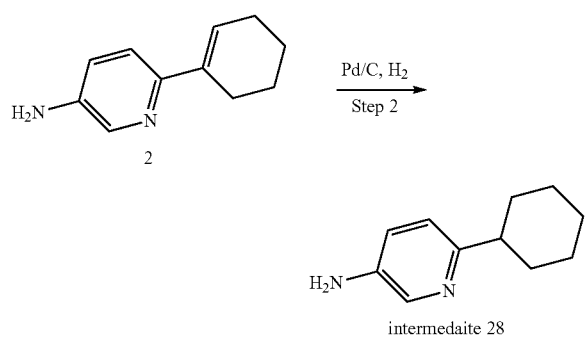

intermedaite 28

6-(Cyclohex-1-en-1-yl)pyridin-3-amine (295.8 mg, 1.7 mmol, 1.0 equiv) was dissolved in MeOH (20.0 mL). Pd/C (27.48 mg, 0.258 mmol, 0.15 equiv) was added under $N_2$ atmosphere and stirred for 16 hours at RT with an atmosphere of H2. The solids were filtered out and resulting mixture was concentrated under vacuum and applied onto a silica gel column with EtOAc/PE (2:1) as an eluent. This resulted in 6-cyclohexylpyridin-3-amine (120.1 mg, 40.1%) of as a yellow solid.

LCMS: Method L, MS-ESI, 177.1 [M+H⁺].

Scheme 29
Synthesis of intermediate 29 (2-amino-N-methyl-3-phenylpropanamide)

intermediate 29

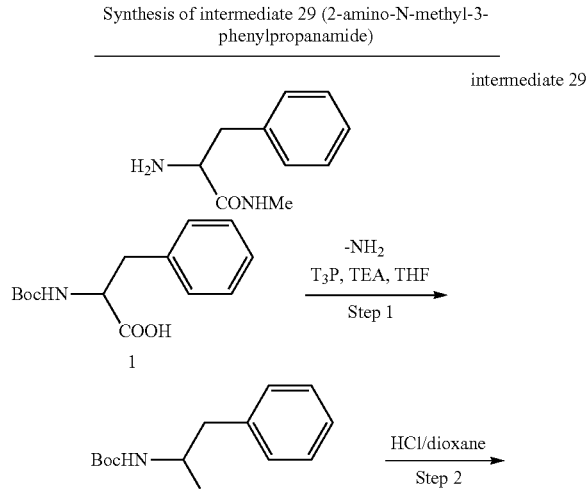

intermediate 29

1. Synthesis of t-butyl (1-(methylamino)-1-oxo-3-phenylpropan-2-yl)carbamate

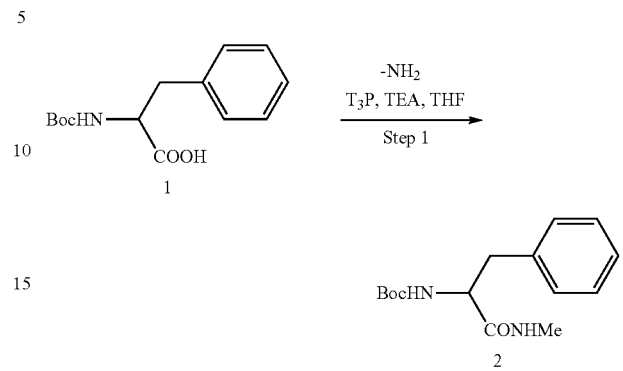

2-[(Tert-butoxycarbonyl)amino]-3-phenylpropanoic acid (500.0 mg, 1.9 mmol, 1.0 equiv) was dissolved in THF (20.0 mL). TEA (381.4 mg, 3.8 mmol, 2.0 equiv), T3P (1199.3 mg, 3.8 mmol, 2.0 equiv) and methylamine (117.1 mg, 3.8 mmol, 2.0 equiv) were added and stirred for 8 hours. The solution was concentrated under vacuum and applied onto a silica gel column with EtOAc/PE (2:1) as an eluent. This resulted in t-butyl N-[1-(methylcarbamoyl)-2-phenylethyl]carbamate (520 mg, 99.1%) of as a brown solid.

LCMS: Method F, MS-ESI, 279.2 [M+H⁺].

2. Synthesis of
2-amino-N-methyl-3-phenylpropanamide

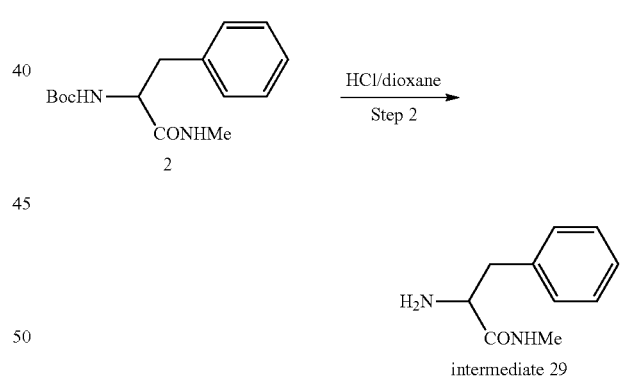

intermediate 29

Synthesized using method as described for Scheme 4.
LCMS: Method L, MS-ESI, 179.1 [M+H⁺].

Scheme 30
Synthesis of intermediate 30 (5-cyclohexylpyridin-2-amine)

intermedaite 30

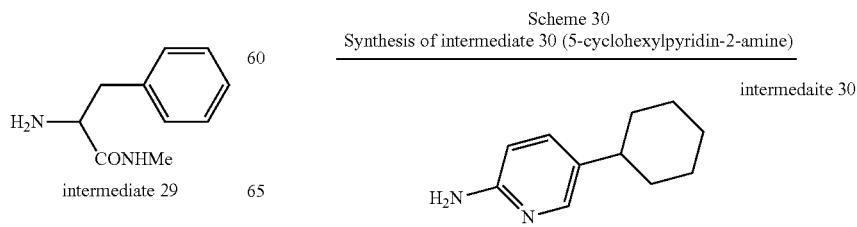

1. Synthesis of 5-(cyclohex-1-en-1-yl)pyridin-2-amine

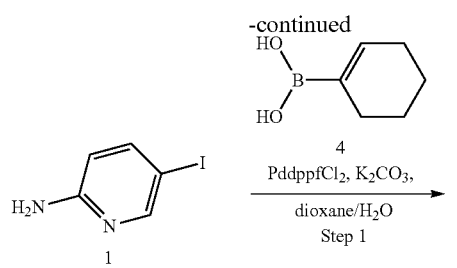

2. Synthesis of 5-cyclohexylpyridin-2-amine

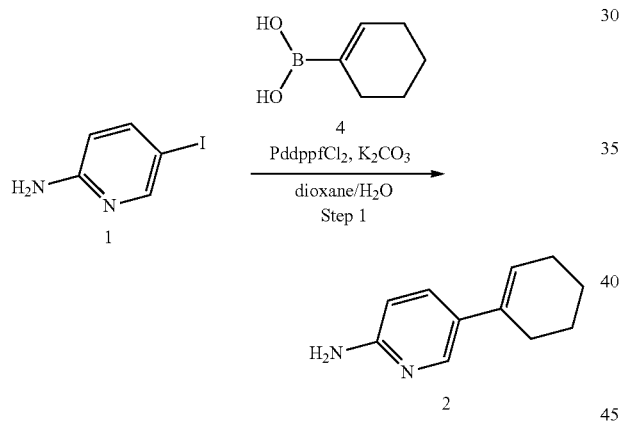

Synthesized using the method as described for Scheme 28. LCMS: Method L, MS-ESI, 175.1 [M+H⁺].

Synthesized using the method as described for Scheme 28. LCMS: Method L, MS-ESI, 177.1 [M+H⁺].

Scheme 31
Synthesis of intermediate 31
(spiro[2.5]octan-6-amine hydrochloride)

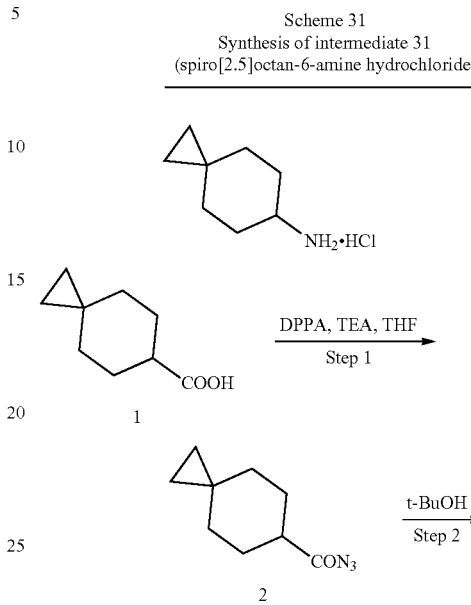

1. Synthesis of spiro[2.5]octane-6-carbonyl azide

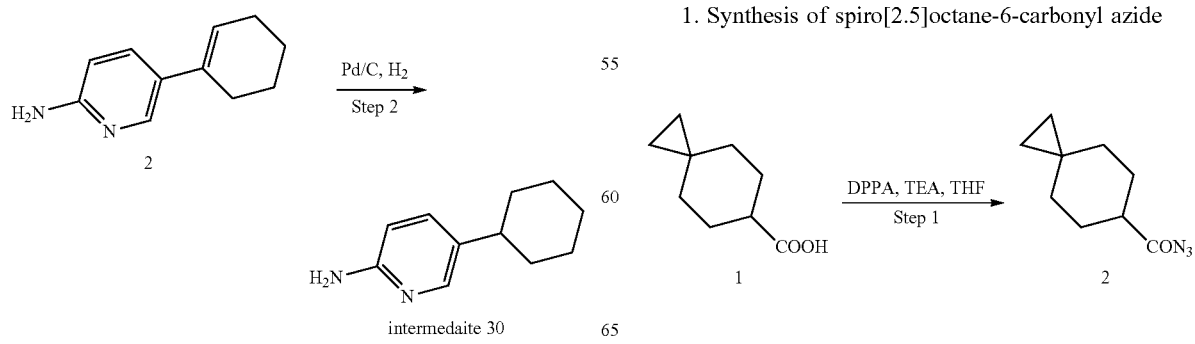

Synthesized using the method as described for Scheme 2. LCMS: Method A, MS-ESI, 180.1 [M+H⁺].

2. Synthesis of t-butyl spiro[2.5]octan-6-ylcarbamate

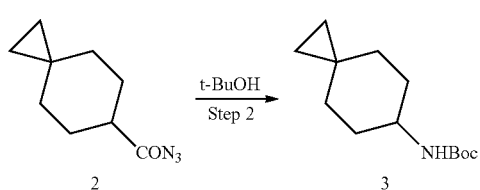

Synthesized using the method as described for Scheme 4. LCMS: Method A, MS-ESI, 226.2 [M+H$^+$].

3. Synthesis of spiro[2.5]octan-6-amine hydrochloride

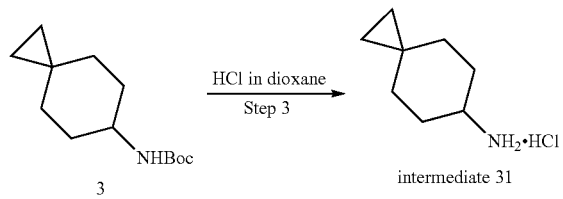

Synthesized using the method as described for Scheme 4. LCMS: Method A, MS-ESI, 162.1 [M+H$^+$].

Scheme 34
Synthesis of intermediate 34
(6-cyclohexylpyridin-2-amine)

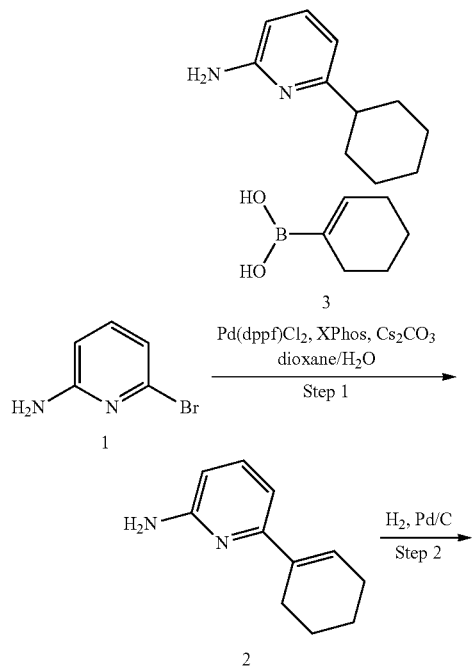

1. Synthesis of 6-(cyclohex-1-en-1-yl)pyridin-2-amine

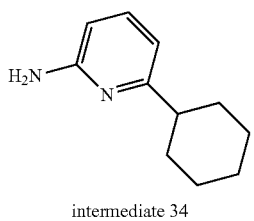

Synthesized using the method as described for Scheme 28. LCMS: Method A, MS-ESI, 175.1 [M+H$^+$].

2. Synthesis of 6-cyclohexylpyridin-2-amine

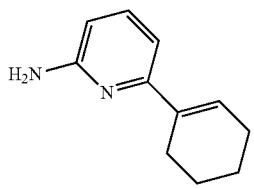

Synthesized using the method as described for Scheme 28. LCMS: Method A, MS-ESI, 177.1 [M+H$^+$].

Scheme 35
Synthesis of intermediate 35
(6-bromo-1H-pyrrolo[2,3-b]pyridin-3-amine)

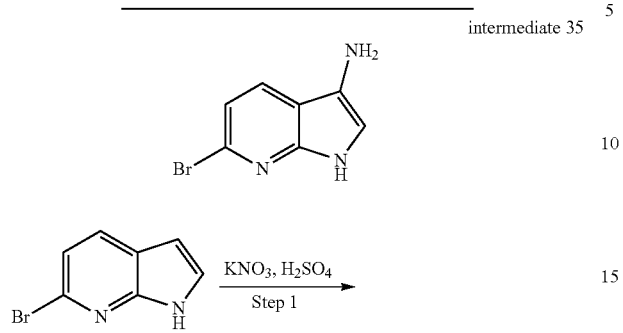

intermediate 35

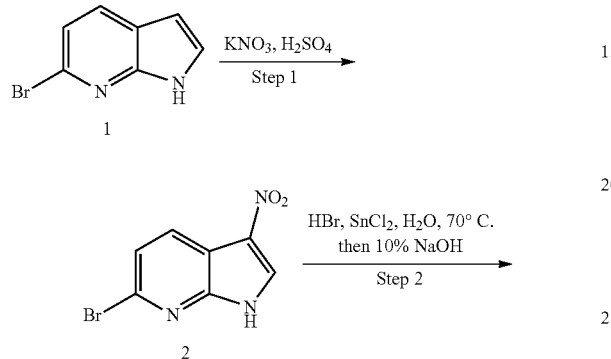

1. Synthesis of 6-bromo-3-nitro-1H-pyrrolo[2,3-b]pyridine

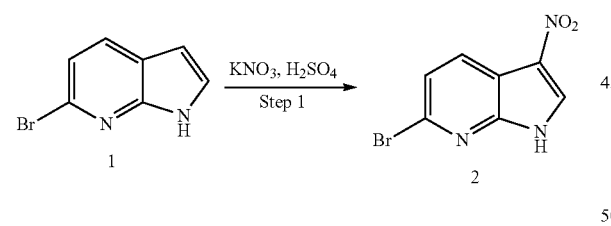

Synthesized using the method as described for Scheme 1.
LCMS: Method A, MS-ESI, 241.9 [M+H$^+$].

2. Synthesis of 6-bromo-1H-pyrrolo[2,3-b]pyridin-3-amine

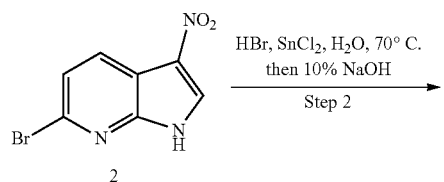

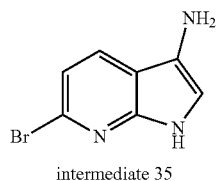

intermediate 35

Synthesized using conditions shown in the scheme above.
LCMS: Method L, MS-ESI, 212.0 [M+H$^+$].

Scheme 36
Synthesis of intermediate 36
(6-butyl-5-fluoropyridin-3-amine)

intermediate 36

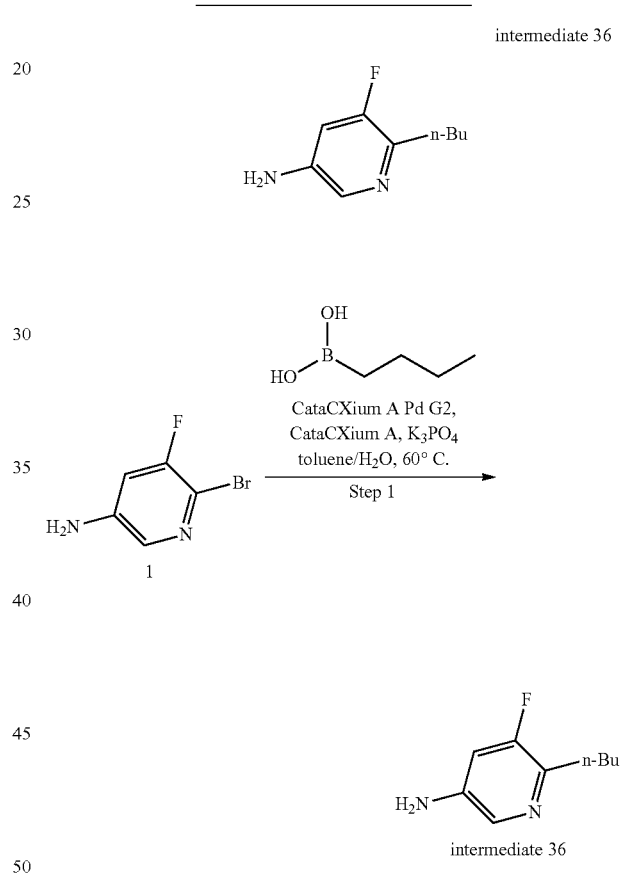

intermediate 36

6-Bromo-5-fluoropyrind-3-amine (1.0 g, 5.2 mmol, 1.0 equiv) and 1-butane boronic acid were dissolved in toluene (8.00 mL). CataCXium A Pd G2 (350.1 mg, 0.5 mmol, 0.1 equiv), CataCXium A (187.7 mg, 0.5 mmol, 0.1) and K$_3$PO$_4$ (2.2 g, 10.5 mmol, 2.0 equiv) were added at RT. The reaction system was evacuated and flushed with N$_2$ for three times and stirred at 60° C. under N$_2$ atmosphere for 16 hours. The mixture was cooled to RT and filtered through Celite. The filtrate was concentrated and diluted with EtOAc (10 mL) and washed with water (4 mL) and brine (4 mL), and then dried over anhydrous Na$_2$SO$_4$ and concentrated under vacuum. The residue was applied onto a silica gel column with EtOAc/PE (1:5) as an eluent. 6-Butyl-5-fluoropyridin-3-amine (468 mg, 53.2%) was isolated as a brown oil. LCMS: Method L, MS-ESI, 169.1 [M+H$^+$].

Scheme 37
Synthesis of intermediate 37
(5-butyl-3-fluropyridin-2-amine)

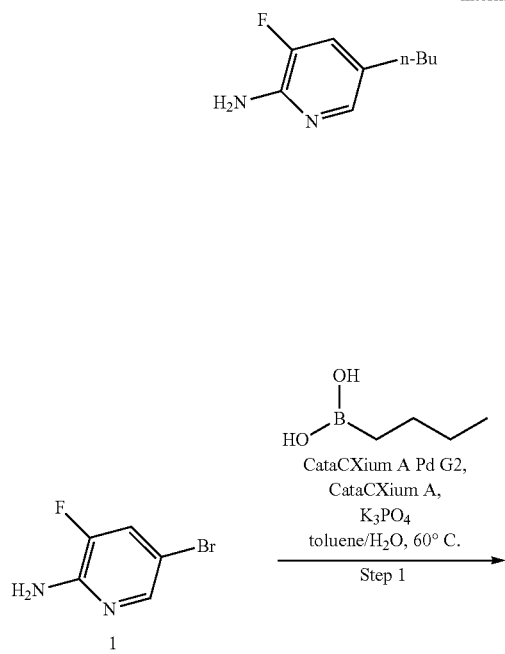

Synthesized using the method as described for Scheme 36. LCMS: Method A, MS-ESI, 169.1 [M+H⁺].

Scheme 38
Synthesis of intermediate 38 (1-(5-bromo-1-((2-(trimethylsilyl)ethoxy)methyl)-1H-pyrrolo[2,3-b]pyridin-3-yl)-3-(4-(trifluoromethyl)phenyl)urea)

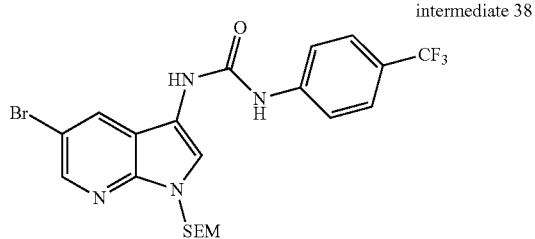

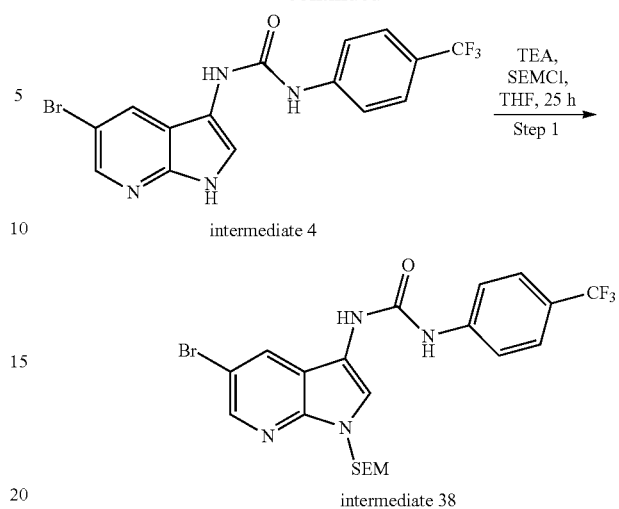

1-(5-Bromo-1H-pyrrolo[2,3-b]pyridin-3-yl)-3-(4-(trifluoromethyl)phenyl)urea (1.0 g, 2.5 mmol, 1.0 equiv) was dissolved in THF (15.0 mL). TEA (505.0 mg, 5.0 mmol, 2.0 equiv) and SEM-Cl (2.1 g, 12.5 mmol, 5.0 equiv) were added at RT and stirred for 16 hours. The mixture was concentrated and applied onto a silica gel column with EtOAc/PE (1:3) as an eluent. 1-(5-Bromo-1-((2-(trimethylsilyl)ethoxy)methyl)-1H-pyrrolo[2,3-b]pyridin-3-yl)-3-(4-(trifluoro-methyl)phenyl)urea (800.0 mg, 60.6%) was isolate as a yellow solid. LCMS: Method A, MS-ESI, 529.1 [M+H⁺].

SCHEMES FOR PREPARATION OF EXAMPLES

Example 1: Synthesis of 1-(5-fluoro-1H-pyrrolo[2,3-b]pyridin-3-yl)-3-(4-(trifluoromethyl)phenyl)urea (Compound 173)

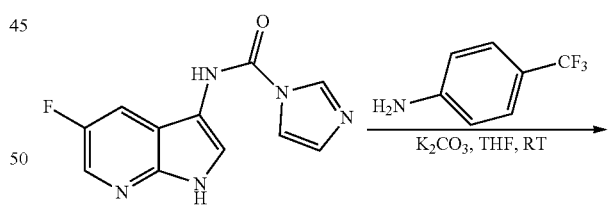

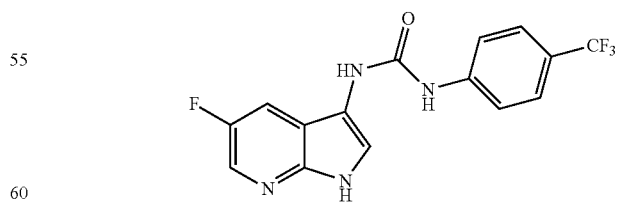

N-(5-fluoro-1H-pyrrolo[2,3-b]pyridin-3-yl)-1H-imidazole-1-carboxamide (80.0 mg, 0.5 mmol, 1.0 equiv) was dissolved in THF (10.0 mL). 4-(trifluoromethyl)aniline (90.1 mg, 0.5 mmol, 1.0 equiv) and K₂CO₃ (138.8 mg, 1.0 mmol, 2.0 equiv) were added and stirred for 1 hour at RT.

The solid was filtered out and filtrate was concentrated under vacuum and the residue was purified by Method P. This resulted in 1-(5-fluoro-1H-pyrrolo[2,3-b]pyridin-3-yl)-3-(4-(trifluoromethyl)phenyl)urea (9.9 mg, 5.8%) was isolated as a white solid.

LCMS: Method K, MS-ESI, 339.1 [M+H$^+$].

$^1$H NMR (400 MHz, DMSO-d$_6$) δ 11.58-11.53 (m, 1H), 9.07 (s, 1H), 8.70-8.65 (m, 1H), 8.22 (dd, J=2.8, 1.7 Hz, 1H), 7.80-7.69 (m, 2H), 7.71-7.59 (m, 5H).

$^{19}$F NMR (400 MHz, DMSO-d$_6$) δ −59.99, −139.94

Analogs Prepared by this Method

| Ex # | Compound Starting # | Material | Final Compound | LCMS and NMR Data |
|---|---|---|---|---|
| 2 | 323 | Intermediate 1 (N-(1H-pyrrolo[3,2-b]pyridin-3-yl)-1H-imidazole-1-carboxamide); 1-phenylpiperidin-4-amine | (structure) | Method M: MS-ESI: 336.2 [M + H$^+$] $^1$HNMR (400 MHz, DMSO-d$_6$) δ 10.75 (brs, 1H), 8.30 (s, 1H), 8.26 (dd, J = 4.4, 1.2 Hz, 1H), 7.72-7.69 (m, 2H), 7.23-7.18 (m, 2H), 7.11 (dd, J = 8.4, 4.8 Hz, 1H), 7.00-6.90 (m, 2H), 6.80-6.72 (m, 1H), 6.65 (d, J = 7.6 Hz, 1H), 3.72-3.69 (m, 1H), 3.56-3.53 (m, 2H), 2.94-2.78 (m, 2H), 2.01-1.91 (m, 2H), 1.52-1.43 (m, 2H). |
| 3 | 325 | Intermediate 1 (N-(1H-pyrrolo[3,2-b]pyridin-3-yl)-1H-imidazole-1-carboxamide); 4-phenylcyclohexan-1-amine | (structure) | Method C: MS-ESI: 335.2 [M + H$^+$] $^1$H NMR (400 MHz, DMSO-d$_6$) δ 10.73 (s, 1H), 8.45 (s, 1H), 8.28 (dd, J = 4.5, 1.4 Hz, 1H), 7.76-7.67 (m, 2H), 7.37-7.25 (m, 5H), 7.24-7.08 (m, 1H), 6.92 (d, J = 8.3 Hz, 1H), 4.10-3.96 (m, 1H), 2.51-2.50 (m, 1H), 2.01-1.67 (m, 8H). |
| 3a | | Intermediate 1 (N-(1H-pyrrolo[3,2-b]pyridin-3-yl)-1H-imidazole-1-carboxamide); 2-fluoro-4-(trifluoromethyl)aniline | (structure) | Method K, MS-ESI, 339.1 [M + H$^+$]. $^1$HNMR: (400 MHz, DMSO-d$_6$) δ 10.97 (s, 1H), 9.51 (s, 1H), 9.36 (s, 1H), 8.55 (t, J = 8.3 Hz, 1H), 8.34 (dd, J = 4.4, 1.2 Hz, 1H), 7.86 (d, J = 2.4 Hz, 1H), 7.76 (dd, J = 8.4, 1.2 Hz, 1H), 7.69 (dd, J = 11.6, 2.0 Hz, 1H), 7.54 (d, J = 8.8 Hz, 1H), 7.16 (dd, J = 8.0, 4.4 Hz, 1H). |
| 3c | 332 | Intermediate 1 (N-(1H-pyrrolo[3,2-b]pyridin-3-yl)-1H-imidazole-1-carboxamide); 3-(trifluoromethyl)aniline | (structure) | Method C: MS-ESI: 321.1 [M + H$^+$] $^1$HNMR (400 MHz, DMSO-d$_6$) δ 10.96 (d, J = 2.7 Hz, 1H), 9.43 (s, 1H), 8.83 (s, 1H), 8.33 (dd, J = 4.8, 1.6 Hz, 1H), 8.10 (d, J = 2.2 Hz, 1H), 7.85 (d, J = 2.5 Hz, 1H), 7.75 (dd, J = 8.0, 1.2 Hz, 1H), 7.54-7.49 (m, 2H), 7.30-7.28 (m, 1H), 7.16 (dd, J = 8.0, 4.4 Hz, 1H). |
| 3d | 146 | Intermediate 1 (N-(1H-pyrrolo[3,2-b]pyridin-3-yl)-1H-imidazole-1-carboxamide); 4-(trifluoromethyl)aniline | (structure) | Method N: MS-ESI: 321.1 [M + H$^+$] $^1$HNMR (400 MHz, DMSO-d$_6$) δ 10.96 (s, 1H), 9.47 (s, 1H), 8.88 (s, 1H), 8.33 (dd, J = 4.5, 1.4 Hz, 1H), 7.84 (s, 1H), 7.76 (dd, J = 8.2, 1.4 Hz, 1H), 7.69-7.62 (m, 4H), 7.16 (dd, J = 8.2, 4.5 Hz, 1H). |

-continued

| Ex # | Compound # | Starting Material | Final Compound | LCMS and NMR Data |
|---|---|---|---|---|
| 4 | 327 | Intermediate 1 (N-(1H-pyrrolo[3,2-b]pyridin-3-yl)-1H-imidazole-1-carboxamide); 5-(tetrahydro-2H-pyran-4-yl)pyridin-2-amine (commercially available) | | Method E: MS-ESI: 338.2 [M + H$^+$] $^1$HNMR (400 MHz, DMSO-d$_6$) δ 10.94 (s, 1H), 10.75 (brs, 1H), 9.58 (s, 1H), 8.34 (dd, J = 4.6, 1.4 Hz, 1H), 8.19 (d, J = 2.4 Hz, 1H), 7.88 (d, J = 2.5 Hz, 1H), 7.75 (dd, J = 8.2, 1.4 Hz, 1H), 7.68 (dd, J = 8.6, 2.4 Hz, 1H), 7.43 (d, J = 8.6 Hz, 1H), 7.15 (dd, J = 8.2, 4.5 Hz, 1H), 3.96 (dt, J = 11.5, 3.1 Hz, 2H), 3.44 (td, J = 11.1, 3.9 Hz, 2H), 2.83-2.75 (m, 1H), 1.75-1.61 (m, 4H). |
| 5 | 331 | Intermediate 1 N-(1H-pyrrolo[3,2-b]pyridin-3-yl)-1H-imidazole-1-carboxamide); Intermediate 28 (6-cyclohexylpyridin-3-amine) | | Method E: MS-ESI: 336.2 [M + H$^+$] $^1$HNMR (300 MHz, DMSO-d$_6$) δ 10.88 (s, 1H), 9.11 (s, 1H), 8.75 (s, 1H), 8.47 (t, J = 2.3 Hz, 1H), 8.31 (d, J = 4.6 Hz, 1H), 7.92-7.83 (m, 1H), 7.80 (t, J = 2.2 Hz, 1H), 7.73 (d, J = 8.2 Hz, 1H), 7.17-7.11 (m, 2H), 2.64-2.58 (m, 1H), 1.85-1.67 (m, 5H), 1.47-1.28 (m, 5H). |
| 6 | 333 | Intermediate 1 N-(1H-pyrrolo[3,2-b]pyridin-3-yl)-1H-imidazole-1-carboxamide); 6-(tetrahydro-2H-pyran-4-yl)pyridin-3-amine (commercially available) | | Method C: MS-ESI: 338.2 [M + H$^+$] $^1$HNMR (300 MHz, DMSO-d$_6$) δ 10.89 (d, J = 2.5 Hz, 1H), 9.14 (s, 1H), 8.76 (s, 1H), 8.50 (d, J = 2.6 Hz, 1H), 8.31 (dd, J = 4.5, 1.4 Hz, 1H), 7.91 (dd, J = 8.5, 2.7 Hz, 1H), 7.80 (d, J = 2.6 Hz, 1H), 7.74 (dd, J = 8.2, 1.4 Hz, 1H), 7.21 (d, J = 8.5 Hz, 1H), 7.14 (dd, J = 8.2, 4.5 Hz, 1H), 3.99-3.88 (m, 2H), 3.44 (td, J = 11.0, 5.3 Hz, 2H), 2.87-2.84 (m, 1H), 1.76-1.64 (m, 4H). |
| 7 | 334 | Intermediate 1 (N-(1H-pyrrolo[3,2-b]pyridin-3-yl)-1H-imidazole-1-carboxamide); (1r,4r)-4-propoxycyclohexan-1-amine | | Method I: MS-ESI: 317.2 [M + H$^+$] $^1$HNMR (400 MHz, MeOH-d4) δ 8.29 (dd, J = 4.8, 1.6 Hz, 1H), 7.79 (d, J = 8.4, 1.6 Hz, 1H), 7.72 (s, 1H), 7.19 (dd, J = 8.0, 4.4 Hz, 1H), 5.01-4.88 (m, 3H), 3.60-3.45 (m, 1H), 2.07 (s, 5H), 1.59-1.55 (m, 2H), 1.45-1.25 (m, 3H), 0.95 (t, J = 7.4 Hz, 3H). |
| 8 | 140 | Intermediate 1 (N-(1H-pyrrolo[3,2-b]pyridin-3-yl)-1H-imidazole-1-carboxamide); 4-butylpiperidine | | Method D: MS-ESI: 301.2 [M + H$^+$] $^1$HNMR (400 MHz, DMSO-d6) δ 10.89 (d, J = 2.8 Hz, 1H), 8.28 (dd, J = 4.5, 1.4 Hz, 1H), 8.03 (s, 1H), 7.74-7.66 (m, 2H), 7.10 (dd, J = 8.2, 4.5 Hz, 1H), 4.18-4.09 (m, 2H), 2.76 (td, J = 12.8, 2.5 Hz, 2H), 1.72-1.63 (m, 2H), 1.47-1.38 (m, 1H), 1.34-1.18 (m, 6H), 1.05 (qd, J = 12.4, 4.1 Hz, 2H), 0.93-0.85 (m, 3H). |

-continued

| Ex # | Compound # | Starting Material | Final Compound | LCMS and NMR Data |
|---|---|---|---|---|
| 9 | 141 | Intermediate 1 (N-(1H-pyrrolo[3,2-b]pyridin-3-yl)-1H-imidazole-1-carboxamide); 4-(trifluoromethyl)cyclohexan-1-amine | (structure: 1H-pyrrolo[3,2-b]pyridin-3-yl urea with 4-CF$_3$-cyclohexyl) | Method B: MS-ESI: 327.1 [M + H$^+$] $^1$HNMR (400 MHz, DMSO-d$_6$) δ 10.78 (s, 1H), 8.41 (s, 1H), 8.29 (d, J = 4.6 Hz, 1H), 7.72 (s, 2H), 7.14 (s, 1H), 6.88 (d, J = 7.7 Hz, 1H), 3.99-3.88 (m, 1H), 2.30 (s, 1H), 1.82-1.42 (m, 8H). |
| 10 | 142 | Intermediate 1 (N-(1H-pyrrolo[3,2-b]pyridin-3-yl)-1H-imidazole-1-carboxamide); spiro[3.5]nonan-7-amine | (structure: 1H-pyrrolo[3,2-b]pyridin-3-yl urea with spiro[3.5]nonan-7-yl) | Method A: MS-ESI: 299.2 [M + H$^+$] $^1$HNMR (400 MHz, DMSO-d$_6$) δ 10.71 (d, J = 2.4 Hz, 1H), 8.26-8.25 (m, 2H), 7.72-7.66 (m, 2H), 7.10 (dd, J = 8.2, 4.5 Hz, 1H), 6.49 (d, J = 7.7 Hz, 1H), 3.50-3.42 (m, 1H), 1.89-1.77 (m, 2H), 1.76-1.65 (m, 8H), 1.36 (t, J = 10.4 Hz, 2H), 1.26-1.15 (m, 2H). |
| 11 | 322 | Intermediate 1 (N-(1H-pyrrolo[3,2-b]pyridin-3-yl)-1H-imidazole-1-carboxamide); 4-butylcyclohexan-1amine | (structure: 1H-pyrrolo[3,2-b]pyridin-3-yl urea with 4-n-Bu-cyclohexyl) | Method A: MS-ESI: 315.2 [M + H$^+$] $^1$HNMR (400 MHz, DMSO-d$_6$) δ 10.71 (d, J = 2.7 Hz, 1H), 8.41 (d, J = 2.0 Hz, 1H), 8.27 (dd, J = 4.5, 1.4 Hz, 1H), 7.70 (d, J = 1.6 Hz, 1H), 7.68 (d, J = 1.4 Hz, 1H), 7.11 (dd, J = 8.2, 4.5 Hz, 1H), 6.74 (d, J = 8.0 Hz, 1H), 3.89-3.79 (m, 1H), 1.65-1.44 (m, 6H), 1.31-1.14 (m, 9H), 0.93-0.85 (m, 3H). |
| 12 | 290 | Intermediate 24 (N-(1H-pyrrolo[2,3-b]pyridin-3-yl)-1H-imidazole-1-carboxamide); isoindoline | (structure: 1H-pyrrolo[2,3-b]pyridin-3-yl urea with isoindoline) | Method A: MS-ESI: 279.1 [M + H$^+$] $^1$HNMR (DMSO-d$_6$, 400 MHz, ppm): δ 11.26 (s, 1H), 8.21-8.18 (m, 2H), 8.11-8.09 (d, J = 8.0 Hz, 1H), 7.49-7.48 (d, J = 2.4 Hz, 1H), 7.40-7.31 (m, 4H), 7.06-7.03 (m, 1H), 4.80 (s, 4H). |
| 13 | 289 | Intermediate 24 (N-(1H-pyrrolo[2,3-b]pyridin-3-yl)-1H-imidazole-1-carboxamide); 3-phenylazetidine | (structure: 1H-pyrrolo[2,3-b]pyridin-3-yl urea with 3-phenylazetidine) | Method A: MS-ESI: 293.1 [M + H$^+$] $^1$HNMR (400 MHz, DMSO-d$_6$) δ 11.25 (s, 1H), 8.36 (s, 1H), 8.20 (dd, J = 4.6, 1.6 Hz, 1H), 8.08 (dd, J = 7.9, 1.6 Hz, 1H), 7.47 (d, J = 2.5 Hz, 1H), 7.44-7.35 (m, 4H), 7.32-7.25 (m, 1H), 7.03 (dd, J = 7.9, 4.6 Hz, 1H), 4.42-4.35 (m, 2H), 3.96 (dd, J = 8.0, 6.0 Hz, 2H), 3.89-3.80 (m, 1H). |
| 14 | 330 | Intermediate 3g (6-fluoro-1H-pyrrolo[3,2-b]pyridin-3-carbonyl-azide); 4-(trifluoromethyl)aniline | (structure: 6-fluoro-1H-pyrrolo[3,2-b]pyridin-3-yl urea with 4-CF$_3$-phenyl) | Method C: MS-ESI: 339.1 [M + H$^+$] $^1$HNMR (400 MHz, DMSO-d$_6$) δ 11.05 (s, 1H), 9.43 (s, 1H), 8.89 (s, 1H), 8.35 (dd, J = 2.5, 1.5 Hz, 1H), 7.84 (d, J = 1.9 Hz, 1H), 7.78-7.60 (m, 5H). FNMR: (400 MHz, DMSO-d$_6$) δ −58.79, −59.97, −136.46 |

-continued

| Ex # | Compound # | Starting Material | Final Compound | LCMS and NMR Data |
|---|---|---|---|---|
| 15 | 163 | Intermediate 3b (5-methyl-1H-pyrrolo[2,3-b]pyridine-3-carbonyl-azide); 4-(trifluoromethyl)aniline | | Method C: MS-ESI: 335.1 [M + H⁺] ¹HNMR (400 MHz, DMSO-d₆) δ 11.21 (s, 1H), 9.01 (s, 1H), 8.62 (s, 1H), 8.09 (s, 1H), 7.74-7.66 (m, 3H), 7.63 (d, J = 8.5 Hz, 2H), 7.51 (d, J = 2.7 Hz, 1H), 2.41 (s, 3H). |
| 16 | 259 | Intermediate 23 (5-fluoro-1H-pyrrolo[2,3-b]pyridin-3-amine hydrochloride); Intermediate 3e (5-butylpicolinyl azide) | | Method A: MS-ESI: 328.1 [M + H⁺] ¹HNMR (400 MHz, DMSO-d₆) δ11.58-11.53 (m, 1H), 10.60 (s, 1H), 9.45 (s, 1H), 8.26-8.17 (m, 2H), 7.78 (dd, J = 9.2, 2.8 Hz, 1H), 7.70 (d, J = 2.4 Hz, 1H), 7.61 (dd, J = 8.5, 2.4 Hz, 1H), 7.36 (d, J = 8.5 Hz, 1H), 2.55 (t, J = 7.6 Hz, 2H), 1.58-1.51 (m, 2H), 1.35-1.25 (m, 2H), 0.91 (t, J = 7.3 Hz, 3H). |
| 17 | 152 | Intermediate 3d (1H-pyrrolo[3,2-b]pyridine-3-carbonyl-azide); 5-(trifluoromethyl)pyridin-2-amine | | Method A: MS-ESI: 322.1 [M + H⁺] ¹HNMR (400 MHz, DMSO-d₆) δ 11.01 (s, 1H), 10.15 (s, 1H), 10.03 (s, 1H), 8.65 (d, J = 2.2 Hz, 1H), 8.35 (dd, J = 4.6, 1.4 Hz, 1H), 8.15-8.10 (m, 1H), 7.95-7.87 (m, 2H), 7.77 (dd, J = 8.2, 1.4 Hz, 1H), 7.17 (dd, J = 8.2, 4.5 Hz, 1H). |
| 18 | 156 | Intermediate 3d (1H-pyrrolo[3,2-b]pyridine-3-carbonyl-azide); 6-(trifluoromethyl)pyridin-3-amine | | Method I: MS-ESI: 322.1 [M + H⁺] ¹HNMR (400 MHz, DMSO-d₆) δ 11.00 (s, 1H), 9.68 (s, 1H), 9.00 (s, 1H), 8.75 (d, J = 2.6 Hz, 1H), 8.35 (d, J = 4.6 Hz, 1H), 8.26 (d, J = 8.8 Hz, 1H), 7.89-7.80 (m, 2H), 7.77 (d, J = 8.2 Hz, 1H), 7.18 (dd, J = 8.4, 4.6 Hz, 1H). |
| 19 | 157 | Intermediate 3d (1H-pyrrolo[3,2-b]pyridine-3-carbonyl-azide); bicyclo[3.2.1]octan-3-amine | | Method N: MS-ESI: 285.2 [M + H⁺] ¹HNMR (400 MHz, MeOH-d₄) δ 8.09 (dd, J = 4.7, 1.3 Hz, 1H), 7.58 (dd, J = 8.2, 1.4 Hz, 1H), 7.51 (s, 1H), 6.98 (dd, J = 8.2, 4.7 Hz, 1H), 3.81-3.71 (m, 1H), 2.08 (s, 2H), 1.73-1.67 (m, 2H), 1.57-1.42 (m, 4H), 1.32-1.20 (m, 2H), 1.10 (t, J = 11.9 Hz, 2H). |
| 20 | 329 | Intermediate 3c (5-methyl-1H-pyrrolo[3,2-b]pyridine-3-carbonyl-azide); 4-(trifluoromethyl)aniline | | Method A: MS-ESI, 335.1 [M + H⁺]. ¹HNMR: (400 MHz, MeOH-d₄) δ 7.77 (s, 1H), 7.73 (d, J = 8.3 Hz, 1H), 7.69 (d, J = 8.6 Hz, 2H), 7.59 (d, J = 8.6 Hz, 2H), 7.11 (d, J = 8.4 Hz, 1H), 2.66 (s, 3H). |

| Ex # | Compound # | Starting Material | Final Compound | LCMS and NMR Data |
|---|---|---|---|---|
| 21 | 314 | Intermediate 2a (1H-pyrrolo[2,3-c]pyridine-3-carbonyl-azide); 4-butylcyclohexan-1-amine | *[structure: 1H-pyrrolo[2,3-c]pyridin-3-yl urea with 4-n-butylcyclohexyl group]* | Method A: MS-ESI: 315.2 [M + H⁺]<br>¹HNMR (400 MHz, DMSO-$d_6$) δ 11.3-11.08 (m, 1H), 8.66 (dd, J = 2.3, 1.1 Hz, 1H), 8.20-8.15 (m, 1H), 8.06 (t, J = 5.6 Hz, 1H), 7.62 (dd, J = 8.4, 2.5 Hz, 1H), 7.42 (d, J = 5.5 Hz, 1H), 6.17-5.87 (m, 1H), 3.80-3.41 (m, 1H), 1.94-1.85 (m, 1H), 1.74 (d, J = 12.7 Hz, 1H), 1.65-1.46 (m, 3H), 1.33-1.07 (m, 9H), 1.01-0.84 (m, 4H). |
| 22 | 137 | Intermediate 2a (1H-pyrrolo[2,3-c]pyridine-3-carbonyl-azide); 4-phenylcyclohexan-1-amine | *[structure: 1H-pyrrolo[2,3-c]pyridin-3-yl urea with 4-phenylcyclohexyl group]* | Method A: MS-ESI: 335.2 [M + H⁺]<br>¹HNMR (400 MHz, DMSO-$d_6$) δ 11.14 (d, J = 2.8 Hz, 1H), 8.23-8.16 (m, 2H), 7.91-7.85 (m, 1H), 7.47 (dd, J = 9.5, 2.4 Hz, 1H), 7.37-7.22 (m, 4H), 7.26-7.14 (m, 1H), 7.04 (dt, J = 7.8, 5.2 Hz, 1H), 5.93 (d, J = 7.8 Hz, 1H), 3.60-3.47 (m, 1H), 2.06-1.98 (m, 2H), 1.87-1.78 (m, 2H), 1.73-1.49 (m, 3H), 1.32 (qd, J = 12.6, 3.4 Hz, 2H). |
| 23 | 153 | Intermediate 2a (1H-pyrrolo[2,3-c]pyridine-3-carbonyl-azide); bicyclo[3.2.1]octan-3-amine | *[structure: 1H-pyrrolo[2,3-c]pyridin-3-yl urea with bicyclo[3.2.1]octan-3-yl group]* | Method A: MS-ESI: 285.2 [M + H⁺]<br>¹HNMR (400 MHz, DMSO-$d_6$) δ 11.15 (s, 1H), 8.67 (dd, J = 3.5, 1.1 Hz, 1H), 8.15 (s, 1H), 8.06 (dd, J = 7.7, 5.5 Hz, 1H), 7.65 (dd, J = 8.8, 2.4 Hz, 1H), 7.44 (dd, J = 10.3, 5.5 Hz, 1H), 5.79 (d, J = 8.3 Hz, 1H), 3.85-3.84 (m, 1H), 2.22 (s, 2H), 1.81-1.74 (m, 2H), 1.68-1.61 (m, 2H), 1.50 (d, J = 7.8 Hz, 2H), 1.38 (d, J = 5.1 Hz, 2H), 1.21 (t, J = 12.2 Hz, 2H). |
| 24 | 312 | Intermediate 2a (1H-pyrrolo[2,3-c]pyridine-3-carbonyl-azide); 6-cyclohexyl-pyridine-3-amine | *[structure: 1H-pyrrolo[2,3-c]pyridin-3-yl urea with 6-cyclohexylpyridin-3-yl group]* | Method N: MS-ESI: 336.2 [M + H⁺]<br>¹HNMR (400 MHz, DMSO-$d_6$) δ 11.29 (s, 1H), 8.71 (d, J = 1.1 Hz, 1H), 8.67 (s, 1H), 8.65 (s, 1H), 8.50 (d, J = 2.7 Hz, 1H), 8.10 (d, J = 5.5 Hz, 1H), 7.88 (dd, J = 8.5, 2.7 Hz, 1H), 7.72 (d, J = 2.5 Hz, 1H), 7.49 (d, J = 5.5 Hz, 1H), 7.16 (d, J = 8.5 Hz, 1H), 2.65-2.54 (m, 1H), 1.87-1.65 (m, 5H), 1.58-1.14 (m, 5H). |
| 25 | 313 | Intermediate 2a (1H-pyrrolo[2,3-c]pyridine-3-carbonyl-azide); 5-cyclohexyl-pyridine-2-amine | *[structure: 1H-pyrrolo[2,3-c]pyridin-3-yl urea with 5-cyclohexylpyridin-2-yl group]* | Method A: MS-ESI: 336.2 [M + H⁺]<br>¹HNMR (400 MHz, DMSO-$d_6$) δ 11.29 (d, J = 2.6 Hz, 1H), 8.55-8.49 (m, 2H), 8.23 (dd, J = 4.7, 1.6 Hz, 1H), 7.92 (dd, J = 7.9, 1.6 Hz, 1H), 7.55 (d, J = 2.4 Hz, 1H), 7.38 (t, J = 2.0 Hz, 1H), 7.28-7.20 (m, 1H), 7.17 (t, J = 7.8 Hz, 1H), 7.08 (dd, J = 7.9, 4.6 Hz, 1H), 6.82 (dt, J = 7.5, 1.5 Hz, 1H), 2.50-2.41 (m, 1H), 1.85-1.68 (m, 5H), 1.46-1.12 (m, 5H). |
| 26 | 311 | Intermediate 2a (1H-pyrrolo[2,3-c]pyridine-3-carbonyl-azide); 5-(trifluoromethyl)pyridin-2-amine | *[structure: 1H-pyrrolo[2,3-c]pyridin-3-yl urea with 5-(trifluoromethyl)pyridin-2-yl group]* | Method A: MS-ESI : 322.2 [M + H⁺]<br>¹HNMR (400 MHz, DMSO-$d_6$) δ 11.39 (s, 1H), 10.15 (s, 1H), 9.92 (s, 1H), 8.79-8.72 (m, 2H), 8.17-8.10 (m, 2H), 7.84-7.75 (m, 3H), 7.56 (d, J = 5.5 Hz, 1H).<br>FNMR (400 MHz, DMSO-$d_6$) δ −59.81, −60.01, −60.04 |

| Ex # | Compound # | Starting Material | Final Compound | LCMS and NMR Data |
|---|---|---|---|---|
| 27 | 310 | Intermediate 2a (1H-pyrrolo[2,3-c]pyridine-3-carbonyl-azide); 6-(trifluoromethyl)pyridin-3-amine | | Method L: MS-ESI: 322.1 [M + H⁺] ¹HNMR (400 MHz, DMSO-d₆) δ 11.39-11.34 (m, 1H), 9.30 (s, 1H), 8.91 (s, 1H), 8.78 (d, J = 2.5 Hz, 1H), 8.72 (d, J = 1.2 Hz, 1H), 8.25 (dd, J = 8.7, 2.5 Hz, 1H), 8.11 (d, J = 5.5 Hz, 1H), 7.82 (d, J = 8.7 Hz, 1H), 7.76 (d, J = 2.5 Hz, 1H), 7.52 (d, J = 5.5 Hz, 1H). FNMR (400 MHz, DMSO-d6) δ −65.32, −65.33, −65.37 |
| 28 | 161 | Intermediate 3f (1H-pyrrolo[3,2-c]pyridine-3-carbonyl-azide); bicyclo[3.2.1]octan-3-amine hydrochloride | | Method H: MS-ESI: 285.2 [M + H⁺] ¹HNMR (400 MHz, MeOH-d₄) δ 8.55 (d, J = 1.1 Hz, 1H), 7.93 (d, J = 5.9 Hz, 1H), 7.26 (s, 1H), 7.17 (dd, J = 5.9, 1.0 Hz, 1H), 3.77 (tt, J = 11.,5 5.6 Hz, 1H), 2.08 (s, 2H), 1.75-1.67 (m, 2H), 1.57-1.41 (m, 4H), 1.32-1.20 (m, 2H), 1.09 (t, J = 11.9 Hz, 2H). |
| 29 | 315 | Intermediate 3f (1H-pyrrolo[3,2-c]pyridine-3-carbonyl-azide); 6-cyclohexyl-pyridin-3-amine | | Method L: MS-ESI: 336.2 [M + H⁺] ¹HNMR (300 MHz, DMSO-d₆) δ 11.16 (s, 1H), 8.82 (s, 1H), 8.81 (s, 1H), 8.67 (s, 1H), 8.50 (d, J = 2.6 Hz, 1H), 8.14 (d, J = 5.7 Hz, 1H), 7.88 (dd, J = 8.5, 2.7 Hz, 1H), 7.54 (d, J = 2.2 Hz, 1H), 7.30 (dd, J = 5.8, 1.1 Hz, 1H), 7.16 (d, J = 8.5 Hz, 1H), 2.65-2.55 (m, 1H), 1.88-1.65 (m, 5H), 1.59-1.09 (m, 5H). |
| 30 | 316 | Intermediate 3f (1H-pyrrolo[3,2-c]pyridine-3-carbonyl-azide); 5-cyclohexyl-pyridin-2-amine | | Method A: MS-ESI: 336.2 [M + H⁺] ¹HNMR (400 MHz, DMSO-d₆) δ 11.21 (s, 1H), 10.90 (s, 1H), 9.47 (d, J = 4.3 Hz, 1H), 8.87 (s, 1H), 8.26 (d, J = 2.3 Hz, 1H), 8.19 (d, J = 5.7 Hz, 1H), 7.69-7.59 (m, 2H), 7.41-7.29 (m, 2H), 2.53 -2.47 (m, 1H), 1.85-1.67 (m, 5H), 1.50-1.12 (m, 5H). |
| 31 | 317 | Intermediate 3f (1H-pyrrolo[3,2-c]pyridine-3-carbonyl-azide); 4-butylcyclo-hexan-1-amine | | Method A: MS-ESI: 315.2 [M + H⁺] ¹HNMR (400 MHz, DMSO-d₆) δ 11.14 (s, 1H), 8.79 (s, 1H), 8.42-8.35 (m, 1H), 8.17-8.11 (m, 1H), 7.49 (s, 1H), 7.33 (s, 1H), 6.25-5.88 (m, 1H), 3.85-3.34 (m, 1H), 1.90 (d, J = 11.9 Hz, 1H), 1.74 (d, J = 12.8 Hz, 1H), 1.65-1.46 (m, 3H), 1.35-1.01 (m, 9H), 1.02-0.84 (m, 4H). |
| 32 | 318 | Intermediate 3f (1H-pyrrolo[3,2-c]pyridine-3-carbonyl-azide); 6-(trifluoromethyl)pyridin-3-amine | | Method L: MS-ESI: 322.1 [M + H⁺] ¹HNMR (400 MHz, DMSO-d₆) δ 11.25 (s, 1H), 9.31 (s, 1H), 9.07 (s, 1H), 8.86 (s, 1H), 8.79 (d, J = 2.5 Hz, 1H), 8.26 (dd, J = 8.6, 2.5 Hz, 1H), 8.17 (d, J = 5.7 Hz, 1H), 7.82 (d, J = 8.7 Hz, 1H), 7.59 (d, J = 2.2 Hz, 1H), 7.34 (d, J = 5.7 Hz, 1H). FNMR (400 MHz, DMSO-d₆) δ −65.32, −65.37 |

| Ex # | Compound # | Starting Material | Final Compound | LCMS and NMR Data |
|---|---|---|---|---|
| 33 | 319 | Intermediate 3f (1H-pyrrolo[3,2-c]pyridine-3-carbonyl-azide); 5-(trifluoromethyl)pyridin-2-amine | | Method A: MS-ESI: 322.1 [M + H⁺] ¹HNMR (400 MHz, MeOH-d₄) δ 8.88 (s, 1H), 8.71 (d, J = 2.1 Hz, 1H), 8.20 (d, J = 5.9 Hz, 1H), 8.04 (dd, J = 8.9, 2.5 Hz, 1H), 7.68 (s, 1H), 7.53 (d, J = 8.9 Hz, 1H), 7.43 (dd, J = 5.9, 1.1 Hz, 1H). FNMR (400 MHz, MeOH-d₄) δ −63.33 |
| 34 | 272 | Intermediate 2 (5-fluoro-1H-pyrrolo[2,3-b]pyridine-3-carbonyl-azide); 6-cyclohexyl-pyridin-3-amine | | Method N: MS-ESI: 354.2 [M + H⁺] ¹HNMR (400 MHz, DMSO-d₆) δ 11.52 (s, 1H), 8.67 (s, 1H), 8.62 (s, 1H), 8.50 (d, J = 2.6 Hz, 1H), 8.24-8.19 (m, 1H), 7.87 (dd, J = 8.5, 2.7 Hz, 1H), 7.75 (dd, J = 9.4, 2.8 Hz, 1H), 7.63 (d, J = 2.6 Hz, 1H), 7.16 (d, J = 8.5, Hz, 1H), 2.65-2.54 (m, 1H), 1.85-1.69 (m, 5H), 1.52-1.31 (m, 4H), 1.29-1.18 (m, 1H). FNMR (400 MHz, DMSO-d₆) δ −140.03 |
| 35 | 273 | Intermediate 2 (5-fluoro-1H-pyrrolo[2,3-b]pyridine-3-carbonyl-azide); 4-butylcyclohexan-1-amine | | Method N: MS-ESI: 333.4 [M + H⁺] ¹HNMR (400 MHz, DMSO-d₆) δ 11.32 (s, 1H), 8.29-8.00 (m, 2H), 7.8-7.40 (m, 2H), 5.95 (m, 1H), 3.40 (m, 1H), 1.89 (m, 1H), 1.75 (d, J = 12.8 Hz, 1H), 1.62-1.49 (m, 3H), 1.40-1.10 (m, 9H), 1.10-0.70 (m, 4H). F NMR (400 MHz, DMSO-d₆) δ −140.48 |
| 36 | 274 | Intermediate 2 (5-fluoro-1H-pyrrolo[2,3-b]pyridine-3-carbonyl-azide); 3-butylaniline | | Method N: MS-ESI: 327.2 [M + H⁺] ¹HNMR (400 MHz, DMSO-d₆) δ 11.49 (s, 1H), 8.53 (s, 2H), 8.49 (s, 2H), 8.21 (t, J = 2.2 Hz, 1H), 7.73 (dd, J = 9.4, 2.8 Hz, 1H), 7.63 (d, J = 2.5 Hz, 1H), 7.34 (t, J = 1.9 Hz, 1H), 7.26 (dt, J = 8.2, 1.6 Hz, 1H), 7.17 (t, J = 7.8 Hz, 1H), 6.79 (d, J = 7.4 Hz, 1H), 2.56 (t, J = 7.6 Hz, 2H), 1.55 (tt, J = 7.7, 6.3 Hz, 2H), 1.37-1.28 (m, 2H), 0.91 (t, J = 7.3 Hz, 3H). FNMR (400 MHz, DMSO-d₆) δ −140.11 |
| 37 | 275 | Intermediate 2 (5-fluoro-1H-pyrrolo[2,3-b]pyridine-3-carbonyl-azide); 4-butylaniline | | Method A: MS-ESI: 327.2 [M + H⁺] ¹HNMR (400 MHz, DMSO-d₆) δ 11.48 (d, J = 2.4 Hz, 1H), 8.49 (s, 1H), 8.47 (s, 1H), 8.21 (t, J = 2.4 Hz, 1H), 7.73 (dd, J = 9.4, 2.8 Hz, 1H), 7.62 (d, J = 2.5 Hz, 1H), 7.37 (d, J = 8.4 Hz, 2H), 7.09 (d, J = 8.4 Hz, 2H), 2.53 (t, J = 8.8 Hz, 2H), 1.59-1.47 (m, 2H), 1.34-1.24 (m, 2H), 0.90 (t, J = 7.3 Hz, 3H). FNMR (400 MHz, DMSO-d₆) δ −139.88 |

| Ex # | Compound # | Starting Material | Final Compound | LCMS and NMR Data |
|---|---|---|---|---|
| 38 | 280 | Intermediate 2 (5-fluoro-1H-pyrrolo[2,3-b]pyridine-3-carbonyl-azide); 5-fluoropyridin-2-amine | | Method E: MS-ESI: 290.1 [M + H$^+$] $^1$HNMR (400 MHz, DMSO-d$_6$): δ 11.57 (s, 1H), 9.84 (s, 1H), 9.47 (s, 1H), 8.33-8.34 (d, J = 0.4 Hz, 1H), 8.23 (s, 1H), 7.65-7.78 (m, 4H). FNMR (400 MHz, DMSO-d$_6$): δ −73.41, −136.73, −139.82 |
| 39 | 281 | Intermediate 2 (5-fluoro-1H-pyrrolo[2,3-b]pyridine-3-carbonyl-azide); 2-trifluoromethyl-5-aminopyridine | | Method G: MS-ESI: 340.1 [M + H$^+$] $^1$HNMR (400 MHz, DMSO-d$_6$) δ 11.61 (s, 1H), 9.32 (s, 1H), 8.87 (s, 1H), 8.78 (d, J = 2.5 Hz, 1H), 8.28-8.20 (m, 2H), 7.85-7.75 (m, 2H), 7.67 (d, J = 2.6 Hz, 1H). FNMR (400 MHz, DMSO-d$_6$) δ −65.37, −139.81 |
| 40 | 282 | Intermediate 2 (5-fluoro-1H-pyrrolo[2,3-b]pyridine-3-carbonyl-azide); 3-chloro-4-(trifluoromethyl)aniline | | Method A: MS-ESI: 373.0 [M + H$^+$] $^1$HNMR (400 MHz, DMSO-d$_6$) δ 11.63-11.58 (m, 1H), 9.28 (s, 1H), 8.81 (s, 1H), 8.23 (s, 1H), 7.96 (d, J = 2.1 Hz, 1H), 7.81-7.70 (m, 2H), 7.66 (d, J = 2.6 Hz, 1H), 7.52 (dd, J = 8.6, 2.1 Hz, 1H). FNMR (400 MHz, DMSO-d$_6$) δ −59.83, −139.82 |
| 41 | 284 | Intermediate 2 (5-fluoro-1H-pyrrolo[2,3-b]pyridine-3-carbonyl-azide); 5,6,7,8-tetrahydro-naphthalen-1-amine | | Method L: MS-ESI: 325.1 [M + H$^+$] $^1$HNMR (400 MHz, DMSO-d$_6$) δ 11.47 (s, 1H), 8.85 (s, 1H), 8.24-8.19 (m, 1H), 7.77-7.70 (m, 2H), 7.69 (d, J = 8.0 Hz, 1H), 7.63 (d, J = 2.6 Hz, 1H), 7.03 (t, J = 7.8 Hz, 1H), 6.77 (d, J = 7.5 Hz, 1H), 2.73 (t, J = 6.2 Hz, 2H), 2.60 (t, J = 6.4 Hz, 2H), 1.81 (dd, J = 7.8, 3.7 Hz, 2H), 1.77-1.67 (m, 2H). F NMR (400 MHz, DMSO-d6) δ −65.37, −140.20 |
| 42 | 286 | Intermediate 2 (5-fluoro-1H-pyrrolo[2,3-b]pyridine-3-carbonyl-azide); 2-methylbenzo[d]thiazol-5-amine | | Method A: MS-ESI: 342.1 [M + H$^+$] $^1$HNMR (400 MHz, DMSO-d$_6$) δ 11.53 (d, J = 2.5 Hz, 1H), 8.87 (s, 1H), 8.64 (s, 1H), 8.25-8.19 (m, 1H), 8.15 (d, J = 2.1 Hz, 1H), 7.89 (d, J = 8.7 Hz, 1H), 7.78 (dd, J = 9.4, 2.8 Hz, 1H), 7.66 (d, J = 2.6 Hz, 1H), 7.45 (dd, J = 8.7, 2.1 Hz, 1H), 2.78 (s, 3H). FNMR (400 MHz, DMSO-d$_6$) δ −140.01, −140.05 |
| 43 | 287 | Intermediate 2 (5-fluoro-1H-pyrrolo[2,3-b]pyridine-3-carbonyl-azide); isoquinolin-7-amine | | Method A: MS-ESI: 322.1 [M + H$^+$] $^1$HNMR (400 MHz, MeOH-d$_4$) δ 8.11-8.09 (d, J = 8.0 Hz, 2H), 7.66-7.60 (m, 2H), 7.56-7.54 (d, J = 8.0 Hz, 1H), 6.68-6.67 (d, J = 6.8 Hz, 1H), 3.65 (s, 3H), 2.94-2.90 (t, J = 8.0 Hz, 2H), 1.61-1.57 (m, 2H), 1.41-1.35 (m, 2H), 0.92-0.88 (t, J = 7.6 Hz, 3H). FNMR (400 MHz, MeOH-d$_4$) δ −139.59, −139.72, −139.97 |

-continued

| Ex # | Compound # | Starting Material | Final Compound | LCMS and NMR Data |
|---|---|---|---|---|
| 44 | 288 | Intermediate 2 (5-fluoro-1H-pyrrolo[2,3-b]pyridine-3-carbonyl-azide); isoquinolin-6-amine | 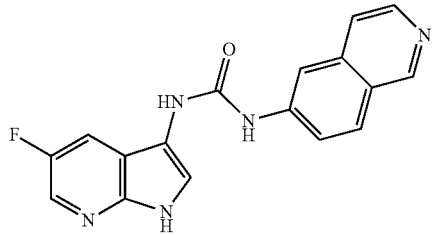 [SMILES: O=C(Nc1ccc2cnccc2c1)Nc1c[nH]c2ncc(F)cc12] | Method A: MS-ESI: 322.1 [M + H+]<br>$^1$HNMR (400 MHz, DMSO-d$_6$) δ 11.58 (s, 1H), 9.15 (d, J = 8.8 Hz, 2H), 8.77 (s, 1H), 8.39 (d, J = 5.8 Hz, 1H), 8.24 (t, J = 2.2 Hz, 1H), 8.19 (d, J = 2.0 Hz, 1H), 8.04 (d, J = 8.8 Hz, 1H), 7.79 (dd, J = 9.4, 2.8 Hz, 1H), 7.72-7.66 (m, 2H), 7.66 (dd, J = 8.9, 2.1 Hz, 1H). |
| 45 | 291 | Intermediate 2 (5-fluoro-1H-pyrrolo[2,3-b]pyridine-3-carbonyl-azide); 4-ethynylaniline | 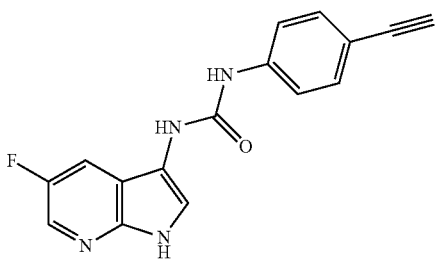 [SMILES: C#Cc1ccc(NC(=O)Nc2c[nH]c3ncc(F)cc23)cc1] | Method L: MS-ESI: 295.1 [M + H+]<br>$^1$HNMR (300 MHz, DMSO-d$_6$) δ 11.51 (s, 1H), 8.81 (s, 1H), 8.56 (s, 1H), 8.21 (t, J = 2.2 Hz, 1H), 7.73 (dd, J = 9.5, 2.8 Hz, 1H), 7.62 (d, J = 2.6 Hz, 1H), 7.50 (d, J = 8.3 Hz, 2H), 7.38 (d, J = 8.3 Hz, 2H), 4.00 (s, 1H). |
| 46 | 292 | Intermediate 2 (5-fluoro-1H-pyrrolo[2,3-b]pyridine-3-carbonyl-azide); benzo[d]thiazol-2-amine | 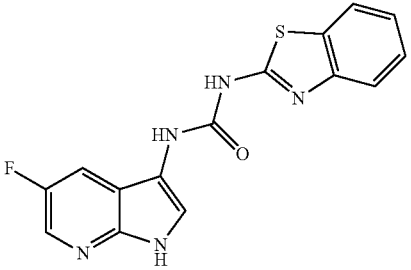 [SMILES: O=C(Nc1nc2ccccc2s1)Nc1c[nH]c2ncc(F)cc12] | Method H: MS-ESI: 328.1 [M + H+]<br>$^1$HNMR (400 MHz, DMSO-d$_6$) δ 11.67 (s, 1H), 10.87 (s, 1H), 9.21 (s, 1H), 8.24 (s, 1H), 7.90 (d, J = 6.8 Hz, 1H), 7.83 (d, J = 13.4 Hz, 1H), 7.72 (s, 1H), 7.65 (s, 1H), 7.39 (t, J = 8.0 Hz, 1H), 7.24 (t, J = 7.6 Hz, 1H).<br>FNMR (400 MHz, DMSO-d6) δ −139.62 |
| 47 | 293 | Intermediate 2 (5-fluoro-1H-pyrrolo[2,3-b]pyridine-3-carbonyl-azide); 5-phenylthiazol-2-amine | 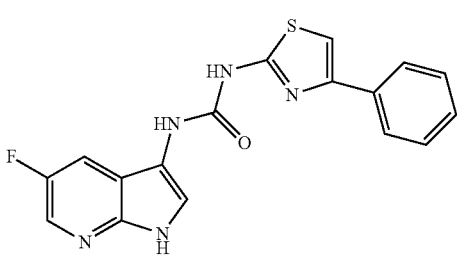 [SMILES: O=C(Nc1nc(-c2ccccc2)cs1)Nc1c[nH]c2ncc(F)cc12] | Method I: MS-ESI: 354.1 [M + H+]<br>$^1$HNMR (400 MHz, DMSO-d$_6$) δ 11.65 (s, 1H), 10.64 (s, 1H), 8.86 (s, 1H), 8.24 (s, 1H), 7.79 (s, 1H), 7.76 (s, 1H), 7.70 (d, J = 2.1 Hz, 1H), 7.59 (d, J = 7.2 Hz, 2H), 7.41 (t, J = 7.7 Hz, 2H), 7.29 (t, J = 7.4 Hz, 1H).<br>FNMR (400 MHz, DMSO-d$_6$) δ −139.72 |
| 48 | 294 | Intermediate 2 (5-fluoro-1H-pyrrolo[2,3-b]pyridine-3-carbonyl-azide); 4-butylpiperidine-hydrochloride | 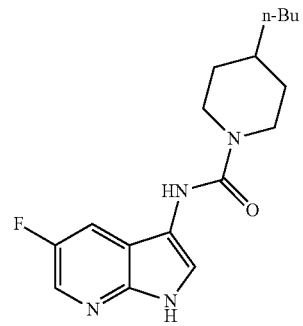 | Method I: MS-ESI: 319.2 [M + H+]<br>$^1$HNMR (300 MHz, DMSO-d$_6$) δ 11.35 (s, 1H), 8.24-8.15 (d, J = 26.9 Hz, 2H), 7.86 (dd, J = 9.8, 2.9 Hz, 1H), 7.51 (d, J = 2.7 Hz, 1H), 4.12 (d, J = 13.8 Hz, 2H), 2.75 (t, J = 12.3 Hz, 2H), 1.67 (d, J = 13.0 Hz, 2H), 1.27 (s, 7H), 1.04 (d, J = 12.2 Hz, 2H), 0.88 (s, 3H). |

-continued

| Ex # | Compound # | Starting Material | Final Compound | LCMS and NMR Data |
|---|---|---|---|---|
| 49 | 295 | Intermediate 2 (5-fluoro-1H-pyrrolo[2,3-b]pyridin-3-carbonyl-azide); 2-phenylthiazol-5-amine | | Method A: MS-ESI: 354.1 [M + H⁺] ¹HNMR (300 MHz, DMSO-d₆) δ 11.62 (s, 1H), 9.93 (s, 1H), 8.83 (s, 1H), 8.22 (s, 1H), 7.88-7.72 (m, 3H), 7.65 (d, J = 2.3 Hz, 1H), 7.55-7.31 (m, 4H). |
| 50 | 296 | Intermediate 2 (5-fluoro-1H-pyrrolo[2,3-b]pyridine-3-carbonyl-azide); 5,6,7,8-tetrahydro-naphthalen-2-amine | | Method A: MS-ESI: 325.1 [M + H⁺] ¹HNMR (300 MHz, DMSO-d₆) δ 11.45 (s, 1H), 8.42 (d, J = 18.6 Hz, 2H), 8.19 (s, 1H), 7.71 (dd, J = 9.4, 2.8 Hz, 1H), 7.60 (d, J = 2.6 Hz, 1H), 7.22-7.09 (m, 2H), 6.93 (d, J = 8.4 Hz, 1H), 2.65 (d, J = 10.5 Hz, 4H), 1.71 (s, 4H). |
| 51 | 297 | Intermediate 2 (5-fluoro-1H-pyrrolo[2,3-b]pyridine-3-carbonyl-azide); 3-(trifluoromethyl)aniline | | Method A: MS-ESI: 339.1 [M + H⁺] ¹HNMR (400 MHz, DMSO-d₆) δ 11.55 (brs, 1H), 9.04 (s, 1H), 8.69 (s, 1H), 8.22 (dd, J = 2.8, 1.7 Hz, 1H), 8.05 (d, J = 2.1 Hz, 1H), 7.77 (dd, J = 9.4, 2.8 Hz, 1H), 7.68-7.59 (m, 2H), 7.51 (t, J = 8.0 Hz, 1H), 7.32-7.26 (m, 1H). FNMR (400 MHz, DMSO-d₆): δ −61.23, −61.26, −139.2 |
| 52 | 298 | Intermediate 2 (5-fluoro-1H-pyrrolo[2,3-b]pyridine-3-carbonyl-azide); 3,5-difluoroaniline | | Method N: MS-ESI: 307.1 [M + H⁺] ¹HNMR (400 MHz, DMSO-d₆) δ 11.60-11.55 (m, 1H), 9.05 (s, 1H), 8.71 (s, 1H), 8.22 (dd, J = 2.7, 1.7 Hz, 1H), 7.76 (dd, J = 9.4, 2.8 Hz, 1H), 7.64 (d, J = 2.5 Hz, 1H), 7.29-7.17 (m, 2H), 6.77 (tt, J = 9.4, 2.3 Hz, 1H). FNMR (400 MHz, DMSO-d₆) δ −109.86, −139.89 |
| 53 | 300 | Intermediate 2 (5-fluoro-1H-pyrrolo[2,3-b]pyridine-3-carbonyl-azide); spiro[5.5]un-decan-3-amine hydrochloride | | Method A: MS-ESI: 345.2 [M + H⁺] ¹HNMR (400 MHz, DMSO-d₆) δ 11.33 (s, 1H), 8.20-8.11 (m, 2H), 7.67 (dd, J = 9.5, 2.8 Hz, 1H), 7.52 (d, J = 2.5 Hz, 1H), 5.91 (d, J = 7.9 Hz, 1H), 3.55-3.42 (m, 1H), 1.69-1.52 (m, 4H), 1.44-1.26 (m, 10H), 1.25-1.08 (m, 4H). FNMR (400 MHz, DMSO-d₆): δ −140.10, −140.24, −140.47 |
| 54 | 305 | Intermediate 2 (5-fluoro-1H-pyrrolo[2,3-b]pyridine-3-carbonyl-azide); Intermediate 31 (spiro[2.5]octan-6-amine hydrochloride) | | Method A: MS-ESI: 303.2 [M + H⁺] ¹HNMR (300 MHz, DMSO-d₆) δ 11.31 (brs, 1H), 8.20-8.09 (m, 2H), 7.65 (dd, J = 9.4, 2.8 Hz, 1H), 7.52 (s, 1H), 5.95 (d, J = 7.9 Hz, 1H), 3.61-3.47 (m, 1H), 1.86-1.75 (m, 2H), 1.65-1.55 (m, 2H), 1.43-1.26 (m, 2H), 1.09-0.98 (m, 2H), 0.34-0.15 (m, 4H). |

-continued

| Ex # | Compound # | Starting Material | Final Compound | LCMS and NMR Data |
|---|---|---|---|---|
| 55 | 138 | Intermediate 2 (5-fluoro-1H-pyrrolo[2,3-b]pyridine-3-carbonyl-azide); 5-(trifluoromethyl)pyridin-2-amine | | Method N: MS-ESI: 340.1 [M + H$^+$] $^1$HNMR (400 MHz, DMSO-d$_6$) δ 11.63 (s, 1H), 10.13 (s, 1H), 9.91 (s, 1H), 8.78 (s, 1H), 8.28-8.22 (m, 1H), 8.13 (dd, J = 8.9, 2.5 Hz, 1H), 7.83 (dd, J = 9.2, 2.7 Hz, 1H), 7.77-7.70 (m, 2H). |
| 56 | 172 | Intermediate 2 (5-fluoro-1H-pyrrolo[2,3-b]pyridine-3-carbonyl-azide); N-methyl-4-(trifluoromethyl)aniline | | Method A: MS-ESI: 353.1 [M + H$^+$] $^1$HNMR (400 MHz, DMSO-d$_6$) δ 11.50 (s, 1H), 8.54 (s, 1H), 8.18-8.17 (m, 1H), 7.84-7.82 (m, 1H), 7.73 (d, J = 8.4 Hz, 2H), 7.60 (d, J = 8.4 Hz, 2H), 7.53 (d, J = 2.0 Hz, 1H), 3.40 (s, 3H). FNMR (400 MHz, DMSO-d$_6$) δ −60.47, −140.44 |
| 57 | 174 | Intermediate 2 (5-fluoro-1H-pyrrolo[2,3-b]pyridine-3-carbonyl-azide); 4-ethylaniline | | Method J: MS-ESI: 299.1 [M + H$^+$] $^1$HNMR (400 MHz, DMSO-d$_6$) δ 11.49 (s, 1H), 8.51 (s, 1H), 8.49 (s, 1H), 8.21 (dd, J = 2.8, 1.7 Hz, 1H), 7.73 (dd, J = 9.4, 2.8 Hz, 1H), 7.62 (d, J = 2.6 Hz, 1H), 7.42-7.34 (m, 2H), 7.14-7.08 (m, 2H), 2.65 (q, J = 7.6 Hz, 2H), 1.16 (t, J = 7.6 Hz, 3H). FNMR (DMSO-d$_6$, 400 MHz, ppm): δ −140.12 |
| 58 | 271 | Intermediate 2 (5-fluoro-1H-pyrrolo[2,3-b]pyridine-3-carbonyl-azide); 3-cyclohexyl-aniline | | Method A: MS-ESI: 353.2 [M + H$^+$] $^1$HNMR (300 MHz, DMSO-d$_6$) δ 11.48 (s, 1H), 8.53 (s, 1H), 8.49 (s, 1H), 8.24-8.16 (m, 1H), 7.72 (dd, J = 9.5, 2.8 Hz, 1H), 7.62 (d, J = 2.6 Hz, 1H), 7.37 (s, 1H), 7.23 (d, J = 8.0 Hz, 1H), 7.16 (t, J = 7.8 Hz, 1H), 6.81 (d, J = 7.5 Hz, 1H), 2.50-2.42 (m, 1H), 1.85-1.66 (m, 5H), 1.45-1.18 (m, 5H). FNMR (400 MHz, DMSO-d$_6$) δ −140.10 |
| 59 | 270 | Intermediate 2 (5-fluoro-1H-pyrrolo[2,3-b]pyridine-3-carbonyl-azide); 4-(trifluoromethyl)cyclohexan-1-amine | | Method A: MS-ESI: 345.1 [M + H$^+$] $^1$HNMR (400 MHz, DMSO-d$_6$) δ 11.35 (s, 1H), 8.19-8.16 (m, 1H), 8.13 (s, 1H), 7.66 (dt, J = 9.4, 2.8 Hz, 1H), 7.53 (dd, J = 7.7, 2.5 Hz, 1H), 6.29 (d, J = 7.4 Hz, 1H), 3.93-3.38 (m, 1H), 2.39-2.25 (m, 1H), 1.98 (d, J = 12.0 Hz, 1H), 1.89 (d, J = 12.6 Hz, 1H), 1.81-1.67 (m, 3H), 1.66-1.43 (m, 2H), 1.41-1.11 (m, 1H). FNMR (400 MHz, DMSO-d$_6$) δ 71.88, −72.05, −14.42, 140.45 |
| 60 | 269 | Intermediate 2 (5-fluoro-1H-pyrrolo[2,3-b]pyridine-3-carbonyl-azide); quinolin-2-amine | | Method A: MS-ESI: 322.1 [M + H$^+$] $^1$HNMR (400 MHz, DMSO-d$_6$) δ 11.66 (s, 1H), 11.60 (s, 1H), 10.11 (s, 1H), 8.31 (d, J = 9.0 Hz, 1H), 8.28-8.25 (m, 1H), 7.92-7.90 (m, 1H), 7.89-7.87 (m, 1H), 7.85-7.73 (m, 3H), 7.51-7.40 (m, 2H). FNMR (400 MHz, DMSO-d$_6$) δ −139.50 |

-continued

| Ex # | Compound # | Starting Material | Final Compound | LCMS and NMR Data |
|---|---|---|---|---|
| 61 | 262 | Intermediate 2 (5-fluoro-1H-pyrrolo[2,3-b]pyridine-3-carbonyl-azide); 4-cyclohexyl-pyridine-2-amine | | Method A: MS-ESI: 354.2 [M + H$^+$] $^1$HNMR (400 MHz, DMSO-d$_6$) δ 11.58-11.53 (m, 1H), 10.64 (s, 1H), 9.45 (s, 1H), 8.26-8.20 (m, 2H), 7.76 (dd, J = 9.3, 2.8 Hz, 1H), 7.70 (d, J = 2.5 Hz, 1H), 7.32 (s, 1H), 6.90 (dd, J = 5.2, 1.5 Hz, 1H), 2.53-2.45 (m, 1H), 1.76 (dd, J = 36.5, 10.5 Hz, 5H), 1.46-1.14 (m, 5H). FNMR (400 MHz, DMSO-d$_6$) δ −139.86 |
| 62 | 261 | Intermediate 2 (5-fluoro-1H-pyrrolo[2,3-b]pyridine-3-carbonyl-azide); 5-cyclohexyl-pyridin-2-amine | | Method L: MS-ESI: 354.2 [M + H$^+$] $^1$HNMR (400 MHz, DMSO-d$_6$) δ 11.55 (s, 1H), 10.64 (s, 1H), 9.42 (s, 1H), 8.27-8.22 (m, 2H), 7.78 (dd, J = 9.3, 2.8 Hz, 1H), 7.71 (d, J = 2.6 Hz, 1H), 7.65 (dd, J = 8.6, 2.5 Hz, 1H), 7.35 (d, J = 8.5 Hz, 1H), 2.54-2.48 (m, 1H), 1.88-1.67 (m, 5H), 1.50-1.18 (m, 5H). FNMR (400 MHz, DMSO-d$_6$) δ −139.86 |
| 63 | 260 | Intermediate 2 (5-fluoro-1H-pyrrolo[2,3-b]pyridine-3-carbonyl-azide); 6-cyclohexyl-pyridin-2-amine | | Method M: MS-ESI: 354.2 [M + H$^+$] $^1$HNMR (300 MHz, DMSO-d$_6$) δ 11.59 (d, J = 2.6 Hz, 1H), 10.92 (s, 1H), 9.54 (s, 1H), 8.28-8.20 (m, 1H), 7.75-7.60 (m, 3H), 7.14 (d, J = 8.2 Hz, 1H), 6.87 (d, J = 7.5 Hz, 1H), 2.74-2.61 (m, 1H), 1.99-1.89 (m, 2H), 1.85-1.68 (m, 3H), 1.58-1.42 (m, 2H), 1.46-1.17 (m, 3H). FNMR (300 MHz, DMSO-d$_6$) δ −140.02 |
| 64 | 255 | Intermediate 2 (5-fluoro-1H-pyrrolo[2,3-b]pyridine-3-carbonyl-azide); Intermediate 36 (6-butyl-5-fluoropyridin-3-amine) | | Method A: MS-ESI: 346.1 [M + H$^+$] $^1$HNMR (400 MHz, DMSO-d$_6$) δ 11.57 (s, 1H), 8.96 (s, 1H), 8.70 (s, 1H), 8.34 (dd, J = 2.2, 1.2 Hz, 1H), 8.25-8.19 (m, 1H), 7.91 (dd, J = 12.4, 2.1 Hz, 1H), 7.76 (dd, J = 9.5, 2.8 Hz, 1H), 7.64 (d, J = 2.4 Hz, 1H), 2.71 (td, J = 7.6, 2.3 Hz, 2H), 1.68-1.56 (m, 2H), 1.36-1.27 (m, 2H), 0.90 (t, J = 7.4 Hz, 3H). FNMR (400 MHz, DMSO-d$_6$) δ −125.99, −126.10, −126.13 −126.36, −126.38, −139.23 −139.24, 139.90 |
| 65 | 254 | Intermediate 2 (5-fluoro-1H-pyrrolo[2,3-b]pyridine-3-carbonyl-azide); 5-chloropyridin-2-amine | | Method O: MS-ESI: 306.0 [M + H$^+$] $^1$HNMR (400 MHz, DMSO-d$_6$) δ 9.88 (s, 1H), 9.55 (s, 1H), 8.43-8.38 (m, 1H), 8.24 (dd, J = 2.8, 1.7 Hz, 1H), 7.87 (dd, J = 9.0, 2.7 Hz, 1H), 7.78 (dd, J = 9.3, 2.8 Hz, 1H), 7.70 (s, 1H), 7.65 (d, J = 9.0 Hz, 1H). FNMR (400 MHz, DMSO-d$_6$) δ −139.79 |

| Ex # | Compound # | Starting Material | Final Compound | LCMS and NMR Data |
|---|---|---|---|---|
| 66 | 253 | Intermediate 2 (5-fluoro-1H-pyrrolo[2,3-b]pyridine-3-carbonyl-azide); Intermediate 37 (5-butyl-3-fluoropyridin-2-amine) | | Method A: MS-ESI: 346.0 [M + H$^+$] $^1$HNMR (400 MHz, DMSO-d$_6$) δ 11.58 (s, 1H), 10.98 (s, 1H), 8.24 (t, J = 2.2 Hz, 1H), 8.15 (d, J = 1.9 Hz, 1H), 7.81 (dd, J = 9.2, 2.8 Hz, 1H), 7.72 (s, 1H), 7.66 (dd, J = 11.6, 1.9 Hz, 1H), 2.60 (t, J = 7.7 Hz, 2H), 1.62-1.54 (m, 2H), 1.37-1.27 (m, 2H), 0.92 (t, J = 7.3 Hz, 3H). FNMR (400 MHz, DMSO-d$_6$) δ −139.82 |
| 67 | 252 | Intermediate 2 (5-fluoro-1H-pyrrolo[2,3-b]pyridine-3-carbonyl-azide); 1-(2,2,2-trifluoroethyl)piperidin-4-amine | | Method A: MS-ESI: 359.1 [M + H$^+$] $^1$HNMR (300 MHz, DMSO-d$_6$) δ 11.34 (s, 1H), 8.17 (s, 1H), 8.15 (s, 1H), 7.66 (dd, J = 9.5, 2.8 Hz, 1H), 7.51 (d, J = 2.2 Hz, 1H), 5.95 (d, J = 7.7 Hz, 1H), 3.54-3.32 (m, 1H), 3.21-2.07 (m, 2H), 2.90-2.80 (m, 2H), 2.53-2.32 (m, 3H), 1.85-1.70 (m, 2H), 1.51-1.33 (m, 2H). FNMR (300 MHz, DMSO-d$_6$) δ −68.08, −140.56 |
| 68 | 251 | Intermediate 2 (5-fluoro-1H-pyrrolo[2,3-b]pyridine-3-carbonyl-azide); 3-ethynylaniline | | Method L: MS-ESI: 295.1 [M + H$^+$] $^1$HNMR (400 MHz, DMSO-d$_6$) δ 11.54 (s, 1H), 8.74 (s, 1H), 8.59 (s, 1H), 8.22 (t, J = 2.2 Hz, 1H), 7.76 (dd, J = 9.4, 2.8 Hz, 1H), 7.71 (t, J = 1.9 Hz, 1H), 7.64 (d, J = 2.3 Hz, 1H), 7.46-7.41 (m, 1H), 7.29 (t, J = 7.9 Hz, 1H), 7.07 (dt, J = 7.6, 1.3 Hz, 1H), 4.16 (s, 1H). FNMR (400 MHz, DMSO-d$_6$) δ −139.98, −139.99 |
| 69 | 250 | Intermediate 2 (5-fluoro-1H-pyrrolo[2,3-b]pyridine-3-carbonyl-azide); 4-cyclobutyl-3-fluoroaniline | | Method A: MS-ESI: 343.1 [M + H$^+$] $^1$HNMR (400 MHz, DMSO-d$_6$) δ 11.53 (s, 1H), 8.74 (s, 1H), 8.54 (s, 1H), 8.24-8.19 (m, 1H), 7.73 (dd, J = 9.3, 2.8 Hz, 1H), 7.63 (d, J = 2.3 Hz, 1H), 7.42 (dd, J = 13.2, 2.1 Hz, 1H), 7.23 (t, J = 8.6 Hz, 1H), 7.12 (dd, J = 8.3, 2.1 Hz, 1H), 3.66-3.57 (m, 1H), 2.32-2.21 (m, 2H), 2.16-2.05 (m, 2H), 2.07-1.89 (m, 1H), 1.85-1.77 (m, 1H). FNMR (400 MHz, DMSO-d$_6$) δ −117.28, −140.01 |
| 70 | 285 | Intermediate 3a (1H-pyrrolo[2,3-b]pyridine-3-carbonyl-azide); 3-butylcyclopentan-1-amine | | Method A: MS-ESI: 301.2 [M + H$^+$] $^1$HNMR (300 MHz, DMSO-d$_6$) δ 11.10 (s, 2H), 8.17 (dd, J = 4.7, 1.6 Hz, 2H), 8.11 (d, J = 5.6 Hz, 2H), 7.85 (dt, J = 8.0, 1.8 Hz, 2H), 7.43 (s, 2H), 7.01 (dd, J = 8.0, 4.7 Hz, 2H), 6.02 (t, J = 7.1 Hz, 2H), 4.03-3.88 (m, 1H), 2.16-2.06 (m, 1H), 2.00-1.56 (m, 4H), 1.49-1.05 (m, 9H), 0.93-0.82 (m, 3H). |

-continued

| Ex # | Compound # | Starting Material | Final Compound | LCMS and NMR Data |
|---|---|---|---|---|
| 71 | 301 | Intermediate 3a (1H-pyrrolo[2,3-b]pyridine-3-carbonyl-azide); 1,2,3,4-tetrahydroquinoline | | Method H: MS-ESI: 293.1 [M + H$^+$] $^1$HNMR (300 MHz, MeOH-d$_4$) δ 8.23-8.16 (m, 1H), 8.00 (dd, J = 8.0, 1.5 Hz, 1H), 7.56-7.43 (m, 2H), 7.25-7.19 (m, 2H), 7.16-7.01 (m, 2H), 3.88-3.78 (m, 2H), 2.84 (t, J = 6.6 Hz, 2H), 2.08-1.99 (m, 2H). |
| 72 | 302 | Intermediate 3a (1H-pyrrolo[2,3-b]pyridine-3-carbonyl-azide); 2,3-dihydro-1H-inden-2-amine | | Method A: MS-ESI: 293.1 [M + H$^+$] $^1$HNMR (400 MHz, DMSO-d$_6$) δ 11.17 (d, J = 12.4 Hz, 1H), 8.26-8.18 (m, 1H), 7.86 (d, J = 7.6 Hz, 1H), 7.49 (d, J = 12.4 Hz, 1H), 7.35-7.12 (m, 4H), 7.07-6.98 (m, 1H), 6.37-6.28 (m, 1H), 4.47 (s, 1H), 3.29-3.16 (m, 2H), 2.73-2.58 (m, 2H). |
| 73 | 303 | Intermediate 3a (1H-pyrrolo[2,3-b]pyridine-3-carbonyl-azide); indoline | | Method A: MS-ESI: 279.1 [M + H$^+$] $^1$HNMR (400 MHz, MeOH-d$_4$) δ 8.23 (dd, J = 4.8, 1.5 Hz, 1H), 8.10 (dd, J = 7.9, 1.5 Hz, 1H), 7.90 (d, J = 8.0 Hz, 1H), 7.48 (s, 1H), 7.26-7.19 (m, 1H), 7.19-7.10 (m, 2H), 6.95 (td, J = 7.4, 1.1 Hz, 1H), 4.21 (dd, J = 9.1, 8.1 Hz, 2H), 3.29 (t, J = 8.6 Hz, 2H). |
| 74 | 304 | Intermediate 3a (1H-pyrrolo[2,3-b]pyridine-3-carbonyl-azide); 3-phenylcyclohexan-1-amine | | Method C: MS-ESI: 335.2 [M + H$^+$] $^1$HNMR (400 MHz, DMSO-d$_6$) δ 11.13 (d, J = 2.5 Hz, 1H), 8.25-8.15 (m, 2H), 7.86 (dd, J = 7.9, 1.6 Hz, 1H), 7.43 (d, J = 2.4 Hz, 1H), 7.34-7.26 (m, 2H), 7.28-.22 (m, 2H), 7.22-7.14 (m, 1H), 7.02 (dd, J = 7.9, 4.6 Hz, 1H), 5.94 (d, J = 7.9 Hz, 1H), 3.66-3.54 (m, 1H), 2.68-2.59 (m, 1H), 2.03 (d, J = 12.1 Hz, 1H), 1.95 (d, J = 12.4 Hz, 1H), 1.85 (dt, J = 12.8, 3.3 Hz, 1H), 1.76 (d, J = 12.4 Hz, 1H), 1.55-1.41 (m, 1H), 1.43-1.27 (m, 1H), 1.25-1.13 (m, 1H). |
| 75 | 306 | Intermediate 3a (1H-pyrrolo[2,3-b]pyridine-3-carbonyl-azide); 1,2,3,4-tetrahydroisoquinoline | | Method C: MS-ESI: 293.1 [M + H$^+$] $^1$HNMR (400 MHz, DMSO-d$_6$) δ 11.24 (brs, 1H), 8.41 (s, 1H), 8.19 (dd, J = 4.6, 1.6 Hz, 1H), 8.04 (dd, J = 8.0, 1.6 Hz, 1H), 7.44 (d, J = 2.4 Hz, 1H), 7.20 (s, 4H), 7.02 (dd, J = 8.0, 4.6 Hz, 1H), 4.67 (s, 2H), 3.74 (t, J = 5.9 Hz, 2H), 2.87 (t, J = 5.9 Hz, 2H). |
| 76 | 307 | Intermediate 3a (1H-pyrrolo[2,3-b]pyridine-3-carbonyl-azide); 3-phenyl-piperidine | | Method K: MS-ESI: 321.2 [M + H$^+$] $^1$HNMR (400 MHz, DMSO-d$_6$) δ 11.21 (s, 1H), 8.37 (s, 1H), 8.18 (dd, J = 4.6, 1.7 Hz, 1H), 8.02 (dd, J = 8.0, 1.6 Hz, 1H), 7.43 (d, J = 2.5 Hz, 1H), 7.36-7.32 (m, 4H), 7.29-7.20 (m, 1H), 7.01 (dd, J = 7.9, 4.6 Hz, 1H), 4.24 (d, J = 12.6 Hz, 2H), 2.95-2.79 (m, 2H), 2.76-2.69 (m, 1H), 1.96 (d, J = 12.9 Hz, 1H), 1.81-1.54 (m, 3H). |

| Ex # | Compound # | Starting Material | Final Compound | LCMS and NMR Data |
|---|---|---|---|---|
| 77 | 308 | Intermediate 3a (1H-pyrrolo[2,3-b]pyridine-3-carbonyl-azide); 4-phenylpiperidine | | Method K: MS-ESI: 321.2 [M + H$^+$] $^1$HNMR (400 MHz, DMSO-d$_6$) δ 11.21 (s, 1H), 8.35 (s, 1H), 8.18 (dd, J = 4.7, 1.6 Hz, 1H), 8.05 (dd, J = 7.9, 1.6 Hz, 1H), 7.45 (d, J = 2.5 Hz, 1H), 7.36-7.25 (m, 4H), 7.25-7.16 (m, 1H), 7.02 (dd, J = 7,9, 4.6 Hz, 1H), 4.36-4.27 (m, 2H), 2.95-2.85 (m, 2H), 2.79-2.69 (m, 1H), 1.86-1.77 (m, 2H), 1.66-1.54 (m, 2H). |
| 78 | 132 | Intermediate 3a (1H-pyrrolo[2,3-b]pyridine-3-carbonyl-azide); 4-butylpiperidine | | Method L: MS-ESI: 301.2 [M + H$^+$] $^1$HNMR (400 MHz, DMSO-d$_6$) δ 11.19 (s, 1H), 8.27 (d, J = 2.6 Hz, 1H), 8.18 (dd, J = 4.8, 2.4 Hz, 1H), 8.02 (d, J = 8.0 Hz, 1H), 7.42 (d, J = 2.6 Hz, 1H), 7.04-6.99 (m, 1H), 4.15 (dd, J = 13.2, 3.4 Hz, 2H), 2.82-2.70 (m, 2H), 1.74-1.64 (m, 2H), 1.46-1.20 (m, 7H), 1.14-0.99 (m, 2H), 0.94-0.85 (m, 3H). |
| 79 | 133 | Intermediate 3a (1H-pyrrolo[2,3-b]pyridine-3-carbonyl-azide); 3-phenylcyclobutan-1-amine | | Method K: MS-ESI: 307.1 [M + H$^+$] $^1$HNMR (400 MHz, DMSO-d$_6$) δ 11.21-11.15 (m, 1H), 8.24-8.15 (m, 2H), 7.89 (dd, J = 8.1, 1.6 Hz, 1H), 7.45 (d, J = 2.4 Hz, 1H), 7.38-7.24 (m, 4H), 7.23-7.14 (m, 1H), 7.08-7.00 (m, 1H), 6.37 (d, J = 8.3 Hz, 1H), 4.25-4.10 (m, 1H), 3.17-3.06 (m, 1H), 2.69-2.59 (m, 1H), 2.45-2.31 (m, 1H), 2.06-1.93 (m, 2H). |
| 80 | 134 | Intermediate 3a (1H-pyrrolo[2,3-b]pyridine-3-carbonyl-azide); 2,3-dihydro-1H-inden-1-amine | | Method L: MS-ESI: 293.1 [M + H$^+$] $^1$HNMR (400 MHz, DMSO-d$_6$) δ 11.19 (s, 1H), 8.27-8.17 (m, 2H), 7.88 (dd, J = 8.0, 1.6 Hz, 1H), 7.51 (d, J = 2.4 Hz, 1H), 7.36-7.30 (m, 1H), 7.30-7.18 (m, 3H), 7.05 (dd, J = 7.9, 4.6 Hz, 1H), 6.37 (d, J = 8.2 Hz, 1H), 5.21 (q, J = 7.8 Hz, 1H), 2.94 (ddd, J = 15.8, 8.7, 3.6 Hz, 1H), 2.82 (dt, J = 15.9, 8.2 Hz, 1H), 2.45 (ddd, J = 11.6, 7.9, 3.8 Hz, 1H), 1.80 (dq, J = 12.5, 8.4 Hz, 1H). |
| 81 | 135 | Intermediate 3a (1H-pyrrolo[2,3-b]pyridine-3-carbonyl-azide); 1,2,3,4-tetrahydronaphthalen-1-amine | | Method L: MS-ESI: 307.1 [M + H$^+$] $^1$HNMR (400 MHz, DMSO-d$_6$) δ 11.19 (s, 1H), 8.23-8.17 (m, 2H), 7.85 (dd, J = 8.0, 1.6 Hz, 1H), 7.51 (d, J = 2.4 Hz, 1H), 7.34-7.30 (m, 1H), 7.19-7.15 (m, 2H), 7.14-7.08 (m, 1H), 7.04 (dd, J = 8.0, 4.7 Hz, 1H), 6.37 (d, J = 8.5 Hz, 1H), 4.92-4.84 (m, 1H), 2.84-2.67 (m, 2H), 1.98-1.74 (h, J = 4.9 Hz, 4H). |
| 82 | 136 | Intermediate 3a (1H-pyrrolo[2,3-b]pyridine-3-carbonyl-azide); 1,2,3,4-tetrahydronaphthalen-2-amine hydrochloride | | Method K: MS-ESI: 307.1 [M + H$^+$] $^1$HNMR (400 MHz, DMSO-d$_6$) δ 11.14 (s, 1H), 8.25 (s, 1H), 8.19 (dd, J = 4.6, 1.6 Hz, 1H), 7.88-7.81 (m, 1H), 7.47 (d, J = 2.4 Hz, 1H), 7.15-7.06 (m, 4H), 7.03 (dd, J = 7.9, 4.6 Hz, 1H), 6.12 (d, J = 7.7 Hz, 1H), 4.02-3.98 (m, 1H), 3.05 (dd, J = 16.4, 5.1 Hz, 1H), 2.89-2.81 (m, 2H), 2.72-2.61 (m, 1H), 2.03-1.94 (m, 1H), 1.79-1.71 (m, 1H). |

-continued

| Ex # | Compound # | Starting Material | Final Compound | LCMS and NMR Data |
|---|---|---|---|---|
| 83 | 150 | Intermediate 3a (1H-pyrrolo[2,3-b]pyridine-3-carbonyl-azide); 3-trifluoromethyl)aniline | | Method M: MS-ESI: 321.1 [M + H⁺] ¹HNMR (400 MHz, MeOH-d₄) δ 8.24 (d, J = 4.8 Hz, 1H), 8.04 (d, J = 7.9 Hz, 1H), 7.94 (s, 1H), 7.64 (d, J = 7.8 Hz, 1H), 7.58 (s, 1H), 7.51-7.46 (m, 1H), 7.31 (d, J = 7.8 Hz, 1H), 7.16 (dd, J = 7.9, 4.8 Hz, 1H). |
| 84 | 160 | Intermediate 3a (1H-pyrrolo[2,3-b]pyridine-3-carbonyl-azide); bicyclo[3.2.1]octan-3-amine hydrochloride | | Method L: MS-ESI: 285.2 [M + H⁺] ¹HNMR (400 MHz, MeOH-d₄) δ 8.02-7.98 (m, 1H), 7.79-7.73 (m, 1H), 7.29-7.22 (m, 1H), 6.94-6.88 (m, 1H), 3.82-3.71 (m, 1H), 2.11-2.01 (m, 2H), 1.72-1.65 (m, 2H), 1.58-1.42 (m, 4H), 1.33-1.19 (m, 2H), 1.12-1.02 (m, 2H). |
| 85 | 166 | Intermediate 3a (1H-pyrrolo[2,3-b]pyridine-3-carbonyl-azide); 4-phenylcyclohexan-1-amine | | Method K: MS-ESI: 335.2 [M + H⁺] ¹HNMR (400 MHz, DMSO-d₆) δ 11.14 (d, J = 2.6 Hz, 1H), 8.23-8.15 (m, 2H), 7.87 (dd, J = 7.9, 1.6 Hz, 1H), 7.46 (d, J = 2.4 Hz, 1H), 7.32-7.22 (m, 4H), 7.24-7.13 (m, 1H), 7.03 (dd, J = 7.9, 4.7 Hz, 1H), 5.93 (d, J = 7.8 Hz, 1H), 3.59-3.48 (m, 1H), 2.55-2.49 (m, 1H), 2.05-1.98 (m, 2H), 1.87-1.78 (m, 2H), 1.62-1.50 (m, 2H), 1.38-1.26 (m, 2H). |
| 86 | 167 | Intermediate 3a (1H-pyrrolo[2,3-b]pyridine-3-carbonyl-azide); 3-butylpiperidine | | Method N: MS-ESI: 301.2 [M + H⁺] ¹HNMR (400 MHz, DMSO-d₆) δ 11.18 (brs, 1H), 8.26 (s, 1H), 8.17 (dd, J = 4.6, 1.6 Hz, 1H), 8.00 (dd, J = 8.0, 1.6 Hz, 1H), 7.41 (d, J = 2.5 Hz, 1H), 7.01 (dd, J = 8.0, 4.6 Hz, 1H), 4.07-3.99 (m, 2H), 2.84-2.75 (m, 1H), 2.51-2.43 (m, 1H), 1.86-1.78 (m, 1H), 1.68-1.59 (m, 1H), 1.46-1.05 (m, 9H), 0.93-0.85 (m, 3H). |
| 87 | 168 | Intermediate 3a (1H-pyrrolo[2,3-b]pyridine-3-carbonyl-azide); 5-ethylthiazol-2-amine | | Method A: MS-ESI: 288.1 [M + H⁺] ¹HNMR (400 MHz, DMSO-d₆) δ 11.39 (s, 1H), 10.27 (brs, 1H), 8.88 (s, 1H), 8.24 (dd, J = 4.7, 1.6 Hz, 1H), 7.91 (d, J = 7.8 Hz, 1H), 7.57 (d, J = 2.5 Hz, 1H), 7.13-7.03 (m, 2H), 2.72 (qd, J = 7.5, 1.2 Hz, 2H), 1.22 (t, J = 7.5 Hz, 3H). |
| 88 | 169 | Intermediate 3a (1H-pyrrolo[2,3-b]pyridine-3-carbonyl-azide); 5-ethylpyridin-2-amine | | Method A: MS-ESI: 282.1 [M + H⁺] ¹HNMR (400 MHz, DMSO-d₆) δ 11.36-11.31 (m, 1H), 10.66 (s, 1H), 9.42 (s, 1H), 8.25 (dd, J = 4.6, 1.6 Hz, 1H), 8.21 (d, J = 2.4 Hz, 1H), 7.96 (dd, J = 7.8, 1.6 Hz, 1H), 7.67-7.59 (m, 2H), 7.38 (d, J = 8.5 Hz, 1H), 7.10 (dd, J = 7.8, 4.6 Hz, 1H), 2.57 (q, J = 7.6 Hz, 2H), 1.19 (t, J = 7.6 Hz, 3H). |

| Ex # | Compound # | Starting Material | Final Compound | LCMS and NMR Data |
|---|---|---|---|---|
| 89 | 170 | Intermediate 3a (1H-pyrrolo[2,3-b]pyridine-3-carbonyl-azide); 4-butylcyclo-hexan-1-amine | | Method E: MS-ESI: 315.2 [M + H+] $^1$HNMR (400 MHz, DMSO-d$_6$) δ 11.11 (d, J = 2.7 Hz, 1H), 8.22-8.13 (m, 2H), 7.87-7.83 (m, 1H), 7.45-7.41 (m, 1H), 7.06-6.99 (m, 1H), 6.17-5.81 (m, 1H), 3.44-3.33 (m, 1H), 1.94-1.86 (m, 1H), 1.78-1.69 (m, 1H), 1.65-1.45 (m, 2H), 1.34-1.07 (m, 9H), 1.02-.83 (m, 4H). |
| 90 | 171 | Intermediate 3a (1H-pyrrolo[2,3-b]pyridine-3-carbonyl-azide); (4-ethylphenyl)meth-anamine | | Method E: MS-ESI: 295.1 [M + H+] $^1$HNMR (400 Mhz, DMSO-d$_6$) δ 11.20-11.15 (m, 1H), 8.34 (s, 1H), 8.19 (dd, J = 4.7, 1.6 Hz, 1H), 7.89 (dd, J = 8.0, 1.6 Hz, 1H), 7.46 (d, J = 2.5 Hz, 1H), 7.23 (d, J = 8.0 Hz, 2H), 7.17 (d, J = 8.0 Hz, 2H), 7.03 (dd, J = 8.0, 4.7 Hz, 1H), 6.46 (t, J = 5.9 Hz, 1H), 4.27 (d, J = 5.9 Hz, 2H), 2.58 (q, J = 7.6 Hz, 2H), 1.17 (t, J = 7.6 Hz, 3H). |
| 91 | 265 | Intermediate 3a (1H-pyrrolo[2,3-b]pyridine-3-carbonyl-azide); 5-(trifluorometh-yl)pyridin-2-amine | | Method A: MS-ESI: 322.1 [M + H+] $^1$HNMR (400 MHz, DMSO-d$_6$) δ 11.44-11.39 (m, 1H), 10.15 (s, 1H), 9.90 (s, 1H), 8.78-8.72 (m, 1H), 8.26 (dd, J = 4.7, 1.6 Hz, 1H), 8.13 (dd, J = 8,9, 2.5 Hz, 1H), 8.00 (dd, J = 8.0, 1.6 Hz, 1H), 7.79 (dd, J = 8.9, 4.0 Hz, 1H), 7.64 (d, J = 2.3 Hz, 1H), 7.11 (dd, J = 7.9, 4.7 Hz, 1H). FNMR (400 MHz, DMSO-d$_6$) δ −60.01, −60.05 |
| 92 | 264 | Intermediate 3a (1H-pyrrolo[2,3-b]pyridine-3-carbonyl-azide); 5-cyclohexyl-pyridin-2-amine | | Method A: MS-ESI: 336.2 [M + H+] $^1$HNMR (400 MHz, DMSO-d$_6$) δ 11.37-11.32 (m, 1H), 10.75 (s, 1H), 9.43 (s, 1H), 8.28-8.21 (m, 2H), 7.97 (dd, J = 7.9, 1.6 Hz, 1H), 7.68-7.59 (m, 2H), 7.35 (d, J = 8.6 Hz, 1H), 7.10 (dd, J = 7.9, 4.7 Hz, 1H), 2.51-2.47 (m, 1H), 1.84-1.66 (m, 5H), 1.49-1.16 (m, 5H). |
| 93 | 263 | Intermediate 3a (1H-pyrrolo[2,3-b]pyridine-3-carbonyl-azide); 6-cyclohexyl-pyridine-3-amine | | Method L: MS-ESI: 336.2 [M + H+] $^1$HNMR (300 MHz, DMSO-d$_6$) δ 11.29 (s, 1H), 8.75 (d, J = 5.5 Hz, 2H), 8.49 (d, J = 2.6 Hz, 1H), 8.21 (dd, J = 4.7, 1.6 Hz, 1H), 7.98-7.91 (m, 1H), 7.87 (dd, J = 8.5, 2.7 Hz, 1H), 7.53 (d, J = 2.5 Hz, 1H), 7.15 (d, J = 8.5 Hz, 1H), 7.06 (dd, J = 7.9, 4.7 Hz, 1H), 2.65-2.53 (m, 1H), 1.87-1.65 (m, 5H), 1.55-1.08 (m, 5H). |
| 94 | 257 | Intermediate 3a (1H-pyrrolo[2,3-b]pyridine-3-carbonyl-azide); 6-(trifluorometh-ylpyridin-3-amine | | Method L: MS-ESI: 322.1 [M + H+] $^1$HNMR (400 MHz, DMSO-d$_6$) δ 11.40 (s, 1H), 9.27 (s, 1H), 8.88 (s, 1H), 8.77 (d, J = 2.5 Hz, 1H), 8.29-8.21 (m, 2H), 7.96 (dd, J = 8.0, 1.6 Hz, 1H), 7.82 (d, J = 8.7 Hz, 1H), 7.58 (d, J = 2.5 Hz, 1H), 7.09 (dd, J = 7.9, 4.7 Hz, 1H). |

Example 95: Synthesis of Compound 159

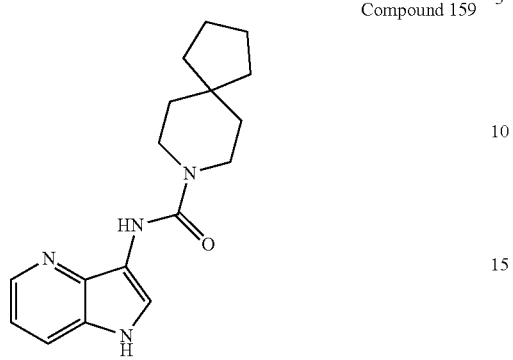

Compound 159

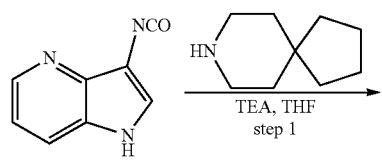

intermediate 17

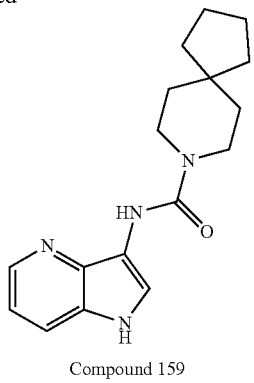

Compound 159

3-Isocyanato-1H-pyrrolo[3,2-b]pyridine (100.0 mg, 0.6 mmol, 1.0 equiv) was dissolved in THF (10 mL). TEA (127.2 mg, 1.3 mmol, 2.0 equiv) and azaspirodecane (87.5 mg, 0.6 mmol, 1.0 equiv) were added and stirred for 30 min at RT. The reaction was then quenched by the addition of water. The resulting solution was extracted with 3×30 mL of DCM. The organic layer was combined and concentrated under vacuum. The crude product was purified by Method P. N-(1H-pyrrolo[3,2-b]pyridin-3-yl)-8-azaspiro[4.5]decane-8-carboxamide (25.0 mg, 13.3%) was isolated as a white solid.

LCMS: Method A, MS-ESI, 299.2 [M+H$^+$].

$^1$HNMR: (400 MHz, DMSO-d$_6$) δ 10.89 (s, 1H), 8.29 (dd, J=4.6, 1.4 Hz, 1H), 8.02 (s, 1H), 7.75-7.67 (m, 2H), 7.11 (dd, J=8.2, 4.5 Hz, 1H), 3.48-3.41 (m, 4H), 1.67-1.55 (m, 4H), 1.48-1.38 (m, 8H).

Analogs Prepared by this Method

| Ex # | Compound # | Starting Material | Final compound | LCMS and NMR Data |
|---|---|---|---|---|
| 96 | 159 | Intermediate 17 (3-isocyanato-1H-pyrrolo[3,2-b]pyridine); 8-azaspiro[4.5]decane | (structure) | Method A: MS-ESI: 299.2 [M + H$^+$] $^1$HNMR (400 MHz, DMSO-d$_6$) δ 10.89 (s, 1H), 8.29 (dd, J = 4.6, 1.4 Hz, 1H), 8.02 (s, 1H), 7.75-7.67 (m, 2H), 7.11 (dd, J = 8.2, 4.5 Hz, 1H), 3.48-3.41 (m, 4H), 1.67-1.55 (m, 4H), 1.48-1.38 (m, 8H). |
| 97 | 151 | Intermediate 6a (3-amino-1H-pyrrolo[2,3-b]pyridine-5-carbonitrile hydrochloride); 1-isocyanato-4-(trifluoromethyl)benzene | (structure) | Method N: MS-ESI: 346.1 [M + H$^+$] $^1$HNMR (400 MHz, DMSO-d$_6$) δ12.12 (s, 1H), 9.18 (s, 1H), 8.96 (s, 1H), 8.62 (d, J = 2.0 Hz, 1H), 8.46 (s, 1H), 7.78-7.68 (m, 3H), 7.64 (d, J = 8.5 Hz, 2H). |

-continued

| Ex # | Compound # | Starting Material | Final compound | LCMS and NMR Data |
|---|---|---|---|---|
| 98 | 266 | Intermediate 35 (6-bromo-1H-pyrrolo[2,3-b]pyridin-3-amine); 1-isocyanato-4-(trifluoromethyl)benzene | 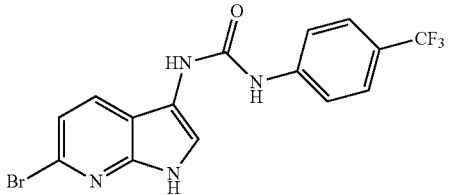 [SMILES: O=C(Nc1ccc(C(F)(F)F)cc1)Nc1c[nH]c2nc(Br)ccc12] | Method L: MS-ESI: 399.0 [M + H⁺] ¹HNMR (400 MHz, DMSO-d₆) δ11.66 (s, 1H), 9.07 (s, 1H), 8.82 (s, 1H), 7.92 (d, J = 8.2 Hz, 1H), 7.70 (d, J = 8.6 Hz, 2H), 7.64 (d, J = 8.6 Hz, 2H), 7.60 (d, J = 2.4 Hz, 1H), 7.27 (d, J = 8.2 Hz, 1H). FNMR: (400 MHz, DMSO-d₆) δ-59.99 |
| 99 | 278 | Intermediate 6c (4-bromo-1H-pyrrolo[2,3-b]pyridin-3-amine); 1-isocyanato-4-(trifluoromethyl)benzene | 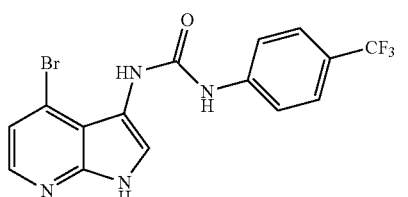 | Method C: MS-ESI: 399.0 [M + H⁺] ¹HNMR (400 MHz, DMSO-d₆) δ11.96-11.91 (m, 1H), 9.40 (br s, 1H), 8.08 (d, J = 5.1 Hz, 1H), 7.97 (s, 1H), 7.72-7.66 (m, 3H), 7.62 (d, J = 8.5 Hz, 2H), 7.32 (d, J = 5.1 Hz, 1H). |
| 100 | 283 | Intermediate 6b (5-chloro-1H-pyrrolo[2,3-b]pyridin-3-amine); 1-isocyanato-4-(trifluoromethyl)benzene | 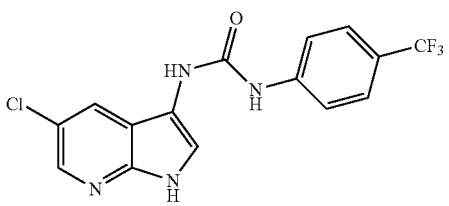 [SMILES: O=C(Nc1ccc(C(F)(F)F)cc1)Nc1c[nH]c2ncc(Cl)cc12] | Method A: MS-ESI: 355.7 [M + H⁺] ¹HNMR (400 MHz, DMSO-d₆) δ 11.66 (s, 1H), 9.06 (s, 1H), 8.77 (s, 1H), 8.23 (s, 1H), 8.02 (s, 1H), 7.70 (d, J = 8.6 Hz, 2H), 7.65-7.61 (m, 3H). FNMR (400 MHz, DMSO-d₆) δ-58.98 |
| 101 | 165 | Intermediate 6 (7-fluoro-1H-pyrrolo[3,2-c]pyridin-3-amine hydrochloride); 1-isocyanato-4-(trifluoromethyl)benzene | 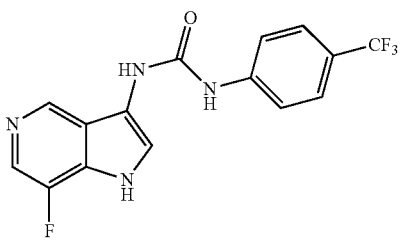 [SMILES: O=C(Nc1ccc(C(F)(F)F)cc1)Nc1c[nH]c2c(F)cncc12] | Method C: MS-ESI: 339.1 [M + H⁺] ¹HNMR (400 MHz, DMSO-d₆) δ11.89 (s, 1H), 9.15 (s, 1H), 9.02 (s, 1H), 8.72 (d, J = 2.6 Hz, 1H), 8.16 (d, J = 3.2 Hz, 1H), 7.82-7.58 (m, 5H). |
| 102 | 164 | Intermediate 6d (4-fluoro-1H-pyrrolo[2,3-c]pyridin-3-amine); 1-isocyanato-4-(trifluoromethyl)benzene | 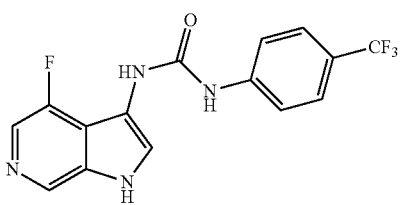 [SMILES: O=C(Nc1ccc(C(F)(F)F)cc1)Nc1c[nH]c2cncc(F)c12] | Method L: MS-ESI: 339.1 [M + H⁺] ¹HNMR (400 MHz, DMSO-d₆) δ11.70 (br s, 1H), 9.49 (s, 1H), 8.59 (d, J = 2.4 Hz, 1H), 8.39 (s, 1H), 8.00 (d, J = 2.4 Hz, 1H), 7.82 (s, 1H), 7.69-7.55 (m, 4H). |
| 103 | 326 | Intermediate 17 (3-isocyanato-1H-pyrrolo[3,2-b]pyridine); Intermediate 30 (5-cyclohexyl-pyridin-2-amine) | 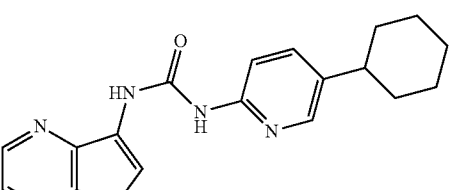 | Method L: MS-ESI: 336.2 [M + H⁺] ¹HNMR (400 MHz, DMSO-d₆) δ 10.95 (d, J = 12.2 Hz, 1H), 10.80 (s, 1H), 9.57 (d, J = 13.2 Hz, 1H), 8.35 (dt, J = 11.2, 5.4 Hz, 1H), 8.17 (d, J = 12.7 Hz, 1H), 7.94-7.84 (m, 1H), 7.75 (dt, J = 15.9, 8.2 Hz, 1H), 7.70-7.60 (m, 1H), 7.41 (s, 1H), 7.17 (ddd, J = 14.6, |

| Ex # | Compound # | Starting Material | Final compound | LCMS and NMR Data |
|---|---|---|---|---|
| | | | | 8.5, 4.6 Hz, 1H), 2.65-2.51 (m, 1H), 2.10-1.65 (m, 5H), 1.51-1.71 (m, 5H). |

Example 158: Synthesis of Compound 328

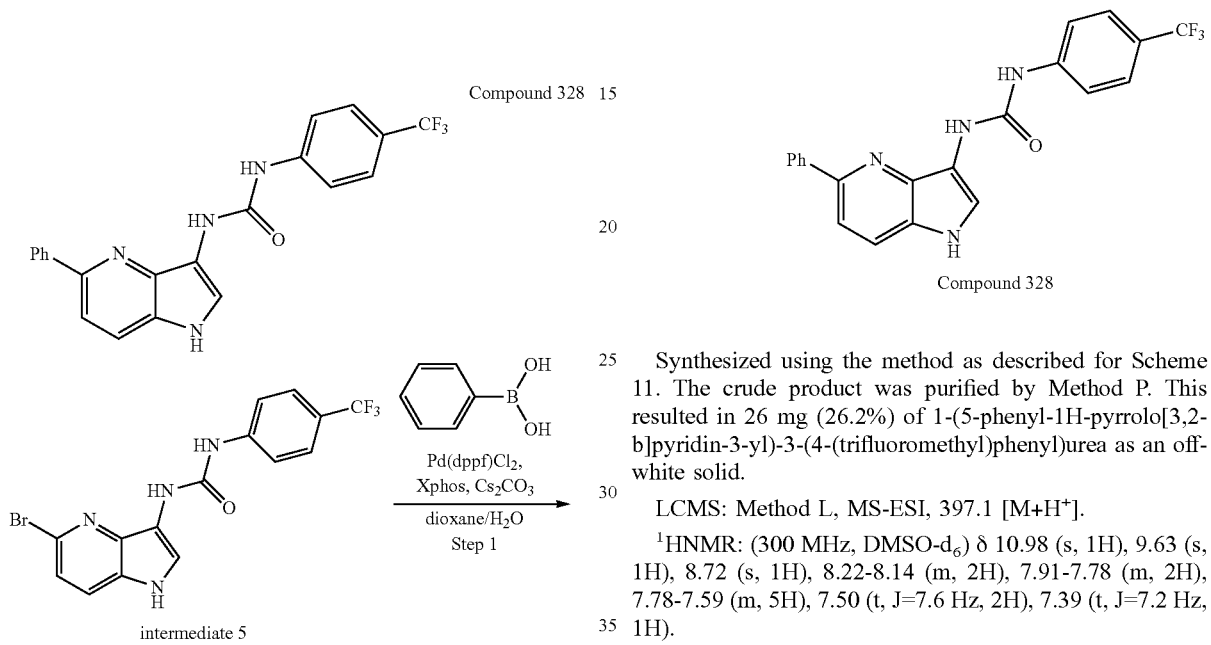

Synthesized using the method as described for Scheme 11. The crude product was purified by Method P. This resulted in 26 mg (26.2%) of 1-(5-phenyl-1H-pyrrolo[3,2-b]pyridin-3-yl)-3-(4-(trifluoromethyl)phenyl)urea as an off-white solid.

LCMS: Method L, MS-ESI, 397.1 [M+H$^+$].

$^1$HNMR: (300 MHz, DMSO-d$_6$) δ 10.98 (s, 1H), 9.63 (s, 1H), 8.72 (s, 1H), 8.22-8.14 (m, 2H), 7.91-7.78 (m, 2H), 7.78-7.59 (m, 5H), 7.50 (t, J=7.6 Hz, 2H), 7.39 (t, J=7.2 Hz, 1H).

Analogs Prepared by this Method

| Example | Compound # | Starting Material | Final compound | LCMS and NMR Data |
|---|---|---|---|---|
| 159 | 328 | Intermediate 4a (1-(5-bromo-1H-pyrrolo[3,2-b]pyridin-3-yl)-3-(4-(trifluoromethyl)phenyl)urea); phenylboronic acid | | Method L: MS-ESI: 397.1 [M + H$^+$] $^1$HNMR: (300 MHz, DMSO-d$_6$) δ 10.98 (s, 1H), 9.63 (s, 1H), 8.72 (s, 1H), 8.22-8.14 (m, 2H), 7.91-7.78 (m, 2H), 7.78-7.59 (m, 5H), 7.50 (t, J = 7.6 Hz, 2H), 7.39 (t, J = 7.2 Hz, 1H). |
| 160 | 335 | Intermediate 20 (1-(5-bromo-1H-pyrrolo[3,2-b]pyridin-3-yl)-3-(4-(trifluoromethyl)cyclohexyl)urea); phenylboronic acid | | Method A: MS-ESI: 403.2 [M + H$^+$] $^1$HNMR: (400 MHz, DMSO-d$_6$) δ10.81 (s, 1H), 8.59 (d, J = 1.9 Hz, 1H), 8.48 (s, 1H), 7.91 (d, J = 1.9 Hz, 1H), 7.76-7.73 (m, 3H), 7.52-7.48 (t, J = 7.7 Hz, 2H), 7.39-7.37 (m, 1H), 6.89 (d, J = 7.7 Hz, 1H), 3.94-3.92 (m, 1H), 2.33-2.25 (m, 1H), 1.78-1.71 (m, 4H), 1.63-1.50 (m, 4H). |

Example 161: Synthesis of Compound 320

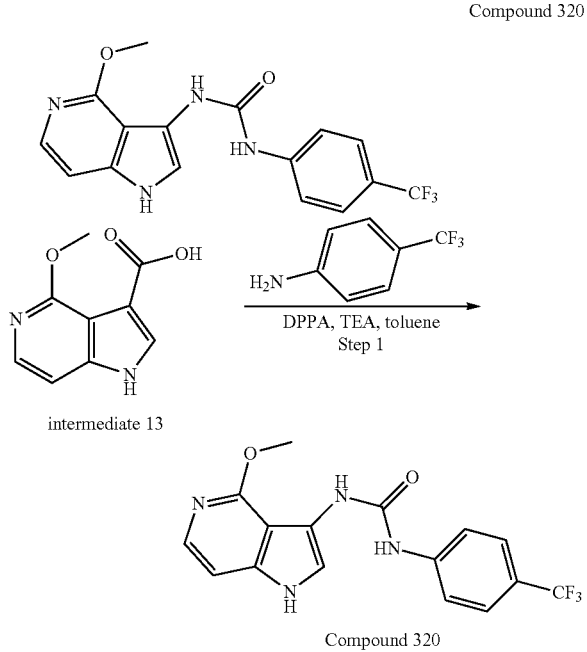

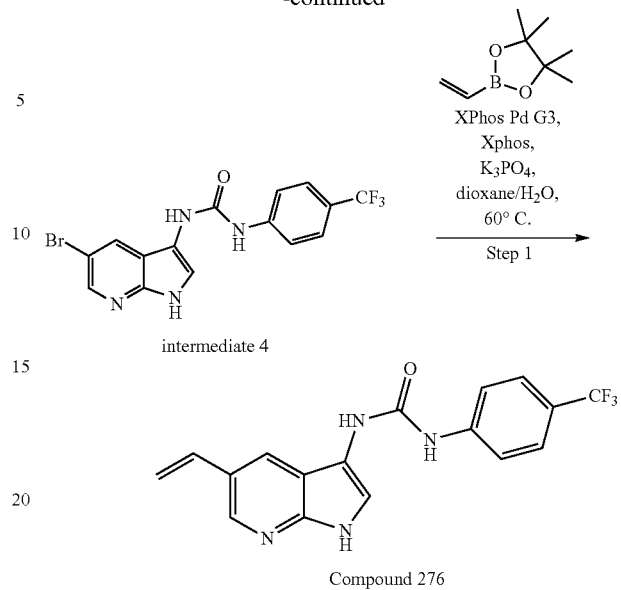

To a stirred solution of 4-methoxy-1H-pyrrolo[3,2-c]Py-3-carboxylic acid (80.0 mg, 0.4 mmol, 1.0 equiv) in toluene (5.0 mL) in a sealed tube under nitrogen were added TEA (126.0 mg, 1.2 mmol, 3.0 equiv) and 4-(trifluoromethyl) aniline (80.0 mg, 0.5 mmol, 1.2 equiv). DPPA (149.0 mg, 0.5 mmol, 1.3 equiv) dropwise to the mixture at RT. The resulting solution was stirred for 4 hr at 95° C. The reaction was quenched with water (20.0 mL). The resulting solution was extracted with 3×20 mL of EtOAc and the organic layers combined and dried over anhydrous sodium sulfate. The resulting mixture was concentrated under vacuum. The crude product was purified by Method R This resulted in 42.1 mg (28.9%) of 1-(4-methoxy-1H-pyrrolo[3,2-c]pyridin-3-yl)-3-(4-(trifluoromethyl)phenyl)urea as a off-white solid.

LCMS: Method L, MS-ESI, 351.1 [M+H⁺].

¹HNMR: (400 MHz, DMSO-d₆) δ 11.4 (s, 1H), 9.36 (s, 2H), 9.32 (s, 1H), 7.71 (d, J=8.8 Hz, 2H), 7.67 (d, J=8.8 Hz, 2H), 7.64 (d, J=7.2 Hz, 1H), 7.01 (d, J=5.6 Hz, 1H), 6.08 (s, 1H), 3.94 (s, 3H).

Example 162: Synthesis of Compound 276

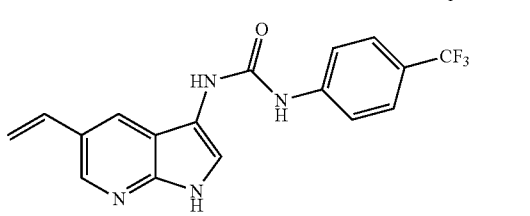

3-[5-Bromo-1H-pyrrolo[2,3-b]pyridin-3-yl]-1-[4-(trifluoromethyl)phenyl]urea (300.0 mg, 0.8 mmol, 1.0 equiv) was dissolved in dioxane (50.0 mL). H₂O (10.0 mL), 2-ethenyl-4,4,5,5-tetramethyl-1,3,2-dioxaborolane (173.7 mg, 1.1 mmol, 1.5 equiv), XPhos Pd G3 (30.0 mg, 0.04 mmol, 0.05 equiv), XPhos (30.0 mg, 0.06 mmol, 0.08 equiv) and K₃PO₄ (319.1 mg, 1.5 mmol, 2.0 equiv) were added under N₂ and stirred for 2 hr at 80° C. Resulting solution was concentrated under vacuum and applied onto a silica gel column with EtOAc as an eluent. The crude product was purified by Method Q. This resulted in 10 mg (3.9%) of 3-[5-ethenyl-1H-pyrrolo[2,3-b]pyridin-3-yl]-1-[4-(trifluoromethyl)phenyl] urea as a white solid.

LCMS: Method G, MS-ESI, 347.1 [M+H⁺].

¹HNMR: (400 MHz, DMSO-d₆) δ 11.40 (s, 1H), 9.25 (s, 1H), 8.93 (s, 1H), 8.37 (d, J=2.1 Hz, 1H), 8.08 (d, J=2.1 Hz, 1H), 7.71 (d, J=8.5 Hz, 2H), 7.63 (d, J=8.5 Hz, 2H), 7.57 (d, J=2.5 Hz, 1H), 6.87 (dd, J=17.7, 11.1 Hz, 1H), 5.82 (dd, J=17.7, 1.0 Hz, 1H), 5.24 (dd, J=11.0, 1.0 Hz, 1H).

Example 163: Synthesis of Compound 268

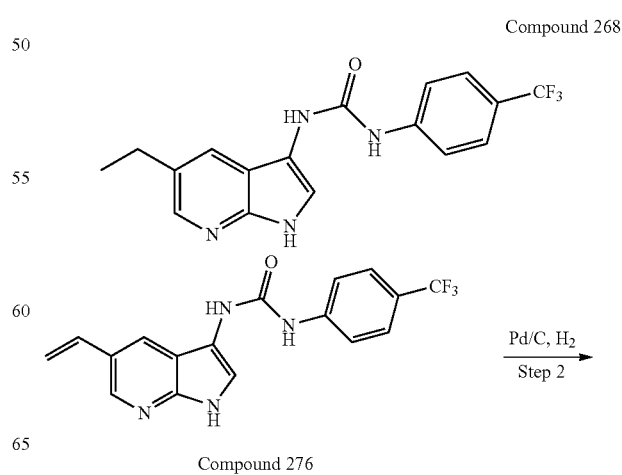

-continued

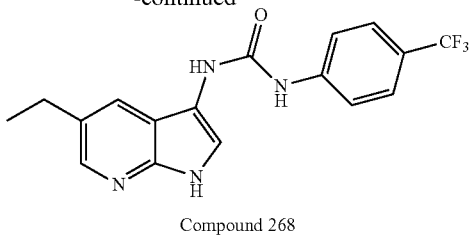

Compound 268

Synthesized using the method as described for Scheme 28. The crude product was purified by Method Q. This resulted in 10 mg (6.6%) of 3-[5-ethyl-1H-pyrrolo[2,3-b]pyridin-3-yl]-1-[4-(trifluoromethyl) phenyl] urea as a white solid.

LCMS: Method D, MS-ESI, 349.1 [M+H$^+$].

$^1$HNMR: (400 MHz, DMSO-d$_6$) δ 11.22 (d, J=2.4 Hz, 1H), 9.02 (s, 1H), 8.67 (s, 1H), 8.12 (d, J=2.0 Hz, 1H), 7.75 (d, J=2.0 Hz, 1H), 7.70 (d, J=8.6 Hz, 2H), 7.63 (d, J=8.7 Hz, 2H), 7.53 (d, J=2.5 Hz, 1H), 2.73 (q, J=7.6 Hz, 2H), 1.26 (t, J=7.6 Hz, 3H).

Example 164: Synthesis of Compound 277

Compound 277

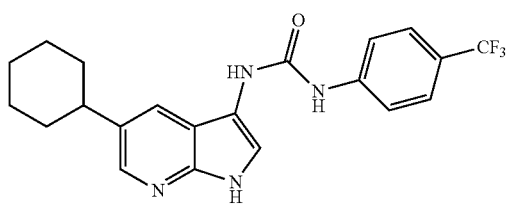

Synthesized using the method as described for Example 162. This resulted in 460 mg (76.5%) of 3-[5-(cyclohex-1-en-1-yl)-1H-pyrrolo[2,3-b]pyridin-3-yl]-1-[4-(trifluoromethyl)phenyl] urea as a off-white crude solid.

LCMS: Method G, MS-ESI, 401.2 [M+H$^+$].

$^1$HNMR: (400 MHz, DMSO-d$_6$) δ 11.26 (s, 1H), 9.35 (s, 1H), 9.05 (s, 1H), 8.33 (d, J=2.2 Hz, 1H), 7.97 (d, J=2.2 Hz, 1H), 7.71 (d, J=8.6 Hz, 2H), 7.62 (d, J=8.6 Hz, 2H), 7.55 (d, J=2.5 Hz, 1H), 6.18-6.11 (m, 1H), 2.48-2.42 (m, 2H), 2.25-2.18 (m, 2H), 1.83-1.73 (m, 2H), 1.70-1.61 (m, 2H).

Example 165: Synthesis of Compound 267

Compound 267

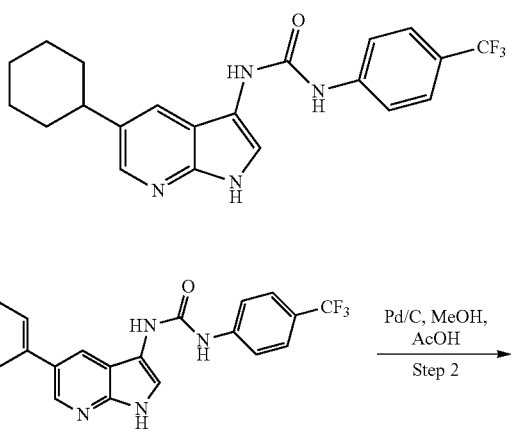

Synthesized using the method as described in Example 163. The crude product was purified by Method P. This resulted in 62 mg (30.9%) of 3-[5-cyclohexyl-1H-pyrrolo[2,3-b]pyridin-3-yl]-1-[4-(trifluoromethyl) phenyl] urea as a off-white solid. LCMS: Method D, MS-ESI, 403.2 [M+H$^+$].

$^1$HNMR: (400 MHz, DMSO-d$_6$) δ 11.21 (d, J=2.6 Hz, 1H), 9.02 (s, 1H), 8.70 (s, 1H), 8.13 (d, J=2.1 Hz, 1H), 7.77 (d, J=2.1 Hz, 1H), 7.70 (d, J=8.6 Hz, 2H), 7.64 (d, J=8.6 Hz, 2H), 7.53 (d, J=2.5 Hz, 1H), 2.69-2.59 (m, 1H), 1.91-1.69 (m, 5H), 1.55-1.21 (m, 5H). $^{19}$FNMR: (400 MHz, DMSO-d$_6$) δ −59.95.

Example 166: Synthesis of Compound 143

Compound 143

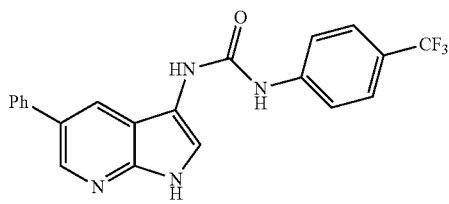

-continued

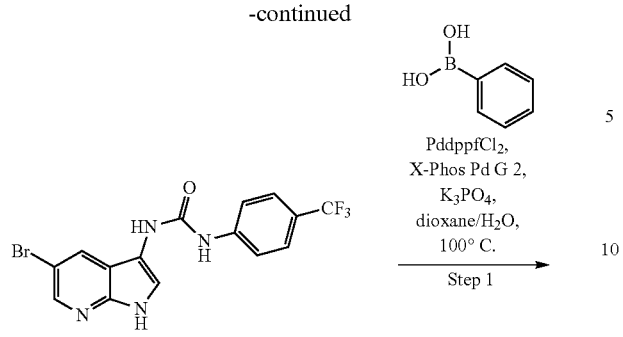

intermediate 4

Compound 143

Synthesized using the method as described for Scheme 11. The crude product was purified by Method P. 1-(5-phenyl-1H-pyrrolo[2,3-b]pyridin-3-yl)-3-(4-(trifluoromethyl)phenyl)urea (30 mg, 21%) was isolated as an off-white solid.

LCMS: Method G, MS-ESI, 397.1 [M+H$^+$].

1HNMR: (400 MHz, DMSO-d$_6$) δ 11.47 (d, J=2.4 Hz, 1H), 9.07 (s, 1H), 8.84 (s, 1H), 8.55 (d, J=2.1 Hz, 1H), 8.19 (d, J=2.1 Hz, 1H), 7.75-7.68 (m, 4H), 7.67-7.60 (m, 3H), 7.52 (t, J=7.6 Hz, 2H), 7.39 (t, J=7.6 Hz, 1H).

$^{19}$FNMR: (400 MHz, DMSO-d$_6$) δ −59.93, −59.97

Example 167: Synthesis of Compound 258

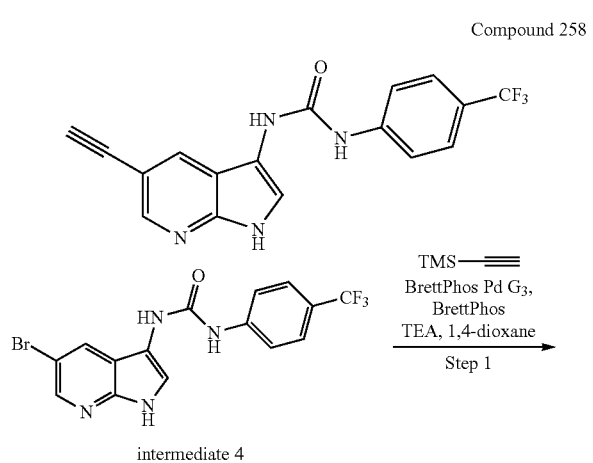

Compound 258

-continued

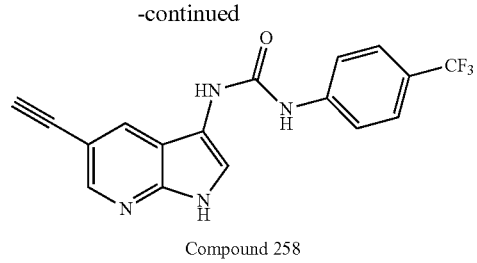

Compound 258

1. Synthesis of 1-(4-(trifluoromethyl)phenyl)-3-(5-((trimethylsilyl)ethynyl)-1H-pyrrolo[2,3-b]pyridin-3-yl)urea

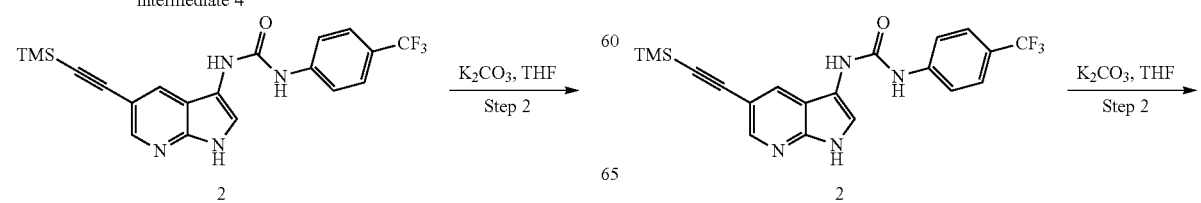

3-[5-Bromo-1H-pyrrolo[2,3-b]pyridin-3-yl]-1-[4-(trifluoromethyl)phenyl]urea (200.0 mg, 0.5 mmol, 1.0 equiv) was dissolved in 1,4-dioxane (10.0 mL). Trimethylsilylacetylene (59.1 mg, 0.6 mmol, 1.2 equiv), BrettPhos (26.9 mg, 0.05 mmol, 0.1 equiv), BrettPhos Pd G3 (45.4 mg, 0.05 mmol, 0.1 equiv) and TEA (101.4 mg, 1.0 mmol, 2.0 equiv) were added, and the reaction mixture was stirred for 16 hours at 90° C. The solids were filtered out and applied onto a silica gel column with EtOAc/PE (1:1) as an eluent. This resulted in 110 mg (52.7%) of 1-[4-(trifluoromethyl)phenyl]-3-[5-[2-(trimethylsilyl)ethynyl]-1H-pyrrolo[2,3-b]pyridin-3-yl]urea as a yellow solid.

LCMS: Method A, MS-ESI, 417.1 [M+H$^+$].

2. Synthesis of 1-(5-ethynyl-1H-pyrrolo[2,3-b]pyridin-3-yl)-3-(4-(trifluoromethyl)phenyl)urea -continued

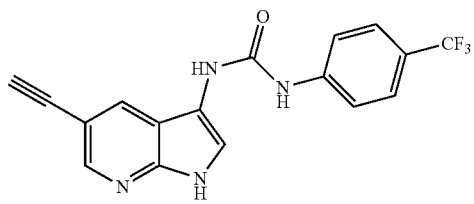

Compound 258

1-[4-(Trifluoromethyl)phenyl]-3-[5-[2-(trimethylsilyl) ethynyl]-1H-pyrrolo[2,3-b]pyridin-3-yl]urea (150.0 mg, 0.4 mmol, 1.0 equiv) was dissolved in THF (5 mL). K$_2$CO$_3$ (149.3 mg, 1.2 mmol, 3.0 equiv) was added and stirred for 4 hours at RT. The resulting mixture was cooled to RT and concentrated under vacuum and then applied onto a silica gel column with EtOAc/PE (1:1) as an eluent. The crude product was purified by Method P. This resulted in 22 mg (17.8%) of 3-[5-ethynyl-1H-pyrrolo[2,3-b]pyridin-3-yl]-1-[4-(trifluoromethyl)phenyl]urea as a off-white solid.

LCMS: Method A, MS-ESI, 345.1 [M+H$^+$].

$^1$HNMR: (400 MHz, DMSO-d$_6$) δ 11.67 (s, 1H), 9.04 (s, 1H), 8.81 (s, 1H), 8.34 (d, J=2.0 Hz, 1H), 8.09 (d, J=2.0 Hz, 1H), 7.71 (d, J=8.6 Hz, 2H), 7.67-7.61 (m, 3H), 4.19 (s, 1H).
$^{19}$FNMR: (400 MHz, DMSO-d$_6$) δ−59.98

Example 168: Synthesis of Compound 256

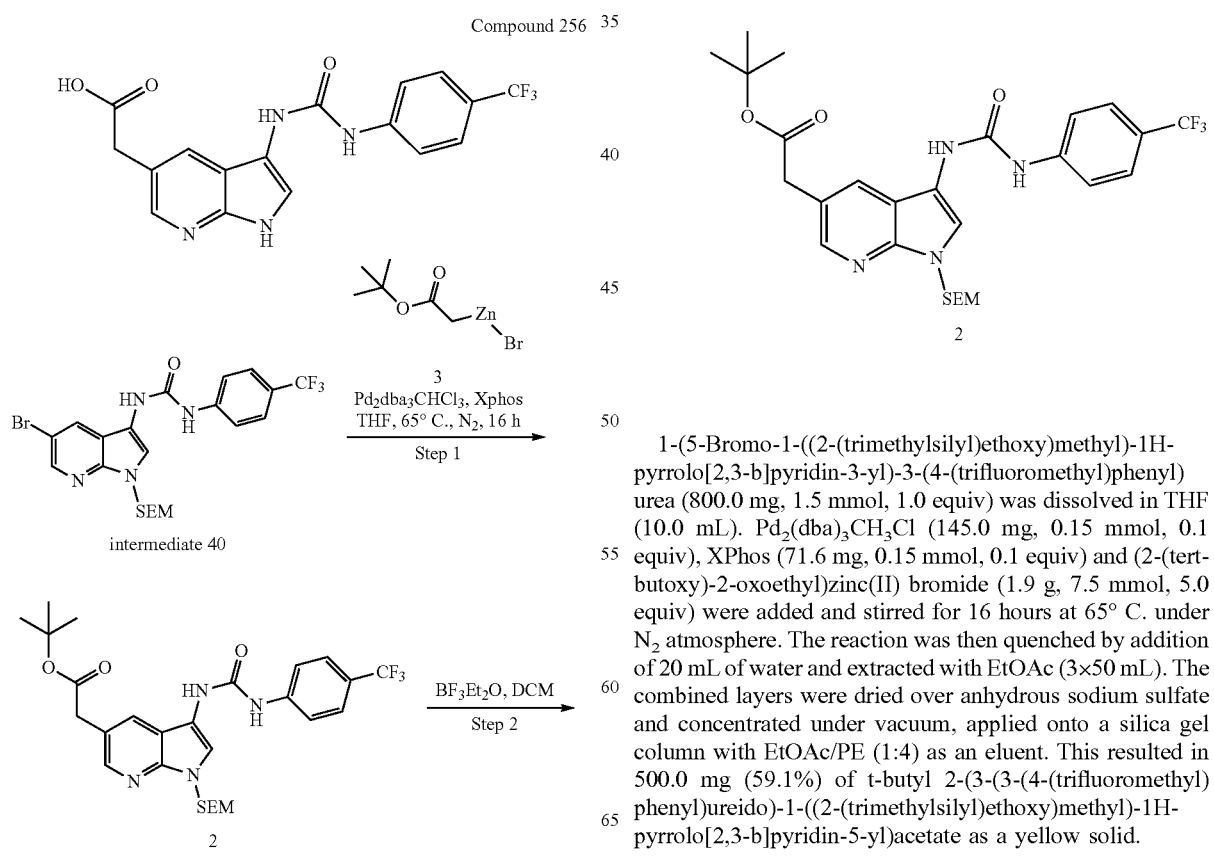

-continued

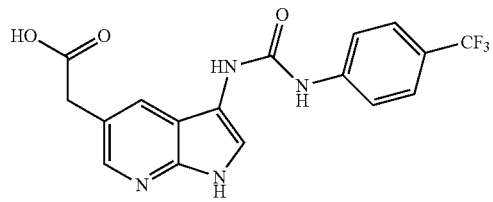

Compound 256

1. Synthesis of t-butyl 2-(3-(3-(4-(trifluoromethyl) phenyl)ureido)-1-((2-(trimethyl-silyl) ethoxy) methyl)-1H-pyrrolo[2,3-b]pyridin-5-yl)acetate

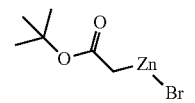

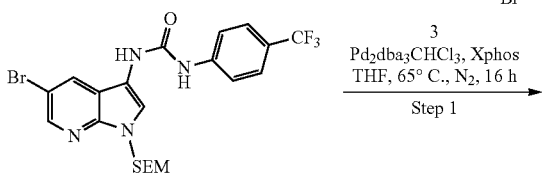

1-(5-Bromo-1-((2-(trimethylsilyl)ethoxy)methyl)-1H-pyrrolo[2,3-b]pyridin-3-yl)-3-(4-(trifluoromethyl)phenyl) urea (800.0 mg, 1.5 mmol, 1.0 equiv) was dissolved in THF (10.0 mL). Pd$_2$(dba)$_3$CH$_3$Cl (145.0 mg, 0.15 mmol, 0.1 equiv), XPhos (71.6 mg, 0.15 mmol, 0.1 equiv) and (2-(tert-butoxy)-2-oxoethyl)zinc(II) bromide (1.9 g, 7.5 mmol, 5.0 equiv) were added and stirred for 16 hours at 65° C. under N$_2$ atmosphere. The reaction was then quenched by addition of 20 mL of water and extracted with EtOAc (3×50 mL). The combined layers were dried over anhydrous sodium sulfate and concentrated under vacuum, applied onto a silica gel column with EtOAc/PE (1:4) as an eluent. This resulted in 500.0 mg (59.1%) of t-butyl 2-(3-(3-(4-(trifluoromethyl) phenyl)ureido)-1-((2-(trimethylsilyl)ethoxy)methyl)-1H-pyrrolo[2,3-b]pyridin-5-yl)acetate as a yellow solid.

LCMS: Method C, MS-ESI, 565.2 [M+H$^+$].

2. Synthesis of 2-(3-(3-(4-(trifluoromethyl)phenyl)ureido)-1H-pyrrolo[2,3-b]pyridin-5-yl)acetic acid

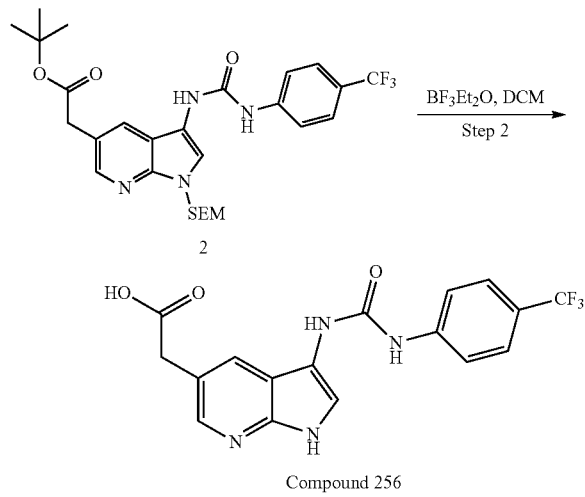

Tert-butyl 2-[3-([[4-(trifluoromethyl)Ph]carbamoyl]amino)-1-[[2-(trimethyl silyl)ethoxy]methyl]pyrrolo[2,3-b]pyridin-5-yl]acetate (50.0 mg, 0.1 mmol, 1.0 equiv) was dissolved in DCM (4.00 mL). Boron trifluoride etherate (25.1 mg, 0.2 mmol, 2.0 equiv) was added dropwise at 0° C. and stirred for 90 min at RT. The mixture was quenched with two drops of ice water and concentrated under vacuum. The resulting residue was purified by Method Q. [3-([[4-(Trifluoromethyl)phenyl]carbamoyl]amino)-1H-pyrrolo[2,3-b]pyridin-5-yl]acetic acid (7.0 mg, 20.9%) was isolated as a white solid.

LCMS: Method O, MS-ESI, 379.1 [M+H⁺].

¹HNMR: (400 MHz, DMSO-d₆) δ 11.04 (s, 1H), 8.32 (brs, 1H), 8.10 (s, 1H), 7.82-7.69 (m, 2H), 7.64-7.54 (m, 3H), 3.57 (s, 2H). ¹⁹FNMR: (400 MHz, DMSO-d₆) δ−59.72

Example 171: Synthesis of Compound 162

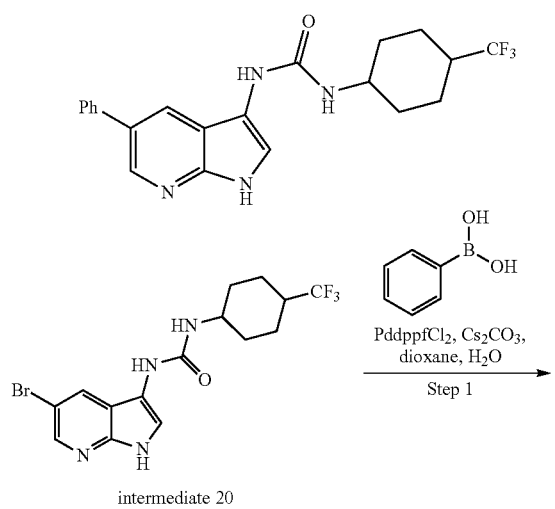

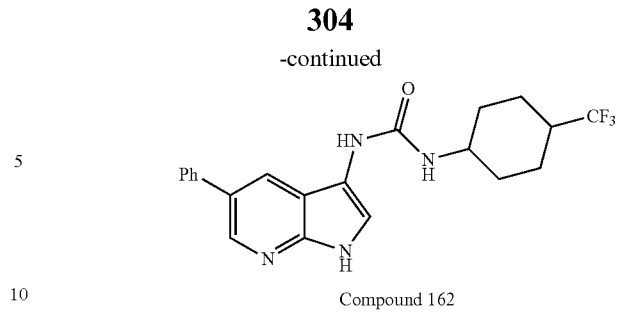

Synthesized using the method as described for Scheme 28. The crude product was further purified by Method Q. This resulted in 6.5 mg (6.6%) of 3-[5-phenyl-1H-pyrrolo[2,3-b]pyridin-3-yl]-1l-[4-(trifluoromethyl)cyclohexyl]urea as a yellow solid.

LCMS: Method L, MS-ESI, 403.2 [M+H⁺].

¹HNMR: (400 MHz, DMSO-d₆) δ 11.24 (s, 1H), 8.51 (s, 1H), 8.34 (s, 1H), 8.10 (s, 1H), 7.74-7.67 (m, 2H), 7.55-7.46 (m, 3H), 7.40-7.36 (m, 1H), 6.34 (d, J=7.6 Hz, 1H), 3.92 (s, 1H), 2.64-2.56 (m, 1H), 1.85-1.71 (m, 4H), 1.66-1.45 (m, 4H).

Example 172: Synthesis of Compound 324

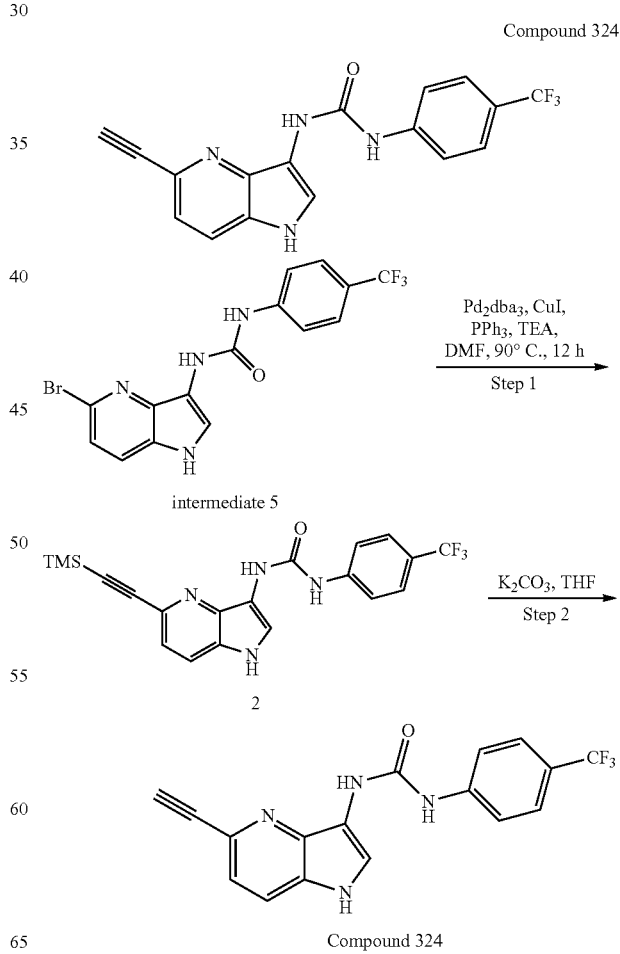

1. Synthesis of 1-(4-(trifluoromethyl)phenyl)-3-(5-((trimethylsilyl)ethynyl)-1H-pyrrolo[3,2-b]pyridin-3-yl)urea

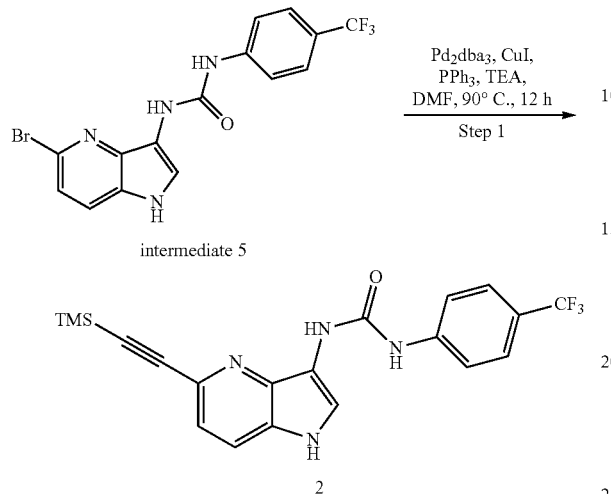

3-[5-Bromo-1H-pyrrolo[3,2-b]pyridin-3-yl]-1-[4-(trifluoromethyl)phenyl]urea (200.0 mg, 0.5 mmol, 1.0 equiv) was dissolved in DMF (5.0 mL) under $N_2$. Trimethylsilylacetylene (49.2 mg, 0.5 mmol, 1.0 equiv), TEA (101.4 mg, 1.0 mmol, 2.0 equiv), CuI (47.7 mg, 0.3 mmol, 0.5 equiv), Pd(dba)$_2$ (28.8 mg, 0.05 mmol, 0.1 equiv) and PPh$_3$ (13.2 mg, 0.05 mmol, 0.1 equiv) were added under $N_2$ and stirred for 12 hr at 90° C. The solids were filtered out and resulting mixture was concentrated under vacuum. The crude product was purified by flash column with EA/PE (1/3). This resulted in 100 mg (47.9%) of 1-[4-(trifluoromethyl)phenyl]-3-[5-[2-(trimethylsilyl)ethynyl]-1H-pyrrolo[3,2-b]pyridin-3-yl]urea as a light yellow solid.

LCMS: Method C, MS-ESI, 417.1 [M+H$^+$].

2. Synthesis of 1-(5-ethynyl-1H-pyrrolo[3,2-b]pyridin-3-yl)-3-(4-(trifluoromethyl)phenyl)urea

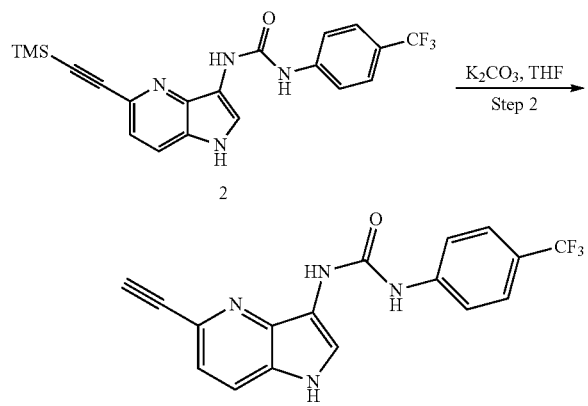

Synthesized using the method method as in Example 167. The crude product was purified by Method P. This resulted in 5.5 mg (7.6%) of 3-[5-ethynyl-1H-pyrrolo[3,2-b]pyridin-3-yl]-1-[4-(trifluoromethyl)phenyl]urea as an off-white solid.

LCMS: Method C, MS-ESI, 345.1 [M+H$^+$].

$^1$HNMR: (300 MHz, DMSO-d$_6$) δ 11.14 (s, 1H), 9.41 (s, 1H), 8.91 (s, 1H), 8.40 (d, J=1.7 Hz, 1H), 7.94 (d, J=2.7 Hz, 1H), 7.87 (d, J=1.7 Hz, 1H), 7.71-7.58 (m, 4H), 4.26 (s, 1H).

Example 173: Synthesis of Compound 240

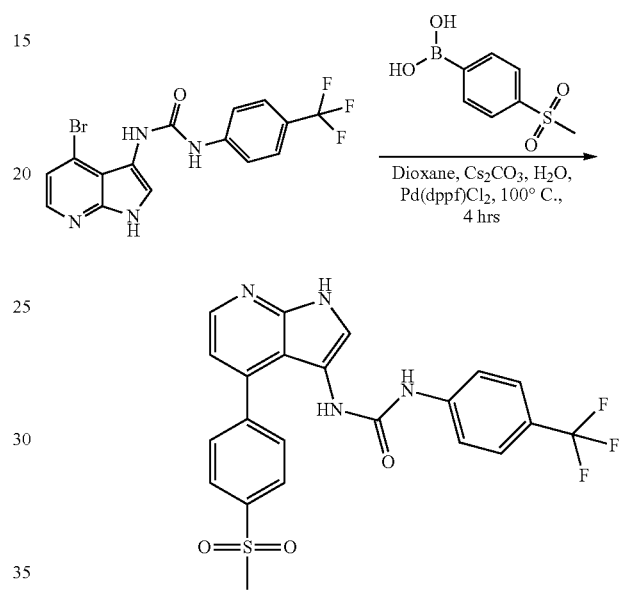

Procedure 1:

1-(4-bromo-1H-pyrrolo[2,3-b]pyridin-3-yl)-3-(4-(trifluoromethyl) phenyl)urea (80 mg, 200 umol, 1.0 eq) and (4-(methylsulfonyl)phenyl)boronic acid (300 mol, 1.5 eq) were mixed in dioxane (2 mL). Cs$_2$CO$_{3\ aq}$. (2.0 M, 2.0 eq, 200 ul) and Pd(dppf)Cl$_2$ (0.05 eq) under $N_2$ atmosphere were then added. The mixture was stirred at 100° C. for 4 hours, after which water (2 mL) was added. The resulting mixture was extract with EtOAc (5 mL*3). The organic layer was collected, and the solvent was removed with Speedvac. The residue was purified by prep. HPLC to give final compound.

Instrument GILSON 281 and Shimadzu LCMS 2010A; Column Name Xtimate C18 150*25 mm*5 um; Mobile phase MeOH-Water (0.225% FA); Begin (%) 42, End (%)67; Gradient Time (min) 12.5; Flow Rate (mL/min) 30; Detector MS Trigger.

Agilent 1200 HPLC/6100series MSD or equivalent API-ES; Gradient: 90% A (0.04% TFA in water) and 10% B (0.02% TFA in Acetonitrile) to 0% A and 100% B within 3.4 min with flow rate 0.8 ml/min; Column:XBridge C18, 2.1*50 mm, 5 μm or equivalent; Temperature:40 Centigrade; Detector: 220 nm by DAD.

MS-ESI, 475.1 [M+H$^+$].

$^1$H NMR (400 MHz, DMSO-d$_6$) δ ppm 11.89 (br s, 1H) 8.78 (br s, 1H) 8.32 (d, J=5.02 Hz, 1H) 7.81-7.90 (m, 2H) 7.76 (d, J=8.28 Hz, 2H) 7.45-7.61 (m, 4H) 7.34 (d, J=8.53 Hz, 2H) 7.08 (d, J=4.77 Hz, 1H) 2.86 (br s, 3H)

Example 174: Synthesis of Compound 234

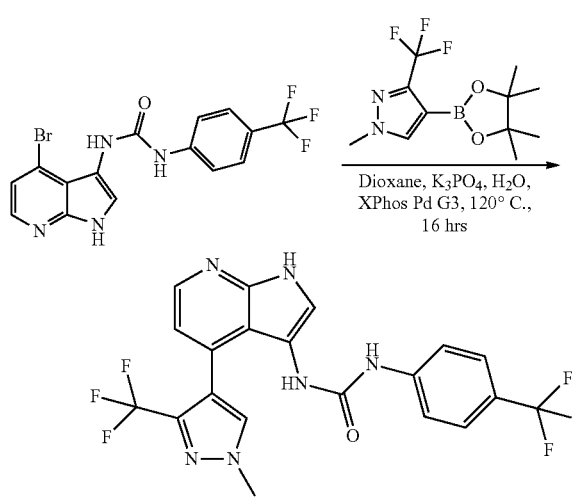

Procedure 2:

1-(4-bromo-1H-pyrrolo[2,3-b]pyridin-3-yl)-3-(4-(trifluoromethyl) phenyl)urea (80 mg, 200 umol, 1.0 eq) and 1-methyl-4-(4,4,5,5-tetramethyl-1,3,2-dioxaborolan-2-yl)-3-(trifluoromethyl)-1H-pyrazole (300 umol, 1.5 eq) were mixed in dioxane (2 mL). To the mixture were then added $K_3PO_{4\ aq}$. (2.0 M, 2.0 eq, 200 μL) and XPhos Pd G3 (0.05 eq) under $N_2$ atmosphere. The mixture was stirred at 120° C. for 16 hours, after which water (2 mL) was added. The resulting mixture was extracted with EtOAc (5 mL*3). The organic layer was collected, and the solvent was removed by Speedvac. The residue was purified by prep.HPLC to give final compound.

Instrument GILSON 281 and Shimadzu LCMS 2010A; Column Name Xtimate C18 150*25 mm*5 um; Mobile phase MeOH-Water (0.225% FA); Begin (%) 51, End (%) 72; Gradient Time (min) 12.5; Flow Rate (mL/min) 30; Detector MS Trigger.

Agilent 1200 HPLC/6100series MSD or equivalent API-ES; Gradient: 90% A (0.04% TFA in water) and 10% B (0.02% TFA in Acetonitrile) to 0% A and 100% B within 3.4 min with flow rate 0.8 ml/min; Column:XBridge C18, 2.1*50 mm, 5 μm or equivalent; Temperature:40 Centigrade; Detector: 220 nm by DAD;

MS-ESI, 469.1 [M+H⁺].

$^1$H NMR (400 MHz, DMSO-$d_6$) δ ppm 11.76 (br s, 1H) 8.99 (br s, 1H) 8.24 (d, J=4.77 Hz, 1H) 7.97 (s, 1H) 7.47-7.59 (m, 5H) 7.34 (br s, 1H) 6.90 (d, J=4.77 Hz, 1H) 3.76 (s, 3H).

The following compounds were synthesized by the above method through the coupling of the intermediate below with the respective boronates:

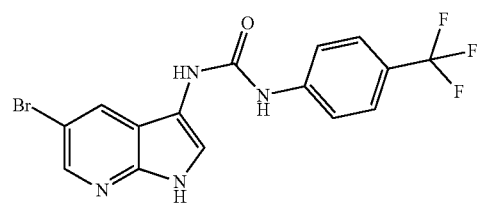 [SMILES: O=C(Nc1ccc(C(F)(F)F)cc1)Nc1c[nH]c2ncc(Br)cc12]

| Example # | Compound # | Final compound | Catalyst Conditions | LC-MS, MS-ESI, — [M + H⁺]. |
|---|---|---|---|---|
| 175 | 212 | | procedure 1 | 403 |
| 176 | 213 | | procedure 1 | 416 |
| 177 | 207 | | procedure 1 | 475.1 |

-continued

| Example # | Compound # | Final compound | Catalyst Conditions | LC-MS, MS-ESI, — [M + H⁺]. |
|---|---|---|---|---|
| 178 | 243 | | procedure 1 | 440 |
| 179 | 200 | | procedure 2 | 417.1 |
| 180 | 185 | | procedure 1 | 398.2 |
| 181 | 197 | | procedure 1 | 495.3 |
| 182 | 242 | | procedure 2 | 418 |
| 183 | 196 | | procedure 1 | 468.2 |

-continued

| Example # | Compound # | Final compound | Catalyst Conditions | LC-MS, MS-ESI, [M + H⁺]. |
|---|---|---|---|---|
| 184 | 210 | | procedure 1 | 398 |
| 185 | 208 | | procedure 1 | 399.2 |
| 186 | 214 | | procedure 1 | 463.1 |
| 187 | 241 | | procedure 1 | 469 |
| 188 | 188 | | procedure 1 | 483.2 |
| 189 | 211 | | procedure 1 | 468.1 |

-continued

| Example # | Compound # | Final compound | Catalyst Conditions | LC-MS, MS-ESI, — [M + H⁺]. |
|---|---|---|---|---|
| 190 | 198 | | procedure 2 | 469.1 |
| 191 | 193 | | procedure 2 | 429.1 |
| 192 | 204 | | procedure 1 | 504.2 |
| 193 | 215 | | procedure 1 | 455.1 |
| 194 | 209 | | procedure 1 | 455.1 |

The following compounds were synthesized by the above method for the following boronate
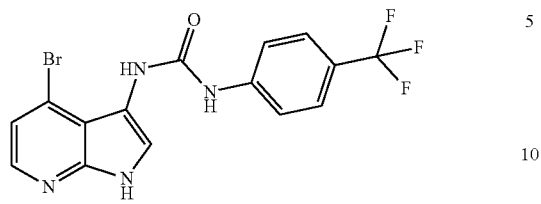
5
10
| Example # | Compound # | Final compound | Catalyst Conditions | LC-MS, MS-ESI, — [M + H⁺]. |
|---|---|---|---|---|
| 195 | 203 | | procedure 1 | 403.2 |
| 196 | 195 | | procedure 1 | 416.1 |
| 197 | 184 | | procedure 1 | 414.1 |
| 173 | 240 | | procedure 1 | 475.1 |

-continued

| Example # | Compound # | Final compound | Catalyst Conditions | LC-MS, MS-ESI, — [M + H+]. |
|---|---|---|---|---|
| 198 | 239 | | procedure 1 | 440.2 |
| 199 | 238 | | procedure 2 | 417.1 |
| 200 | 206 | | procedure 1 | 398.1 |
| 201 | 187 | | procedure 1 | 495.2 |
| 202 | 202 | | procedure 1 | 476.1 |

-continued

| Example # | Compound # | Final compound | Catalyst Conditions | LC-MS, MS-ESI, — [M + H+]. |
|---|---|---|---|---|
| 203 | 237 | | procedure 2 | 418 |
| 204 | 192 | | procedure 1 | 468.1 |
| 205 | 189 | | procedure 1 | 398.1 |
| 206 | 236 | | procedure 1 | 399 |
| 207 | 201 | | procedure 1 | 463.2 |

-continued

| Example # | Compound # | Final compound | Catalyst Conditions | LC-MS, MS-ESI, — [M + H⁺]. |
|---|---|---|---|---|
| 208 | 194 | | procedure 1 | 469.1 |
| 209 | 191 | | procedure 1 | 483.1 |
| 210 | 235 | | procedure 1 | 468.2 |
| 174 | 234 | | procedure 2 | 469.1 |

-continued

| Example # | Compound # | Final compound | Catalyst Conditions | LC-MS, MS-ESI, — [M + H⁺]. |
|---|---|---|---|---|
| 211 | 186 | | procedure 2 | 429.2 |
| 212 | 199 | | procedure 1 | 504.2 |
| 213 | 205 | | procedure 1 | 455.2 |
| 214 | 190 | | procedure 1 | 455.1 |

The following compounds were synthesized by the above method for the following boronate
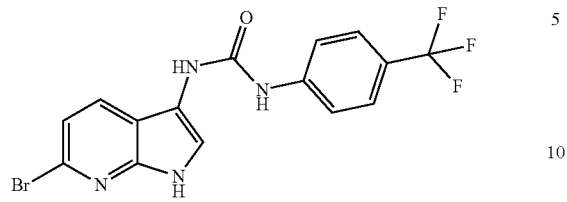
| Example # | Compound # | Final compound | Catalyst Conditions | LC-MS, MS-ESI, — [M + H⁺]. |
|---|---|---|---|---|
| 215 | 233 | | procedure 1 | 403 |
| 216 | 232 | | procedure 1 | 475 |
| 217 | 231 | | procedure 1 | 440 |
| 218 | 230 | | procedure 2 | 417 |

-continued

| Example # | Compound # | Final compound | Catalyst Conditions | LC-MS, MS-ESI, — [M + H⁺]. |
|---|---|---|---|---|
| 219 | 229 | | procedure 1 | 398 |
| 220 | 228 | | procedure 1 | 495.2 |
| 221 | 227 | | procedure 1 | 476 |
| 222 | 226 | | procedure 1 | 468 |
| 223 | 225 | | procedure 1 | 398 |

-continued

| Example # | Compound # | Final compound | Catalyst Conditions | LC-MS, MS-ESI, — [M + H+]. |
|---|---|---|---|---|
| 224 | 224 | | procedure 1 | 399 |
| 225 | 223 | | procedure 1 | 463 |
| 226 | 222 | | procedure 1 | 483 |
| 227 | 221 | | procedure 1 | 468.2 |
| 228 | 220 | | procedure 1 | 504 |

| Example # | Compound # | Final compound | Catalyst Conditions | LC-MS, MS-ESI, — [M + H+]. |
|---|---|---|---|---|
| 229 | 219 | 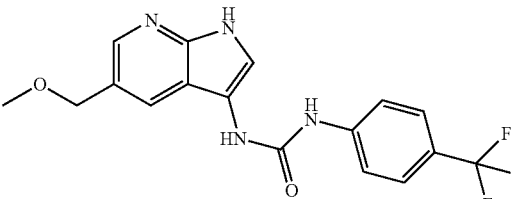 | procedure 1 | 455 |
| 230 | 218 | 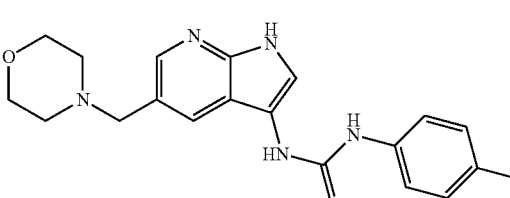 | procedure 1 | 455.2 |
The following compounds are synthesized using methods similar to those described elsewhere herein.
| Example # | Compound # | Final compound |
|---|---|---|
| 231 | 338 | 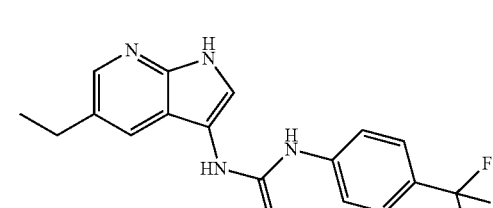 |
| 232 | 339 | |
| 233 | 340 | |

-continued
| Example # | Compound # | Final compound |
|---|---|---|
| 234 | 341 | 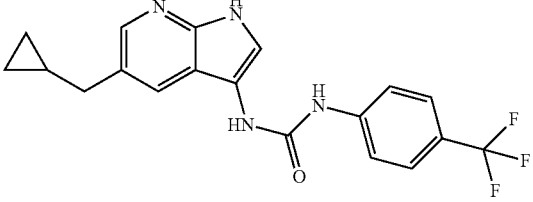 |
| 235 | 342 | 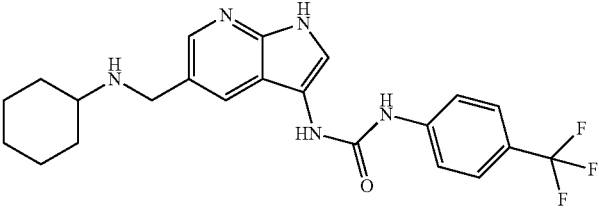 [SMILES: O=C(Nc1ccc(C(F)(F)F)cc1)Nc1c[nH]c2ncc(CNC3CCCCC3)cc12] |
| 236 | 343 | 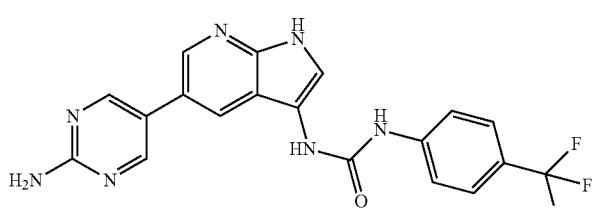 |
| 237 | 344 | 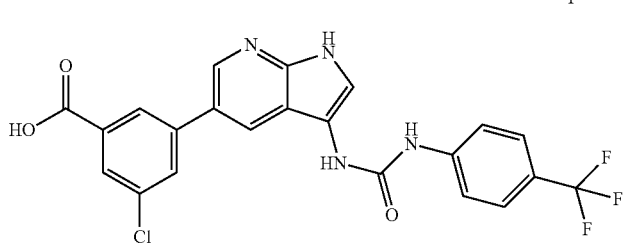 |
| 238 | 345 | 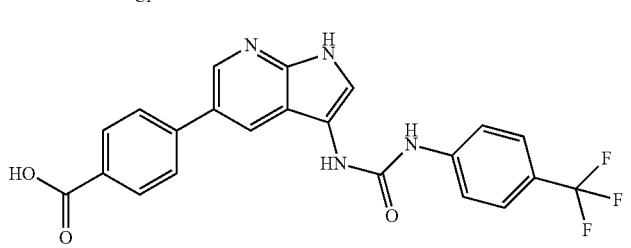 |
| 239 | 346 | 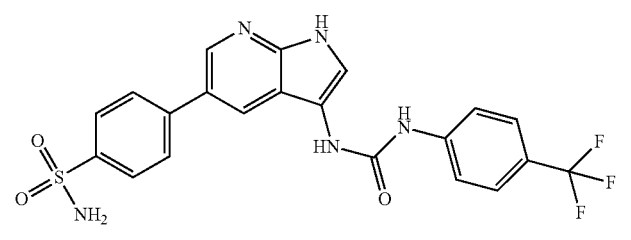 [SMILES: NS(=O)(=O)c1ccc(-c2cnc3[nH]cc(NC(=O)Nc4ccc(C(F)(F)F)cc4)c3c2)cc1] |
| 240 | 347 | 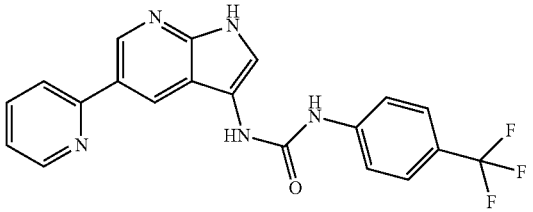 [SMILES: O=C(Nc1ccc(C(F)(F)F)cc1)Nc1c[nH]c2ncc(-c3ccccn3)cc12] |

-continued
| Example # | Compound # | Final compound |
|---|---|---|
| 241 | 348 | 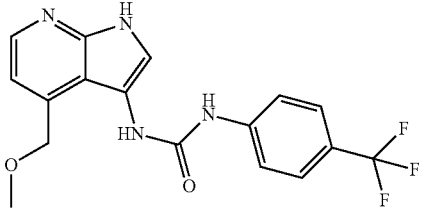 [SMILES: COCc1ccnc2[nH]cc(NC(=O)Nc3ccc(C(F)(F)F)cc3)c12] |
| 242 | 349 | 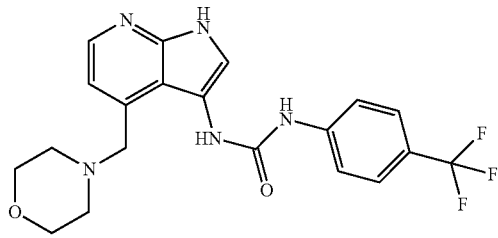 [SMILES: O=C(Nc1ccc(C(F)(F)F)cc1)Nc1c[nH]c2nccc(CN3CCOCC3)c12] |
| 243 | 350 | 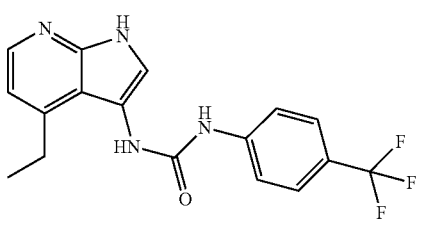 [SMILES: CCc1ccnc2[nH]cc(NC(=O)Nc3ccc(C(F)(F)F)cc3)c12] |
| 244 | 351 | 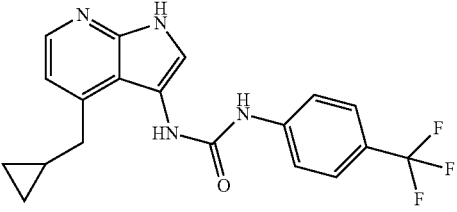 [SMILES: O=C(Nc1ccc(C(F)(F)F)cc1)Nc1c[nH]c2nccc(CC3CC3)c12] |
| 245 | 352 | 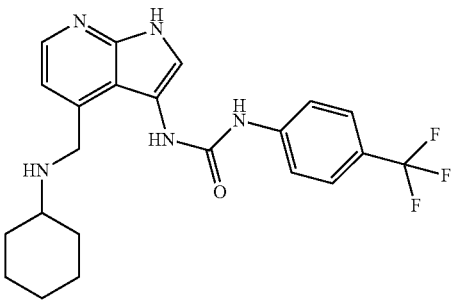 [SMILES: O=C(Nc1ccc(C(F)(F)F)cc1)Nc1c[nH]c2nccc(CNC3CCCCC3)c12] |
| 246 | 353 | 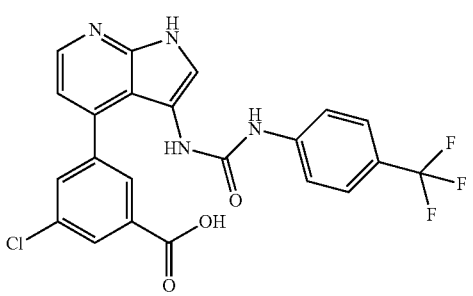 [SMILES: O=C(Nc1ccc(C(F)(F)F)cc1)Nc1c[nH]c2nccc(-c3cc(Cl)cc(C(=O)O)c3)c12] |

-continued
| Example # | Compound # | Final compound |
|---|---|---|
| 247 | 354 | 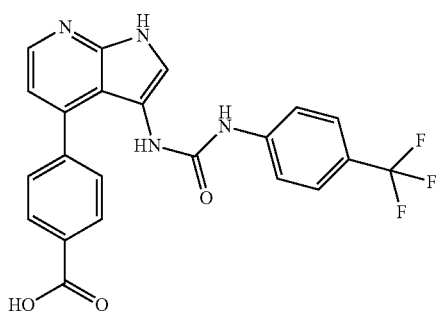 [SMILES: O=C(Nc1ccc(C(F)(F)F)cc1)Nc1c[nH]c2nccc(-c3ccc(C(=O)O)cc3)c12] |
| 248 | 355 | 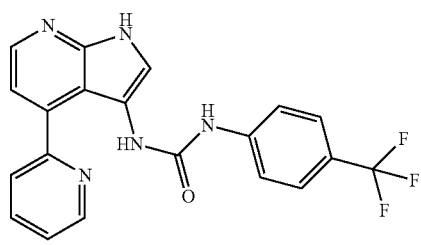 [SMILES: O=C(Nc1ccc(C(F)(F)F)cc1)Nc1c[nH]c2nccc(-c3ccccn3)c12] |
| 249 | 356 | 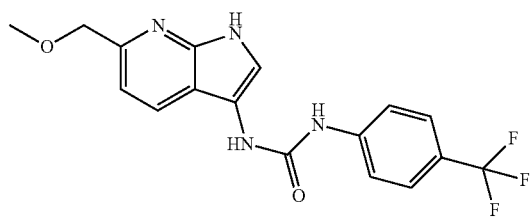 [SMILES: COCc1ccc2c(NC(=O)Nc3ccc(C(F)(F)F)cc3)c[nH]c2n1] |
| 250 | 357 | 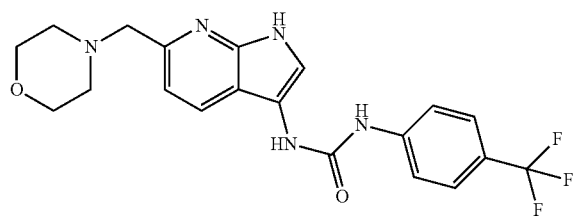 [SMILES: O=C(Nc1ccc(C(F)(F)F)cc1)Nc1c[nH]c2nc(CN3CCOCC3)ccc12] |
| 251 | 358 | 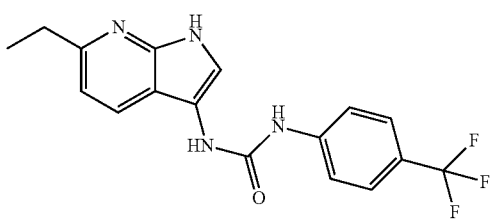 [SMILES: CCc1ccc2c(NC(=O)Nc3ccc(C(F)(F)F)cc3)c[nH]c2n1] |
| 252 | 359 | 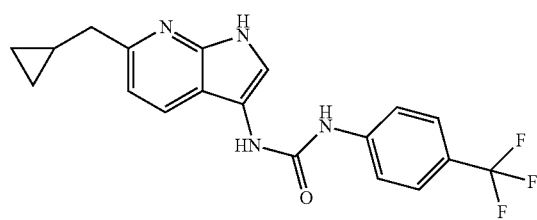 [SMILES: O=C(Nc1ccc(C(F)(F)F)cc1)Nc1c[nH]c2nc(CC3CC3)ccc12] |

-continued
| Example # | Compound # | Final compound |
|---|---|---|
| 253 | 360 | 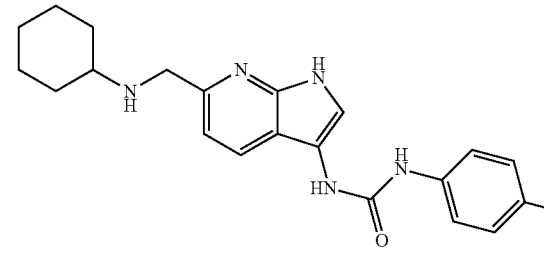 |
| 254 | 361 | 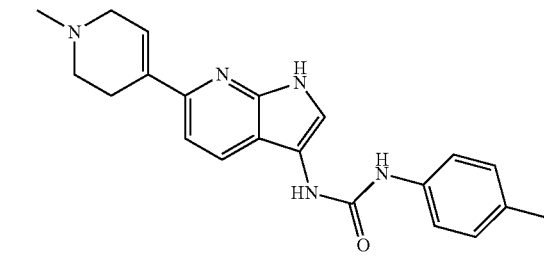 |
| 255 | 362 | 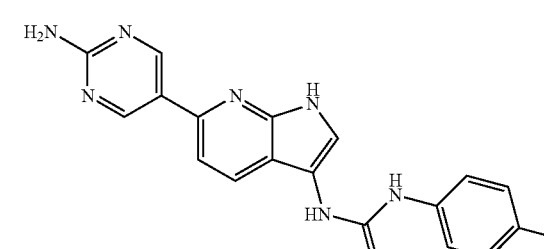 |
| 256 | 363 | 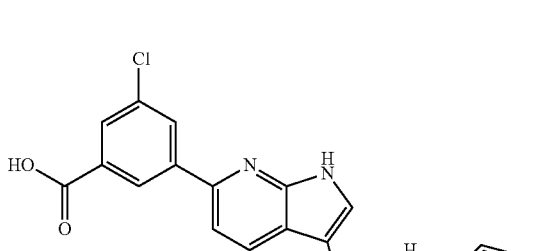 |
| 257 | 364 | 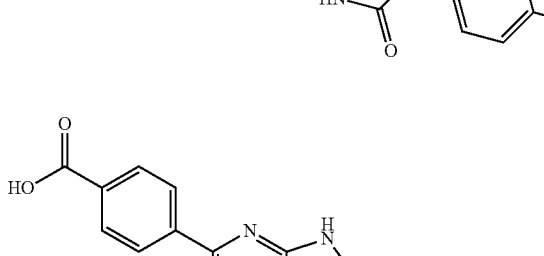 |

-continued
| Example # | Compound # | Final compound |
|---|---|---|
| 258 | 365 | 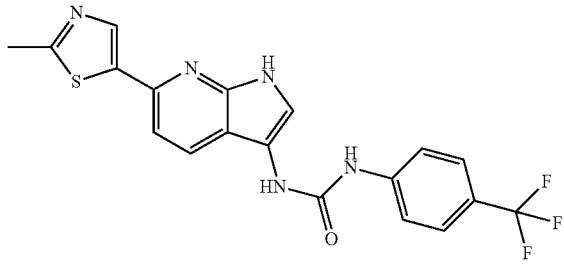 [SMILES: Cc1ncc(-c2ccc3c(NC(=O)Nc4ccc(C(F)(F)F)cc4)c[nH]c3n2)s1] |
| 259 | 366 | 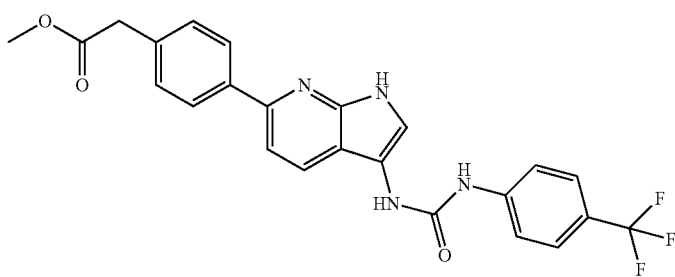 [SMILES: COC(=O)Cc1ccc(-c2ccc3c(NC(=O)Nc4ccc(C(F)(F)F)cc4)c[nH]c3n2)cc1] |
| 260 | 367 | 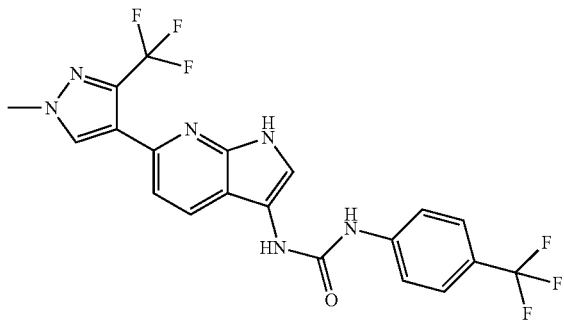 [SMILES: Cn1cc(-c2ccc3c(NC(=O)Nc4ccc(C(F)(F)F)cc4)c[nH]c3n2)c(C(F)(F)F)n1] |
| 261 | 368 | 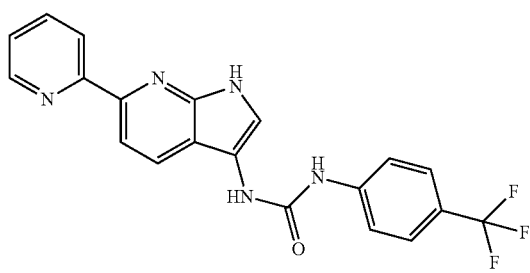 [SMILES: O=C(Nc1ccc(C(F)(F)F)cc1)Nc1c[nH]c2nc(-c3ccccn3)ccc12] |
| 262 | 369 | 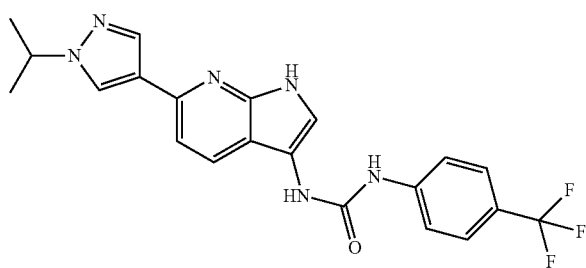 [SMILES: CC(C)n1cc(-c2ccc3c(NC(=O)Nc4ccc(C(F)(F)F)cc4)c[nH]c3n2)cn1] |

-continued

| Example # | Compound # | Final compound |
|---|---|---|
| 263 | 370 | |
| 264 | 371 | |
| 265 | 372 | |
| 266 | 373 | |
| 267 | 374 | |
| 268 | 375 | |
| 269 | 376 | |

-continued

| Example # | Compound # | Final compound |
|---|---|---|
| 270 | 377 | *structure: 4-(2-methylphenyl)-7-azaindole-3-yl urea with 4-(trifluoromethyl)phenyl* |
| 271 | 378 | *structure: 4-(2-chlorophenyl)-7-azaindole-3-yl urea with 4-(trifluoromethyl)phenyl* |
| 272 | 379 | *structure: 4-[2-(hydroxymethyl)phenyl]-7-azaindole-3-yl urea with 4-(trifluoromethyl)phenyl* |
| 273 | 380 | *structure: 4-[3-(hydroxymethyl)phenyl]-7-azaindole-3-yl urea with 4-(trifluoromethyl)phenyl* |
| 274 | 381 | *structure: 4-{3-[(methylamino)methyl]phenyl}-7-azaindole-3-yl urea with 4-(trifluoromethyl)phenyl* |
| 275 | 382 | *structure: 6-(pyrimidin-2-yl)-7-azaindole-3-yl urea with 4-(trifluoromethyl)phenyl* |

| Example # | Compound # | Final compound |
|---|---|---|
| 276 | 383 | *structure: 6-(2-methylphenyl)-7-azaindole with 3-NH-C(O)-NH-(4-trifluoromethylphenyl) urea* |
| 277 | 384 | *structure: 6-(2-chlorophenyl)-7-azaindole with 3-NH-C(O)-NH-(4-trifluoromethylphenyl) urea* |
| 278 | 385 | *structure: 6-(2-hydroxymethylphenyl)-7-azaindole with 3-NH-C(O)-NH-(4-trifluoromethylphenyl) urea* |
| 279 | 386 | *structure: 6-(3-hydroxymethylphenyl)-7-azaindole with 3-NH-C(O)-NH-(4-trifluoromethylphenyl) urea* |
| 280 | 387 | *structure: 6-(3-(methylaminomethyl)phenyl)-7-azaindole with 3-NH-C(O)-NH-(4-trifluoromethylphenyl) urea* |

Biological Assays

STING pathway activation by the compounds described herein is measured using THP1-Dual™ cells (KO-IFNAR2).

THP1-Dual™ KO-IFNAR2 Cells (obtained from invivogen) are maintained in RPMI, 10% FCS, 5 ml P/S, 2 mM L-glut, 10 mM Hepes, and 1 mM sodium pyruvate. Compounds are spotted in empty 384 well tissue culture plates (Greiner 781182) by Echo for a final concentration of 0.0017-100 M. Cells are plated into the TC plates at 40 μL per well, 2×10E6 cells/mL. For activation with STING ligand, 2'3'cGAMP (MW 718.38, obtained from Invivogen), is prepared in Optimem media.

The following solutions are prepared for each 1×384 plate:

Solution A: 2 mL Optimem with one of the following stimuli:
60 uL of 10 mM 2'3'cGAMP→150 μM stock
Solution B: 2 mL Optimem with 60 μL Lipofectamine 2000→Incubate 5 min at RT 2 mL of solution A and 2 ml Solution B is mixed and incubated for 20 min at room temperature (RT). 20 uL of transfection solution (A+B) is added on top of the plated cells, with a final 2'3'cGAMP concentration of 15 μM. The plates are then centrifuged immediately at 340 g for 1 minute, after which they are incubated at 37° C., 5% $CO_2$, >98% humidity for 24 h. Luciferase reporter activity is then measured. $EC_{50}$ values were calculated by using standard methods known in the art.

Luciferase Reporter Assay:

10 μL of supernatant from the assay is transferred to white 384-plate with flat bottom and squared wells. one pouch of QUANTI-Luc™ Plus is dissolved in 25 mL of water. 100 μL of QLC Stabilizer per 25 mL of QUANTI-Luc™ Plus solution was added. 50 μL of QUANTI-Luc™ Plus/QLC solution per well is then added. Luminescence is measured on a Platereader (e.g., Spectramax I3X (Molecular Devices GF3637001)).

Luciferase reporter activity is then measured. $EC_{50}$ values are calculated by using standard methods known in the art.

Table A shows the activity of compounds in STING reporter assay: <0.008 μM="++++++"; ≥0.008 and <0.04 μM="+++++"; ≥0.04 and <0.2 μM="++++"; >0.2 and <1 μM="+++"; ≥1 and <5 μM="++"; ≥5 and <100 μM="+" μM.

TABLE A

| Compound # | hSTING: $EC_{50}$ (μM) |
|---|---|
| 132 | ++ |
| 133 | + |
| 135 | + |
| 136 | + |
| 137 | ++ |
| 138 | +++ |
| 139 | +++ |
| 140 | ++ |
| 141 | + |
| 142 | ++ |
| 143 | ++ |
| 144 | ++ |
| 145 | +++ |
| 146 | ++ |
| 147 | ++++ |
| 148 | ++ |
| 149 | + |
| 150 | ++ |
| 151 | +++ |
| 152 | + |
| 154 | + |
| 156 | + |
| 157 | + |
| 159 | + |
| 160 | + |
| 161 | + |
| 162 | + |
| 163 | +++ |
| 164 | + |
| 165 | +++ |
| 166 | +++ |
| 167 | + |
| 168 | + |
| 169 | + |
| 170 | +++ |
| 171 | + |
| 172 | + |
| 173 | ++++ |

TABLE A-continued

| Compound # | hSTING: $EC_{50}$ (μM) |
|---|---|
| 174 | ++++ |
| 180 | + |
| 183 | + |
| 183b | + |
| 186 | + |
| 188 | + |
| 189 | + |
| 192 | + |
| 193 | +++ |
| 195 | + |
| 196 | + |
| 197 | ++ |
| 198 | ++ |
| 203 | + |
| 204 | ++ |
| 205 | + |
| 206 | + |
| 207 | + |
| 209 | ++ |
| 210 | ++ |
| 211 | +++ |
| 212 | ++ |
| 213 | + |
| 214 | + |
| 215 | ++ |
| 245 | + |
| 246 | ++ |
| 247 | ++ |
| 248 | +++ |
| 249 | + |
| 250 | +++ |
| 251 | +++ |
| 252 | + |
| 255 | +++ |
| 257 | + |
| 258 | +++ |
| 259 | +++ |
| 260 | ++ |
| 261 | ++++ |
| 263 | +++ |
| 264 | +++ |
| 265 | +++ |
| 267 | ++ |
| 268 | +++ |
| 270 | + |
| 271 | +++ |
| 272 | ++++ |
| 273 | +++ |
| 274 | ++++ |
| 275 | ++++ |
| 276 | +++ |
| 279 | + |
| 280 | ++ |
| 281 | ++ |
| 282 | +++ |
| 283 | ++++ |
| 284 | ++ |
| 285 | ++ |
| 286 | ++ |
| 287 | ++ |
| 288 | + |
| 289 | + |
| 291 | ++++ |
| 292 | +++ |
| 293 | +++ |
| 294 | + |
| 295 | +++ |
| 296 | ++++ |
| 297 | +++ |
| 298 | ++ |
| 299 | + |
| 300 | +++ |
| 301 | + |
| 302 | + |
| 303 | + |
| 304 | + |
| 305 | ++ |
| 306 | + |

TABLE A-continued

| Compound # | hSTING: EC$_{50}$ (μM) |
|---|---|
| 307 | + |
| 309 | |
| 312 | ++ |
| 313 | ++ |
| 314 | ++ |
| 315 | ++ |
| 316 | +++ |
| 317 | +++ |
| 318 | + |
| 319 | ++ |
| 320 | + |
| 321 | + |
| 322 | ++ |
| 324 | + |
| 325 | + |
| 326 | +++ |
| 328 | + |
| 329 | +++ |
| 330 | ++ |
| 331 | ++ |
| 332 | ++ |
| 335 | ++ |
| 336 | +++ |
| 337 | + |

What is claimed is:

1. A compound of Formula (I):

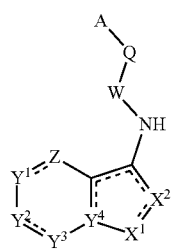

(I)

or a pharmaceutically acceptable salt thereof, or an N-oxide thereof, wherein:

Z is CH;
each of $Y^1$ and $Y^2$ is an independently selected $CR^1$, and $Y^3$ is N;
$Y^4$ is C;
$X^1$ is $NR^2$;
$X^2$ is CH;
each ≡ is independently a single bond or a double bond, provided that the five-membered ring comprising $Y^4$, $X^1$, and $X^2$ is heteroaryl; and wherein the ring that includes Z, $Y^1$, $Y^2$, $Y^3$, and $Y^4$:

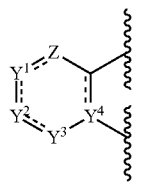

is aromatic;
W is selected from the group consisting of:
(i) C(=O);
(ii) C(=S);
(iv) C(=$NR^d$); and
(v) C(=NH);

Q-A is defined according to (A) or (B) below:
(A)
Q is NH or N(C$_{1-6}$ alkyl) wherein the C$_{1-6}$ alkyl is optionally substituted with 1-2 independently selected $R^a$, and A is:
(i) —(Y$^{A1}$)$_n$—Y$^{A2}$, wherein:
n is 0;
and
Y$^{A2}$ is:
(a) C$_{3-20}$ cycloalkyl, which is optionally substituted with from 1-4 $R^b$,
(b) C$_{6-20}$ aryl, which is optionally substituted with from 1-4 $R^c$;
(c) heteroaryl including from 5-20 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-4 independently selected R$^c$, or
(d) heterocyclyl including from 3-16 ring atoms, wherein from 1-3 ring atoms are heteroatoms, each independently selected from the group consisting of N, N(H), N(R$^b$), N(R$^d$), and O, and wherein one or more of the heterocyclyl ring carbon atoms are optionally substituted with from 1-4 independently selected R$^b$, OR
(ii) —Z$^1$—Z$^2$—Z$^3$, wherein:
Z$^1$ is C$_{1-3}$ alkylene, which is optionally substituted with from 1-4 R$^a$;
Z$^2$ is —N(H)—, —N(R$^d$)—, —O—, or —S—; and
Z$^3$ is C$_{2-7}$ alkyl, which is optionally substituted with from 1-4 R$^a$;
or
(B)
Q and A, taken together, form:

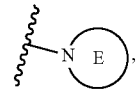

wherein / denotes point of attachment to W; and
E is a ring including from 3-16 ring atoms, wherein aside from the nitrogen atom present, from 0-3 additional ring atoms are heteroatoms, each independently selected from the group consisting of N, N(H), N(R$^d$), and O, and wherein one or more of the heterocyclyl ring carbon atoms are optionally substituted with from 1-4 independently selected R$^b$,
each occurrence of R$^1$ is independently selected from the group consisting of H; halo; cyano; C$_{1-6}$ alkyl optionally substituted with 1-2 R$^a$; C$_{2-6}$ alkenyl; C$_{2-6}$ alkynyl; C$_{1-4}$ haloalkyl; C$_{1-4}$ alkoxy; C$_{1-4}$ haloalkoxy; —(C$_{0-3}$ alkylene)-C$_{3-6}$ cycloalkyl optionally substituted with from 1-4 independently selected R$^g$; —(C$_{0-3}$ alkylene)-C$_{6-10}$ aryl optionally substituted with from 1-4 independently selected R$^g$; —(C$_{0-3}$ alkylene)-5-10 membered heteroaryl, wherein from 1-3 ring atoms of the heteroaryl are heteroatoms each independently selected from the group consisting of N, NH, NR$^d$, O, and S, wherein the heteroaryl is optionally substituted with from 1-4 independently selected R$^g$; —(C$_{0-3}$ alkylene)-

5-10 membered heterocyclyl, wherein from 1-3 ring atoms of the heterocyclyl are heteroatoms each independently selected from the group consisting of N, NH, $NR^d$, O, and S, wherein the heterocyclyl is optionally substituted with 1-4 independently selected $R^g$; —S(O)$_{1-2}$(C$_{1-4}$ alkyl); —NR$^e$R$^f$; —OH; oxo; —S(O)$_{1-2}$(NR'R"); —C$_{1-4}$ thioalkoxy; —NO$_2$; —C(=O)(C$_{1-4}$ alkyl); —C(=O)O(C$_{1-4}$ alkyl); —C(=O)OH; and —C(=O)N(R')(R");

each occurrence of $R^2$ is independently selected from the group consisting of:
(i) C$_{1-6}$ alkyl, which is optionally substituted with from 1-2 independently selected $R^a$;
(ii) C$_{3-6}$ cycloalkyl;
(iii) heterocyclyl including from 3-10 ring atoms, wherein from 1-3 ring atoms are heteroatoms, each independently selected from the group consisting of N, N(H), N(R$^d$), and O;
(iv) —C(O)(C$_{1-4}$ alkyl);
(v) —C(O)O(C$_{1-4}$ alkyl);
(vi) —CON(R')(R");
(vii) —S(O)$_{1-2}$(NR'R");
(viii) —S(O)$_{1-2}$(C$_{1-4}$ alkyl);
(ix) —OH;
(x) C$_{1-4}$ alkoxy; and
(xi) H;

each occurrence of $R^a$ is independently selected from the group consisting of: —OH; —F; —Cl; —Br; —NR$^e$R$^f$; C$_{1-4}$ alkoxy; C$_{1-4}$ haloalkoxy; —C(=O)O(C$_{1-4}$ alkyl); —C(=O)(C$_{1-4}$ alkyl); —C(=O)OH; —CON(R')(R"); —S(O)$_{1-2}$(NR'R"); —S(O)$_{1-2}$(C$_{1-4}$ alkyl); cyano, and C$_{3-6}$ cycloalkyl optionally substituted with from 1-4 independently selected C$_{1-4}$ alkyl;

each occurrence of $R^b$ is independently selected from the group consisting of: C$_{1-10}$ alkyl optionally substituted with from 1-6 independently selected $R^a$; C$_{1-4}$ haloalkyl; —OH; oxo; —F; —Cl; —Br; —NR$^e$R$^f$; C$_{1-4}$ alkoxy; C$_{1-4}$ haloalkoxy; —C(=O)(C$_{1-4}$ alkyl); —C(=O)O(C$_{1-4}$ alkyl); —C(=O)OH; —C(=O)N(R')(R"); —S(O)$_{1-2}$(NR'R"); —S(O)$_{1-2}$(C$_{1-4}$ alkyl); cyano; (C$_{0-3}$ alkylene)-C$_{6-10}$ aryl optionally substituted with 1-4 independently selected C$_{1-4}$ alkyl; and (C$_{0-3}$ alkylene)-C$_{3-6}$ cycloalkyl optionally substituted with from 1-4 independently selected C$_{1-4}$ alkyl;

each occurrence of $R^c$ is independently selected from the group consisting of:
(i) halo;
(ii) cyano;
(iii) C$_{1-10}$ alkyl which is optionally substituted with from 1-6 independently selected $R^a$;
(iv) C$_{2-6}$ alkenyl;
(v) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl, wherein the heterocyclyl includes from 3-16 ring atoms, wherein from 1-3 ring atoms are heteroatoms, each independently selected from the group consisting of N, N(H), N(R$^d$), and O;
(xi) —S(O)$_{1-2}$(C$_{1-4}$ alkyl);
(xii) —NR$^e$R$^f$;
(xiii) —OH;
(xiv) —S(O)$_{1-2}$(NR'R");
(xv) —C$_{1-4}$ thioalkoxy;
(xvi) —NO$_2$;
(xvii) —C(=O)(C$_{1-4}$ alkyl);
(xviii) —C(=O)O(C$_{1-4}$ alkyl);
(xix) —C(=O)OH;
(xx) —C(=O)N(R')(R");
(xxi) —(C$_{0-3}$ alkylene)-C$_{6-10}$ aryl optionally substituted with from 1-4 independently selected C$_{1-4}$ alkyl; and
(xxii) —(C$_{0-3}$ alkylene)-5-10 membered heteroaryl, wherein from 1-3 ring atoms of the heteroaryl are heteroatoms each independently selected from the group consisting of N, NH, NR$^d$, O, and S, wherein the heteroaryl is optionally substituted with from 1-4 independently selected C$_{1-4}$ alkyl;

$R^d$ is selected from the group consisting of: C$_{1-6}$ alkyl; C$_{3-6}$ cycloalkyl; —C(O)(C$_{1-4}$ alkyl); —C(O)O(C$_{1-4}$ alkyl); —CON(R')(R"); —S(O)$_{1-2}$(NR'R"); —S(O)$_{1-2}$(C$_{1-4}$ alkyl); —CN; —OH; and C$_{1-4}$ alkoxy;

each occurrence of $R^e$ and $R^f$ is independently selected from the group consisting of: H; C$_{1-6}$ alkyl; C$_{1-6}$ haloalkyl; C$_{3-6}$ cycloalkyl; —C(O)(C$_{1-4}$ alkyl); —C(O)O(C$_{1-4}$ alkyl); —CON(R')(R"); —S(O)$_{1-2}$(NR'R"); —S(O)$_{1-2}$(C$_{1-4}$ alkyl); —OH; and C$_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from the group consisting of H and C$_{1-3}$ alkyl; and (b) from 0-3 ring heteroatoms (in addition to the nitrogen atom attached to $R^e$ and $R^f$), which are each independently selected from the group consisting of N(R$^d$), O, and S;

each occurrence of $R^g$ is independently selected from the group consisting of: halo; cyano; C$_{1-6}$ alkyl optionally substituted with from 1-2 independently selected $R^a$; C$_{1-4}$ haloalkyl; C$_{1-6}$ alkoxy optionally substituted with 1-2 independently selected $R^a$; C$_{1-4}$ haloalkoxy; S(O)$_{1-2}$(C$_{1-4}$ alkyl); —NR$^e$R$^f$; —OH; oxo; —S(O)$_{1-2}$(NR'R"); —C$_{1-4}$ thioalkoxy; —NO$_2$; —C(=O)(C$_{1-4}$ alkyl); —C(=O)O(C$_{1-4}$ alkyl); —C(=O)OH; and —C(=O)N(R')(R"); and each occurrence of R' and R" is independently selected from the group consisting of: H and C$_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from the group consisting of: H and C$_{1-3}$ alkyl; and (b) from 0-3 ring heteroatoms (in addition to the nitrogen atom attached to R' and R"), which are each independently selected from the group consisting of N(R$^d$), O, and S, and provided that when Q-A is defined according to (A), and A is C$_6$ aryl mono-substituted with C$_4$ alkyl, then the ring that includes Z, Y$^1$, Y$^2$, Y$^3$, and Y$^4$ must be substituted with one or more $R^1$ that is other than hydrogen.

2. The compound of claim 1, wherein W is C(=O).

3. The compound of claim 1, wherein Q and A are defined according to (A).

4. The compound of claim 3, wherein A is —(Y$^{A1}$)$_n$—Y$^{A2}$.

5. The compound of claim 4, wherein Y$^{A2}$ is C$_{6-20}$ aryl, which is optionally substituted with from 1-4 R$^c$.

6. The compound of claim 4, wherein Y$^{A2}$ is heteroaryl including from 5-20 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-4 independently selected $R^c$.

7. The compound of claim 4, wherein $Y^{A2}$ is $C_{3-20}$ cycloalkyl, which is optionally substituted with from 1-4 $R^b$.

8. The compound of claim 4, wherein $Y^{A2}$ is heterocyclyl including from 3-12 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

9. The compound of claim 1, wherein Q and A are defined according to (B).

10. The compound of claim 1, wherein
each occurrence of $R^1$ is independently selected from the group consisting of H; halo; cyano; $C_{1-6}$ alkyl optionally substituted with 1-2 $R^a$; $C_{2-6}$ alkenyl; $C_{2-6}$ alkynyl; $C_{1-4}$ haloalkyl; $C_{1-4}$ alkoxy; $C_{1-4}$ haloalkoxy —S(O)$_{1-2}$($C_{1-4}$ alkyl); —NR$^e$R$^f$; —OH; oxo; —S(O)$_{1-2}$(NR'R''); —$C_{1-4}$ thioalkoxy; —NO$_2$; —C(=O)($C_{1-4}$ alkyl); —C(=O)O($C_{1-4}$ alkyl); —C(=O)OH; and —C(=O)N(R')(R'').

11. A compound selected from the group consisting of the following compounds

| Compound # | Final Structure |
|---|---|
| 115 | |
| 116 | |
| 132 | |
| 133 | |

| Compound # | Final Structure |
|---|---|
| 134 | 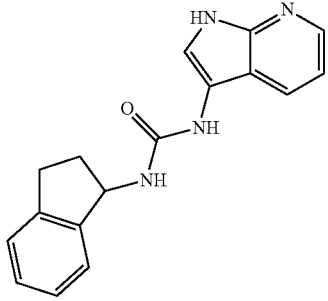 [SMILES: O=C(Nc1c[nH]c2ncccc12)NC1CCc2ccccc21] |
| 135 | 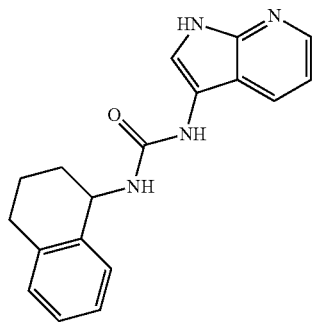 [SMILES: O=C(Nc1c[nH]c2ncccc12)NC1CCCc2ccccc21] |
| 136 | 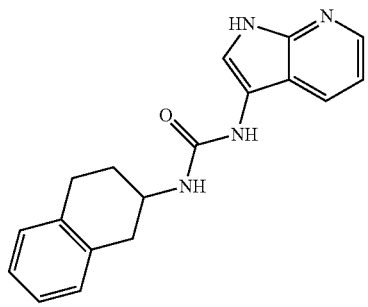 [SMILES: O=C(Nc1c[nH]c2ncccc12)NC1CCc2ccccc2C1] |
| 138 | 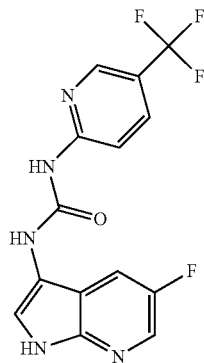 |

-continued
| Compound # | Final Structure |
|---|---|
| 143 | 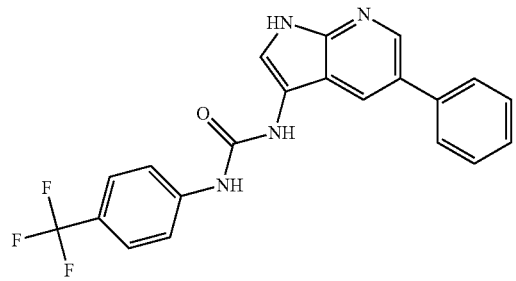 [SMILES: O=C(Nc1ccc(C(F)(F)F)cc1)Nc1c[nH]c2ncc(-c3ccccc3)cc12] |
| 147 | 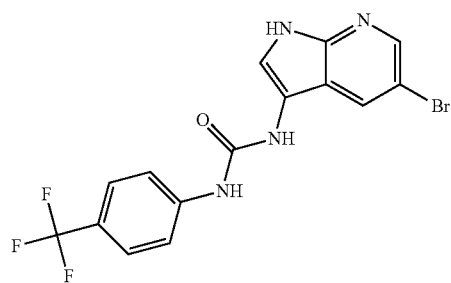 [SMILES: O=C(Nc1ccc(C(F)(F)F)cc1)Nc1c[nH]c2ncc(Br)cc12] |
| 150 | 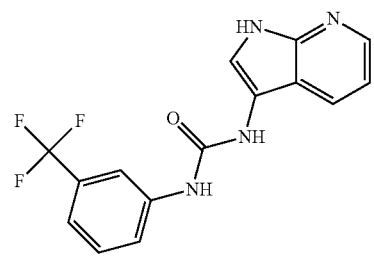 [SMILES: O=C(Nc1cccc(C(F)(F)F)c1)Nc1c[nH]c2ncccc12] |
| 151 | 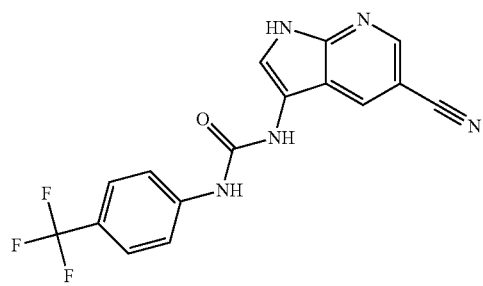 [SMILES: N#Cc1cnc2[nH]cc(NC(=O)Nc3ccc(C(F)(F)F)cc3)c2c1] |
| 160 | 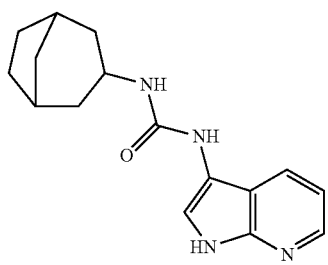 [SMILES: O=C(Nc1c[nH]c2ncccc12)NC1CC2CCC(C2)C1] |

-continued
| Compound # | Final Structure |
|---|---|
| 162 | 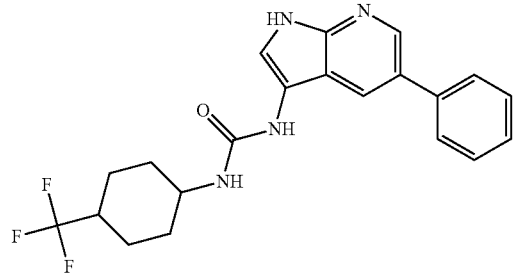 [SMILES: O=C(Nc1c[nH]c2ncc(-c3ccccc3)cc12)NC1CCC(C(F)(F)F)CC1] |
| 163 | 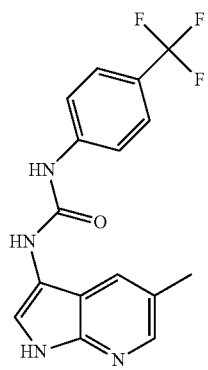 |
| 166 | 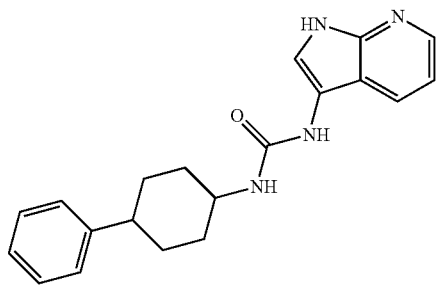 [SMILES: O=C(Nc1c[nH]c2ncccc12)NC1CCC(c2ccccc2)CC1] |
| 167 | 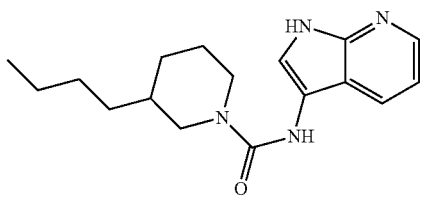 [SMILES: CCCCC1CCCN(C(=O)Nc2c[nH]c3ncccc23)C1] |
| 168 | 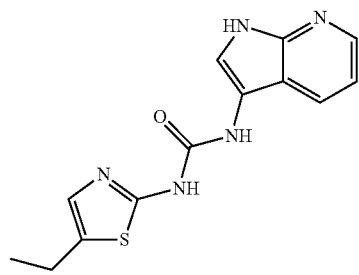 [SMILES: CCc1cnc(NC(=O)Nc2c[nH]c3ncccc23)s1] |

-continued

| Compound # | Final Structure |
|---|---|
| 169 | |
| 170 | |
| 172 | |
| 173 | |
| 174 | |

-continued

| Compound # | Final Structure |
|---|---|
| 179 | |
| 185 | |
| 188 | |
| 193 | |
| 196 | |

-continued

| Compound # | Final Structure |
|---|---|
| 197 | |
| 198 | |
| 200 | |
| 207 | |

-continued

| Compound # | Final Structure |
|---|---|
| 208 | |
| 209 | |
| 210 | |
| 211 | |
| 212 | |

-continued
| Compound # | Final Structure |
|---|---|
| 213 | 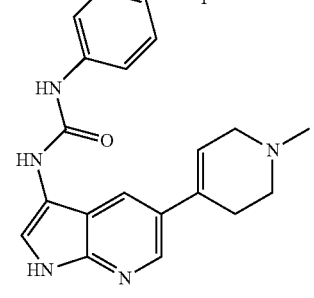 |
| 214 | 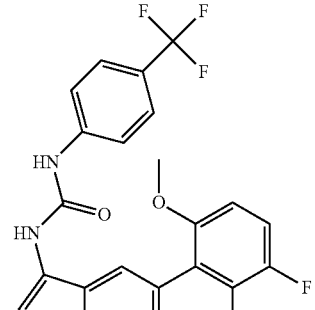 |
| 215 | 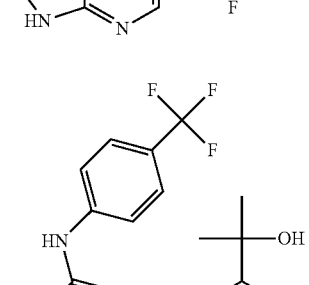 |
| 216 | 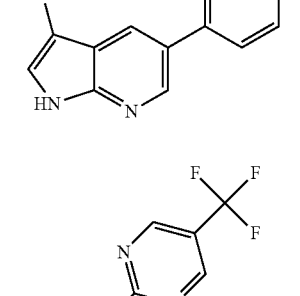 |

| Compound # | Final Structure |
|---|---|
| 217 | 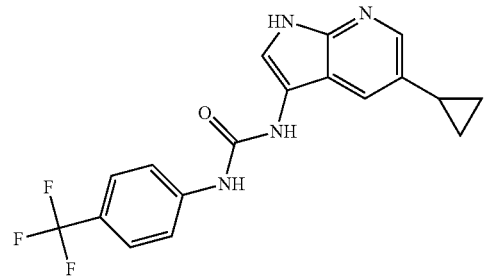 [SMILES: O=C(Nc1ccc(C(F)(F)F)cc1)Nc1c[nH]c2ncc(C3CC3)cc12] |
| 218 | 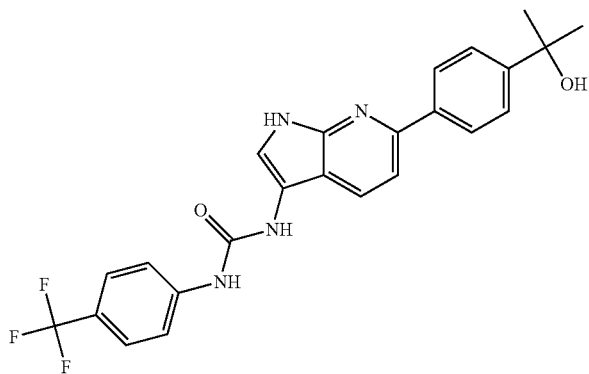 [SMILES: CC(C)(O)c1ccc(-c2ccc3c(NC(=O)Nc4ccc(C(F)(F)F)cc4)c[nH]c3n2)cc1] |
| 219 | 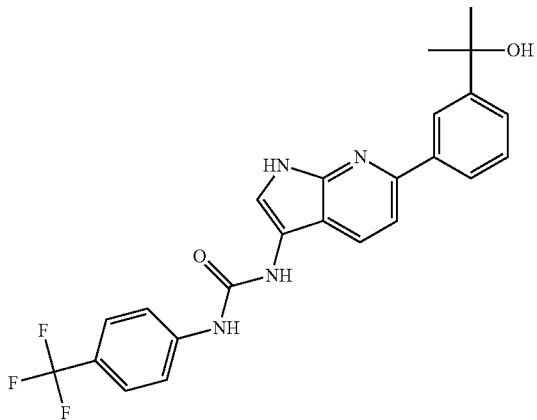 [SMILES: CC(C)(O)c1cccc(-c2ccc3c(NC(=O)Nc4ccc(C(F)(F)F)cc4)c[nH]c3n2)c1] |
| 220 | 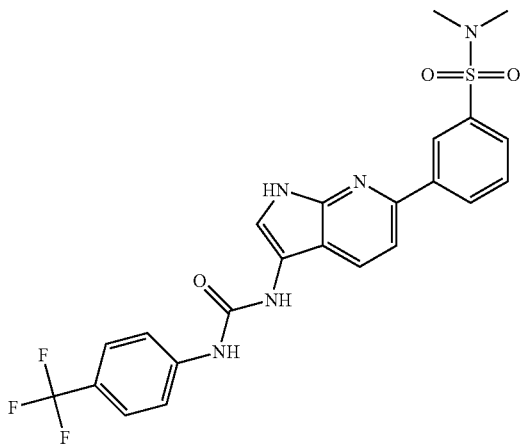 [SMILES: CN(C)S(=O)(=O)c1cccc(-c2ccc3c(NC(=O)Nc4ccc(C(F)(F)F)cc4)c[nH]c3n2)c1] |

-continued
| Compound # | Final Structure |
|---|---|
| 221 | 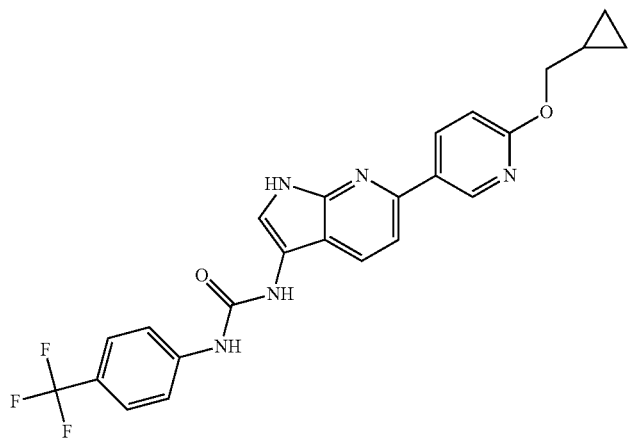 [SMILES: O=C(Nc1ccc(C(F)(F)F)cc1)Nc1c[nH]c2nc(-c3ccc(OCC4CC4)nc3)ccc12] |
| 222 | 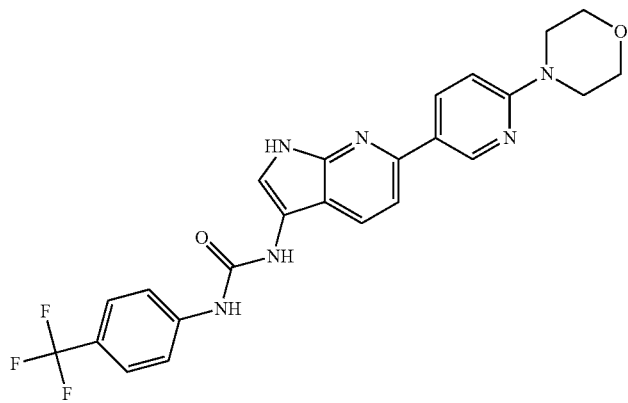 [SMILES: O=C(Nc1ccc(C(F)(F)F)cc1)Nc1c[nH]c2nc(-c3ccc(N4CCOCC4)nc3)ccc12] |
| 223 | 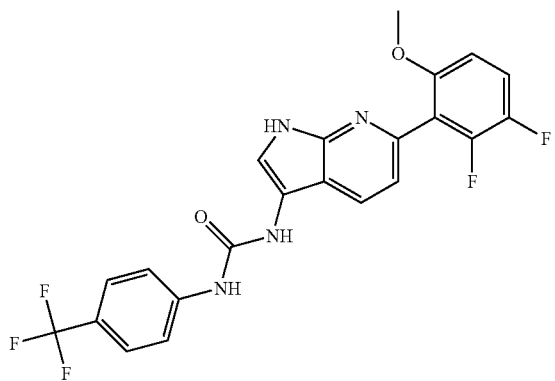 [SMILES: COc1ccc(F)c(F)c1-c1ccc2c(NC(=O)Nc3ccc(C(F)(F)F)cc3)c[nH]c2n1] |
| 224 | 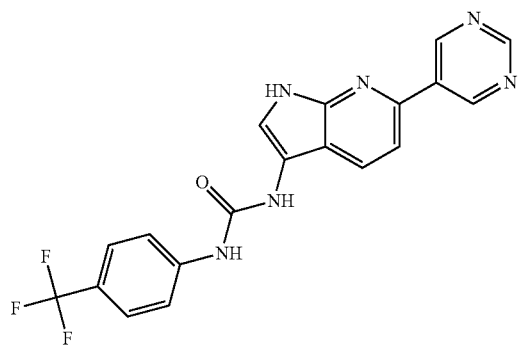 [SMILES: O=C(Nc1ccc(C(F)(F)F)cc1)Nc1c[nH]c2nc(-c3cncnc3)ccc12] |

-continued

| Compound # | Final Structure |
|---|---|
| 225 | |
| 226 | |
| 227 | |
| 228 | |

| Compound # | Final Structure |
|---|---|
| 229 | 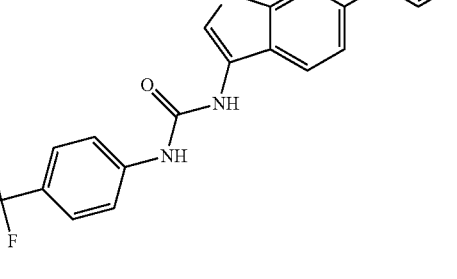 |
| 230 | 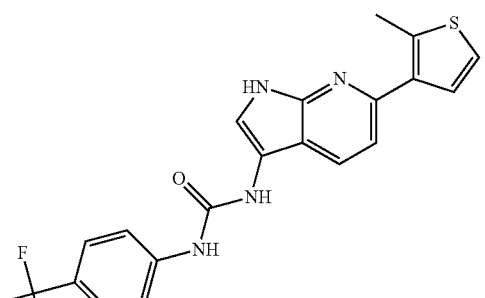 |
| 231 | 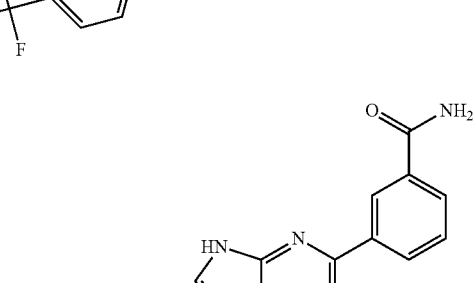 |
| 232 | 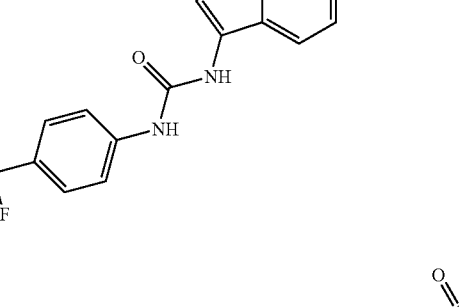 |

| Compound # | Final Structure |
|---|---|
| 233 | |
| 241 | |
| 242 | |
| 243 | |
| 244 | |

-continued
| Compound # | Final Structure |
|---|---|
| 245 | 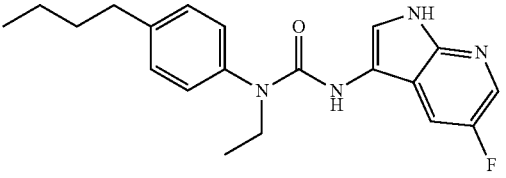 [SMILES: CCCCc1ccc(N(CC)C(=O)Nc2c[nH]c3ncc(F)cc23)cc1] |
| 246 | 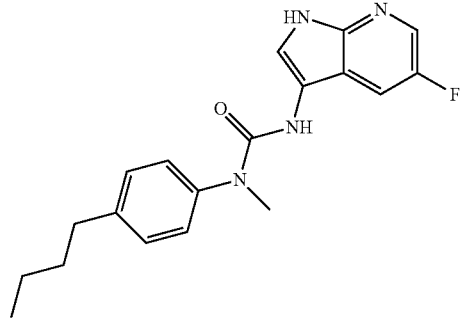 [SMILES: CCCCc1ccc(N(C)C(=O)Nc2c[nH]c3ncc(F)cc23)cc1] |
| 247 | 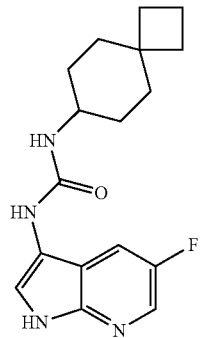 |
| 248 | 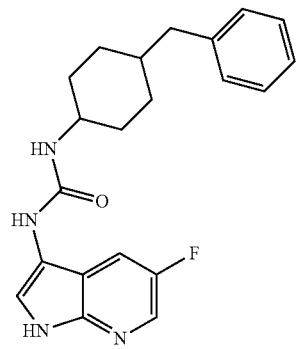 [SMILES: O=C(Nc1c[nH]c2ncc(F)cc12)NC1CCC(Cc2ccccc2)CC1] |
| 249 | 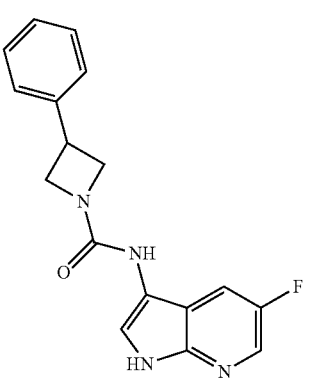 [SMILES: O=C(Nc1c[nH]c2ncc(F)cc12)N1CC(c2ccccc2)C1] |

-continued
| Compound # | Final Structure |
|---|---|
| 250 | 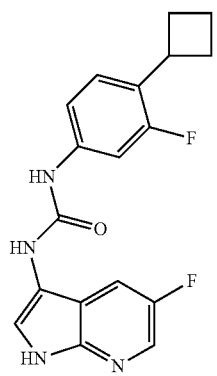 [SMILES: O=C(Nc1ccc(C2CCC2)c(F)c1)Nc1c[nH]c2ncc(F)cc12] |
| 251 | 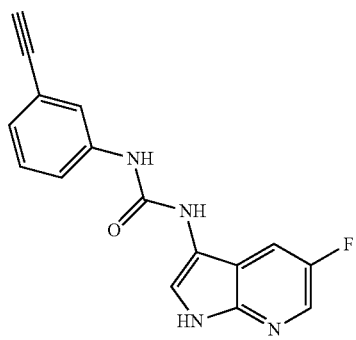 [SMILES: C#Cc1cccc(NC(=O)Nc2c[nH]c3ncc(F)cc23)c1] |
| 252 | 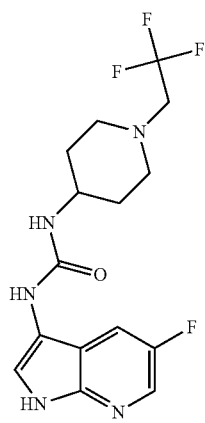 |
| 253 | 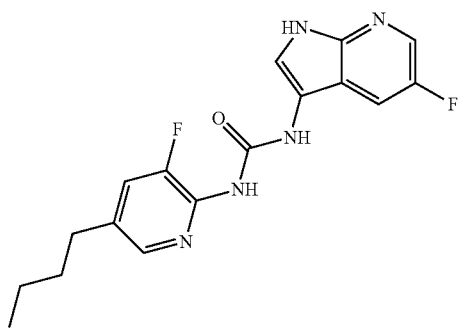 [SMILES: CCCCc1cnc(NC(=O)Nc2c[nH]c3ncc(F)cc23)c(F)c1] |

-continued
| Compound # | Final Structure |
|---|---|
| 254 | 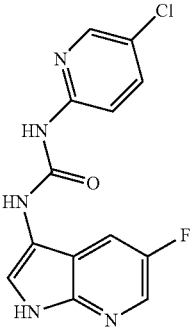 |
| 255 | 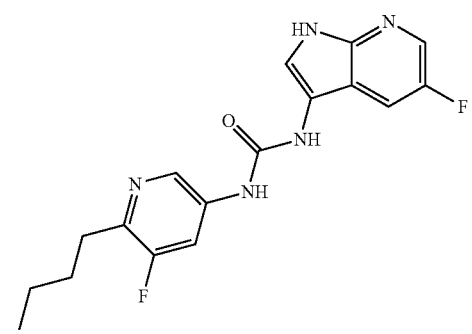 [SMILES: CCCCc1ncc(NC(=O)Nc2c[nH]c3ncc(F)cc23)cc1F] |
| 256 | 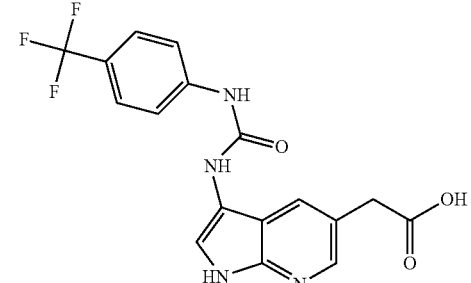 |
| 257 | 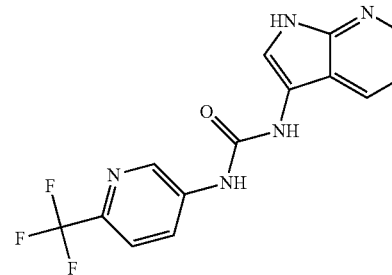 |
| 258 | 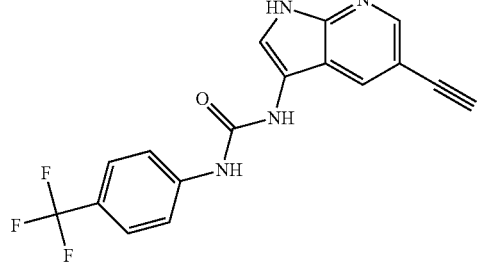 |

-continued
| Compound # | Final Structure |
|---|---|
| 259 | 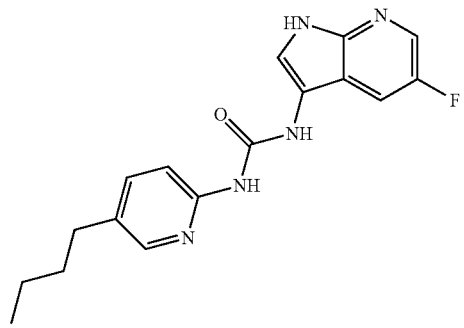 [SMILES: CCCCc1ccc(NC(=O)Nc2c[nH]c3ncc(F)cc23)nc1] |
| 260 | 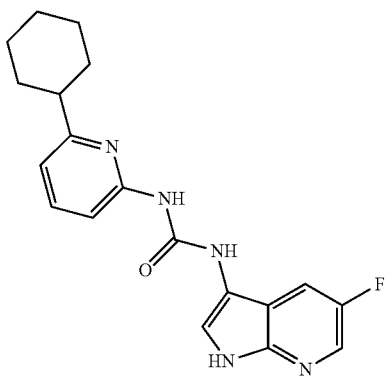 [SMILES: O=C(Nc1cccc(C2CCCCC2)n1)Nc1c[nH]c2ncc(F)cc12] |
| 261 | 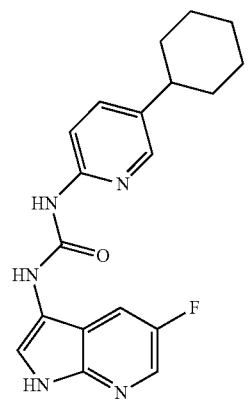 [SMILES: O=C(Nc1ccc(C2CCCCC2)cn1)Nc1c[nH]c2ncc(F)cc12] |
| 262 | 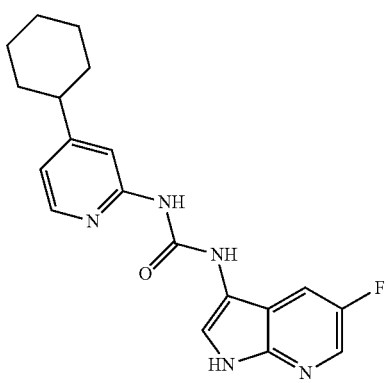 [SMILES: O=C(Nc1cc(C2CCCCC2)ccn1)Nc1c[nH]c2ncc(F)cc12] |

-continued

| Compound # | Final Structure |
|---|---|
| 263 | |
| 264 | |
| 265 | |
| 266 | |
| 267 | |

| Compound # | Final Structure |
|---|---|
| 268 | 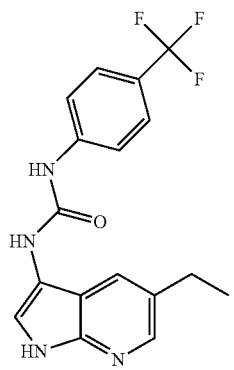 |
| 269 | 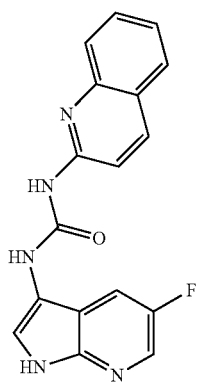 |
| 270 | 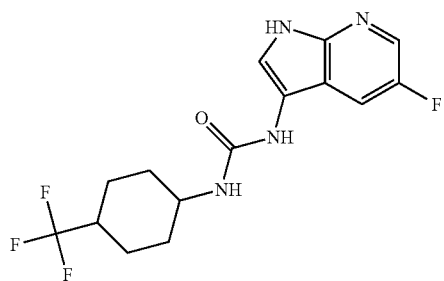 [SMILES: O=C(Nc1c[nH]c2ncc(F)cc12)NC1CCC(C(F)(F)F)CC1] |
| 271 | 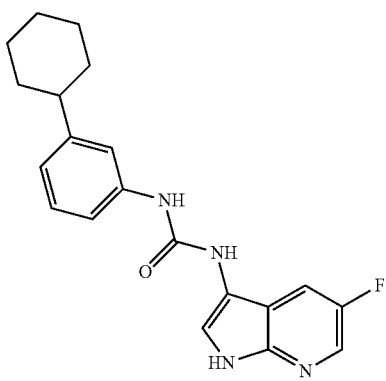 [SMILES: O=C(Nc1cccc(C2CCCCC2)c1)Nc1c[nH]c2ncc(F)cc12] |

-continued

| Compound # | Final Structure |
|---|---|
| 272 | |
| 273 | |
| 274 | |
| 275 | |
| 276 | |

| Compound # | Final Structure |
|---|---|
| 277 | |
| 280 | |
| 281 | |
| 282 | |
| 283 | |

-continued

| Compound # | Final Structure |
|---|---|
| 284 | |
| 285 | |
| 286 | |
| 287 | |
| 288 | |

-continued
| Compound # | Final Structure |
|---|---|
| 289 | 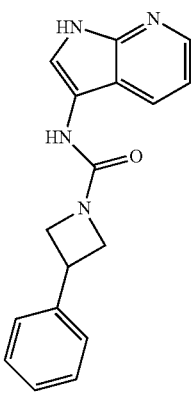 [SMILES: O=C(Nc1c[nH]c2ncccc12)N1CC(c2ccccc2)C1] |
| 290 | 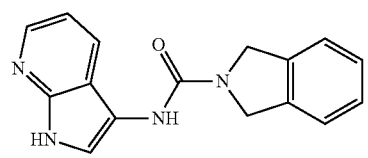 [SMILES: O=C(Nc1c[nH]c2ncccc12)N1Cc2ccccc2C1] |
| 291 | 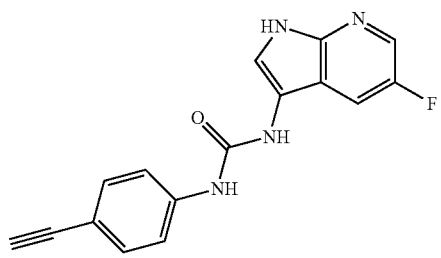 [SMILES: C#Cc1ccc(NC(=O)Nc2c[nH]c3ncc(F)cc23)cc1] |
| 292 | 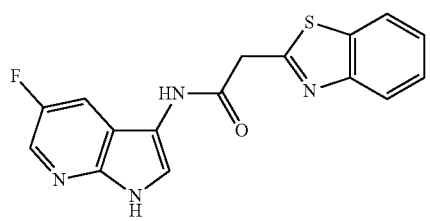 [SMILES: O=C(Cc1nc2ccccc2s1)Nc1c[nH]c2ncc(F)cc12] |
| 293 | 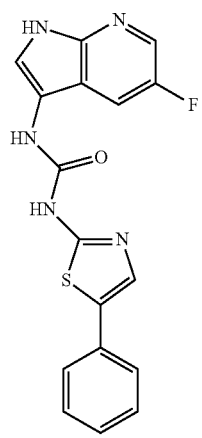 [SMILES: O=C(Nc1ncc(-c2ccccc2)s1)Nc1c[nH]c2ncc(F)cc12] |

-continued

| Compound # | Final Structure |
|---|---|
| 294 | (structure) |
| 295 | (structure) |
| 296 | (structure) |
| 297 | (structure) |

-continued
| Compound # | Final Structure |
|---|---|
| 298 | 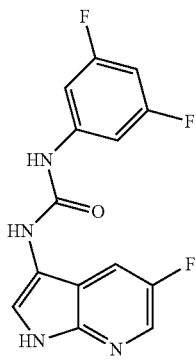 |
| 299 | 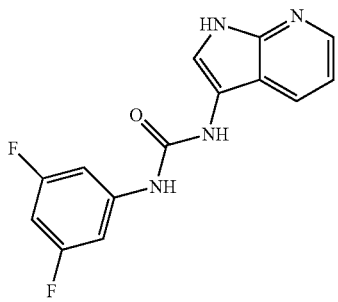 |
| 300 | 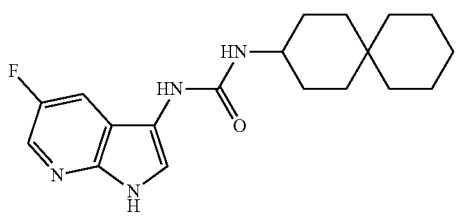 [SMILES: O=C(Nc1c[nH]c2ncc(F)cc12)NC1CCC2(CCCCC2)CC1] |
| 301 | 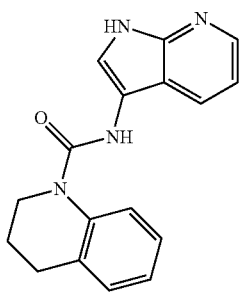 [SMILES: O=C(Nc1c[nH]c2ncccc12)N1CCCc2ccccc21] |
| 302 | 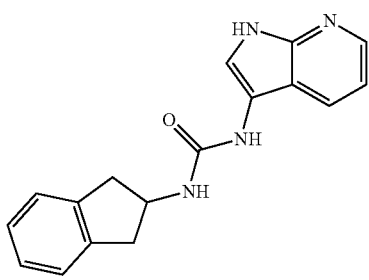 [SMILES: O=C(Nc1c[nH]c2ncccc12)NC1Cc2ccccc2C1] |

| Compound # | Final Structure |
|---|---|
| 303 | |
| 304 | |
| 305 | |
| 306 | |
| 307 | |

| Compound # | Final Structure |
|---|---|
| 308 | |
| 338 | |
| 339 | |
| 340 | |
| 341 | |
| 342 | |

| Compound # | Final Structure |
|---|---|
| 343 | (structure) |
| 344 | (structure) |
| 345 | (structure) |
| 346 | (structure) |
| 347 | (structure) |
| 356 | (structure) |
| 357 | (structure) |

-continued
| Compound # | Final Structure |
|---|---|
| 358 | 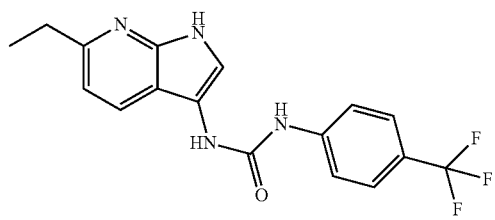 [SMILES: CCc1ccc2c(NC(=O)Nc3ccc(C(F)(F)F)cc3)c[nH]c2n1] |
| 359 | 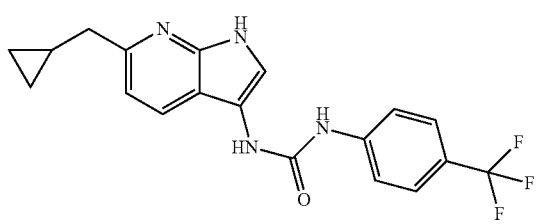 [SMILES: O=C(Nc1ccc(C(F)(F)F)cc1)Nc1c[nH]c2nc(CC3CC3)ccc12] |
| 360 | 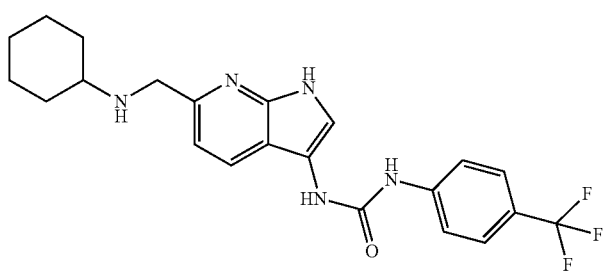 [SMILES: O=C(Nc1ccc(C(F)(F)F)cc1)Nc1c[nH]c2nc(CNC3CCCCC3)ccc12] |
| 361 | 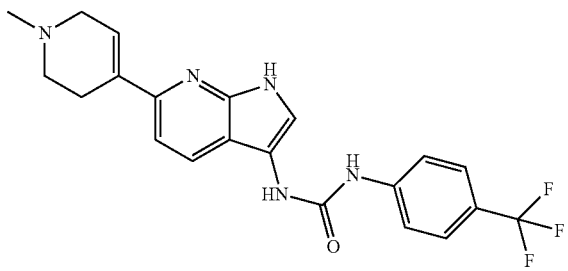 [SMILES: CN1CC=C(c2ccc3c(NC(=O)Nc4ccc(C(F)(F)F)cc4)c[nH]c3n2)CC1] |
| 362 | 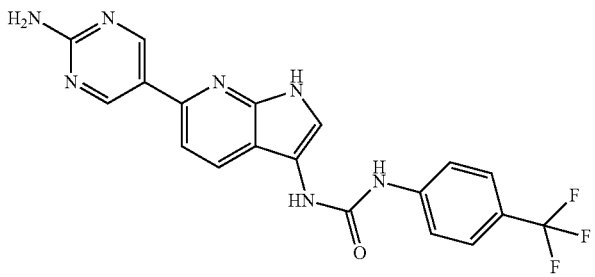 [SMILES: Nc1ncc(-c2ccc3c(NC(=O)Nc4ccc(C(F)(F)F)cc4)c[nH]c3n2)cn1] |

| Compound # | Final Structure |
|---|---|
| 363 | 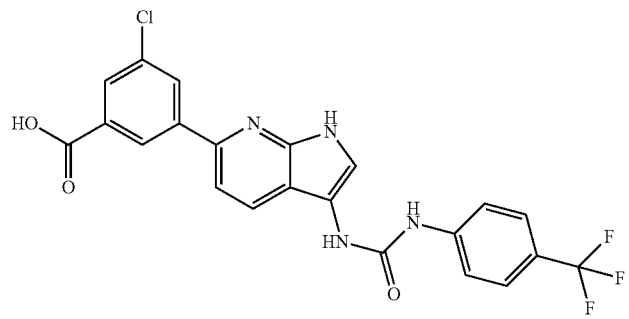 [SMILES: O=C(Nc1ccc(C(F)(F)F)cc1)Nc1c[nH]c2nc(-c3cc(Cl)cc(C(=O)O)c3)ccc12] |
| 364 | 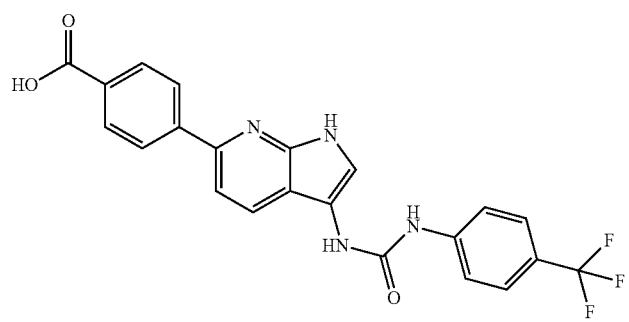 [SMILES: O=C(Nc1ccc(C(F)(F)F)cc1)Nc1c[nH]c2nc(-c3ccc(C(=O)O)cc3)ccc12] |
| 365 | 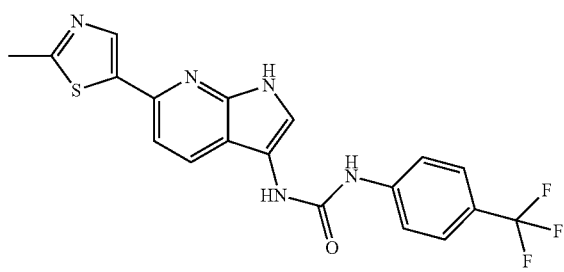 [SMILES: Cc1ncc(-c2ccc3c(NC(=O)Nc4ccc(C(F)(F)F)cc4)c[nH]c3n2)s1] |
| 366 | 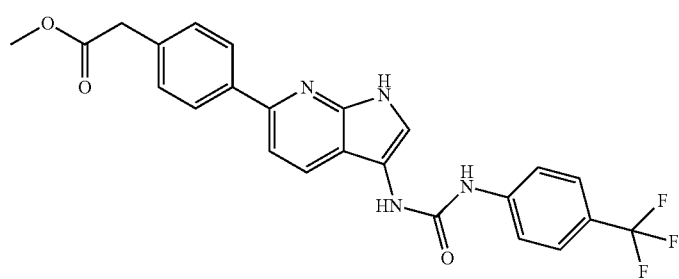 [SMILES: COC(=O)Cc1ccc(-c2ccc3c(NC(=O)Nc4ccc(C(F)(F)F)cc4)c[nH]c3n2)cc1] |
| 367 | 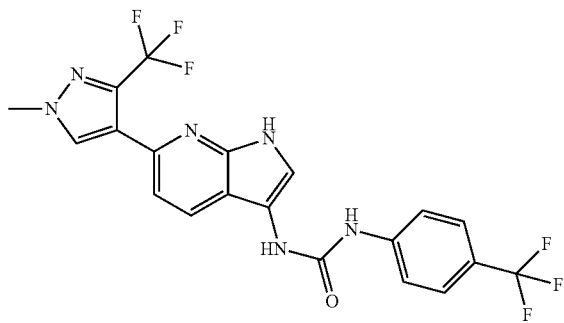 [SMILES: Cn1cc(-c2ccc3c(NC(=O)Nc4ccc(C(F)(F)F)cc4)c[nH]c3n2)c(C(F)(F)F)n1] |

| Compound # | Final Structure |
|---|---|
| 368 | |
| 369 | |
| 370 | |
| 371 | |
| 372 | |
| 373 | |

| Compound # | Final Structure |
|---|---|
| 374 | 3-(hydroxymethyl)phenyl at 5-position of 7-azaindole; 3-position bears NHC(O)NH-(4-trifluoromethylphenyl) urea |
| 375 | 3-(methylaminomethyl)phenyl at 5-position of 7-azaindole; 3-position bears NHC(O)NH-(4-trifluoromethylphenyl) urea |
| 382 | pyrimidin-2-yl at 6-position of 7-azaindole; 3-position bears NHC(O)NH-(4-trifluoromethylphenyl) urea |
| 383 | 2-methylphenyl at 6-position of 7-azaindole; 3-position bears NHC(O)NH-(4-trifluoromethylphenyl) urea |
| 384 | 2-chlorophenyl at 6-position of 7-azaindole; 3-position bears NHC(O)NH-(4-trifluoromethylphenyl) urea |
| 385 | 2-(hydroxymethyl)phenyl at 6-position of 7-azaindole; 3-position bears NHC(O)NH-(4-trifluoromethylphenyl) urea |

| Compound # | Final Structure |
|---|---|
| 386 | 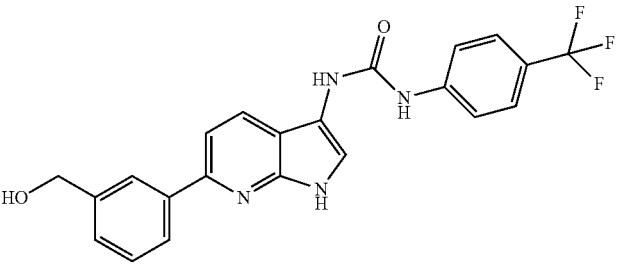 [SMILES: O=C(Nc1ccc(C(F)(F)F)cc1)Nc1c[nH]c2nc(-c3cccc(CO)c3)ccc12] |
| 387 | 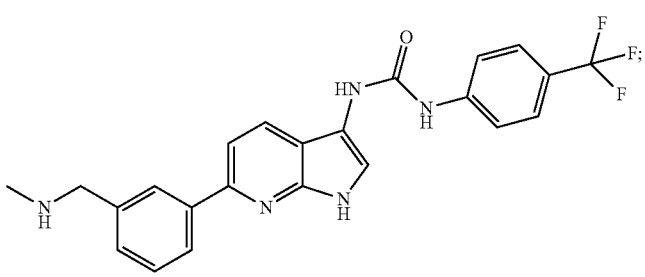 [SMILES: CNCc1cccc(-c2ccc3c(NC(=O)Nc4ccc(C(F)(F)F)cc4)c[nH]c3n2)c1] |
or a pharmaceutically acceptable salt thereof.
12. A pharmaceutical composition comprising a compound of claim 1 and one or more pharmaceutically acceptable excipients.
* * * * *